(12) United States Patent
Bloom

(10) Patent No.: US 9,944,687 B2
(45) Date of Patent: Apr. 17, 2018

(54) COMPOUNDS AND THEIR EFFECTS ON FEEDING BEHAVIOUR

(75) Inventor: Stephen Robert Bloom, London (GB)

(73) Assignee: Imperial Innovations Limited, London (GB)

(*) Notice: Subject to any disclaimer, the term of this patent is extended or adjusted under 35 U.S.C. 154(b) by 285 days.

(21) Appl. No.: 14/128,081

(22) PCT Filed: Jul. 4, 2011

(86) PCT No.: PCT/GB2011/001010
§ 371 (c)(1),
(2), (4) Date: Mar. 10, 2014

(87) PCT Pub. No.: WO2013/004983
PCT Pub. Date: Jan. 10, 2013

(65) Prior Publication Data
US 2014/0221280 A1     Aug. 7, 2014

(51) Int. Cl.
*C07K 14/605* (2006.01)

(52) U.S. Cl.
CPC .................. *C07K 14/605* (2013.01)

(58) Field of Classification Search
CPC .................................................. C07K 14/605
See application file for complete search history.

(56) References Cited

U.S. PATENT DOCUMENTS

| | | | |
|---|---|---|---|
| 4,179,337 A | 12/1979 | Davis et al. | |
| 5,665,705 A | 9/1997 | Merrifield et al. | |
| 5,936,092 A | 8/1999 | Shen et al. | |
| 6,093,692 A | 7/2000 | Shen et al. | |
| 6,225,445 B1 | 5/2001 | Shen et al. | |
| 6,410,707 B2 | 6/2002 | Wagner et al. | |
| 7,186,683 B2 * | 3/2007 | Henriksen | A61K 38/26 514/10.7 |
| 8,329,648 B2 | 12/2012 | Fineman et al. | |
| 2003/0032588 A1 * | 2/2003 | Marshall et al. | 514/12 |
| 2004/0052862 A1 * | 3/2004 | Henriksen | A61K 38/26 424/617 |
| 2007/0135345 A1 * | 6/2007 | Henriksen | A61K 31/573 514/5.8 |
| 2010/0099619 A1 | 4/2010 | Levy et al. | |

FOREIGN PATENT DOCUMENTS

| | | |
|---|---|---|
| EP | 2330125 | 6/2011 |
| WO | WO88/09341 | 12/1988 |
| WO | WO91/11457 | 8/1991 |
| WO | WO92/04042 | 3/1992 |
| WO | WO95/05848 | 3/1995 |
| WO | WO98/05351 | 2/1998 |
| WO | WO98/30231 | 7/1998 |
| WO | WO99/07404 | 2/1999 |
| WO | WO99/25727 | 5/1999 |
| WO | WO99/25728 | 5/1999 |
| WO | WO03/057235 | 7/2003 |
| WO | WO2004/005342 | 1/2004 |
| WO | WO2004/056763 | 7/2004 |
| WO | WO2004/105781 | 12/2004 |
| WO | WO2004/105790 | 12/2004 |
| WO | WO2006/024275 | 3/2006 |
| WO | WO2006/073890 | 7/2006 |
| WO | WO2006/097535 | 9/2006 |
| WO | WO2006/134340 | 12/2006 |
| WO | WO2007/022123 | 2/2007 |
| WO | WO2007/022518 | 2/2007 |
| WO | WO2007/024700 | 3/2007 |
| WO | WO2007/056362 | 5/2007 |
| WO | WO2007/124461 | 11/2007 |
| WO | WO2008/062420 | 5/2008 |
| WO | WO2008/071972 | 6/2008 |
| WO | WO2008/086086 | 7/2008 |
| WO | WO2008/101017 | 8/2008 |
| WO | WO2008/152403 | 12/2008 |
| WO | WO2009/058734 | 5/2009 |
| WO | WO2009/099763 | 8/2009 |
| WO | WO2009/143014 | 11/2009 |
| WO | WO2009/155258 | 12/2009 |
| WO | WO2010/011439 | 1/2010 |
| WO | WO2010/070253 | 6/2010 |
| WO | WO2010/070255 | 6/2010 |
| WO | WO2010/071807 | 6/2010 |
| WO | WO2010/096142 | 8/2010 |
| WO | WO2010/148089 | 12/2010 |
| WO | WO2011/075393 | 6/2011 |

OTHER PUBLICATIONS

Ahn et al., "A New Approach to Search for the Bioactive Conformation of Glucagon: Positional Cyclization Scanning", *J. Med. Chem.*, 44: 3109-3116 (2001).

Al-Sabah and Donnelly, "Structure/function studies of glucagon-like peptide-1 and exendin 4", In *Astbury Centre of Structural Molecular Biology, University of Leeds, Annual Report 2002* (The University of Leeds, U.K., 2003), pp. 17-19.

Claus et al., "Dual-acting peptide with prolonged glucagon-like peptide-1 receptor agonist and glucagon receptor antagonist activity for the treatment of type 2 diabetes," *J. Endocrinol.*, 192: 371-380 (2007).

Day et al., "A new glucagon and GLP-1 co-agonist eliminates obesity in rodents," *Nature Chem. Biol.*, 5(10): 749-757 (2009).

Gelfanov et al., "Discovery and Structural Optimization of High Affinity Co-Agonists at the Glucagon and GLP-1 Receptors," In *Understanding Biology Using Peptides, Proceedings of the Nineteenth American Peptide Symposium* (Blondelle, Sylvie E., ed.) (Springer, New York, 2006) pp. 763-764.

(Continued)

*Primary Examiner* — Amber D Steele
(74) *Attorney, Agent, or Firm* — Thomas R. Berka; Leon R. Yankwich; Yankwich & Associates, P.C.

(57) ABSTRACT

Peptide containing sequence from both the GLP-1 peptide and glucagon peptide, compositions comprising said peptides and methods of using said peptides for the treatment and prevention of metabolic disorders, for example disorders of energy metabolism such as obesity or diabetes, are provided.

15 Claims, 52 Drawing Sheets

(56) References Cited

OTHER PUBLICATIONS

Gelling et al., "Localization of the Domains Involved in Ligand Binding and Activation of the Glucose-Dependent Insulinotropic Polypeptide Receptor," *Endocrinology*, 138(6): 2640-2643 (1997).
Gengler et al., "Val(8)GLP-1 rescues synaptic plasticity and reduces dense core plaques in APP/PS1 mice,"—Article in Press—*Neurobiology of Aging*, xx (2010) xxx, published online Apr. 2, 2010 (12 pages).
Hjorth et al., "Glucagon and Glucagon-like Peptide 1: Selective Receptor Recognition via Distinct Peptide Epitopes," *J. Biol. Chem.*, 269(48): 30121-30124 (1994).
Holst, J.J., Review: "On the Physiology of GIP and GLP-1," *Horm. Metab. Res.*, 36(11-12): 747-754 (2004).
Li, Pengyun, et al., "Design, synthesis and crystallization of a novel glucagon analog as a therapeutic agent," *Acta Crystallographica Section F: Structural Biology and Crystallization Communications*, 63(7): 599-601 (2007).
Pan et al., "Design of a Long Acting Peptide Functioning as Both a Glucagon-like Peptide-1 Receptor Agnoist and a Glucagon Receptor Antagonist," *J. Biol. Chem.*, 281(18): 12506-12515 (2006).
Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," *Biochem. J.*, 362(2): 389-394 (2002).
Ruczynski et al., "Synthesis and Biological Properties of New Chimeric Galanin Analogue GAL(1-13)-[Ala$^{10,\ 11}$]ET-1(6-21)-NH$_2$," *J. Physiol. Pharmacol.*, 56(2): 273-285 (2005).
Runge et al., "Different domains of the glucagon and glucagon-like peptide-1 receptors provide the critical determinants of ligand selectivity," *Br. J. Pharmacol.*, 138: 787-794 (2003).
Teramoto et al., "Exendin-4, a glucagon-like peptide-1 receptor agonist, provides neuroprotection in mice transient focal cerebral ischemia,"*J. Cereb. Blood Flow Metab.*, 31: 1696-1705 (2011) published online Apr. 13, 2011 www.jcbfm.com.
Unson et al., "Roles of Aspartic Acid 15 and 21 in Glucagon Action: Receptor Anchor and Surrogates for Aspartic Acid 9," *Biochemistry*, 33: 6884-6887 (1994).
International Search Report (ISR) dated Dec. 20, 2011, issued in PCT/GB2011/001010.
International Preliminary Report on Patentability (Chapter I) dated Jan. 7, 2014, issued in PCT/GB2011/001010.
Krstenansky et al., "Importance of the C-terminal α-helical structure for glucagon's biological activity," *Int. J. Peptide Protein Res.*, 32: 468-475 (1988).
Day et al., "Charge inversion at position 68 of the glucagon and glucagon-like peptide-1 receptors supports selectivity in hormone action," J. Peptide Sci., 17: 218-225 (2011) doi:10.1002/psc.1317.

* cited by examiner

FIG. 1A

| SEQ ID No. | Compound no. / G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 1 | Gluc | His | Ser | Gln | Gly | Thr | Phe | Thr | Ser | Asp | Tyr | Ser | Lys | Tyr | Leu | Asp | Ser | Arg | Arg | Ala | Gln |
| 2 | GLP1 7-36NH2 | His | Ala | Glu | Gly | Thr | Phe | Thr | Ser | Asp | Val | Ser | Ser | Tyr | Leu | Glu | Gly | Gln | Ala | Ala | Lys |
| 3 | Exen | His | Gly | Glu | Gly | Thr | Phe | Thr | Ser | Asp | Leu | Ser | Lys | Gln | Met | Glu | Glu | Glu | Ala | Val | Arg |
| 4 | 11 | DHis | Ala | Gln | Gly | Thr | Phe | Thr | Ser | Asp | Tyr | Ser | Lys | Tyr | Leu | Glu | Gln | Glu | Leu | Val | Lys |
| 5 | 14 | His | Ala | Glu | Gly | Thr | Phe | Thr | Ser | Asp | Val | Ser | Ser | Tyr | Leu | Glu | Gln | Glu | Ala | Val | Arg |
| 6 | 15 | His | AIB | Glu | Gly | Thr | Phe | Thr | Ser | Asp | Val | Ser | Ser | Tyr | Leu | Glu | Gln | Glu | Ala | Val | Lys |
| 7 | 17 | His | AIB | Glu | Gly | Thr | Phe | Thr | Ser | Asp | Val | Ser | Ser | Tyr | Leu | Glu | Gln | Glu | Ile | Val | Lys |
| 8 | 18 | His | AIB | Glu | Gly | Thr | Phe | Thr | Ser | Asp | Val | Ser | Ser | Tyr | Leu | Glu | Gln | His | Ile | Val | Lys |
| 9 | 21 | His | AIB | Glu | Gly | Thr | Phe | Thr | Ser | Asp | Val | Ser | Ser | Tyr | Leu | Glu | Gly | Gln | Ile | Val | Lys |
| 10 | 22 | His | AIB | Glu | Gly | Thr | Phe | Thr | Ser | Asp | Val | Ser | Ser | Tyr | Leu | Glu | Gly | Gln | Ile | Val | Lys |
| 11 | 32 | His | Ser | Gln | Gly | Thr | Phe | Thr | Ser | Asp | Tyr | Ser | Lys | Tyr | Leu | Asp | Ser | Arg | Arg | Ala | Gln |
| 12 | 33 | His | Ser | Gln | Gly | Thr | Phe | Thr | Ser | Asp | Tyr | Ser | Ser | Tyr | Leu | Asp | Ser | Arg | Arg | Ala | Gln |
| 13 | 38 | His | AIB | Gln | Gly | Thr | Phe | Thr | Ser | Asp | Tyr | Ser | Lys | Tyr | Leu | Asp | Ser | Arg | Arg | Ala | Gln |
| 14 | 41 | His | AIB | Glu | Gly | Thr | Phe | Thr | Ser | Asp | Val | Ser | Arg | Tyr | Leu | Asp | Gly | Gln | Arg | Val | Lys |
| 15 | 42 | His | AIB | Glu | Gly | Thr | Phe | Thr | Ser | Asp | Val | Ser | Arg | Tyr | Leu | Glu | Gly | Arg | Arg | Val | Lys |
| 16 | 43 | His | AIB | Glu | Gly | Thr | Phe | Thr | Ser | Asp | Val | Ser | Arg | Tyr | Leu | Glu | Gly | Arg | Arg | Val | Lys |
| 17 | 44 | His | AIB | Glu | Gly | Thr | Phe | Thr | Ser | Asp | Val | Ser | His | Tyr | Leu | Glu | Gly | Gln | Ala | Val | Arg |
| 18 | 45 | His | AIB | Glu | Gly | Thr | Phe | Thr | Ser | Asp | Val | Ser | Ser | Tyr | Leu | Glu | Gly | Gln | Ile | Val | Lys |
| 19 | 48 | His | AIB | Gln | Gly | Thr | Phe | Thr | Ser | Asp | Val | Ser | Ser | Tyr | Leu | Asp | Gly | Gln | Ile | Val | Lys |
| 20 | 49 | His | AIB | Gln | Gly | Thr | Phe | Thr | Ser | Asp | Tyr | Ser | Lys | Tyr | Leu | Asp | Ser | Arg | Arg | Ala | Gln |
| 21 | 50 | His | AIB | Gln | Gly | Thr | Phe | Thr | Ser | Asp | Tyr | Ser | Lys | Tyr | Leu | Asp | Gly | Arg | Arg | Val | Arg |
| 22 | 52 | His | Ser | Gln | Gly | Thr | Phe | Thr | Ser | Asp | Tyr | Ser | Lys | Tyr | Leu | Asp | Ser | Gln | Arg | Ala | Gln |
| 23 | 53 | His | Ser | Gln | Gly | Thr | Phe | Thr | Ser | Asp | Tyr | Ser | Lys | Tyr | Leu | Asp | Ser | Arg | Ala | Ala | Gln |
| 24 | 54 | His | AIB | Gln | Gly | Thr | Phe | Thr | Ser | Asp | Tyr | Ser | Lys | Tyr | Leu | Asp | Ser | Arg | Arg | Ala | Gln |
| 25 | 55 | His | Ser | Gln | Gly | Thr | Phe | Thr | Ser | Asp | Tyr | Ser | Lys | Tyr | Leu | Asp | Ser | Glu | Arg | Ala | Gln |
| 26 | 56 | His | Ser | Gln | Gly | Thr | Phe | Thr | Ser | Asp | Tyr | Ser | Lys | Tyr | Leu | Asp | Ser | Arg | Ala | Ala | Gln |
| 27 | 57 | His | AIB | Gln | Gly | Thr | Phe | Thr | Ser | Asp | Tyr | Ser | Lys | Tyr | Leu | Asp | Ser | Arg | Arg | Ala | Gln |
| 28 | 58 | His | AIB | Gln | Gly | Thr | Phe | Thr | Ser | Asp | Tyr | Ser | Lys | Tyr | Leu | Asp | Ser | Arg | Arg | Ala | Gln |
| 29 | 59 | His | Ser | Gln | Gly | Thr | Phe | Thr | Ser | Asp | Tyr | Ser | Lys | Tyr | Leu | Asp | Ser | Arg | Arg | Ala | Gln |
| 30 | 60 | His | Ser | Gln | Gly | Thr | Phe | Thr | Ser | Asp | Tyr | Ser | Lys | Tyr | Leu | Glu | Ser | Glu | Arg | Ala | Gln |
| 31 | 62 | His | Ser | Gln | Gly | Thr | Phe | Thr | Ser | Asp | Tyr | Ser | Lys | Tyr | Leu | Glu | Gly | Gln | Ala | Val | Lys |
| 32 | 63 | His | AIB | Gln | Gly | Thr | Phe | Thr | Ser | Asp | Tyr | Ser | Lys | Tyr | Leu | Glu | Gly | Glu | Ile | Val | Lys |
| 33 | 65 | His | AIB | Gln | Gly | Thr | Phe | Thr | Ser | Asp | Tyr | Ser | Lys | Tyr | Leu | Glu | Gly | Glu | Ile | Val | Lys |
| 34 | 71 | His | Ser | Gln | Gly | Thr | Phe | Thr | Ser | Asp | Tyr | Ser | Lys | Tyr | Leu | Asp | Ser | Lys | Lys | Ala | Gln |

FIG. 1B

| SEQ ID No. | Compound no. / G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| 1 | Gluc | Asp | Phe | Val | Gln | Trp | Leu | Met | Asn | Thr | Arg | | | | | | | | | | |
| 2 | GLP1 7-36NH2 | Glu | Phe | Ile | Ala | Trp | Leu | Val | Lys | Gly | Gly | NH2 | | | | | | | | | |
| 3 | Exen | Leu | Phe | Ile | Glu | Trp | Leu | Lys | Asn | Gly | Gly | Pro | Ser | Ser | Gly | Ala | Pro | Pro | Pro | Ser | |
| 4 | 11 | Tyr | Phe | Ile | Gln | Trp | Leu | Val | Lys | Ala | Gly | Pro | Ser | Lys | Asn | Asn | Ile | Ala | Pro | | |
| 5 | 14 | Leu | Phe | Ile | Glu | Trp | Leu | Val | Asn | Gly | Gly | NH2 | | | | | | | | | |
| 6 | 15 | Tyr | Phe | Ile | Gln | Trp | Leu | Val | Lys | Ala | Arg | NH2 | | | | | | | | | |
| 7 | 17 | Tyr | Phe | Ile | Glu | Trp | Leu | Val | Lys | Gly | Arg | NH2 | | | | | | | | | |
| 8 | 18 | Tyr | Phe | Ile | Glu | Trp | Leu | Val | Lys | Gly | Arg | NH2 | | | | | | | | | |
| 9 | 21 | Tyr | Phe | Ile | Gln | Trp | Leu | Val | Lys | Gly | Arg | NH2 | | | | | | | | | |
| 10 | 22 | Tyr | Phe | Ile | His | Trp | Leu | Val | Lys | Gly | Arg | NH2 | | | | | | | | | |
| 11 | 32 | Asp | Phe | Val | Gln | Trp | Leu | Met | Asn | Thr | Gly | Pro | Ser | Ser | Gly | Ala | Pro | Pro | Pro | Ser | |
| 12 | 33 | Asp | Phe | Val | Gln | Trp | Leu | Met | Asn | Gly | Gly | Pro | Ser | Ser | Gly | Ala | Pro | Pro | Pro | Ser | |
| 13 | 38 | Asp | Phe | Val | Gln | Trp | Leu | Lys | Asn | Gly | Gly | Pro | Ser | Ser | Gly | Ala | Pro | Pro | Pro | Ser | |
| 14 | 41 | Tyr | Phe | Ile | Glu | Trp | Leu | Val | Lys | Gly | Arg | NH2 | | | | | | | | | |
| 15 | 42 | Tyr | Phe | Ile | Glu | His | Leu | Val | Lys | Gly | Arg | NH2 | | | | | | | | | |
| 16 | 43 | Tyr | Phe | Ile | Glu | Trp | Leu | Val | Lys | Gly | Arg | NH2 | | | | | | | | | |
| 17 | 44 | Leu | Phe | Ile | Glu | Trp | Leu | Val | Lys | Gly | Arg | NH2 | | | | | | | | | |
| 18 | 45 | Tyr | Phe | Ile | Glu | Lys | Leu | Val | Lys | Gly | Arg | NH2 | | | | | | | | | |
| 19 | 48 | Tyr | Phe | Ile | Glu | Trp | Leu | Val | Lys | Gly | Arg | NH2 | | | | | | | | | |
| 20 | 49 | Asp | Phe | Val | Gln | Trp | Leu | Met | Asn | Gly | Arg | NH2 | | | | | | | | | |
| 21 | 50 | Leu | Phe | Val | Gln | Trp | Leu | Val | Lys | Gly | Arg | NH2 | | | | | | | | | |
| 22 | 52 | Asp | Phe | Ile | Glu | Trp | Leu | Met | Asn | Gly | Gly | Pro | Ser | Ser | Gly | Ala | Pro | Pro | Pro | Ser | |
| 23 | 53 | Asp | Phe | Ile | Gln | Trp | Leu | Lys | Asn | Gly | Gly | Pro | Ser | Ser | Gly | Ala | Pro | Pro | Pro | Ser | |
| 24 | 54 | Asp | Phe | Ile | Gln | Trp | Leu | Lys | Asn | Gly | Gly | Pro | Ser | Ser | Gly | Ala | Pro | Pro | Pro | Ser | |
| 25 | 55 | Tyr | Phe | Ile | Glu | Trp | Leu | Lys | Asn | Gly | Gly | Pro | Ser | Ser | Gly | Ala | Pro | Pro | Pro | Ser | |
| 26 | 56 | Tyr | Phe | Ile | Glu | Trp | Leu | Lys | Asn | Gly | Gly | Pro | Ser | Ser | Gly | Ala | Pro | Pro | Pro | Ser | |
| 27 | 57 | Asp | Phe | Val | Gln | Trp | Leu | Leu | Asn | Asn | Gly | | | | | | | | | | |
| 28 | 58 | Asp | Phe | Val | Gln | Trp | Leu | Leu | Asn | Asn | Gly | | | | | | | | | | |
| 29 | 59 | Asp | Phe | Val | Gln | Trp | Leu | Leu | Asn | Gly | Gly | Pro | Ser | Ser | Gly | Ala | Pro | Pro | Pro | Ser | |
| 30 | 60 | Asp | Phe | Val | Gln | Trp | Leu | Leu | Asn | Gly | Arg | NH2 | | | | | | | | | |
| 31 | 62 | Tyr | Phe | Ile | Glu | Trp | Leu | Val | Asn | Gly | Arg | NH2 | | | | | | | | | |
| 32 | 63 | Tyr | Phe | Ile | Glu | Trp | Leu | Val | Asn | Gly | Gly | NH2 | | | | | | | | | |
| 33 | 65 | Tyr | Phe | Ile | Gln | Trp | Leu | Val | Asn | Gly | Gly | Pro | Ser | Ser | Gly | Ala | Pro | Pro | Pro | Ser | |
| 34 | 71 | Glu | Phe | Ile | Ala | Trp | Leu | Val | Lys | Gly | Gly | Pro | Ser | Ser | Gly | Ala | Pro | Pro | Pro | Ser | |

FIG. 1C

| SEQ ID No. | Compound no. / G no. | hGLP1R Man | rGLP1R Rat | mGLP1R Mouse | hGLP1R cAMP | hGlucR Man | hGluc cAMP | 0-1 Mouse | 0-4 Mouse | 0-8 Mouse | 4-8 Mouse | 8-24 Mouse | 0-24 Mouse |
|---|---|---|---|---|---|---|---|---|---|---|---|---|---|
| 1 | Gluc | | 3817.273 | | 288.8301388 | 1.4678213 | 0.957657 | 10 | 0.45 | 0.1 | 0.1 | 0.1 | 0.25 |
| 2 | GLP1 7-36NH2 | 1 | 1.059051 | | 0.985671984 | 7692.3077 | 31.19399 | 1 | 1 | 1 | 1 | 0.1 | 0.1 |
| 3 | Exen | | 1.632857 | | 2.36417657 | | | 10 | 6 | 8 | 8 | 0.1 | 8 |
| 4 | 11 | | 0 | | | | | | | | | | |
| 5 | 14 | | 2.467143 | | | | | 0.9 | 1.5 | 1.3 | 1.3 | 0.8 | 1.9 |
| 6 | 15 | | 2.45 | | | | | 2 | 3 | 3.5 | 8 | 2 | 4 |
| 7 | 17 | | 3.671635 | | | 471.53846 | 67385.44 | 1 | 3.875 | 4.075 | 6.75 | 2.825 | 5.875 |
| 8 | 18 | | 1.05 | | | | | 0.3 | 1.3 | 2 | 5 | 1 | 2.3 |
| 9 | 21 | | 2.7625 | | | | | 0.8 | 2.2 | 2 | 4 | 3 | 3 |
| 10 | 22 | | 2.6875 | | | | | 0.7 | 2 | 2 | 4 | 1 | 2.3 |
| 11 | 32 | | 270.7 | | | 3.8133333 | | 5.33333 | 1 | 0.8333333 | 0.633333 | 0.4 | 1.166667 |
| 12 | 33 | | 21.55962 | | | 2.7603846 | | 4.6 | 2.18 | 1.36 | 0.14 | 0.46 | 1.18 |
| 13 | 38 | | 10.84727 | | | 32.003846 | | 5.75 | 1.6 | 1.25 | 0.1 | 0.1 | 1 |
| 14 | 41 | | 6.504292 | | | | | | | | | | |
| 15 | 42 | | 1.233654 | | | | | 5 | 3 | 2 | 0.1 | 0.3 | 2.5 |
| 16 | 43 | | 2.892692 | | | | | 3 | 4.5 | 3.7 | 0.3 | 0.2 | 3.3 |
| 17 | 44 | | 1.842078 | | | | | | | | | | |
| 18 | 45 | | 2.094091 | | | | | 3 | 4.5 | 1.5 | 0.1 | 0.3 | 0.5 |
| 19 | 48 | | 4.793091 | | | | 67385.44 | 2.5 | 2.2 | 3 | 0.3 | 0.1 | 3 |
| 20 | 49 | | 2.255128 | | | 20.107692 | | 4.5 | 2.75 | 1.6 | 0.55 | 0.1 | 1.7 |
| 21 | 50 | | 1.703007 | | | | | | | | | | |
| 22 | 52 | | 49.23958 | | | 2.1911538 | | 6.5 | 1.75 | 1.45 | 0.1 | 0.3 | 1.25 |
| 23 | 53 | | 11.025 | | | 9.9326923 | | 7 | 1.75 | 1.8 | 0.1 | 0.3 | 1.75 |
| 24 | 54 | | 7.944444 | | | 65.615385 | | 6 | 2.5 | 1.5 | 0.1 | 0.1 | 2.5 |
| 25 | 55 | | 4.562857 | | | 317.84615 | | 10 | 3 | 4 | 3.5 | 1 | 3.5 |
| 26 | 56 | | 1.812778 | | | 369.05385 | | 4.875 | 3.75 | 4.5 | 4.525 | 2 | 5.5 |
| 27 | 57 | | 203.506 | | | 0.1629808 | | 2.5 | 1.4 | 1.25 | 0.8 | 1.05 | 1.4 |
| 28 | 58 | | 10.67857 | | | 2.845641 | | 3.5 | 1.55 | 0.9 | 0.1 | 1 | 1.2 |
| 29 | 59 | | 34.0319 | | | 1.0898077 | | 4.83333 | 3 | 1.4 | 3.5 | 0.7 | 1.366667 |
| 30 | 60 | | 47.54827 | | | 1.6397436 | | 5 | 1.6 | 1.8 | 0.333333 | 0.55 | 1.5 |
| 31 | 62 | | 33.92592 | | | 73.1 | | 0.55 | 1.85 | 1.5 | 0.8 | 2 | 2.2 |
| 32 | 63 | | 19.40952 | | | 152.69231 | | 4 | 1.3 | 1.5 | 1.5 | 1 | 6 |
| 33 | 65 | | 3.803571 | | | 311.53846 | | 4.33333 | 3.5 | 4 | 3.5 | 0.733333 | 5 |
| 34 | 71 | | 9.458242 | | | 5.4487179 | | 6 | 3.333333 | 4.333333 | 5.166667 | 0.1 | 2 |

| SEQ ID No. | Compound no. / G no. | Pair feeding | mouse 8+24 | rat 8+24 | sol pH<5 | sol pH 7.4 | pK peak | PK3d/4d | PK 7d | PK rating |
|---|---|---|---|---|---|---|---|---|---|---|
| 1 | Gluc | | | | | | | | | |
| 2 | GLP1 7-36NH2 | 0.1 | | | | | | | | |
| 3 | Exen | | | | | | | | | |
| 4 | 11 | | | | | | | | | |
| 5 | 14 | | | | | | | | | |
| 6 | 15 | | | | 7 | | | | | |
| 7 | 17 | | | | 3 | 5 | | | | |
| 8 | 18 | | | | | | | | | |
| 9 | 21 | | | | | | | | | |
| 10 | 22 | | | | | | | | | |
| 11 | 32 | | | | 1 | | | | | |
| 12 | 33 | | | | | | | | | |
| 13 | 38 | | | | 7 | 5 | | | | |
| 14 | 41 | | | | | | | | | |
| 15 | 42 | | | | | | | | | |
| 16 | 43 | | | | | | | | | |
| 17 | 44 | | | | 7 | | | | | |
| 18 | 45 | | | | 2 | 5 | | | | |
| 19 | 48 | | | | | | | | | |
| 20 | 49 | | | | | | | | | |
| 21 | 50 | | | | | | | | | |
| 22 | 52 | | | | | | | | | |
| 23 | 53 | | | | | | | | | |
| 24 | 54 | | | | | | | | | |
| 25 | 55 | | | | | | | | | |
| 26 | 56 | | | | 1 | 5 | | | | |
| 27 | 57 | | | | | | | | | |
| 28 | 58 | | | | | | | | | |
| 29 | 59 | | | | | | | | | |
| 30 | 60 | | | | | | | | | |
| 31 | 62 | | | | 7 | | | | | |
| 32 | 63 | | | | 7 | | | | | |
| 33 | 65 | | | | | | | | | |
| 34 | 71 | | | | | | | | | |

| SEQ ID No. | Compound no. / G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 35 | 74 | His | Ser | Gln | Gly | Thr | Phe | Thr | Ser | Asp | Tyr | Ser | Lys | Tyr | Leu | Asp | Glu | Glu | Ile | Val | Lys |
| 36 | 75 | His | Aib | Gln | Gly | Thr | Phe | Thr | Ser | Asp | Tyr | Ser | Lys | Tyr | Leu | Asp | Ser | Arg | Ala | Val | Arg |
| 37 | 80 | His | Aib | Gln | Gly | Thr | Phe | Thr | Ser | Asp | Tyr | Ser | Lys | Tyr | Leu | Asp | Ser | Arg | Ile | Val | Lys |
| 38 | 85 | His | Ser | Gln | Gly | Thr | Phe | Thr | Ser | Asp | Tyr | Ser | Lys | Tyr | Leu | Asp | Glu | Glu | Ile | Val | Lys |
| 39 | 89 | His | Aib | Gln | Gly | Thr | Phe | Thr | Ser | Asp | Tyr | Ser | Lys | Tyr | Leu | Asp | Ser | Lys | Lys | Ala | Gln |
| 40 | 91 | His | Aib | Gln | Gly | Thr | Phe | Thr | Ser | Asp | Tyr | Ser | Lys | Tyr | Leu | Asp | Ser | Lys | Lys | Ala | Gln |
| 41 | 92 | His | Ser | Gln | Gly | Thr | Phe | Thr | Ser | Asp | Tyr | Ser | Lys | Tyr | Leu | Asp | Ser | Arg | Ala | Val | Arg |
| 42 | 104 | His | Ser | Gln | Gly | Thr | Phe | Thr | Ser | Asp | Tyr | Ser | Lys | Tyr | Leu | Asp | Ser | Arg | Ile | Val | Lys |
| 43 | 105 | His | Ser | Gln | Gly | Thr | Phe | Thr | Ser | Asp | Tyr | Ser | Lys | Tyr | Leu | Asp | Ser | Arg | Ala | Val | Gln |
| 44 | 108 | His | Ser | Gln | Gly | Thr | Phe | Thr | Ser | Asp | Tyr | Ser | Lys | Tyr | Leu | Asp | Glu | Arg | Ile | Val | Arg |
| 45 | 114 | His | Aib | Gln | Gly | Thr | Phe | Thr | Ser | Asp | Tyr | Ser | Lys | Tyr | Leu | Asp | Ser | Arg | Ala | Ala | Gln |
| 46 | 115 | His | Aib | Gln | Gly | Thr | Phe | Thr | Ser | Asp | Tyr | Ser | Lys | Tyr | Leu | Asp | Ser | Arg | Arg | Ala | Arg |
| 47 | 120 | His | Ser | Gln | Gly | Thr | Phe | Thr | Ser | Asp | Tyr | Ser | Lys | Tyr | Leu | Asp | Ser | Arg | Ala | Ala | Gln |
| 48 | 124 | His | Ser | Gln | Gly | Thr | Phe | Thr | Ser | Asp | Tyr | Ser | Lys | Tyr | Leu | Asp | Ser | Arg | Ala | Val | Arg |
| 49 | 125 | His | Ser | Gln | Gly | Thr | Phe | Thr | Ser | Asp | Tyr | Ser | Lys | Tyr | Leu | Asp | Ser | Arg | Ala | Val | Arg |
| 50 | 126 | His | Ser | Gln | Gly | Thr | Phe | Thr | Ser | Asp | Tyr | Ser | Lys | Tyr | Leu | Asp | Ser | Arg | Ala | Val | Arg |
| 51 | 127 | His | Ser | Gln | Gly | Thr | Phe | Thr | Ser | Asp | Tyr | Ser | Lys | Tyr | Leu | Asp | Ser | Arg | Ala | Val | Arg |
| 52 | 129 | His | Ser | Gln | Gly | Thr | Phe | Thr | Ser | Asp | Tyr | Ser | Lys | Tyr | Leu | Asp | Ser | Gln | Ala | Val | Arg |
| 53 | 130 | His | Ser | Gln | Gly | Thr | Phe | Thr | Ser | Asp | Tyr | Ser | Lys | Tyr | Leu | Asp | Gln | Glu | Ala | Val | Arg |
| 54 | 131 | His | Ser | Gln | Gly | Thr | Phe | Thr | Ser | Asp | Tyr | Ser | Arg | Tyr | Leu | Glu | Ser | Gln | Ala | Val | Arg |
| 55 | 148 | His | Ser | Gln | Gly | Thr | Phe | Thr | Ser | Asp | Tyr | Ser | Lys | Tyr | Leu | Glu | Gly | Glu | Ala | Val | Arg |
| 56 | 149 | His | Ser | Gln | Gly | Thr | Phe | Thr | Ser | Asp | Tyr | Ser | Lys | Tyr | Leu | Glu | Gly | Glu | Ala | Val | Arg |
| 57 | 150 | His | Ser | Gln | Gly | Thr | Phe | Thr | Ser | Asp | Tyr | Ser | Lys | Tyr | Leu | Asp | Ser | Glu | Ala | Val | Arg |
| 58 | 151 | His | Ser | Gln | Gly | Thr | Phe | Thr | Ser | Asp | Tyr | Ser | Lys | Tyr | Leu | Asp | Ser | Gln | Ala | Val | Arg |
| 59 | 152 | His | Ser | Gln | Gly | Thr | Phe | Thr | Ser | Asp | Tyr | Ser | Lys | Tyr | Leu | Asp | Ser | Gln | Ala | Val | Arg |
| 60 | 153 | His | Ser | Gln | Gly | Thr | Phe | Thr | Ser | Asp | Tyr | Ser | Lys | Tyr | Leu | Asp | Ser | Gln | Ala | Val | Arg |
| 61 | 154 | His | Ser | Gln | Gly | Thr | Phe | Thr | Ser | Asp | Tyr | Ser | Lys | Tyr | Leu | Asp | Ser | Gln | Ala | Val | Arg |
| 62 | 155 | His | Aib | Gln | Gly | Thr | Phe | Thr | Ser | Asp | Tyr | Ser | Lys | Tyr | Leu | Asp | Ser | Arg | Ala | Val | Arg |
| 63 | 166 | His | Ser | Gln | Gly | Thr | Phe | Thr | Ser | Asp | Tyr | Ser | Lys | Tyr | Leu | Asp | Ser | Arg | Ala | Val | Arg |
| 64 | 168 | His | Aib | Gln | Gly | Thr | Phe | Thr | Ser | Asp | Tyr | Ser | Lys | Tyr | Leu | Asp | Ser | Lys | Ile | Val | Lys |
| 65 | 171 | His | Ser | Gln | Gly | Thr | Phe | Thr | Ser | Asp | Tyr | Ser | Lys | Tyr | Leu | Asp | Ser | Gln | Ile | Val | Lys |
| 66 | 177 | His | Aib | Gln | Gly | Thr | Phe | Thr | Ser | Asp | Tyr | Ser | Lys | Tyr | Leu | Asp | Ser | Arg | Ala | Val | His |
| 67 | 179 | His | Ser | Gln | Gly | Thr | Phe | Thr | Ser | Asp | Tyr | Ser | Lys | Tyr | Leu | Asp | Ser | Lys | Ala | Val | Lys |
| 68 | 181 | His | Ser | Gln | Gly | Thr | Phe | Thr | Ser | Asp | Tyr | Ser | Lys | Tyr | Leu | Asp | Ser | Arg | Ala | Val | Arg |
| 69 | 182 | His | Ser | Gln | Gly | Thr | Phe | Thr | Ser | Asp | Tyr | Ser | Lys | Tyr | Leu | Glu | Gly | Gln | Ile | Val | Lys |

FIG. 1F

| SEQ ID No. | Compound no. / G no. | | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|
| 35 | | 74 | Lys | Tyr | Phe | Ile | Glu | Leu | Leu | Met | Asn | Gly | Gly | Pro | Ser | Ser | Gly | Ala | Pro | Pro | Pro | Ser |
| 36 | | 75 | Arg | Leu | Phe | Ile | Glu | Trp | Leu | Met | Asn | Thr | | | | | | | | | | |
| 37 | | 80 | Lys | Tyr | Phe | Ile | Glu | Trp | Leu | Met | Asn | Gly | Gly | Pro | Ser | Ser | Gly | Ala | Pro | Pro | Pro | Ser |
| 38 | | 85 | Lys | Tyr | Phe | Val | Gln | Trp | Leu | Met | Asn | Thr | Arg | NH2 | | | | | | | | |
| 39 | | 89 | Gln | Glu | Phe | Val | Gln | Trp | Leu | Met | Asn | Thr | | | | | | | | | | |
| 40 | | 91 | Gln | Glu | Phe | Val | Gln | Trp | Leu | Met | Asn | Thr | Arg | NH2 | | | | | | | | |
| 41 | | 92 | Gln | Glu | Phe | Ile | Glu | Trp | Leu | Lys | Asn | Gly | Gly | Pro | Ser | Ser | Gly | Ala | Pro | Pro | Pro | Ser |
| 42 | | 104 | Arg | Leu | Phe | Ile | Gln | Trp | Leu | Leu | Asn | Gly | Gly | Pro | Ser | Ser | Gly | Ala | Pro | Pro | Pro | Ser |
| 43 | | 105 | Lys | Tyr | Phe | Ile | Glu | Trp | Leu | Leu | Asn | Gly | Gly | Pro | Ser | Ser | Gly | Ala | Pro | Pro | Pro | Ser |
| 44 | | 108 | Gln | Glu | Phe | Ile | Glu | Trp | Leu | Leu | Asn | Gly | Gly | Pro | Ser | Ser | Gly | Ala | Pro | Pro | Pro | Ser |
| 45 | | 114 | Arg | Leu | Phe | Ile | Gln | Trp | Leu | Leu | Asn | Thr | NH2 | | | | | | | | | |
| 46 | | 115 | Gln | Asp | Phe | Val | Gln | Trp | Leu | Leu | Asn | Gly | Gly | Pro | Ser | Ser | Gly | Ala | Pro | Pro | Pro | Ser |
| 47 | | 120 | Arg | Leu | Phe | Ile | Gln | Trp | Leu | Met | Asn | Thr | NH2 | | | | | | | | | |
| 48 | | 124 | Arg | Leu | Phe | Val | Gln | Trp | Leu | Leu | Asn | Gly | NH2 | | | | | | | | | |
| 49 | | 125 | Arg | Leu | Phe | Val | Gln | Trp | Leu | Leu | Asn | Thr | NH2 | | | | | | | | | |
| 50 | | 126 | Arg | Leu | Phe | Val | Glu | Trp | Leu | Leu | Asn | Gly | NH2 | | | | | | | | | |
| 51 | | 127 | Arg | Leu | Phe | Val | Gln | Trp | Leu | Leu | Asn | Gly | Gly | Pro | Ser | Ser | Gly | Ala | Pro | Pro | Pro | Ser |
| 52 | | 129 | Arg | Leu | Phe | Ile | Gln | Trp | Leu | Leu | Asn | Thr | NH2 | | | | | | | | | |
| 53 | | 130 | Arg | Leu | Phe | Ile | Glu | Trp | Leu | Leu | Asn | Thr | NH2 | | | | | | | | | |
| 54 | | 131 | Arg | Leu | Phe | Ile | Glu | Trp | Leu | Leu | Asn | Thr | NH2 | | | | | | | | | |
| 55 | | 148 | Arg | Leu | Phe | Ile | Glu | Trp | Leu | Val | Asn | Thr | NH2 | | | | | | | | | |
| 56 | | 149 | Arg | Leu | Phe | Ile | Gln | Trp | Leu | Leu | Asn | Gly | Gly | Pro | Ser | Ser | Gly | Ala | Pro | Pro | Pro | Ser |
| 57 | | 150 | Arg | Leu | Phe | Ile | Glu | Trp | Leu | Leu | Asn | Gly | Gly | Pro | Ser | Ser | Gly | Ala | Pro | Pro | Pro | Ser |
| 58 | | 151 | Arg | Leu | Phe | Ile | Gln | Trp | Leu | Leu | Asn | Gly | Gly | Pro | Ser | Ser | Gly | Ala | Pro | Pro | Pro | Ser |
| 59 | | 152 | Arg | Leu | Phe | Ile | Glu | Trp | Leu | Leu | Asn | Gly | Gly | Pro | Ser | Ser | Gly | Ala | Pro | Pro | Pro | Ser |
| 60 | | 153 | Arg | Leu | Phe | Ile | Glu | Trp | Leu | Leu | Asn | Gly | Gly | Pro | Ser | Ser | Gly | Ala | Pro | Pro | Pro | Ser |
| 61 | | 154 | Lys | Tyr | Phe | Ile | Glu | Trp | Leu | Leu | Asn | Thr | Arg | NH2 | | | | | | | | |
| 62 | | 155 | Lys | Tyr | Phe | Ile | Glu | Trp | Leu | Leu | Asn | Gly | Gly | Pro | Ser | Ser | Gly | Ala | Pro | Pro | Pro | Ser |
| 63 | | 166 | Lys | Tyr | Phe | Ile | Gln | Trp | Leu | Leu | Asn | Gly | Gly | Pro | Ser | Ser | Gly | Ala | Pro | Pro | Pro | Ser |
| 64 | | 168 | Arg | Leu | Phe | Ile | Glu | Trp | Leu | Leu | Asn | Thr | NH2 | | | | | | | | | |
| 65 | | 171 | His | Leu | Phe | Ile | Glu | Trp | Leu | Leu | Asn | Thr | NH2 | | | | | | | | | |
| 66 | | 177 | Lys | Tyr | Phe | Ile | Glu | Trp | Leu | Leu | Asn | Thr | NH2 | | | | | | | | | |
| 67 | | 179 | Arg | Leu | Phe | Ile | Glu | Trp | Leu | Leu | Asn | Thr | NH2 | | | | | | | | | |
| 68 | | 181 | Arg | Leu | Phe | Ile | Glu | Trp | Leu | Leu | Asn | Thr | Gly | Pro | Ser | Ser | Gly | Ala | Pro | Pro | Pro | |
| 69 | | 182 | Lys | Tyr | Phe | Ile | Glu | Trp | Leu | Leu | Asn | Gly | Gly | Pro | Ser | Ser | Gly | Ala | Pro | Pro | Pro | Ser |

FIG. 1G

| SEQ ID No. | Compound no. / G no. | hGLP1R Man | rGLP1R Rat | mGLP1R Mouse | hGLP1R cAMP | hGlucR Man | hGluc cAMP | 0-1 Mouse | 0-4 Mouse | 0-8 Mouse | 4-8 Mouse | 8-24 Mouse | 0-24 Mouse |
|---|---|---|---|---|---|---|---|---|---|---|---|---|---|
| 35 | 74 | | 5773.4066 | | | 7692.30769 | | 3 | 2.8 | 2 | 0.1 | 0.1 | 2 |
| 36 | 75 | | 99 | | | 621.538462 | | 1.5 | 3 | 3 | 1.5 | 4 | 5 |
| 37 | 80 | | 8.2757692 | | | 1196.36364 | | 4 | 2.5 | 4 | 7 | 0.1 | 3.8 |
| 38 | 85 | | 1583.5417 | | | 4762.69231 | | 2.9 | 2.5 | 3.75 | 2.55 | 0.1 | 3.25 |
| 39 | 89 | | 4080.7372 | | | 0.27307692 | | 2 | 1.5 | 2 | 4 | 2 | 3 |
| 40 | 91 | | 21.411538 | | | 19.2307692 | | 4.25 | 1.5 | 1.25 | 0.75 | 1.5 | 1.45 |
| 41 | 92 | | 2.7203846 | | | 253.076923 | | 5 | 3 | 2.3 | 0.1 | 0.7 | 1.5 |
| 42 | 104 | | 4.4160684 | | | 42.3456439 | | 4.75 | 3 | 3 | 5.5 | 2.1 | 4.35 |
| 43 | 105 | | 68.230769 | | | 56.0481935 | 32.417266 | 2.5 | 3 | 3 | 6.25 | 1.3 | 3.25 |
| 44 | 108 | | 91.138462 | | | 0.57645455 | | 3 | 1.7 | 1.2 | 0.1 | 0.5 | 1.5 |
| 45 | 114 | | 19.867647 | | | 68.3068182 | | 0.4 | 1.1 | 1.85 | 3.75 | 0.75 | 3 |
| 46 | 115 | | 3.7629808 | | | 18.5272727 | | 3 | 1.3 | 1.1 | 0.1 | 0.5 | 1 |
| 47 | 120 | | 8.6825658 | | | | | 0.4 | 1.2 | 1.2 | 0.2 | 0.5 | 1.5 |
| 48 | 124 | | 1.3131579 | | | | | 4 | 2.4 | 2.5 | 0.1 | 0.1 | 0.9 |
| 49 | 125 | | 4.0784211 | | | 1478.18182 | | 2.5 | 2 | 2.5 | 3 | 1 | 3 |
| 50 | 126 | | 3.4531579 | | | 981.818182 | | 3 | 2 | 2.5 | 4 | 1 | 3.5 |
| 51 | 127 | | 3.9852632 | | | | | 6 | 3 | 3 | 3 | 0.1 | 1 |
| 52 | 129 | | 25.787576 | | | 13.2158333 | | 0.5 | 1.5 | 2.5 | 6 | 2 | 4 |
| 53 | 130 | | 101.28711 | | | 102.657143 | | 1.5 | 2.5 | 3.5 | 8 | 0.1 | 2 |
| 54 | 131 | | 19.806029 | | 1.058403467 | 16.8875 | 1.7305936 | 0.766667 | 1.4 | 1.9666667 | 3.8333333 | 0.7666667 | 3 |
| 55 | 148 | | 89.984561 | | 1.1616478 | 44.9264069 | 10.129573 | 1.2 | 1.75 | 3 | 5.5 | 0.3 | 4.5 |
| 56 | 149 | | 250.89474 | | 1.036221591 | 45.0454545 | 2.5371585 | 2 | 2 | 3 | 5 | 0.1 | 3 |
| 57 | 150 | | 2.1591729 | | | 705.363636 | | 8 | 3.5 | 4 | 6 | 1 | 5 |
| 58 | 151 | | 1.7581328 | | | 537.272727 | | 3 | 2 | 2.5 | 3 | 0.1 | 3.5 |
| 59 | 152 | | 3.5391353 | | | | | 2.8 | 2 | 2.5 | 4 | 1 | 3.5 |
| 60 | 153 | | 5.5735139 | | | | | 3.5 | 2.5 | 3.5 | 4 | 0.1 | 5 |
| 61 | 154 | | 5.1415414 | | | 350 | | 3 | 2 | 2.3 | 2.5 | 0.5 | 2.5 |
| 62 | 155 | | 6.8898496 | | | 213.636364 | | 2.5 | 2 | 2.5 | 4 | 1 | 3.5 |
| 63 | 166 | | 152.89773 | | | 12500 | | | | | | | |
| 64 | 168 | | 30.871212 | | | 57.7625 | | | | | | | |
| 65 | 171 | | 2.5151515 | | | 42.3041667 | | | | | | | |
| 66 | 177 | | 9.2170868 | | | 41.2875 | 31.735575 | | | | | | |
| 67 | 179 | | 177.38235 | | | 59.20625 | | | | | | | |
| 68 | 181 | | 29.886368 | | | 14.9 | | | | | | | |
| 69 | 182 | | 9.95 | | | 17.375 | 3.0171739 | | | | | | |

| SEQ ID No. | Compound no./ G no. | Pair feeding | mouse 8 + 24 | rat 8+24 | sol pH<5 | sol pH 7.4 | pK peak | PK3d/4d | PK 7d | PK rating |
|---|---|---|---|---|---|---|---|---|---|---|
| 35 | 74 | | | | | | | | | |
| 36 | 75 | | | | | | | | | |
| 37 | 80 | | | | | | | | | |
| 38 | 85 | | | | 6 | | | | | |
| 39 | 89 | | | | | | | | | |
| 40 | 91 | | | | | | | | | |
| 41 | 92 | | | | | | | | | |
| 42 | 104 | | | | | | | | | |
| 43 | 105 | | | | 1 | 3 | | | | |
| 44 | 108 | | | | | | | | | |
| 45 | 114 | | | | | | | | | |
| 46 | 115 | | | | 1 | 5 | | | | |
| 47 | 120 | | | | 1 | 5 | | | | |
| 48 | 124 | | | | | | | | | |
| 49 | 125 | | | | | | | | | |
| 50 | 126 | | | | | | | | | |
| 51 | 127 | | | | | | | | | |
| 52 | 129 | | | | 4 | 4 | 4 | | | |
| 53 | 130 | | | | 7 | 4 | | | | |
| 54 | 131 | | 2.4 | 0.7 | 1 | 5 | 24 | 0.3 | 0.01 | 2 |
| 55 | 148 | | | | 3 | 4 | 4 | 0.2 | 0.1 | 1.5 |
| 56 | 149 | | 3.1 | 0.3 | 1 | 5 | 4 | 0.3 | 0.3 | 3 |
| 57 | 150 | | | | | | | | | |
| 58 | 151 | | | | | | | | | |
| 59 | 152 | | | | | | | | | |
| 60 | 153 | | | | | | | | | |
| 61 | 154 | | | | | | | | | |
| 62 | 155 | | | | | | | | | |
| 63 | 166 | | | | 1 | 5 | | | | |
| 64 | 168 | | | | | | | | | |
| 65 | 171 | | | | | | | | | |
| 66 | 177 | | | | 3 | 4 | | | | |
| 67 | 179 | | | | 1 | 4 | | | | |
| 68 | 181 | | | | 1 | 5 | | | | |
| 69 | 182 | | | | 7 | 4 | | | | |

| SEQ ID No. | Compound no. / G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 70 | 183 | His | Ser | Gln | Gly | Thr | Phe | Thr | Ser | Asp | Tyr | Ser | Lys | Tyr | Leu | Glu | Gly | Lys | Ile | Val | Lys |
| 71 | 189 | His | Ser | Gln | Gly | Thr | Phe | Thr | Ser | Asp | Tyr | Ser | Lys | His | Leu | Asp | Ser | Arg | Ala | Val | Arg |
| 72 | 191 | His | Ser | Gln | Gly | Thr | Phe | Thr | Ser | Asp | Tyr | Ser | Lys | Tyr | Leu | Asp | Ser | Arg | Ala | Val | Arg |
| 73 | 193 | His | Ser | Gln | Gly | Thr | Phe | Thr | Ser | Asp | Tyr | Ser | Lys | Tyr | Leu | Asp | Ser | Arg | Ala | Val | Arg |
| 74 | 194 | His | Ser | Gln | Gly | Thr | Phe | Thr | Ser | Asp | Tyr | Ser | Lys | Tyr | Leu | Asp | Ser | Arg | Ile | Val | Lys |
| 75 | 197 | His | Ser | Gln | Gly | Thr | Phe | Thr | Ser | Asp | Tyr | Ser | Lys | Tyr | Leu | Asp | Ser | Gln | Ala | Val | Arg |
| 76 | 208 | His | Ser | Gln | Gly | Thr | Phe | Thr | Ser | Asp | Tyr | Ser | Lys | Tyr | Leu | Asp | Ser | Gln | Ala | Val | Lys |
| 77 | 216 | His | Ser | Gln | Gly | Thr | Phe | Thr | Ser | Asp | Tyr | Ser | Lys | Tyr | Leu | Asp | Ser | Glu | Ala | Val | Lys |
| 78 | 223 | His | Ser | Gln | Gly | Thr | Phe | Thr | Ser | Asp | Tyr | Ser | Lys | Tyr | Leu | Asp | Ser | Glu | Ala | Val | Lys |
| 79 | 224 | His | Ser | Gln | Gly | Thr | Phe | Thr | Ser | Asp | Tyr | Ser | Lys | Tyr | Leu | Glu | Ser | Gln | Ala | Val | Arg |
| 80 | 233 | His | Ser | Gln | Gly | Thr | Phe | Thr | Ser | Asp | Tyr | Ser | Lys | Tyr | Leu | Asp | Ser | Glu | Ala | Val | Arg |
| 81 | 237 | His | Aib | Gln | Gly | Thr | Phe | Thr | Ser | Asp | Tyr | Ser | Lys | Tyr | Leu | Asp | Ser | Gln | Ala | Val | His |
| 82 | 243 | His | Ser | Gln | Gly | Thr | Phe | Thr | Ser | Asp | Tyr | Ser | Lys | Tyr | Leu | Asp | Ser | Gln | Ile | Val | Lys |
| 83 | 244 | His | Aib | Gln | Gly | Thr | Phe | Thr | Ser | Asp | Tyr | Ser | His | Tyr | Leu | Asp | Ser | Gln | Ala | Val | Arg |
| 84 | 247 | His | Ser | Gln | Gly | Thr | Phe | Thr | Ser | Asp | Tyr | Ser | His | Tyr | Leu | Asp | Ser | Gln | Ile | Val | Arg |
| 85 | 253 | His | Ser | Gln | Gly | Thr | Phe | Thr | Ser | Asp | Tyr | Ser | His | Tyr | Leu | Asp | Ser | Gln | Ala | Val | Arg |
| | 278 | His | Ser | Gln | Gly | Thr | Phe | Thr | Ser | Asp | Tyr | Ser | His | Tyr | Leu | Asp | Ser | Gln | Ala | Val | His |
| 86 | 283 | His | Ser | Gln | Gly | Thr | Phe | Thr | Ser | Asp | Tyr | Ser | His | Tyr | Leu | Asp | Ser | Arg | Ala | Val | His |
| 87 | 285 | His | Ser | Gln | Gly | Thr | Phe | Thr | Ser | Asp | Tyr | Ser | His | Tyr | Leu | Asp | Ser | Lys | Ala | Val | His |
| 88 | 288 | His | Ser | Gln | Gly | Thr | Phe | Thr | Ser | Asp | Tyr | Ser | Lys | Tyr | Leu | Glu | Gly | Glu | Ala | Val | Lys |
| | 289 | His | Ser | Gln | Gly | Thr | Phe | Thr | Ser | Asp | Tyr | Ser | Lys | Tyr | Leu | Glu | Gly | Glu | Ala | Val | Arg |
| 89 | 291 | His | Ser | Gln | Gly | Thr | Phe | Thr | Ser | Asp | Tyr | Ser | Lys | Tyr | Leu | Glu | Gly | Gln | Ala | Val | Gln |
| 90 | 298 | His | Ser | Gln | Gly | Thr | Phe | Thr | Ser | Asp | Tyr | Ser | Lys | Tyr | Leu | Asp | Ser | Gln | Ala | Val | Arg |
| 91 | 311 | His | Ser | Gln | Gly | Thr | Phe | Thr | Ser | Asp | Tyr | Ser | His | Tyr | Leu | Asp | Ser | Gln | Ala | Val | Lys |
| 92 | 312 | His | Ser | Gln | Gly | Thr | Phe | Thr | Ser | Asp | Tyr | Ser | His | Tyr | Leu | Asp | Ser | Gln | Ala | Val | Lys |
| 93 | 313 | His | Ser | Gln | Gly | Thr | Phe | Thr | Ser | Asp | Tyr | Ser | Lys | Tyr | Leu | Asp | Ser | Gln | Ala | Val | Lys |
| 94 | 314 | His | Ser | Gln | Gly | Thr | Phe | Thr | Ser | Asp | Tyr | Ser | His | Tyr | Leu | Asp | Ser | Gln | Ala | Val | Arg |
| 95 | 328 | His | Ser | Gln | Gly | Thr | Phe | Thr | Ser | Asp | Tyr | Ser | Lys | Tyr | Leu | Asn | Ser | Gln | Ala | Val | His |
| 124 | 329 | His | Ser | Gln | Gly | Thr | Phe | Thr | Ser | Asp | Tyr | Ser | His | Tyr | Leu | Asp | Ser | Gln | Ala | Val | Lys |
| 96 | 332 | His | Ser | Gln | Gly | Thr | Phe | Thr | Ser | Asp | Tyr | Ser | Lys | Tyr | Leu | Asp | Ser | Gln | Ala | Val | Lys |
| | 333 | His | Ser | Gln | Gly | Thr | Phe | Thr | Ser | Asp | Tyr | Ser | Lys | Tyr | Leu | Asp | Ser | Gln | Ala | Val | Lys |
| 97 | 339 | His | Ser | Gln | Gly | Thr | Phe | Thr | Ser | Asp | Tyr | Ser | His | Tyr | Leu | Asp | Glu | Gln | Ala | Val | Arg |
| 98 | 340 | His | Ser | Gln | Gly | Thr | Phe | Thr | Ser | Asp | Tyr | Ser | Lys | Tyr | Leu | Asp | Glu | Gln | Ala | Val | Lys |
| 99 | 366 | His | Ser | Gln | Gly | Thr | Phe | Thr | Ser | Asp | Tyr | Ser | Lys | Tyr | Leu | Asp | Ser | Gln | Ala | Val | Arg |
| 100 | 368 | His | Ser | Gln | Gly | Thr | Phe | Thr | Ser | Asp | Tyr | Ser | His | Tyr | Leu | Asp | Ser | Gln | Ala | Val | Lys |

| SEQ ID No. | Compound no./G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| 70 | 183 | Tyr | Phe | Ile | Gln | Trp | Leu | Leu | Asn | Gly | Gly | Pro | Ser | Ser | Gly | Ala | Pro | Pro | Pro | Ser | |
| 71 | 189 | Leu | Phe | Ile | Glu | Trp | Leu | Leu | Asn | Gly | Gly | Pro | Ser | Ser | Gly | Ala | Pro | Pro | Pro | Ser | |
| 72 | 191 | Leu | Phe | Ile | Glu | Trp | Leu | Leu | Asn | Gly | His | Pro | Ser | Ser | Gly | Ala | Pro | Pro | Pro | Ser | |
| 73 | 193 | Leu | Phe | Ile | Gln | Trp | Leu | Lys | Asn | Gly | Gly | Pro | Ser | Ser | Gly | Ala | Pro | Pro | Pro | Ser | |
| 74 | 194 | Tyr | Phe | Ile | Glu | Trp | Leu | Leu | Asn | Gly | Gly | Pro | Ser | Ser | Gly | Ala | Pro | Pro | Pro | Ser | |
| 75 | 197 | Leu | Phe | Ile | Gln | Trp | Leu | Leu | Asn | Gly | Gly | Pro | Ser | Ser | Gly | Ala | Pro | Pro | Pro | Ser | |
| 76 | 208 | Leu | Phe | Ile | Gln | Trp | Leu | Leu | Asn | Thr | NH2 | | | | | | | | | | |
| 77 | 216 | Leu | Phe | Ile | Gln | Trp | Leu | Leu | Asn | Thr | NH2 | | | | | | | | | | |
| 78 | 223 | Leu | Phe | Ile | Glu | Trp | Leu | Leu | Asn | Thr | NH2 | | | | | | | | | | |
| 79 | 224 | Leu | Phe | Ile | Glu | Trp | Leu | Leu | Asn | Thr | NH2 | | | | | | | | | | |
| 80 | 233 | Leu | Phe | Ile | Gln | Trp | Leu | Leu | Asn | Gly | Arg | NH2 | | | | | | | | | |
| 81 | 237 | Tyr | Phe | Ile | Gln | Trp | Leu | Met | Asn | Gly | Gly | Pro | Ser | Ser | Gly | Ala | Pro | Pro | Pro | Ser | |
| 82 | 243 | Leu | Phe | Ile | Glu | Trp | Leu | Lys | Asn | Thr | Arg | NH2 | | | | | | | | | |
| 83 | 244 | Leu | Phe | Ile | Gln | Trp | Leu | Leu | Asn | Gly | Gly | Pro | Ser | Ser | Gly | Ala | Pro | Pro | Pro | Ser | |
| 84 | 247 | Tyr | Phe | Ile | Gln | Trp | Leu | Leu | Asn | Gly | Gly | NH2 | | | | | | | | | |
| 85 | 253 | Leu | Phe | Ile | Gln | Trp | Leu | Leu | Asn | Thr | NH2 | | | | | | | | | | |
| | 278 | Leu | Phe | Ile | Gln | Trp | Leu | Leu | Asn | Thr | NH2 | | | | | | | | | | |
| 86 | 283 | Leu | Phe | Ile | Gln | Trp | Leu | Leu | Asn | Thr | NH2 | | | | | | | | | | |
| 87 | 285 | Leu | Phe | Ile | Glu | Trp | Leu | Leu | Asn | Gly | Gly | Pro | Ser | Ser | Gly | Ala | Pro | Pro | Pro | Ser | |
| 88 | 288 | Leu | Phe | Ile | Glu | Trp | Leu | Leu | Asn | Thr | NH2 | | | | | | | | | | |
| | 289 | Leu | Phe | Ile | Glu | Leu | Leu | Leu | Asn | Gly | Gly | Pro | Ser | Ser | Gly | Ala | Pro | Pro | Pro | Ser | |
| 89 | 291 | Leu | Phe | Ile | Glu | Trp | Leu | Leu | Asn | Gly | Gly | Pro | Ser | Ser | Gly | Ala | Pro | Pro | Pro | Ser | |
| 90 | 298 | Leu | Phe | Ile | Gln | Trp | Leu | Leu | Asn | Gly | NH2 | | | | | | | | | | |
| 91 | 311 | Leu | Phe | Ile | Gln | Trp | Leu | Leu | Asn | Thr | NH2 | | | | | | | | | | |
| 92 | 312 | Leu | Phe | Ile | Glu | Trp | Leu | Leu | Asn | Gly | NH2 | | | | | | | | | | |
| 93 | 313 | Leu | Phe | Ile | Gln | Trp | Leu | Leu | Asn | Gly | NH2 | | | | | | | | | | |
| 94 | 314 | Leu | His | Ile | Gln | Trp | Leu | Leu | Asn | Thr | NH2 | | | | | | | | | | |
| 95 | 328 | Lys | Phe | Ile | Gln | Trp | Leu | Leu | Asn | Gly | NH2 | | | | | | | | | | |
| 124 | 329 | His | Phe | Ile | Glu | Trp | Leu | Leu | Asn | Gly | NH2 | | | | | | | | | | |
| 96 | 332 | Asp | Phe | Asp | Gln | Trp | Leu | Leu | Asn | Gly | NH2 | | | | | | | | | | |
| | 333 | Leu | Phe | Ile | Gln | Trp | Leu | Leu | Asn | Thr | NH2 | Tyr | Tyr | Tyr | | | | | | | |
| 97 | 339 | Leu | Phe | Ile | Glu | Trp | Leu | Leu | Asn | Gly | NH2 | | | | | | | | | | |
| 98 | 340 | Leu | Phe | Ile | Glu | Trp | Leu | Leu | Asn | Gly | NH2 | | | | | | | | | | |
| 99 | 366 | Leu | Phe | Ile | Glu | Trp | Leu | Thr | Asn | Thr | NH2 | | | | | | | | | | |
| 100 | 368 | Leu | Phe | Ile | Glu | Trp | Leu | Leu | Asn | Thr | NH2 | | | | | | | | | | |

FIG. 1J

| SEQ ID No. | Compound no./G no. | hGLP1R Man | hGLP1R Rat | mGLP1R Mouse | hGLP1R cAMP | hGlucR Man | hGluc cAMP | 0-1 Mouse | 0-4 Mouse | 0-8 Mouse | 4-8 Mouse | 8-24 Mouse | 0-24 Mouse |
|---|---|---|---|---|---|---|---|---|---|---|---|---|---|
| 70 | 183 | | 13.246032 | | | 21.0125 | | | | | | | |
| 71 | 189 | | 8.6009314 | | | 34.20625 | | | | | | | |
| 72 | 191 | | 11.898599 | | | 47.05625 | | | | | | | |
| 73 | 193 | | 1.6397339 | | | 25.39375 | 98.864153 | | | | | | |
| 74 | 194 | | 32.578968 | | | 71.50625 | 391.29496 | | | | | | |
| 75 | 197 | | 4.3945658 | | 0.81032561 | 16.92125 | 16.733484 | | | | | | |
| 76 | 208 | | 578.81818 | | 1.858982609 | 6.25 | 18.14439 | | | | | | |
| 77 | 216 | | 17.857143 | | 4.50539277 | 8.625 | 18.928688 | | | | | | |
| 78 | 223 | 83 | | | 1.836830756 | | 29.955561 | | | | | | |
| 79 | 224 | | 518.18182 | | 3.362960013 | 25.3666667 | 5.9701612 | | | | | | |
| 80 | 233 | | 40.904762 | | 3.752732899 | 118.3875 | 9.3430931 | | | | | | |
| 81 | 237 | 4.53333333 | 4.8106061 | | 0.389628512 | 5 | 1.0120683 | | | | | | |
| 81 | 243 | | 309.16667 | | 1.659440711 | 1.93333333 | 531.90398 | | | | | | |
| 82 | 244 | | 1.8181818 | | | 58.2 | | | | | | | |
| 83 | 247 | | 12.770202 | | | 48.3833333 | 2851.0791 | | | | | | |
| 84 | 253 | | 317.91667 | | 2.196999166 | 9.625 | 0.362459 | | | | | | |
| 85 | 278 | | 42.5 | | 0.878075959 | 37.7206451 | 5.6885744 | 2 | 1.4 | 2.2 | | | 6.6 |
| 86 | 283 | | 88.333333 | | 1.454745082 | 161.275862 | 0.7574466 | | | | | | |
| 87 | 285 | | 73 | | 0.908598373 | 205.275862 | 6.3069715 | | | | | | |
| 88 | 288 | | 65.877698 | | 1.097731635 | 84.7586207 | 14.233111 | | | | | | |
| | 289 | | 257.69784 | | 0.362832112 | 222 | 2.7579143 | | | | | | |
| 89 | 291 | | | | 8.695444887 | 124.933333 | 6.867378 | | | | | | |
| 90 | 298 | | 104.02878 | | | 503.655172 | | | | | | | |
| 91 | 311 | | | | | | | | | | | | |
| 92 | 312 | 29.5666667 | 72.214286 | | 4.731128128 | 50.8574661 | 8.9552262 | 1.3 | 1.2 | 1.9 | 4 | 1 | 3.6 |
| 93 | 313 | | | | | 909.502262 | | 0.3 | 0.2 | 0.3 | 1 | 0.1 | 0.1 |
| 94 | 314 | | | | | 1248.19005 | | | | | | | |
| 95 | 328 | | 19.517986 | | 20.3325792 | | | | | | | | |
| 124 | 329 | | 28.597122 | | 2.068869417 | 23.959276 | 11.568245 | | | | | | |
| 96 | 332 | | | | | 51.6515837 | | | | | | | |
| | 333 | | | | | 2262.44344 | | | | | | | |
| 97 | 339 | | | | | | | | | | | | |
| 98 | 340 | | | | | | | | | | | | |
| 99 | 366 | | | | 4.449754041 | | 10.098002 | | | | | | |
| 100 | 368 | | | | 0.963425224 | | 3.1022429 | | | | | | |

FIG. 1K

| SEQ ID No. | Compound no./G no. | Pair feeding | mouse 8+24 | rat 8+24 | sol pH<5 | sol pH 7.4 | pK peak | PK3d/4d | PK 7d | PK rating |
|---|---|---|---|---|---|---|---|---|---|---|
| 70 | 183 | | | | | | | | | |
| 71 | 189 | | | | | | | | | |
| 72 | 191 | | | | | | | | | |
| 73 | 193 | | | | | | | | | |
| 74 | 194 | | | | | 1 | 5 | | | |
| 75 | 197 | | | | | 1 | 5 | 4 | 0.4 | 0.01 | 1.5 |
| 76 | 208 | | 2.5 | 0.7 | | 1 | 5 | 4 | 0.3 | 0.1 | 2 |
| 77 | 216 | | 2 | 0.7 | | 2 | 5 | 4 | 0.3 | 0.2 | 2.5 |
| 78 | 223 | 4 | 3 | 1.7 | | 1 | 5 | 48 | 0.6 | 0.3 | 3.5 |
| 79 | 224 | 3 | 2.5 | 2.1 | | 1 | 4 | 24 | 0.1 | 0.01 | 2 |
| 80 | 233 | 0.1 | 1.7 | 3.4 | | 1 | 5 | 4 | 0.2 | 0.2 | 2 |
| | 237 | 3 | | | | 1 | 5 | | 0.01 | 0.01 | 1 |
| 81 | 243 | | | | | 1 | | | | | |
| 82 | 244 | | | | | 1 | | | | | |
| 83 | 247 | | | | | 2 | 5 | | | | |
| 84 | 253 | | | | | 2 | 5 | | | | 3.5 |
| 85 | 278 | 4 | 2.2 | 0.9 | | 1 | 5 | 24 | 0.4 | 0.3 | 3.5 |
| 86 | 283 | 3.5 | 1.5 | 0.6 | | 1 | 5 | 24 | 0.7 | 0.6 | 4 |
| 87 | 285 | 2 | 2.1 | 1.9 | | 1 | 5 | 48 | 0.6 | 0.1 | 4 |
| 88 | 288 | | 0.8 | 1.3 | | 2 | 5 | 48 | 0.3 | 0.4 | 4 |
| | 289 | 2.5 | | | | 2 | 5 | 4 | 0.2 | 0.01 | 1.5 |
| 89 | 291 | | 1.2 | 1.7 | | 3 | 4 | 4 | 0.4 | 0.25 | 2 |
| 90 | 298 | | | | | 7 | | | | | |
| 91 | 311 | | | | | 5 | 3 | | | | |
| 92 | 312 | 4 | 2 | 0.8 | | 1 | 5 | 24 | 0.3 | 0.3 | 3.5 |
| 93 | 313 | | | | | 1 | 5 | | | | |
| 94 | 314 | | | | | 7 | | | | | |
| 95 | 328 | | | | | 7 | | | | | |
| 124 | 329 | 4 | 1.4 | 0.7 | | 2 | 5 | 24 | 0.3 | 0.2 | 2.5 |
| 96 | 332 | | | | | 5 | 5 | | | | |
| | 333 | | | | | 1 | 5 | | | | |
| 97 | 339 | | | | | 7 | 3 | | | | |
| 98 | 340 | | | | | 7 | | | | | |
| 99 | 366 | | | | | 2 | 4 | | | | |
| 100 | 368 | 1 | 1.5 | 1.3 | | 1 | 5 | 4 | 0.4 | 0.15 | 2.5 |

| SEQ ID No. | Compound no. / G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 101 | 372 | His | Ser | Gln | Gly | Thr | Phe | Thr | Ser | Asp | Tyr | Ser | Lys | Tyr | Leu | Asp | Ser | Gln | Ala | Val | His |
| 102 | 373 | His | Ser | Gln | Gly | Thr | Phe | Thr | Ser | Asp | Tyr | Ser | Lys | Tyr | Leu | Glu | Ser | Gln | Ala | Val | His |
|  | 374 | His | Ser | Gln | Gly | Thr | Phe | Thr | Ser | Asp | Tyr | Ser | Lys | Tyr | Leu | Asp | Ser | Glu | Ala | Val | Lys |
| 103 | 382 | His | Ser | Gln | Gly | Thr | Phe | Thr | Ser | Asp | Tyr | Ser | Lys | Tyr | Leu | Asp | Ser | Gln | Ala | Val | Lys |
| 104 | 384 | His | Ser | Gln | Gly | Thr | Phe | Thr | Ser | Asp | Tyr | Ser | Arg | Tyr | Leu | Glu | Ser | Gln | Ala | Val | Arg |
| 105 | 385 | His | Ser | Gln | Gly | Thr | Phe | Thr | Ser | Asp | Tyr | Ser | Lys | Tyr | Leu | Glu | Ser | Gln | Ala | Val | Lys |
| 106 | 386 | His | Ser | Gln | Gly | Thr | Phe | Thr | Ser | Asp | Tyr | Ser | His | Tyr | Leu | Glu | Ser | Gln | Ala | Val | Arg |
| 107 | 387 | His | Ser | Gln | Gly | Thr | Phe | Thr | Ser | Asp | Tyr | Ser | His | Tyr | Leu | Glu | Ser | Gln | Ala | Val | Arg |
| 108 | 397 | His | Ser | Gln | Gly | Thr | Phe | Thr | Ser | Asp | Tyr | Ser | Lys | Tyr | Leu | Asp | Ser | Gln | Ala | Val | Arg |
| 109 | 398 | His | Ser | Gln | Gly | Thr | Phe | Thr | Ser | Asp | Tyr | Ser | Lys | Tyr | Leu | Asp | Ser | Gln | Ala | Val | Arg |
| 110 | 399 | His | Ser | Gln | Gly | Thr | Phe | Thr | Ser | Asp | Tyr | Ser | Lys | Tyr | Leu | Asp | Ser | Gln | Ala | Val | Arg |
| 111 | 400 | His | Ser | Gln | Gly | Thr | Phe | Thr | Ser | Asp | Tyr | Ser | Lys | Tyr | Leu | Glu | Ser | Gln | Ala | Val | Arg |
| 112 | 404 | His | Ser | Gln | Gly | Thr | Phe | Thr | Ser | Asp | Tyr | Ser | Lys | Tyr | Leu | Glu | Ser | Gln | Ala | Val | His |
| 113 | 405 | His | Ser | Gln | Gly | Thr | Phe | Thr | Ser | Asp | Tyr | Ser | Lys | Tyr | Leu | Asp | Ser | Gln | Ala | Val | Arg |
| 114 | 407 | His | Ser | Gln | Gly | Thr | Phe | Thr | Ser | Asp | Tyr | Ser | His | Tyr | Leu | Glu | Ser | Gln | Ala | Val | Arg |
| 115 | 408 | His | Ser | Gln | Gly | Thr | Phe | Thr | Ser | Asp | Tyr | Ser | His | Tyr | Leu | Glu | Ser | Gln | Ala | Val | Arg |
| 116 | 409 | His | Ser | Gln | Gly | Thr | Phe | Thr | Ser | Asp | Tyr | Ser | Lys | Tyr | Leu | Glu | Ser | Gln | Ala | Val | His |
| 117 | 410 | His | Ser | Gln | Gly | Thr | Phe | Thr | Ser | Asp | Tyr | Ser | His | Tyr | Leu | Glu | Ser | Glu | Ala | Val | His |
|  | 417 | His | Ser | Gln | Gly | Thr | Phe | Thr | Ser | Asp | Tyr | Ser | Lys | Tyr | Leu | Glu | Ser | Glu | Ala | Val | Arg |
| 118 | 418 | His | Ser | Gln | Gly | Thr | Phe | Thr | Ser | Asp | Tyr | Ser | His | Tyr | Leu | Asp | Ser | Glu | Ala | Val | Arg |
| 119 | 420 | His | Ser | Gln | Gly | Thr | Phe | Thr | Ser | Asp | Tyr | Ser | Lys | Tyr | Leu | Asp | Ser | Glu | Ala | Val | Arg |
| 120 | 421 | His | Ser | Gln | Gly | Thr | Phe | Thr | Ser | Asp | Tyr | Ser | Ser | Tyr | Leu | Glu | Ser | Gln | Ala | His | Arg |
|  | 425 | His | Ser | Gln | Gly | Thr | Phe | Thr | Ser | Asp | Tyr | Ser | Lys | Tyr | Leu | Glu | Ser | Glu | Ala | Val | Arg |
|  | 426 | His | Ser | Gln | Gly | Thr | Phe | Thr | Ser | Asp | Tyr | Ser | Lys | Tyr | Leu | Glu | Ser | Gln | Ala | Val | Arg |
|  | 429 | His | Ser | Glu | Gly | Thr | Phe | Thr | Ser | Asp | Tyr | Ser | Lys | Tyr | Leu | Asp | Gly | Gln | Ala | Val | Lys |
|  | 433 | His | Aib | Gln | Gly | Thr | Phe | Thr | Ser | Asp | Val | Ser | Ser | Tyr | Leu | Glu | Gly | Gln | Ala | Ala | Lys |
| 121 | 436 | His | Ser | Gln | Gly | Thr | Phe | Thr | Ser | Asp | Tyr | Ser | Lys | Tyr | Leu | Glu | Gly | Gln | Ala | Val | Lys |
| 122 | 438 | His | Ser | Gln | Gly | Thr | Phe | Thr | Ser | Asp | Tyr | Ser | His | Tyr | Leu | Asn | Ser | Gln | Ala | Val | His |
|  | 439 | His | Ser | Gln | Gly | Thr | Phe | Thr | Ser | Asp | Tyr | Ser | His | Tyr | Leu | Glu | Ser | Gln | Ala | Val | His |
|  | 441 | His | Ser | Gln | Gly | Thr | Phe | Thr | Ser | Asp | Tyr | Ser | Lys | Tyr | Leu | Glu | Ser | Gln | Ala | Val | Lys |
| 123 | 442 | His | Ser | Gln | Gly | Thr | Phe | Thr | Ser | Asp | Tyr | Ser | Lys | Tyr | Leu | Gln | Ser | Gln | Ala | Val | Lys |
|  | 443 | His | Ser | Gln | Gly | Thr | Phe | Thr | Ser | Asp | Tyr | Ser | His | Tyr | Leu | Glu | Ser | Gln | Ala | Val | His |
|  | 444 | His | Ser | Gln | Gly | Thr | Phe | Thr | Ser | Asp | Tyr | Ser | His | Tyr | Leu | Glu | Ser | Gln | Ala | Val | Lys |
|  | 445 | His | Ser | Gln | Gly | Thr | Phe | Thr | Ser | Asp | Tyr | Ser | His | Tyr | Leu | Glu | Ser | Gln | Ala | Val | Lys |
|  | 446 | His | Ser | Gln | Gly | Thr | Phe | Thr | Ser | Asp | Tyr | Ser | His | Tyr | Leu | Asp | Ser | Gln | Ala | Val | Arg |

FIG. 1N

| SEQ ID No. | Compound no. / G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| 101 | 372 | Leu | Phe | Ile | Glu | Trp | Leu | Leu | Asn | Thr | NH2 | | | | | | | | | | |
| 102 | 373 | Leu | Phe | Ile | Glu | Trp | Leu | Lys | Asn | Gly | NH2 | | | | | | | | | | |
| | 374 | Leu | Phe | Ile | Glu | Trp | Leu | Lys | Asn | Thr | NH2 | | | | | | | | | | |
| 103 | 382 | Leu | Phe | Ile | Glu | Trp | Leu | Val | Asn | Thr | NH2 | | | | | | | | | | |
| 104 | 384 | Leu | Phe | Ile | Glu | Trp | Leu | Val | Asn | Thr | NH2 | | | | | | | | | | |
| 105 | 385 | Leu | Phe | Ile | Gln | Trp | Leu | Leu | Asn | Thr | NH2 | | | | | | | | | | |
| 106 | 386 | Leu | Phe | Ile | Glu | Trp | Leu | Leu | Asn | Thr | NH2 | | | | | | | | | | |
| 107 | 387 | Leu | Phe | Ile | Gln | Trp | Leu | Val | Asn | Thr | NH2 | | | | | | | | | | |
| 108 | 397 | Leu | Phe | Ile | Glu | Trp | Leu | Leu | Asn | Gly | Gly | | | | | | | | | | |
| 109 | 398 | Leu | Phe | Ile | Glu | Trp | Leu | Leu | Asn | Gly | NH2 | | | | | | | | | | |
| 110 | 399 | Leu | Phe | Ile | Glu | Trp | Leu | Leu | Asn | Gly | Arg | NH2 | | | | | | | | | |
| 111 | 400 | Leu | Phe | Ile | Glu | Trp | Leu | Leu | Asn | Gly | Gly | Pro | Ser | | | | | | | | |
| 112 | 404 | Leu | Phe | Ile | Gln | Trp | Leu | Leu | Asn | Gly | Arg | Pro | | | | | | | | | |
| 113 | 405 | Leu | Phe | Ile | Glu | Trp | Leu | Val | Asn | Gly | Gly | | Ser | Ser | Gly | | | | | | |
| 114 | 407 | Leu | Phe | Ile | Glu | Trp | Leu | Lys | Asn | Thr | NH2 | | | | | | | | | | |
| 115 | 408 | Leu | Phe | Ile | Glu | Trp | Leu | Leu | Asn | Thr | NH2 | | | | | | | | | | |
| 116 | 409 | Leu | Phe | Ile | Glu | Trp | Leu | Leu | Asn | Thr | NH2 | | | | | | | | | | |
| 117 | 410 | Leu | Phe | Ile | Glu | Trp | Leu | Leu | Asn | Thr | NH2 | | | | | | | | | | |
| | 417 | Leu | Phe | Ile | Glu | Trp | Leu | Leu | Asn | Thr | His | NH2 | | | | | | | | | |
| 118 | 418 | Leu | Phe | Ile | Glu | Trp | Leu | Leu | Asn | Thr | His | NH2 | | | | | | | | | |
| 119 | 420 | Leu | Phe | Ile | Glu | Trp | Leu | Val | Asn | Thr | His | NH2 | | | | | | | | | |
| 120 | 421 | Leu | Phe | Ile | Glu | Trp | Leu | Lys | Asn | Thr | His | | | | | | | | | | |
| | 425 | Leu | Phe | Ile | Glu | Trp | Leu | Leu | Asn | Thr | NH2 | | | | | | | | | | |
| | 426 | His | Phe | Ile | Glu | Trp | Leu | His | Asn | AIB | Arg | NH2 | | | | | | | | | |
| | 429 | Leu | Phe | Ile | Ala | Trp | Leu | Val | Lys | Thr | NH2 | | | | | | | | | | |
| | 433 | Glu | Phe | Ile | Glu | Trp | Leu | Leu | Asn | Thr | NH2 | | | | | | | | | | |
| 121 | 436 | Leu | Phe | Ile | Glu | Trp | Leu | Leu | Asn | Gly | NH2 | | | | | | | | | | |
| 122 | 438 | Leu | Phe | Ile | Glu | Trp | Leu | Val | Asn | Thr | NH2 | | | | | | | | | | |
| | 439 | Leu | Phe | Ile | Glu | Trp | Leu | Lys | Asn | Thr | NH2 | | | | | | | | | | |
| 123 | 441 | Leu | Phe | Ile | Gln | Trp | Leu | Leu | Asn | Thr | NH2 | | | | | | | | | | |
| | 442 | Leu | Phe | Ile | Gln | Trp | Leu | Val | Asn | Thr | NH2 | | | | | | | | | | |
| | 443 | Leu | Phe | Ile | Gln | Trp | Leu | Leu | Asn | Thr | NH2 | | | | | | | | | | |
| | 444 | Leu | Phe | Ile | Gln | Trp | Leu | Leu | Asn | Thr | NH2 | | | | | | | | | | |
| | 445 | Leu | Phe | Ile | Gln | Trp | Leu | Leu | Asn | Thr | NH2 | | | | | | | | | | |
| | 446 | Leu | Phe | Ile | Gln | Trp | Leu | Leu | Asn | Thr | His | NH2 | | | | | | | | | |

| SEQ ID No. | Compound no. / G no. | hGLP1R Man | rGLP1R Rat | mGLP1R Mouse | hGLP1R cAMP | hGlucR Man | hGluc cAMP | 0-1 Mouse | 0-4 Mouse | 0-8 Mouse | 4-8 Mouse | 8-24 Mouse | 0-24 Mouse |
|---|---|---|---|---|---|---|---|---|---|---|---|---|---|
| 101 | 372 | | | | 0.41148858 | | 24.817073 | | | | | | |
| 102 | 373 | | | | 1.898132428 | | 8.3628991 | | | | | | |
| | 374 | | | | 1.121652931 | | 8.0716574 | | | | | | |
| 103 | 382 | | | | 0.310470836 | | 10.302255 | | | | | | |
| 104 | 384 | | | | | | | | | | | | |
| 105 | 385 | | | | 1.18891491 | | 10.720006 | | | | | | |
| 106 | 386 | | | | 1.197410532 | | | | | | | | |
| 107 | 387 | | | | 1.716287814 | | 8.5458808 | | | | | | |
| 108 | 397 | 14.8845687 | | | 1.265704584 | | 16.325891 | | | | | | |
| 109 | 398 | 23.8703524 | | | 20.09337861 | | 5.291489 | | | | | | |
| 110 | 399 | 14.8166667 | | | 10.90831919 | | 34.536993 | | | | | | |
| 111 | 400 | 45.5650061 | | | 1.598778004 | | 7.0064121 | | | | | | |
| 112 | 404 | | | | | | 14.095628 | | | | | | |
| 113 | 405 | | | 133.66086 | 6.358873659 | | 1.8175371 | | | | | | |
| 114 | 407 | | | | | | | | | | | | |
| 115 | 408 | | | | | | 0.1130242 | | | | | | |
| 116 | 409 | | | | | | 4.1169216 | | | | | | |
| 117 | 410 | 22.782503 | | | 1.037096305 | | 42.768141 | | | | | | |
| | 417 | | 131.53193 | | 1.182009838 | | 0 | | | | | | |
| 118 | 418 | | | | 2.857847976 | | 31.160542 | | | | | | |
| 119 | 420 | | 25.398243 | | 1.363215732 | | 44.646226 | | | | | | |
| 120 | 421 | | | | 0.900039762 | | 5.950775 | | | | | | |
| | 425 | | | | | | | | | | | | |
| | 426 | | | | 1.572592377 | | 0.41306 | | | | | | |
| | 429 | | | | 0.656630471 | | 2.2140554 | | | | | | |
| | 433 | | 0.5190881 | | | | | | | | | | |
| 121 | 436 | | | | 1.294630808 | | 1.5115934 | | | | | | |
| 122 | 438 | | | | 1.241053244 | | 7.6394912 | | | | | | |
| | 439 | | | | | | | | | | | | |
| 123 | 441 | | | | 1.96171575 | | 1.5128032 | | | | | | |
| | 442 | | | | | | | | | | | | |
| | 443 | | | | | | | | | | | | |
| | 444 | | | | | | | | | | | | |
| | 445 | | | | | | | | | | | | |
| | 446 | | | | | | 20.713661 | | | | | | |

| SEQ ID No. | Compound no./G no. | Pair feeding | mouse 8+24 | rat 8+24 | sol pH<5 | sol pH 7.4 | pK peak | PK3d/4d | PK 7d | PK rating |
|---|---|---|---|---|---|---|---|---|---|---|
| 101 | 372 | | | | 5 | | | 4 | 0.3 | 0.2 | 3 |
| 102 | 373 | 1 | | | 1 | 5 | 24 | 0.3 | 0.2 | 3 |
| | 374 | 3 | 0.6 | 2.4 | 1 | 5 | 4 | 0.2 | 0.1 | 2 |
| 103 | 382 | | | | 7 | | 4 | 0.1 | 0.01 | 1 |
| 104 | 384 | | | | 7 | | | | | |
| 105 | 385 | | | | 7 | | | | | |
| 106 | 386 | | | | 1 | 4 | 24 | 0.4 | 0.2 | 3 |
| 107 | 387 | 1 | 1.9 | 2.2 | 1 | 4 | 4 | 0.4 | 0.3 | 2.5 |
| 108 | 397 | 4 | 2.1 | 1.5 | 3 | | | | | |
| 109 | 398 | 5 | 1.9 | 1.6 | 2 | 5 | 24 | 0.5 | 0.3 | 3.5 |
| 110 | 399 | 3.5 | 1.6 | 1.6 | 1 | 5 | 24 | 0.6 | 0.3 | 3 |
| 111 | 400 | | 1 | 1.1 | 4 | | | | | |
| 112 | 404 | | | | 1 | 5 | | | | |
| 113 | 405 | | | | 1 | 5 | | | | |
| 114 | 407 | | | | 7 | | | | | |
| 115 | 408 | | | | 7 | | | | | |
| 116 | 409 | | | | 7 | | | | | |
| 117 | 410 | | | | 7 | | | | | |
| | 417 | | | | 1 | 5 | 4 | 0.7 | 0.3 | 2.5 |
| 118 | 418 | | | | 1 | 4 | | | | |
| 119 | 420 | | | | 2 | 5 | 4 | 0.2 | 0.01 | 1.5 |
| 120 | 421 | 0.1 | | | 1 | 5 | 4 | 0.4 | 0.01 | 2 |
| | 425 | | | | 7 | | | | | |
| | 426 | 4 | | | 1 | 5 | 24 | 0.8 | 1 | 4 |
| | 429 | | | | 1 | 5 | 4 | | | |
| | 433 | | | | 1 | 5 | | | | |
| | 436 | | | | 1 | 5 | 4 | 0.1 | 0.04 | 1 |
| 121 | 438 | | | | 1 | 4 | | | | |
| 122 | 439 | | | | 7 | | | | | |
| | 441 | | | | 1 | 5 | | | | |
| 123 | 442 | | | | 1 | 5 | | | | |
| | 443 | | | | 4 | 4 | | | | |
| | 444 | | | | 1 | 5 | | | | |
| | 445 | | | | 1 | 5 | | | | |
| | 446 | | | | 1 | | | | | |

| Compound no./ G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 447 | His | Ser | Gln | Gly | Thr | Phe | Thr | Ser | Asp | Tyr | Ser | Lys | Tyr | Leu | Asp | Ser | Gln | Ala | Val | Arg |
| 448 | His | Ser | Gln | Gly | Thr | Phe | Thr | Ser | Asp | Tyr | Ser | His | Tyr | Leu | Asp | Ser | Gln | Ala | Val | Arg |
| 449 | His | Ser | Gln | Gly | Thr | Phe | Thr | Ser | Asp | Tyr | Ser | His | Tyr | Leu | Asp | Ser | Gln | Ala | Val | Arg |
| 450 | His | Ser | Gln | Gly | Thr | Phe | Thr | Ser | Asp | Tyr | Ser | His | Tyr | Leu | Asp | Ser | Gln | Ala | Val | Lys |
| 451 | His | Ser | Gln | Gly | Thr | Phe | Thr | Ser | Asp | Tyr | Ser | His | Tyr | Leu | Asp | Ser | Arg | Ala | Val | Lys |
| 452 | His | Ser | Gln | Gly | Thr | Phe | Thr | Ser | Asp | Tyr | Ser | His | Tyr | Leu | Asp | Ser | Arg | Ala | Val | His |
| 453 | His | Ser | Gln | Gly | Thr | Phe | Thr | Ser | Asp | Tyr | Ser | His | Tyr | Leu | Glu | Ser | Gln | Ala | Val | His |
| 454 | His | Ser | Gln | Gly | Thr | Phe | Thr | Ser | Asp | Tyr | Ser | His | Tyr | Leu | Asp | Ser | Gln | Ala | Val | Arg |
| 455 | His | Ser | Gln | Gly | Thr | Phe | Thr | Ser | Asp | Tyr | Ser | His | Tyr | Leu | Glu | Ser | Gln | Ala | Val | Arg |
| 456 | His | Ser | Gln | Gly | Thr | Phe | Thr | Ser | Asp | Tyr | Ser | His | Tyr | Leu | Glu | Ser | Glu | Ala | Val | Arg |
| 457 | His | Ser | Gln | Gly | Thr | Phe | Thr | Ser | Asp | Tyr | Ser | Lys | Tyr | Leu | Glu | Ser | Glu | Ala | Val | Arg |
| 458 | His | Ser | Gln | Gly | Thr | Phe | Thr | Ser | Asp | Tyr | Ser | His | Tyr | Leu | Glu | Ser | Gln | Ala | Val | Arg |
| 459 | His | Ser | Gln | Gly | Thr | Phe | Thr | Ser | Asp | Tyr | Ser | Lys | Tyr | Leu | Asp | Arg | Ala | Ala | Val | Asp |
| 460 | His | Gly | Glu | Gly | Thr | Phe | Thr | Ser | Asp | Leu | Ser | His | Gln | Met | Glu | Glu | Glu | Arg | Ala | Arg |
| 461 | His | Ser | Gln | Gly | Thr | Phe | Thr | Ser | Asp | Tyr | Ser | Lys | Tyr | Leu | Asp | Ser | Gln | Ala | Val | Arg |
| 462 | His | Ser | Gln | Gly | Thr | Phe | Thr | Ser | Asp | Tyr | Ser | His | Tyr | Leu | Glu | Ser | Gln | Ala | Val | His |
| 463 | His | Ser | Gln | Gly | Thr | Phe | Thr | Ser | Asp | Tyr | Ser | His | Tyr | Leu | Glu | Ser | Lys | Ala | Val | His |
| 464 | His | Ser | Gln | Gly | Thr | Phe | Thr | Ser | Asp | Tyr | Ser | His | Tyr | Leu | Glu | Ser | Arg | Ala | Val | His |
| 465 | His | Ser | Gln | Gly | Thr | Phe | Thr | Ser | Asp | Tyr | Ser | Lys | Tyr | Leu | Asp | Ser | Glu | Ala | Val | Lys |
| 466 | His | Ser | Gln | Gly | Thr | Phe | Thr | Ser | Asp | Tyr | Ser | His | Tyr | Leu | Glu | Ser | Gln | Ala | Val | His |
| 467 | His | Ser | Gln | Gly | Thr | Phe | Thr | Ser | Asp | Tyr | Ser | Lys | Tyr | Leu | Asp | Ser | Glu | Ala | Val | Arg |
| 468 | His | Ser | Gln | Gly | Thr | Phe | Thr | Ser | Asp | Tyr | Ser | His | Tyr | Leu | Glu | Ser | Glu | Ala | Val | Lys |
| 469 | His | Ser | Gln | Gly | Thr | Phe | Thr | Ser | Asp | Tyr | Ser | Lys | Tyr | Leu | Asp | Ser | Glu | Ala | Val | Arg |
| 470 | His | Ser | Gln | Gly | Thr | Phe | Thr | Ser | Asp | Tyr | Ser | Lys | Tyr | Leu | Glu | Ser | Glu | Ala | Val | Arg |
| 471 | His | Ser | Gln | Gly | Thr | Phe | Thr | Ser | Asp | Tyr | Ser | His | Tyr | Leu | Glu | Ser | Gln | Ala | Val | Arg |
| 472 | His | Ser | Gln | Gly | Thr | Phe | Thr | Ser | Asp | Tyr | Ser | Lys | Tyr | Leu | Asp | Ser | Gln | Ala | Val | His |
| 473 | His | Ser | Gln | Gly | Thr | Phe | Thr | Ser | Asp | Tyr | Ser | Lys | Tyr | Leu | Glu | Ser | Gln | Ala | Val | His |
| 474 | His | Ser | Gln | Gly | Thr | Phe | Thr | Ser | Asp | Tyr | Ser | His | Tyr | Leu | Glu | Ser | Glu | Ala | Val | His |
| 475 | His | Ser | Gln | Gly | Thr | Phe | Thr | Ser | Asp | Tyr | Ser | Lys | Tyr | Leu | Asp | Ser | Glu | Ala | Val | His |
| 476 | His | Ser | Gln | Gly | Thr | Phe | Thr | Ser | Asp | Tyr | Ser | His | Tyr | Leu | Glu | Ser | Glu | Ala | Val | His |
| 477 | His | Ser | Gln | Gly | Thr | Phe | Thr | Ser | Asp | Tyr | Ser | Lys | Tyr | Leu | Glu | Glu | Glu | Ala | Val | His |
| 478 | His | Ser | Gln | Gly | Thr | Phe | Thr | Ser | Asp | Tyr | Ser | His | Tyr | Leu | Glu | Glu | Glu | Ala | Val | His |
| 479 | His | Ser | Gln | Gly | Thr | Phe | Thr | Ser | Asp | Tyr | Ser | Lys | Tyr | Leu | Glu | Glu | Glu | Ala | Val | His |
| 480 | His | Ser | Gln | Gly | Thr | Phe | Thr | Ser | Asp | Tyr | Ser | Lys | Tyr | Leu | Glu | Glu | Glu | Ala | Val | Arg |
| 481 | His | Ser | Gln | Gly | Thr | Phe | Thr | Ser | Asp | Tyr | Ser | Lys | Tyr | Leu | Asp | Ser | Gln | Ala | Val | Arg |

FIG. 1Q

| SEQ ID No. | Compound no./G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| | 447 | Leu | Phe | Ile | Glu | Trp | Leu | Leu | Asn | Gly | His | NH2 | | | | | | | | | |
| | 448 | Leu | Phe | Ile | Gln | Trp | Leu | Leu | Asn | Gly | NH2 | | | | | | | | | | |
| | 449 | Leu | Phe | Ile | Glu | Trp | Leu | Leu | Asn | Gly | NH2 | | | | | | | | | | |
| | 450 | Leu | Phe | Ile | Gln | Trp | Leu | Leu | Asn | Gly | NH2 | | | | | | | | | | |
| | 451 | Leu | Phe | Ile | Gln | Trp | Leu | Leu | Asn | Thr | His | NH2 | | | | | | | | | |
| | 452 | Leu | Phe | Ile | Gln | Trp | Leu | Leu | Asn | Thr | NH2 | | | | | | | | | | |
| | 453 | Leu | Phe | Ile | Gln | Trp | Leu | Leu | Asn | Gly | His | NH2 | | | | | | | | | |
| | 454 | Leu | Phe | Ile | Gln | Trp | Leu | Leu | Asn | Thr | NH2 | | | | | | | | | | |
| | 455 | Leu | Phe | Ile | Glu | Trp | Leu | Leu | Asn | Gly | Arg | NH2 | | | | | | | | | |
| | 456 | Leu | Phe | Ile | Glu | Trp | Leu | Leu | Asn | Gly | Arg | NH2 | | | | | | | | | |
| | 457 | Leu | Phe | Ile | Gln | Trp | Leu | Leu | Asn | Gly | Arg | NH2 | | | | | | | | | |
| | 458 | Leu | Phe | Ile | Glu | Trp | Leu | Leu | Asn | Thr | NH2 | | | | | | | | | | |
| | 459 | Asp | Phe | Val | Ala | Trp | Leu | Lys | Ser | Thr | NH2 | | | | | | | | | | |
| | 460 | Leu | Phe | Ile | Glu | Trp | Leu | Lys | Asn | Gly | Gly | Pro | Ser | Ser | Gly | Ala | Pro | Pro | Ser | Kx6 | NH2 |
| | 461 | Leu | Phe | Ile | Glu | Trp | Leu | Val | Asn | Gly | NH2 | | | | | | | | | | |
| | 462 | Leu | Phe | Ile | Glu | Trp | Leu | Leu | Asn | Thr | NH2 | | | | | | | | | | |
| | 463 | Leu | Phe | Ile | Gln | Trp | Leu | Leu | Asn | Gly | NH2 | | | | | | | | | | |
| | 464 | Leu | Phe | Ile | Gln | Trp | Leu | Leu | Asn | Gly | NH2 | | | | | | | | | | |
| | 465 | Leu | Phe | Ile | Glu | Trp | Leu | Leu | Asn | Gly | NH2 | | | | | | | | | | |
| | 466 | Leu | Phe | Ile | Glu | Trp | Leu | Lys | Asn | Gly | NH2 | | | | | | | | | | |
| | 467 | His | Phe | Ile | Glu | Trp | Leu | Leu | Asn | Gly | NH2 | | | | | | | | | | |
| | 468 | Leu | Phe | Ile | Glu | Trp | Leu | Leu | Asn | Gly | NH2 | | | | | | | | | | |
| | 469 | Leu | Phe | Ile | Glu | Trp | Leu | Leu | Asn | Gly | NH2 | | | | | | | | | | |
| | 470 | Leu | Phe | Ile | Glu | Trp | Leu | Val | Asn | Gly | NH2 | | | | | | | | | | |
| | 471 | Leu | Phe | Ile | Glu | Trp | Leu | Leu | Asn | Gly | NH2 | | | | | | | | | | |
| | 472 | Leu | Phe | Ile | Glu | Trp | Leu | Leu | Asn | Gly | NH2 | | | | | | | | | | |
| | 473 | Leu | Phe | Ile | Glu | Trp | Leu | Leu | Asn | Gly | NH2 | | | | | | | | | | |
| | 474 | Leu | Phe | Ile | Glu | Trp | Leu | Leu | Asn | Gly | NH2 | | | | | | | | | | |
| | 475 | Leu | Phe | Ile | Glu | Trp | Leu | Leu | Asn | Thr | NH2 | | | | | | | | | | |
| | 476 | Leu | Phe | Ile | Glu | Trp | Leu | Leu | Asn | Thr | NH2 | | | | | | | | | | |
| | 477 | Leu | Phe | Ile | Glu | Trp | Leu | Leu | Asn | Thr | NH2 | | | | | | | | | | |
| | 478 | Leu | Phe | Ile | Glu | Trp | Leu | Leu | Asn | Gly | NH2 | | | | | | | | | | |
| | 479 | Leu | Phe | Ile | Glu | Trp | Leu | Lys | Asn | Thr | NH2 | | | | | | | | | | |
| | 480 | Leu | Phe | Ile | Glu | Trp | Leu | Leu | Asn | Thr | NH2 | | | | | | | | | | |
| | 481 | Leu | Phe | Ile | Glu | Trp | Leu | Leu | Asn | Thr | Gly | Pro | | | | | | | | | |

| SEQ ID No. | Compound no. / G no. | hGLP1R Man | rGLP1R Rat | mGLP1R Mouse | hGLP1R cAMP | hGlucR Man | hGluc cAMP | 0-1 Mouse | 0-4 Mouse | 0-8 Mouse | 4-8 Mouse | 8-24 Mouse | 0-24 Mouse |
|---|---|---|---|---|---|---|---|---|---|---|---|---|---|
| | 447 | | | | | | 9.6029999 | | | | | | |
| | 448 | | | | | | | | | | | | |
| | 449 | | | | | | | | | | | | |
| | 450 | | | | 0.36707124 | | 9.7098646 | | | | | | |
| | 451 | | | | 0.721618954 | | 48.55577 | | | | | | |
| | 452 | | | | | | 0 | | | | | | |
| | 453 | | | | 0.119683377 | | 6.827853 | | | | | | |
| | 454 | | | | | | | | | | | | |
| | 455 | | | | | | 3.8728504 | | | | | | |
| | 456 | | | | 1.076011846 | | 119.29356 | | | | | | |
| | 457 | | | | | | 27.529387 | | | | | | |
| | 458 | | | | | | 78.06149 | | | | | | |
| | 459 | | | | | | | | | | | | |
| | 460 | | | | | | | | | | | | |
| | 461 | | | | | | 19.651577 | | | | | | |
| | 462 | | | | | | 1.8278244 | | | | | | |
| | 463 | | | | 4.199843872 | | 9.7187963 | | | | | | |
| | 464 | | | | 1.013270882 | | 9.210238 | | | | | | |
| | 465 | | | | | | | | | | | | |
| | 466 | | | | | | 113.70899 | | | | | | |
| | 467 | | | | | | 1.8676607 | | | | | | |
| | 468 | | | | | | 8.9103804 | | | | | | |
| | 469 | | | | | | 3.021707 | | | | | | |
| | 470 | | | | | | 14.178976 | | | | | | |
| | 471 | | | | | | 2.9329058 | | | | | | |
| | 472 | | | | | | | | | | | | |
| | 473 | | | | | | 10.001092 | | | | | | |
| | 474 | | | | | | 2.7306364 | | | | | | |
| | 475 | | | | | | 4.0367486 | | | | | | |
| | 476 | | | | | | 57.079428 | | | | | | |
| | 477 | | | | | | | | | | | | |
| | 478 | | | | | | | | | | | | |
| | 479 | | | | | | 4.4573261 | | | | | | |
| | 480 | | | | | | 12.481672 | | | | | | |
| | 481 | | | | | | | | | | | | |

| SEQ ID No. | Compound no. / G no. | Pair feeding | mouse 8 + 24 | rat 8+24 | sol pH<5 | sol pH 7.4 | pK peak | PK3d/4d | PK 7d | PK rating |
|---|---|---|---|---|---|---|---|---|---|---|
| | 447 | 2 | | | 1 | 4 | | | 0.15 | 3 |
| | 448 | | | | 4 | | | | | |
| | 449 | | | | 2 | 5 | | | | |
| | 450 | | | | 1 | 5 | 24 | 0.6 | 0.01 | 3 |
| | 451 | | | | 1 | 5 | | | | |
| | 452 | | | | 1 | 4 | | | | |
| | 453 | | | | 1 | 5 | | | | |
| | 454 | | | | 1 | 5 | | | | |
| | 455 | | | | 1 | 5 | 24 | 0.3 | 0.01 | 2 |
| | 456 | | | | 1 | 5 | 24 | 0.2 | 0.01 | 2.5 |
| | 457 | | | | 1 | 5 | | | | |
| | 458 | | | | 1 | 5 | | | | |
| | 459 | | | | 1 | 1 | | | | |
| | 460 | | | | 1 | 5 | | | | |
| | 461 | | | | 2 | | | | | |
| | 462 | | | | 7 | | | | | |
| | 463 | | | | 4 | | | | | |
| | 464 | | | | 4 | | 24 | 0.4 | 0.3 | 3 |
| | 465 | | | | 7 | | | | | |
| | 466 | | | | 1 | 5 | 4 | 0.05 | 0.01 | 1 |
| | 467 | 4 | | | 1 | 5 | | | | |
| | 468 | | | | 1 | 5 | | | | |
| | 469 | | | | 7 | | | | | |
| | 470 | | | | 1 | 5 | 48 | 0.2 | 0.05 | 2 |
| | 471 | 2.5 | | | 7 | | | | | |
| | 472 | | | | 4 | | | | | |
| | 473 | 4 | | | 4 | | | | | |
| | 474 | | | | 1 | 4 | | | | |
| | 475 | | | | 4 | | | | | |
| | 476 | | | | 7 | | | | | |
| | 477 | | | | 7 | | | | | |
| | 478 | | | | 7 | | | | | |
| | 479 | | | | 7 | | | | | |
| | 480 | | | | 1 | 5 | | | | |
| | 481 | | | | 1 | 5 | | | | |

| SEQ ID No. | Compound no./ G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| | 482 | His | Ser | Gln | Gly | Thr | Phe | Thr | Ser | Asp | Tyr | Ser | Lys | Tyr | Leu | Asp | Ser | Gln | Ala | Val | Arg |
| | 483 | His | Ser | Gln | Gly | Thr | Phe | Thr | Ser | Asp | Tyr | Ser | His | Tyr | Leu | Asp | Ser | Gln | Ala | Val | Arg |
| | 484 | His | Ser | Gln | Gly | Thr | Phe | Thr | Ser | Asp | Tyr | Ser | Lys | Tyr | Leu | Asp | Ser | Gln | Ala | Val | His |
| | 485 | His | Ser | Gln | Gly | Thr | Phe | Thr | Ser | Asp | Tyr | Ser | His | Tyr | Leu | Asp | Ser | Gln | Ala | Val | His |
| | 486 | His | Ser | Gln | Gly | Thr | Phe | Thr | Ser | Asp | Tyr | Ser | His | Tyr | Leu | Glu | Ser | Glu | Ala | Val | His |
| | 487 | His | Ser | Gln | Gly | Thr | Phe | Thr | Ser | Asp | Tyr | Ser | Lys | Tyr | Leu | Glu | Glu | Glu | Ala | Val | Arg |
| | 488 | His | Ser | Gln | Gly | Thr | Phe | Thr | Ser | Asp | Tyr | Ser | Lys | Tyr | Leu | Glu | Glu | Glu | Ala | Val | Arg |
| | 489 | His | Ser | Gln | Gly | Thr | Phe | Thr | Ser | Asp | Tyr | Ser | Lys | Tyr | Leu | Glu | Glu | Glu | Ala | Val | Arg |
| | 490 | His | Ser | Gln | Gly | Thr | Phe | Thr | Ser | Asp | Tyr | Ser | Lys | Tyr | Leu | Glu | Glu | Glu | Ala | Val | His |
| | 491 | His | Ser | Gln | Gly | Thr | Phe | Thr | Ser | Asp | Tyr | Ser | Lys | Tyr | Leu | Asp | Ser | Gln | Ala | Val | His |
| | 492 | His | Ser | Gln | Gly | Thr | Phe | Thr | Ser | Asp | Tyr | Ser | His | Tyr | Leu | Asp | Ser | Arg | Ala | Val | Arg |
| | 493 | His | Ser | Gln | Gly | Thr | Phe | Thr | Ser | Asp | Tyr | Ser | Lys | Tyr | Leu | Asp | Ser | Gln | Ala | Val | Arg |
| | 494 | His | Ser | Gln | Gly | Thr | Phe | Thr | Ser | Asp | Tyr | Ser | His | Tyr | Leu | Glu | Glu | Glu | Ala | Val | Arg |
| | 495 | His | Ser | Gln | Gly | Thr | Phe | Thr | Ser | Asp | Tyr | Ser | Lys | Tyr | Leu | Glu | Ser | Gln | Ala | Val | Arg |
| | 496 | His | Ser | Gln | Gly | Thr | Phe | Thr | Ser | Asp | Tyr | Ser | His | Tyr | Leu | Asp | Ser | Gln | Ala | Val | Arg |
| | 497 | His | Ser | Gln | Gly | Thr | Phe | Thr | Ser | Asp | Tyr | Ser | His | Tyr | Leu | Glu | Ser | Arg | Ala | Val | His |
| | 498 | His | Ser | Gln | Gly | Thr | Phe | Thr | Ser | Asp | Tyr | Ser | His | Tyr | Leu | Asp | Ser | Gln | Ala | Val | His |
| | 499 | His | Ser | Gln | Gly | Thr | Phe | Thr | Ser | Asp | Tyr | Ser | His | Tyr | Leu | Asp | Ser | Lys | Ala | Val | His |
| | 500 | His | Ser | Gln | Gly | Thr | Phe | Thr | Ser | Asp | Tyr | Ser | His | Tyr | Leu | Glu | Ser | Gln | Ala | Val | Arg |
| | 501 | His | Ser | Gln | Gly | Thr | Phe | Thr | Ser | Asp | Tyr | Ser | Lys | Tyr | Leu | Asp | Ser | Gln | Ala | Val | Arg |
| | 502 | His | Ser | Gln | Gly | Thr | Phe | Thr | Ser | Asp | Tyr | Ser | His | Tyr | Leu | Glu | Ser | Glu | Ala | Val | Arg |
| | 503 | His | Ser | Gln | Gly | Thr | Phe | Thr | Ser | Asp | Tyr | Ser | Lys | Tyr | Leu | Asp | Glu | Glu | Ala | Val | Arg |
| | 504 | His | Ser | Gln | Gly | Thr | Phe | Thr | Ser | Asp | Tyr | Ser | His | Tyr | Leu | Glu | Glu | Gln | Ala | Val | Arg |
| | 505 | His | Ser | Gln | Gly | Thr | Phe | Thr | Ser | Asp | Tyr | Ser | Lys | Tyr | Leu | Asp | Ser | Gln | Ala | Val | Arg |
| | 506 | His | Ser | Gln | Gly | Thr | Phe | Thr | Ser | Asp | Tyr | Ser | His | Tyr | Leu | Asp | Glu | Gln | Ala | Val | Arg |
| | 507 | His | Ser | Gln | Gly | Thr | Phe | Thr | Ser | Asp | Tyr | Ser | Lys | Tyr | Leu | Glu | Ser | Arg | Ala | Val | His |
| | 508 | His | Ser | Gln | Gly | Thr | Phe | Thr | Ser | Asp | Tyr | Ser | His | Tyr | Leu | Glu | Ser | Arg | Ala | Val | His |
| | 509 | His | Ser | Gln | Gly | Thr | Phe | Thr | Ser | Asp | Tyr | Ser | Lys | Tyr | Leu | Glu | Glu | Arg | Ala | Val | His |
| | 510 | His | Ser | Gln | Gly | Thr | Phe | Thr | Ser | Asp | Tyr | Ser | His | Tyr | Leu | Asp | Ser | Gln | Ala | Val | His |
| | 511 | His | Ser | Gln | Gly | Thr | Phe | Thr | Ser | Asp | Tyr | Ser | His | Tyr | Leu | Glu | Ser | Gln | Ala | Val | His |
| | 512 | His | Ser | Gln | Gly | Thr | Phe | Thr | Ser | Asp | Tyr | Ser | Lys | Tyr | Leu | Asp | Glu | Gln | Ala | Val | His |
| | 514 | His | Ser | Gln | Gly | Thr | Phe | Thr | Ser | Asp | Tyr | Ser | His | Tyr | Leu | Glu | Ser | Arg | Ala | Val | Arg |
| | 515 | His | Ser | Gln | Gly | Thr | Phe | Thr | Ser | Asp | Tyr | Ser | His | Tyr | Leu | Glu | Ser | Gln | Ala | Val | His |
| | 516 | His | Ser | Gln | Gly | Thr | Phe | Thr | Ser | Asp | Tyr | Ser | His | Tyr | Leu | Glu | Glu | Gln | Ala | Val | His |
| | 517 | His | Ser | Gln | Gly | Thr | Phe | Thr | Ser | Asp | Tyr | Ser | Lys | Tyr | Leu | Glu | Glu | Gln | Ala | Val | Arg |

| SEQ ID No. | Compound no. / G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| | 482 | Arg | Leu | Phe | Ile | Glu | Trp | Leu | Leu | Asn | Gly | Gly | Pro | | | | | | | | |
| | 483 | Arg | Leu | Phe | Ile | Glu | Trp | Leu | Leu | Asn | Gly | Gly | Pro | | | | | | | | |
| | 484 | His | Leu | Phe | Ile | Glu | Trp | Leu | Leu | Asn | Gly | Gly | Pro | | | | | | | | |
| | 485 | His | Leu | Phe | Ile | Glu | Trp | Leu | Leu | Asn | Gly | Gly | Pro | | | | | | | | |
| | 486 | His | Leu | Phe | Ile | Gln | Trp | Leu | Leu | Asn | Gly | Gly | Pro | | | | | | | | |
| | 487 | Arg | Leu | Phe | Ile | Glu | Trp | Leu | Leu | Asn | Gly | Gly | Pro | | | | | | | | |
| | 488 | Arg | Leu | Phe | Ile | Glu | Trp | Leu | Leu | Asn | Gly | Gly | His | | | | | | | | |
| | 489 | Arg | Leu | Phe | Ile | Glu | Trp | Leu | Leu | Asn | Gly | His | NH2 | | | | | | | | |
| | 490 | Arg | Leu | Phe | Ile | Glu | Trp | Leu | Leu | Asn | Gly | His | His | | | | | | | | |
| | 491 | His | Leu | Phe | Ile | Glu | Trp | Leu | Leu | Asn | Gly | Gly | His | | | | | | | | |
| | 492 | His | Leu | Phe | Ile | Glu | Trp | Leu | Leu | Asn | Gly | Gly | Pro | | | | | | | | |
| | 493 | Arg | Leu | Phe | Ile | Glu | Trp | Leu | Leu | Asn | Thr | His | | | | | | | | | |
| | 494 | His | Leu | Phe | Ile | Glu | Trp | Leu | Leu | Asn | Thr | His | | | | | | | | | |
| | 495 | Arg | His | Phe | Ile | Glu | Trp | Leu | Leu | Asn | Thr | His | | | | | | | | | |
| | 496 | Arg | Leu | Phe | Ile | Gln | Trp | Leu | Leu | Asn | Thr | His | | | | | | | | | |
| | 497 | His | Leu | Phe | Ile | Gln | Trp | Leu | Leu | Asn | Thr | His | | | | | | | | | |
| | 498 | His | Leu | Phe | Ile | Gln | Trp | Leu | Leu | Asn | Thr | His | | | | | | | | | |
| | 499 | His | Leu | Phe | Ile | Gln | Trp | Leu | Leu | Asn | Gly | His | | | | | | | | | |
| | 500 | Arg | Leu | Phe | Ile | Gln | Trp | Val | Asn | Thr | His | | | | | | | | | | |
| | 501 | Arg | Leu | Phe | Ile | Glu | Trp | Leu | Leu | Asn | Gly | His | | | | | | | | | |
| | 502 | Arg | Leu | Phe | Ile | Glu | Trp | Leu | Leu | Asn | Gly | Arg | | | | | | | | | |
| | 503 | Arg | Leu | Phe | Ile | Glu | Trp | Leu | Leu | Asn | Thr | NH2 | | | | | | | | | |
| | 504 | Arg | Leu | Phe | Ile | Glu | Trp | Leu | Leu | Asn | Thr | His | NH2 | | | | | | | | |
| | 505 | Arg | Leu | Phe | Ile | Gln | Trp | Leu | Lys | Asn | Thr | Arg | NH2 | | | | | | | | |
| | 506 | His | Leu | Phe | Ile | Glu | Trp | Leu | Lys | Asn | Thr | His | NH2 | | | | | | | | |
| | 507 | His | Leu | Phe | Ile | Glu | Trp | Leu | Lys | Asn | Thr | Arg | NH2 | | | | | | | | |
| | 508 | His | Leu | Phe | Ile | Gln | Trp | Leu | Leu | Asn | Thr | His | NH2 | | | | | | | | |
| | 509 | His | Leu | Phe | Ile | Gln | Trp | Leu | Lys | Asn | Thr | His | NH2 | | | | | | | | |
| | 510 | His | Leu | Phe | Ile | Glu | Trp | Leu | Lys | Asn | Thr | His | NH2 | | | | | | | | |
| | 511 | His | Leu | Phe | Ile | Glu | Trp | Leu | Lys | Asn | Thr | His | NH2 | | | | | | | | |
| | 512 | His | Leu | Phe | Ile | Gln | Trp | Leu | Lys | Asn | Thr | His | NH2 | | | | | | | | |
| | 514 | Arg | Leu | Phe | Ile | Glu | Trp | Leu | Lys | Asn | Thr | His | NH2 | | | | | | | | |
| | 515 | His | Leu | Phe | Ile | Gln | Trp | Leu | Leu | Asn | Thr | His | NH2 | | | | | | | | |
| | 516 | His | Leu | Phe | Ile | Gln | Trp | Leu | Leu | Asn | Thr | His | NH2 | | | | | | | | |
| | 517 | Arg | Leu | Phe | Ile | Glu | Trp | Leu | Leu | Asn | Thr | NH2 | | | | | | | | | |

FIG. 1V

| SEQ ID No. | Compound no. / G no. | hGLP1R Man | rGLP1R Rat | mGLP1R Mouse | hGLP1R cAMP | hGlucR Man | hGluc cAMP | 0-1 Mouse | 0-4 Mouse | 0-8 Mouse | 4-8 Mouse | 8-24 Mouse | 0-24 Mouse |
|---|---|---|---|---|---|---|---|---|---|---|---|---|---|
| | 482 | | | | | | | | | | | | |
| | 483 | | | | | | | | | | | | |
| | 484 | | | | | | | | | | | | |
| | 485 | | | | | | | | | | | | |
| | 486 | | | | | | 33.278364 | | | | | | |
| | 487 | | | | | | 3.2066805 | | | | | | |
| | 488 | | | | | | 4.2198503 | | | | | | |
| | 489 | | | | | | 4.4586104 | | | | | | |
| | 490 | | | | | | 3.2771116 | | | | | | |
| | 491 | | | | | | 10.480874 | | | | | | |
| | 492 | | | | | | | | | | | | |
| | 493 | | | | | | | | | | | | |
| | 494 | | | | | | | | | | | | |
| | 495 | | | | | | 10.135224 | | | | | | |
| | 496 | | | | | | 7.3825137 | | | | | | |
| | 497 | | | | | | | | | | | | |
| | 498 | | | | | | | | | | | | |
| | 499 | | | | | | | | | | | | |
| | 500 | | | | | | | | | | | | |
| | 501 | | | | | | 3.6147541 | | | | | | |
| | 502 | | | | | | | | | | | | |
| | 503 | | | | | | | | | | | | |
| | 504 | | | | | | | | | | | | |
| | 505 | | | | | | | | | | | | |
| | 506 | | | | | | | | | | | | |
| | 507 | | | | | | | | | | | | |
| | 508 | | | | | | | | | | | | |
| | 509 | | | | | | | | | | | | |
| | 510 | | | | | | | | | | | | |
| | 511 | | | | | | | | | | | | |
| | 512 | | | | | | | | | | | | |
| | 514 | | | | | | | | | | | | |
| | 515 | | | | | | | | | | | | |
| | 516 | | | | | | | | | | | | |
| | 517 | | | | | | | | | | | | |

FIG. 1W

| SEQ ID No. | Compound no./G no. | Pair feeding | mouse 8+24 | rat 8+24 | sol pH<5 | sol pH 7.4 | pK peak | PK3d/4d | PK 7d | PK rating |
|---|---|---|---|---|---|---|---|---|---|---|
| | 482 | | | | 7 | | | | | |
| | 483 | | | | 4 | | | | | |
| | 484 | | | | | | | | | |
| | 485 | | | | 1 | 5 | | | | |
| | 486 | | | | | | | | | |
| | 487 | | | | 4 | | | | | |
| | 488 | | | | 1 | 5 | | | | |
| | 489 | | | | 1 | 5 | | | | |
| | 490 | | | | 1 | 5 | | | | |
| | 491 | | | | 1 | 5 | | | | |
| | 492 | | | | 1 | 5 | | | | |
| | 493 | | | | 1 | 5 | | | | |
| | 494 | | | | 2 | 5 | | | | |
| | 495 | | | | 2 | 5 | | | | |
| | 496 | | | | 1 | 5 | | | | |
| | 497 | | | | 1 | 5 | | | | |
| | 498 | | | | 1 | 5 | | | | |
| | 499 | | | | 2 | 5 | | | | |
| | 500 | | | | 1 | 5 | | | | |
| | 501 | | | | 1 | 5 | | | | |
| | 502 | | | | | | | | | |
| | 503 | | | | | | | | | |
| | 504 | | | | | | | | | |
| | 505 | | | | | | | | | |
| | 506 | | | | | | | | | |
| | 507 | | | | | | | | | |
| | 508 | | | | | | | | | |
| | 509 | | | | | | | | | |
| | 510 | | | | | | | | | |
| | 511 | | | | | | | | | |
| | 512 | | | | | | | | | |
| | 513 | | | | | | | | | |
| | 514 | | | | | | | | | |
| | 515 | | | | | | | | | |
| | 516 | | | | | | | | | |
| | 517 | | | | | | | | | |

| SEQ ID No. | Compound no./ G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| | 518 | His | Ser | Gln | Gly | Thr | Phe | Thr | Ser | Asp | Tyr | Ser | Lys | Tyr | Leu | Glu | Gln | Glu | Ala | Val | Arg |
| | 519 | His | Ser | Gln | Gly | Thr | Phe | Thr | Ser | Asp | Tyr | Ser | Lys | Tyr | Leu | Gln | Glu | Glu | Ala | Val | Arg |
| | 520 | His | Ser | Gln | Gly | Thr | Phe | Thr | Ser | Asp | Tyr | Ser | Lys | Tyr | Leu | Gln | Gln | Glu | Ala | Val | Arg |
| | 521 | His | Ser | Gln | Gly | Thr | Phe | Thr | Ser | Asp | Tyr | Ser | Lys | Tyr | Leu | Glu | Gln | Gln | Ala | Val | Arg |
| | 522 | His | Ser | Gln | Gly | Thr | Phe | Thr | Ser | Asp | Tyr | Ser | Lys | Tyr | Leu | Gln | Gln | Gln | Ala | Val | Arg |
| | 523 | His | Ser | Gln | Gly | Thr | Phe | Thr | Ser | Asp | Tyr | Ser | Lys | Tyr | Leu | Gln | Glu | Gln | Ala | Val | Arg |
| | 524 | His | Ser | Gln | Gly | Thr | Phe | Thr | Ser | Asp | Tyr | Ser | His | Tyr | Leu | Asp | Glu | Arg | Ala | Val | His |
| | 525 | His | Ser | Gln | Gly | Thr | Phe | Thr | Ser | Asp | Tyr | Ser | Lys | Tyr | Leu | Asp | Glu | Gln | Ala | Val | His |
| | 526 | His | Ser | Gln | Gly | Thr | Phe | Thr | Ser | Asp | Tyr | Ser | His | Tyr | Leu | Glu | Glu | Gln | Ala | Val | Arg |
| | 527 | His | Ser | Gln | Gly | Thr | Phe | Thr | Ser | Asp | Tyr | Ser | His | Tyr | Leu | Asp | Glu | Gln | Ala | Val | His |
| | 528 | His | Ser | Gln | Gly | Thr | Phe | Thr | Ser | Asp | Tyr | Ser | His | Tyr | Leu | Asp | Glu | Gln | Ala | Val | His |
| | 529 | His | Ser | Gln | Gly | Thr | Phe | Thr | Ser | Asp | Tyr | Ser | Lys | Tyr | Leu | Glu | Glu | Gln | Ala | Val | Arg |
| | 530 | His | Ser | Gln | Gly | Thr | Phe | Thr | Ser | Asp | Tyr | Ser | His | Tyr | Leu | Asp | Glu | Gln | Ala | Val | Lys |
| | 531 | His | Ser | Gln | Gly | Thr | Phe | Thr | Ser | Asp | Tyr | Ser | Lys | Tyr | Leu | Glu | Glu | Gln | Ala | Val | Arg |
| | 532 | His | Ser | Gln | Gly | Thr | Phe | Thr | Ser | Asp | Tyr | Ser | His | Tyr | Leu | Asp | Glu | Gln | Ala | Val | His |
| | 533 | His | Ser | Gln | Gly | Thr | Phe | Thr | Ser | Asp | Tyr | Ser | His | Tyr | Leu | Glu | Glu | Gln | Ala | Val | His |
| | 534 | His | Ser | Gln | Gly | Thr | Phe | Thr | Ser | Asp | Tyr | Ser | Lys | Tyr | Leu | Glu | Glu | Gln | Ala | Val | Arg |
| | 536 | His | Ser | Gln | Gly | Thr | Phe | Thr | Ser | Asp | Tyr | Ser | Lys | Tyr | Leu | Glu | Glu | Glu | Ala | Val | Arg |
| | 537 | His | Ser | Gln | Gly | Thr | Phe | Thr | Ser | Asp | Tyr | Ser | His | Tyr | Leu | Glu | Glu | Glu | Ala | Val | Arg |
| | 538 | His | Ser | Gln | Gly | Thr | Phe | Thr | Ser | Asp | Tyr | Ser | Lys | Tyr | Leu | Glu | Ser | Glu | Ala | Val | Arg |
| | 539 | His | Ser | Gln | Gly | Thr | Phe | Thr | Ser | Asp | Tyr | Ser | His | Tyr | Leu | Glu | Ser | Glu | Ala | Val | His |
| | 540 | His | Ser | Gln | Gly | Thr | Phe | Thr | Ser | Asp | Tyr | Ser | Lys | Tyr | Leu | Glu | Ser | Glu | Ala | Val | His |
| | 541 | His | Ser | Gln | Gly | Thr | Phe | Thr | Ser | Asp | Tyr | Ser | Lys | Tyr | Leu | Glu | Glu | Glu | Ala | Val | Arg |
| | 542 | His | Ser | Gln | Gly | Thr | Phe | Thr | Ser | Asp | Tyr | Ser | His | Tyr | Leu | Glu | Glu | Glu | Ala | Val | Arg |
| | 543 | His | Ser | Gln | Gly | Thr | Phe | Thr | Ser | Asp | Tyr | Ser | His | Tyr | Leu | Glu | Glu | Glu | Ala | Val | His |
| | 544 | His | Ser | Gln | Gly | Thr | Phe | Thr | Ser | Asp | Tyr | Ser | His | Tyr | Leu | Glu | Glu | Gln | Ala | Val | Arg |
| | 545 | His | Ser | Gln | Gly | Thr | Phe | Thr | Ser | Asp | Tyr | Ser | Lys | Tyr | Leu | Glu | Glu | Glu | Ala | Val | Arg |
| | 546 | His | Ser | Gln | Gly | Thr | Phe | Thr | Ser | Asp | Tyr | Ser | Lys | Tyr | Leu | Glu | Glu | Gln | Ala | Val | Arg |
| | 547 | His | Ser | Gln | Gly | Thr | Phe | Thr | Ser | Asp | Tyr | Ser | His | Tyr | Leu | Glu | Glu | Gln | Ala | Val | Arg |
| | 548 | His | Ser | Gln | Gly | Thr | Phe | Thr | Ser | Asp | Tyr | Ser | Lys | Tyr | Leu | Asp | Ser | Gln | Ala | Val | Arg |
| | 549 | His | Ser | Gln | Gly | Thr | Phe | Thr | Ser | Asp | Tyr | Ser | His | Tyr | Leu | Glu | Glu | Gln | Ala | Val | Arg |
| | 550 | His | Ser | Gln | Gly | Thr | Phe | Thr | Ser | Asp | Tyr | Ser | Lys | Tyr | Leu | Glu | Ser | Gln | Ala | Val | Arg |
| | 551 | His | Ser | Gln | Gly | Thr | Phe | Thr | Ser | Asp | Tyr | Ser | His | Tyr | Leu | Glu | Ser | Gln | Ala | Val | Arg |
| | 552 | His | Ser | Gln | Gly | Thr | Phe | Thr | Ser | Asp | Tyr | Ser | Lys | Tyr | Leu | Glu | Ser | Glu | Ala | Val | Arg |
| | 553 | His | Ser | Gln | Gly | Thr | Phe | Thr | Ser | Asp | Tyr | Ser | His | Tyr | Leu | Asp | Ser | Arg | Ala | Val | His |

| SEQ ID No. | Compound no. / G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| | 518 | Leu | Phe | Ile | Glu | Trp | Leu | Leu | Asn | Thr | NH2 | | | | | | | | | | |
| | 519 | Leu | Phe | Ile | Glu | Trp | Leu | Leu | Asn | Thr | NH2 | | | | | | | | | | |
| | 520 | Leu | Phe | Ile | Glu | Trp | Leu | Leu | Asn | Thr | NH2 | | | | | | | | | | |
| | 521 | Leu | Phe | Ile | Glu | Trp | Leu | Leu | Asn | Thr | NH2 | | | | | | | | | | |
| | 522 | Leu | Phe | Ile | Glu | Trp | Leu | Leu | Asn | Thr | NH2 | | | | | | | | | | |
| | 523 | Leu | Phe | Ile | Gln | Trp | Leu | Leu | Asn | Thr | NH2 | | | | | | | | | | |
| | 524 | Leu | Phe | Ile | Glu | Trp | Leu | Leu | Asn | Thr | NH2 | | | | | | | | | | |
| | 525 | Leu | Phe | Ile | Glu | Trp | Leu | Lys | Asn | Gly | NH2 | | | | | | | | | | |
| | 526 | His | Phe | Ile | Glu | Trp | Leu | Leu | Asn | Thr | NH2 | | | | | | | | | | |
| | 527 | Leu | Phe | Ile | Glu | Trp | Leu | Leu | Asn | Gly | NH2 | | | | | | | | | | |
| | 528 | Leu | Phe | Ile | Glu | Trp | Leu | Lys | Asn | Gly | His | NH2 | | | | | | | | | | |
| | 529 | Leu | Phe | Ile | Glu | Trp | Leu | Lys | Asn | Thr | His | NH2 | | | | | | | | | | |
| | 530 | Leu | Phe | Ile | Glu | Trp | Leu | Val | Asn | Thr | His | NH2 | | | | | | | | | | |
| | 531 | Leu | Phe | Ile | Glu | Trp | Leu | Val | Asn | Thr | His | NH2 | | | | | | | | | | |
| | 532 | Leu | Phe | Ile | Glu | Trp | Leu | Val | Asn | Gly | NH2 | | | | | | | | | | | |
| | 533 | Leu | Phe | Ile | Glu | Trp | Leu | Lys | Asn | Gly | NH2 | | | | | | | | | | | |
| | 534 | Leu | Phe | Ile | Glu | Trp | Leu | Lys | Asn | Gly | NH2 | | | | | | | | | | | |
| | 536 | Leu | Phe | Ile | Glu | Trp | Leu | Leu | Asn | Thr | Gly | His | | | | | | | | | | |
| | 537 | Leu | Phe | Ile | Glu | Trp | Leu | Lys | Asn | Gly | Gly | His | | | | | | | | | | |
| | 538 | Leu | Phe | Ile | Gln | Trp | Leu | Leu | Asn | Gly | Gly | His | | | | | | | | | | |
| | 539 | Leu | Phe | Ile | Glu | Trp | Leu | Leu | Asn | Gly | Gly | His | | | | | | | | | | |
| | 540 | Leu | Phe | Ile | Glu | Trp | Leu | Leu | Asn | Gly | Gly | His | | | | | | | | | | |
| | 541 | Leu | Phe | Ile | Glu | Trp | Leu | Leu | Asn | Gly | Lys | His | | | | | | | | | | |
| | 542 | His | Phe | Ile | Gln | Trp | Leu | Leu | Asn | Gly | Gly | His | | | | | | | | | | |
| | 543 | Leu | Phe | Ile | Gln | Trp | Leu | Leu | Asn | Thr | Gly | His | | | | | | | | | | |
| | 544 | Leu | Phe | Ile | Glu | Trp | Leu | Leu | Asn | Thr | Gly | His | | | | | | | | | | |
| | 545 | Leu | Phe | Ile | Glu | Trp | Leu | Leu | Asn | Thr | Gly | His | NH2 | | | | | | | | | |
| | 546 | Leu | Phe | Ile | Glu | Trp | Leu | Leu | Asn | Gly | Gly | His | NH2 | | | | | | | | | |
| | 547 | Leu | Phe | Ile | Glu | Trp | Leu | Leu | Asn | Gly | Gly | His | | | | | | | | | | |
| | 548 | Leu | Phe | Ile | Glu | Trp | Leu | Leu | Asn | Thr | NH2 | | | | | | | | | | | |
| | 549 | His | Phe | Ile | Glu | Trp | Leu | Leu | Asn | Thr | NH2 | | | | | | | | | | | |
| | 550 | Leu | Phe | Ile | Glu | Trp | Leu | Leu | Asn | Gly | Gly | His | | | | | | | | | | |
| | 551 | Leu | Phe | Ile | Gln | Trp | Leu | Leu | Asn | Gly | Gly | His | | | | | | | | | | |
| | 552 | His | Phe | Ile | Glu | Trp | Leu | Leu | Asn | Gly | Gly | His | | | | | | | | | | |
| | 553 | Leu | Phe | Ile | Gln | Trp | Leu | Leu | Asn | Gly | Gly | His | | | | | | | | | | |

FIG. 1Z

| SEQ ID No. | Compound no. / G no. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| | 554 | His | Ser | Gln | Gly | Thr | Phe | Thr | Ser | Asp | Tyr | Ser | His | Tyr | Leu | Asp | Ser | Gln | Ala | Val | Arg |
| | 555 | His | Ser | Gln | Gly | Thr | Phe | Thr | Ser | Asp | Tyr | Ser | Lys | Tyr | Leu | Glu | Ser | Glu | Ala | Val | Arg |
| | 556 | His | Ser | Gln | Gly | Thr | Phe | Thr | Ser | Asp | Tyr | Ser | His | Tyr | Leu | Asp | Ser | Arg | Ala | Val | His |
| | 557 | His | Ser | Gln | Gly | Thr | Phe | Thr | Ser | Asp | Tyr | Ser | Lys | Tyr | Leu | Glu | Glu | Gln | Ala | Val | Arg |
| | 558 | His | Ser | Gln | Gly | Thr | Phe | Thr | Ser | Asp | Tyr | Ser | Lys | Tyr | Leu | Glu | Glu | Gln | Ala | Val | Arg |
| | 559 | His | Ser | Gln | Gly | Thr | Phe | Thr | Ser | Asp | Tyr | Ser | His | Tyr | Leu | Glu | Glu | Gln | Ala | Val | His |
| | 560 | His | Ser | Gln | Gly | Thr | Phe | Thr | Ser | Asp | Tyr | Ser | Lys | Tyr | Leu | Glu | Glu | Gln | Ala | Val | Arg |
| | 561 | His | Ser | Gln | Gly | Thr | Phe | Thr | Ser | Asp | Tyr | Ser | Lys | Tyr | Leu | Glu | Ser | Gln | Ala | Val | Arg |
| | 562 | His | Ser | Gln | Gly | Thr | Phe | Thr | Ser | Asp | Tyr | Ser | Lys | Tyr | Leu | Glu | Glu | Glu | Ala | Val | Arg |
| | 563 | His | Ser | Gln | Gly | Thr | Phe | Thr | Ser | Asp | Tyr | Ser | Lys | Tyr | Leu | Glu | Glu | Glu | Ala | Val | Arg |
| | 564 | His | Ser | Gln | Gly | Thr | Phe | Thr | Ser | Asp | Tyr | Ser | Lys | Tyr | Leu | Glu | Glu | Glu | Ala | Val | Arg |
| | 565 | His | Ser | Gln | Gly | Thr | Phe | Thr | Ser | Asp | Tyr | Ser | Lys | Tyr | Leu | Glu | Glu | Glu | Ala | Val | Arg |
| | 566 | His | Ser | Gln | Gly | Thr | Phe | Thr | Ser | Asp | Tyr | Ser | Lys | Tyr | Leu | Glu | Glu | Glu | Ala | Val | Arg |

FIG. 1AA

| SEQ ID No. | Compound no./ G no. | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| | 554 | Leu | Phe | Ile | Gln | Trp | Leu | Leu | Asn | Thr | Gly | His | | | | | | | | | |
| | 555 | His | Phe | Ile | Glu | Trp | Leu | Leu | Asn | Thr | Gly | His | | | | | | | | | |
| | 556 | Leu | Phe | Ile | Gln | Trp | Leu | Leu | Asn | Thr | Gly | His | | | | | | | | | |
| | 557 | Leu | Phe | Ile | Glu | Trp | Leu | Leu | Asn | Thr | Gly | His | | | | | | | | | |
| | 558 | His | Phe | Ile | Glu | Trp | Leu | Leu | Asn | Gly | Gly | His | | | | | | | | | |
| | 559 | Leu | Phe | Ile | Glu | Trp | Leu | Leu | Asn | Gly | Gly | His | | | | | | | | | |
| | 560 | Leu | Phe | Ile | Gln | Trp | Leu | Leu | Asn | Gly | Gly | His | | | | | | | | | |
| | 561 | Leu | Phe | Ile | Glu | Trp | Leu | Leu | Asn | Thr | Gly | His | | | | | | | | | |
| | 562 | Leu | Phe | Ile | Glu | Trp | Leu | Leu | Asn | Thr | Gly | His | | | | | | | | | |
| | 563 | Leu | Phe | Ile | Gln | Trp | Leu | Leu | Asn | Thr | Gly | His | | | | | | | | | |
| | 564 | Leu | Phe | Ile | Glu | Trp | Leu | Val | Asn | Gly | Gly | His | | | | | | | | | |
| | 565 | Leu | Phe | Ile | Glu | Trp | Leu | Leu | Asn | Thr | | | | | | | | | | | |
| | 566 | Leu | Phe | Ile | Glu | Trp | Leu | Leu | Asn | Gly | | | | | | | | | | | |

FIG. 1BB

Total BW Change Day 10

Total FI Day 10

Day 10 Summary

```
                          SEQUENCE LISTING

<160> NUMBER OF SEQ ID NOS: 343

<210> SEQ ID NO 1
   <211> LENGTH: 29
   <212> TYPE: PRT
   <213> ORGANISM: Homo Sapiens

<400> SEQUENCE: 1

His Ser Gln Gly Thr Phe Thr Ser Asp Tyr Ser Lys Tyr Leu Asp Ser
   1               5                   10                  15

Arg Arg Ala Gln Asp Phe Val Gln Trp Leu Met Asn Thr
               20                  25

<210> SEQ ID NO 2
   <211> LENGTH: 30
   <212> TYPE: PRT
   <213> ORGANISM: Homo sapiens
   <220> FEATURE:
   <221> NAME/KEY: MOD_RES
   <222> LOCATION: (30)..(30)
   <223> OTHER INFORMATION: AMIDATION

<400> SEQUENCE: 2

His Ala Glu Gly Thr Phe Thr Ser Asp Val Ser Ser Tyr Leu Glu Gly
   1               5                   10                  15

Gln Ala Ala Lys Glu Phe Ile Ala Trp Leu Val Lys Gly Arg
               20                  25                  30

<210> SEQ ID NO 3
   <211> LENGTH: 39
   <212> TYPE: PRT
   <213> ORGANISM: Homo sapiens

<400> SEQUENCE: 3

His Gly Glu Gly Thr Phe Thr Ser Asp Leu Ser Lys Gln Met Glu Glu
   1               5                   10                  15

Glu Ala Val Arg Leu Phe Ile Glu Trp Leu Lys Asn Gly Gly Pro Ser
               20                  25                  30

Ser Gly Ala Pro Pro Pro Ser
               35

<210> SEQ ID NO 4
   <211> LENGTH: 30
   <212> TYPE: PRT
   <213> ORGANISM: Artificial Sequence
   <220> FEATURE:
   <223> OTHER INFORMATION: GLP/glucagon analogue
   <220> FEATURE:
   <221> NAME/KEY: MISC_FEATURE
   <222> LOCATION: (2)..(2)
   <223> OTHER INFORMATION: Xaa is alpha-amino isobutyric acid
   <220> FEATURE:
   <221> NAME/KEY: MOD_RES
   <222> LOCATION: (30)..(30)
   <223> OTHER INFORMATION: AMIDATION

<400> SEQUENCE: 4
```

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 5

His Ala Glu Gly Thr Phe Thr Ser Asp Val Ser Ser Tyr Leu Glu Glu
1               5                   10                  15

Glu Ala Val Arg Leu Phe Ile Glu Trp Leu Val Lys Gly Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 6

His Xaa Glu Gly Thr Phe Thr Ser Asp Val Ser Ser Tyr Leu Glu Gly
1               5                   10                  15

Glu Ile Val Lys Tyr Phe Ile Glu Trp Leu Val Lys Gly Arg
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 7

His Xaa Glu Gly Thr Phe Thr Ser Asp Val Ser Ser Tyr Leu Glu Gly
1               5                   10                  15

Gln Ile Val Lys Tyr Phe Ile Glu Trp Leu Val Lys Gly Arg
            20                  25                  30

<210> SEQ ID NO 8
<211> LENGTH: 30
<212> TYPE: PRT
```

```
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 8

His Xaa Glu Gly Thr Phe Thr Ser Asp Val Ser Ser Tyr Leu Glu Gly
1               5                   10                  15

His Ile Val Lys Tyr Phe Ile Glu Trp Leu Val Lys Gly Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 9

His Xaa Glu Gly Thr Phe Thr Ser Asp Val Ser Ser Tyr Leu Glu Gly
1               5                   10                  15

Gln Ile Val Lys Tyr Phe Ile Gln Trp Leu Val Lys Gly Arg
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 10

His Xaa Glu Gly Thr Phe Thr Ser Asp Val Ser Ser Tyr Leu Glu Gly
1               5                   10                  15

Gln Ile Val Lys Tyr Phe Ile His Trp Leu Val Lys Gly Arg
            20                  25                  30

<210> SEQ ID NO 11
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 11

His Ser Gln Gly Thr Phe Thr Ser Asp Tyr Ser Lys Tyr Leu Asp Ser
```

```
1               5                   10                  15
Arg Arg Ala Gln Asp Phe Val Gln Trp Leu Met Asn Thr Gly Pro Ser
            20                  25                  30

Ser Gly Ala Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 12

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Gly Gly Pro Ser
            20                  25                  30

Ser Gly Ala Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 13

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Gly Gly Pro Ser
            20                  25                  30

Ser Gly Ala Pro Pro Ser
        35

<210> SEQ ID NO 14
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 14

His Xaa Glu Gly Thr Phe Thr Ser Asp Val Ser Arg Tyr Leu Glu Gly
1               5                   10                  15

Gln Ile Val Lys Tyr Phe Ile Glu Trp Leu Val Lys Gly Arg
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
```

```
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 15

His Xaa Glu Gly Thr Phe Thr Ser Asp Val Ser Arg Tyr Leu Glu Gly
1               5                   10                  15

Gln Ile Val Lys Tyr Phe Ile Glu His Leu Val Lys Gly Arg
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 16

His Xaa Glu Gly Thr Phe Thr Ser Asp Val Ser His Tyr Leu Glu Gly
1               5                   10                  15

Gln Ile Val Lys Tyr Phe Ile Glu Trp Leu Val Lys Gly Arg
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 17

His Xaa Glu Gly Thr Phe Thr Ser Asp Val Ser Ser Tyr Leu Glu Gly
1               5                   10                  15

Gln Ala Val Arg Leu Phe Ile Glu Trp Leu Val Lys Gly Arg
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION
```

```
<400> SEQUENCE: 18

His Xaa Glu Gly Thr Phe Thr Ser Asp Val Ser Ser Tyr Leu Glu Gly
1               5                   10                  15

Gln Ile Val Lys Tyr Phe Ile Glu Lys Leu Val Lys Gly Arg
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 19

His Xaa Gln Gly Thr Phe Thr Ser Asp Val Ser Ser Tyr Leu Glu Gly
1               5                   10                  15

Gln Ile Val Lys Tyr Phe Ile Glu Trp Leu Val Lys Gly Arg
            20                  25                  30

<210> SEQ ID NO 20
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid

<400> SEQUENCE: 20

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Gly Gly Pro Ser
            20                  25                  30

Ser Gly Ala Pro Pro Pro Ser
        35

<210> SEQ ID NO 21
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 21

His Xaa Gln Gly Thr Phe Thr Ser Asp Val Ser Ser Tyr Leu Glu Gly
1               5                   10                  15

Gln Ala Val Arg Leu Phe Ile Glu Trp Leu Val Lys Gly Arg
            20                  25                  30
```

<210> SEQ ID NO 22
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 22

His Ser Gln Gly Thr Phe Thr Ser Asp Tyr Ser Lys Tyr Leu Asp Ser
1               5                   10                  15

Arg Arg Ala Gln Asp Phe Ile Glu Trp Leu Met Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 23

His Ser Gln Gly Thr Phe Thr Ser Asp Tyr Ser Lys Tyr Leu Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid

<400> SEQUENCE: 24

His Xaa Gln Gly Thr Phe Thr Ser Asp Tyr Ser Lys Tyr Leu Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 25

His Ser Gln Gly Thr Phe Thr Ser Asp Tyr Ser Lys Tyr Leu Asp Ser
1               5                   10                  15

Arg Ile Val Lys Tyr Phe Ile Glu Trp Leu Lys Asn Gly Gly Pro Ser
            20                  25                  30

Ser Gly Ala Pro Pro Pro Ser
        35

```
<210> SEQ ID NO 26
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 26

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 27
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 27

His Ser Gln Gly Thr Phe Thr Ser Asp Tyr Ser Arg Tyr Leu Asp Ser
1               5                   10                  15

Arg Arg Ala Gln Asp Phe Val Gln Trp Leu Leu Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (29)..(29)
<223> OTHER INFORMATION: AMIDATION

<400> SEQUENCE: 28

His Xaa Gln Gly Thr Phe Thr Ser Asp Tyr Ser Arg Tyr Leu Asp Ser
1               5                   10                  15

Arg Arg Ala Gln Asp Phe Val Gln Trp Leu Leu Asn Thr
            20                  25

<210> SEQ ID NO 29
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 29

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Gly Gly Pro Ser
            20                  25                  30
```

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 30

His Ser Gln Gly Thr Phe Thr Ser Asp Tyr Ser Arg Tyr Leu Asp Ser
1               5                   10                  15

Arg Arg Ala Gln Asp Phe Val Gln Trp Leu Leu Asn Gly Gly Pro Ser
            20                  25                  30

Ser Gly Ala Pro Pro Pro Ser
        35

<210> SEQ ID NO 31
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 31

His Ser Gln Gly Thr Phe Thr Ser Asp Tyr Ser Lys Tyr Leu Glu Gly
1               5                   10                  15

Gln Ile Val Lys Tyr Phe Ile Glu Trp Leu Val Asn Gly Arg
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 32

His Xaa Gln Gly Thr Phe Thr Ser Asp Tyr Ser Lys Tyr Leu Glu Gly
1               5                   10                  15

Glu Ile Val Lys Tyr Phe Ile Glu Trp Leu Val Asn Gly Arg
            20                  25                  30

<210> SEQ ID NO 33
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid

```
<400> SEQUENCE: 33

His Xaa Gln Gly Thr Phe Thr Ser Asp Tyr Ser Lys Tyr Leu Glu Gly
1               5                   10                  15

Gln Ile Val Lys Tyr Phe Ile Gln Trp Leu Val Asn Gly Gly Pro Ser
            20                  25                  30

Ser Gly Ala Pro Pro Pro Ser
        35

<210> SEQ ID NO 34
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 34

His Ser Gln Gly Thr Phe Thr Ser Asp Tyr Ser Lys Tyr Leu Asp Ser
1               5                   10                  15

Lys Lys Ala Gln Glu Phe Ile Ala Trp Leu Val Lys Gly Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 35

His Ser Gln Gly Thr Phe Thr Ser Asp Tyr Ser Lys Tyr Leu Asp Glu
1               5                   10                  15

Glu Ile Val Lys Tyr Phe Ile Glu Leu Leu Met Asn Gly Gly Pro Ser
            20                  25                  30

Ser Gly Ala Pro Pro Pro Ser
        35

<210> SEQ ID NO 36
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid

<400> SEQUENCE: 36

His Xaa Gln Gly Thr Phe Thr Ser Asp Tyr Ser Lys Tyr Leu Asp Ser
1               5                   10                  15

Arg Ala Val Arg Leu Phe Ile Glu Trp Leu Met Asn Thr
            20                  25

<210> SEQ ID NO 37
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
```

```
<223> OTHER INFORMATION: Xaa is alpha-amino isobutyric acid

<400> SEQUENCE: 37

His Xaa Gln Gly Thr Phe Thr Ser Asp Tyr Ser Lys Tyr Leu Asp Ser
1               5                   10                  15

Arg Ile Val Lys Tyr Phe Ile Glu Trp Leu Met Asn Gly Gly Pro Ser
            20                  25                  30

Ser Gly Ala Pro Pro Pro Ser
        35

<210> SEQ ID NO 38
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 38

His Ser Gln Gly Thr Phe Thr Ser Asp Tyr Ser Lys Tyr Leu Asp Glu
1               5                   10                  15

Glu Ile Val Lys Tyr Phe Ile Gln Trp Leu Met Asn Thr Arg
            20                  25                  30

<210> SEQ ID NO 39
<211> LENGTH: 29
<212> TYPE: PRT
<213> ORGANISM: Artificial Sequence
<220> FEATURE:
<223> OTHER INFORMATION: GLP/glucagon analogue

<400> SEQUENCE: 39

His Ser Gln Gly Thr Phe Thr Ser Asp Tyr Ser Lys Tyr Leu Asp Ser
1               5                   10                  15

Lys Lys Ala Gln Glu Phe Val Gln Trp Leu Met Asn Thr
            20                  25

<210> SEQ ID NO 40
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 40

His Xaa Gln Gly Thr Phe Thr Ser Asp Tyr Ser Lys Tyr Leu Asp Ser
1               5                   10                  15

Lys Lys Ala Gln Glu Phe Val Gln Trp Leu Met Asn Thr Arg
            20                  25                  30

<210> SEQ ID NO 41
<211> LENGTH: 39
<212> TYPE: PRT
<213> ORGANISM: Artificial Sequence
<220> FEATURE:
```

```
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid

<400> SEQUENCE: 41

His Xaa Gln Gly Thr Phe Thr Ser Asp Tyr Ser Lys Tyr Leu Asp Ser
1               5                   10                  15

Lys Lys Ala Gln Glu Phe Val Gln Trp Leu Lys Asn Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 42

His Ser Gln Gly Thr Phe Thr Ser Asp Tyr Ser Lys Tyr Leu Asp Ser
1               5                   10                  15

Arg Ala Val Arg Leu Phe Ile Glu Trp Leu Leu Asn Gly Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 43

His Ser Gln Gly Thr Phe Thr Ser Asp Tyr Ser Lys Tyr Leu Asp Ser
1               5                   10                  15

Arg Ile Val Lys Tyr Phe Ile Glu Trp Leu Leu Asn Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 44

His Ser Gln Gly Thr Phe Thr Ser Asp Tyr Ser Lys Tyr Leu Asp Ser
1               5                   10                  15

Lys Lys Ala Gln Glu Phe Ile Glu Trp Leu Leu Asn Gly Gly Pro Ser
            20                  25                  30

Ser Gly Ala Pro Pro Pro Ser
        35

<210> SEQ ID NO 45
<211> LENGTH: 29
<212> TYPE: PRT
<213> ORGANISM: Artificial Sequence
```

```
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid
<220> FEATURE:
<221> NAME/KEY: MOD_RES
<222> LOCATION: (29)..(29)
<223> OTHER INFORMATION: AMIDATION

<400> SEQUENCE: 45

His Xaa Gln Gly Thr Phe Thr Ser Asp Tyr Ser Lys Tyr Leu Asp Ser
1               5                   10                  15

Arg Ala Val Arg Leu Phe Ile Glu Trp Leu Leu Asn Thr
            20                  25

<210> SEQ ID NO 46
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (2)..(2)
<223> OTHER INFORMATION: Xaa is alpha-amino isobutyric acid

<400> SEQUENCE: 46

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Gly Gly Pro Ser
            20                  25                  30

Ser Gly Ala Pro Pro Pro Ser
        35

<210> SEQ ID NO 47
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 47

His Ser Gln Gly Thr Phe Thr Ser Asp Tyr Ser Lys Tyr Leu Asp Ser
1               5                   10                  15

Arg Ala Val Arg Leu Phe Ile Gln Trp Leu Met Asn Thr
            20                  25

<210> SEQ ID NO 48
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 48

His Ser Gln Gly Thr Phe Thr Ser Asp Tyr Ser Lys Tyr Leu Asp Ser
1               5                   10                  15

Arg Ala Val Arg Leu Phe Ile Gln Trp Leu Met Asn Gly Gly Pro Ser
            20                  25                  30

Ser Gly Ala Pro Pro Pro Ser
```

-continued

35

<210> SEQ ID NO 49
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 49

His Ser Gln Gly Thr Phe Thr Ser Asp Tyr Ser Lys Tyr Leu Asp Glu
1               5                   10                  15

Glu Ala Val Arg Leu Phe Val Gln Trp Leu Leu Asn Gly Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 50

His Ser Gln Gly Thr Phe Thr Ser Asp Tyr Ser Lys Tyr Leu Asp Ser
1               5                   10                  15

Glu Ala Val Arg Leu Phe Val Gln Trp Leu Leu Asn Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 51

His Ser Gln Gly Thr Phe Thr Ser Asp Tyr Ser Lys Tyr Leu Asp Ser
1               5                   10                  15

Gln Ala Val Arg Leu Phe Val Gln Trp Leu Leu Asn Gly Gly Pro Ser
            20                  25                  30

Ser Gly Ala Pro Pro Pro Ser
        35

<210> SEQ ID NO 52
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 52

His Ser Gln Gly Thr Phe Thr Ser Asp Tyr Ser Lys Tyr Leu Asp Ser
1               5                   10                  15

Gln Ala Val Arg Leu Phe Ile Gln Trp Leu Leu Asn Thr
            20                  25

<210> SEQ ID NO 53
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 53

His Ser Gln Gly Thr Phe Thr Ser Asp Tyr Ser Lys Tyr Leu Asp Ser
1               5                   10                  15

Glu Ala Val Arg Leu Phe Ile Gln Trp Leu Leu Asn Thr
            20                  25

<210> SEQ ID NO 54
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 54

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Thr
            20                  25

<210> SEQ ID NO 55
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 55

His Ser Gln Gly Thr Phe Thr Ser Asp Tyr Ser Lys Tyr Leu Asp Ser
1               5                   10                  15

Glu Ala Val Arg Leu Phe Ile Glu Trp Leu Leu Asn Thr
            20                  25

<210> SEQ ID NO 56
<211> LENGTH: 29
<212> TYPE: PRT
<213> ORGANISM: Artificial Sequence
<220> FEATURE:
<223> OTHER INFORMATION: GLP/glucagon analogue

<400> SEQUENCE: 56

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Thr
            20                  25

<210> SEQ ID NO 57
<211> LENGTH: 39

```
<212> TYPE: PRT
<213> ORGANISM: Artificial Sequence
<220> FEATURE:
<223> OTHER INFORMATION: GLP/glucagon analogue

<400> SEQUENCE: 57

His Ser Gln Gly Thr Phe Thr Ser Asp Tyr Ser Lys Tyr Leu Asp Glu
1               5                   10                  15

Glu Ala Val Arg Leu Phe Ile Gln Trp Leu Leu Asn Gly Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 58

His Ser Gln Gly Thr Phe Thr Ser Asp Tyr Ser Lys Tyr Leu Asp Gln
1               5                   10                  15

Glu Ala Val Arg Leu Phe Ile Gln Trp Leu Leu Asn Gly Gly Pro Ser
            20                  25                  30

Ser Gly Ala Pro Pro Pro Ser
        35

<210> SEQ ID NO 59
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 59

His Ser Gln Gly Thr Phe Thr Ser Asp Tyr Ser Lys Tyr Leu Asp Ser
1               5                   10                  15

Glu Ala Val Arg Leu Phe Ile Gln Trp Leu Leu Asn Gly Gly Pro Ser
            20                  25                  30

Ser Gly Ala Pro Pro Pro Ser
        35

<210> SEQ ID NO 60
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 60

His Ser Gln Gly Thr Phe Thr Ser Asp Tyr Ser Arg Tyr Leu Asp Ser
1               5                   10                  15

Glu Ala Val Arg Leu Phe Ile Gln Trp Leu Leu Asn Gly Gly Pro Ser
            20                  25                  30

Ser Gly Ala Pro Pro Pro Ser
        35

<210> SEQ ID NO 61
<211> LENGTH: 39
<212> TYPE: PRT
<213> ORGANISM: Artificial Sequence
<220> FEATURE:
```

<223> OTHER INFORMATION: GLP/glucagon analogue

<400> SEQUENCE: 61

His Ser Gln Gly Thr Phe Thr Ser Asp Tyr Ser Lys Tyr Leu Glu Gly
1               5                   10                  15

Gln Ile Val Lys Tyr Phe Ile Gln Trp Leu Val Asn Gly Gly Pro Ser
            20                  25                  30

Ser Gly Ala Pro Pro Pro Ser
        35

<210> SEQ ID NO 62
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 62

His Ser Gln Gly Thr Phe Thr Ser Asp Tyr Ser Lys Tyr Leu Glu Gly
1               5                   10                  15

Gln Ile Val Lys Tyr Phe Ile Gln Trp Leu Leu Asn Gly Gly Pro Ser
            20                  25                  30

Ser Gly Ala Pro Pro Pro Ser
        35

<210> SEQ ID NO 63
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 63

His Xaa Gln Gly Thr Phe Thr Ser Asp Tyr Ser Lys Tyr Leu Asp Glu
1               5                   10                  15

Glu Ile Val Lys Tyr Phe Ile Gln Trp Leu Leu Asn Thr Arg
            20                  25                  30

<210> SEQ ID NO 64
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 64

His Ser Gln Gly Thr Phe Thr Ser Asp Tyr Ser Lys Tyr Leu Asp Ser
1               5                   10                  15

Arg Ala Val Arg Leu Phe Ile Glu Trp Leu Leu Asn Thr Gly Pro Ser
            20                  25                  30

Ser Gly Ala Pro Pro Pro Ser
        35

<210> SEQ ID NO 65
<211> LENGTH: 39
<212> TYPE: PRT

<213> ORGANISM: Artificial Sequence
<220> FEATURE:
<223> OTHER INFORMATION: GLP/glucagon analogue

<400> SEQUENCE: 65

His Ser Gln Gly Thr Phe Thr Ser Asp Tyr Ser Lys Tyr Leu Asp Ser
1               5                   10                  15

Lys Ala Val His Leu Phe Ile Glu Trp Leu Leu Asn Gly Gly Pro Ser
            20                  25                  30

Ser Gly Ala Pro Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is alpha-amino isobutyric acid

<400> SEQUENCE: 66

His Xaa Gln Gly Thr Phe Thr Ser Asp Tyr Ser Lys Tyr Leu Asp Ser
1               5                   10                  15

Gln Ile Val Lys Tyr Phe Ile Gln Trp Leu Leu Asn Gly Gly Pro Ser
            20                  25                  30

Ser Gly Ala Pro Pro Pro Ser
        35

<210> SEQ ID NO 67
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 67

His Ser Gln Gly Thr Phe Thr Ser Asp Tyr Ser Lys Tyr Leu Asp Ser
1               5                   10                  15

Arg Ala Val Arg Leu Phe Ile Glu Trp Leu Leu Asn Thr
            20                  25

<210> SEQ ID NO 68
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 68

His Ser Gln Gly Thr Phe Thr Ser Asp Tyr Ser Lys Tyr Leu Asp Ser
1               5                   10                  15

Lys Ala Val Arg Leu Phe Ile Glu Trp Leu Leu Asn Thr
            20                  25

```
<210> SEQ ID NO 69
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 69

His Ser Gln Gly Thr Phe Thr Ser Asp Tyr Ser Lys Tyr Leu Glu Gly
1               5                   10                  15

Gln Ile Val Lys Tyr Phe Ile Glu Trp Leu Leu Asn Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 70

His Ser Gln Gly Thr Phe Thr Ser Asp Tyr Ser Lys Tyr Leu Glu Gly
1               5                   10                  15

Lys Ile Val Lys Tyr Phe Ile Gln Trp Leu Leu Asn Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 71

His Ser Gln Gly Thr Phe Thr Ser Asp Tyr Ser Lys His Leu Asp Ser
1               5                   10                  15

Arg Ala Val Arg Leu Phe Ile Glu Trp Leu Leu Asn Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 72

His Ser Gln Gly Thr Phe Thr Ser Asp Tyr Ser Lys Tyr Leu Asp Ser
1               5                   10                  15

Arg Ala Val Arg Leu Phe Ile Glu Trp Leu Leu Asn Gly His Pro Ser
            20                  25                  30

Ser Gly Ala Pro Pro Pro Ser
        35

<210> SEQ ID NO 73
<211> LENGTH: 39
<212> TYPE: PRT
```

```
<213> ORGANISM: Artificial Sequence
<220> FEATURE:
<223> OTHER INFORMATION: GLP/glucagon analogue

<400> SEQUENCE: 73

His Ser Gln Gly Thr Phe Thr Ser Asp Tyr Ser Lys Tyr Leu Asp Ser
1               5                   10                  15

Arg Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 74
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 74

His Ser Gln Gly Thr Phe Thr Ser Asp Tyr Ser Lys Tyr Leu Asp Ser
1               5                   10                  15

Arg Ile Val Lys Tyr Phe Ile Gln Trp Leu Leu Asn Gly Gly Pro Ser
            20                  25                  30

Ser Gly Ala Pro Pro Pro Ser
        35

<210> SEQ ID NO 75
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 75

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly Gly Pro Ser
            20                  25                  30

Ser Gly Ala Pro Pro Pro Ser
        35

<210> SEQ ID NO 76
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 76

His Ser Gln Gly Thr Phe Thr Ser Asp Tyr Ser Lys Tyr Leu Asp Ser
1               5                   10                  15

Gln Ala Val Lys Leu Phe Ile Glu Trp Leu Leu Asn Thr
            20                  25

<210> SEQ ID NO 77
<211> LENGTH: 29
<212> TYPE: PRT
<213> ORGANISM: Artificial Sequence
<220> FEATURE:
```

```
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 77

His Ser Gln Gly Thr Phe Thr Ser Asp Tyr Ser Lys Tyr Leu Asp Ser
1               5                   10                  15

Gln Ala Val Lys Leu Phe Ile Gln Trp Leu Leu Asn Thr
            20                  25

<210> SEQ ID NO 78
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 78

His Ser Gln Gly Thr Phe Thr Ser Asp Tyr Ser Lys Tyr Leu Asp Ser
1               5                   10                  15

Glu Ala Val Lys Leu Phe Ile Glu Trp Leu Leu Asn Thr
            20                  25

<210> SEQ ID NO 79
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 79

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Thr
            20                  25

<210> SEQ ID NO 80
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 80

His Ser Gln Gly Thr Phe Thr Ser Asp Tyr Ser Lys Tyr Leu Asp Ser
1               5                   10                  15

Glu Ala Val Arg Leu Phe Ile Glu Trp Leu Leu Asn Gly Arg
            20                  25                  30

<210> SEQ ID NO 81
<211> LENGTH: 30
<212> TYPE: PRT
<213> ORGANISM: Artificial Sequence
```

```
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 81

His Xaa Gln Gly Thr Phe Thr Ser Asp Tyr Ser Lys Tyr Leu Asp Glu
1               5                   10                  15

Glu Ile Val Lys Tyr Phe Ile Glu Trp Leu Met Asn Thr Arg
            20                  25                  30

<210> SEQ ID NO 82
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 82

His Ser Gln Gly Thr Phe Thr Ser Asp Tyr Ser His Tyr Leu Asp Ser
1               5                   10                  15

Gln Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 83
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is alpha-amino isobutyric acid

<400> SEQUENCE: 83

His Xaa Gln Gly Thr Phe Thr Ser Asp Tyr Ser His Tyr Leu Asp Ser
1               5                   10                  15

Gln Ile Val Lys Tyr Phe Ile Gln Trp Leu Leu Asn Gly Gly Pro Ser
            20                  25                  30

Ser Gly Ala Pro Pro Pro Ser
        35

<210> SEQ ID NO 84
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 84

His Ser Gln Gly Thr Phe Thr Ser Asp Tyr Ser His Tyr Leu Asp Ser
1               5                   10                  15

Gln Ala Val Arg Leu Phe Ile Gln Trp Leu Leu Asn Thr
            20                  25
```

20                  25

<210> SEQ ID NO 85
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 85

His Ser Gln Gly Thr Phe Thr Ser Asp Tyr Ser His Tyr Leu Asp Ser
1               5                   10                  15

Gln Ala Val His Leu Phe Ile Gln Trp Leu Leu Asn Thr
            20                  25

<210> SEQ ID NO 86
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 86

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Thr
            20                  25

<210> SEQ ID NO 87
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 87

His Ser Gln Gly Thr Phe Thr Ser Asp Tyr Ser His Tyr Leu Asp Ser
1               5                   10                  15

Lys Ala Val His Leu Phe Ile Gln Trp Leu Leu Asn Gly
            20                  25

<210> SEQ ID NO 88
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 88

His Ser Gln Gly Thr Phe Thr Ser Asp Tyr Ser Lys Tyr Leu Glu Gly
1               5                   10                  15

-continued

Glu Ala Val Lys Leu Phe Ile Glu Trp Leu Leu Asn Thr
            20                  25

<210> SEQ ID NO 89
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 89

His Ser Gln Gly Thr Phe Thr Ser Asp Tyr Ser Lys Tyr Leu Glu Gly
1               5                   10                  15

Glu Ala Val Lys Leu Phe Ile Glu Trp Leu Leu Asn Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 90

His Ser Gln Gly Thr Phe Thr Ser Asp Tyr Ser Lys Tyr Leu Asp Ser
1               5                   10                  15

Gln Ala Val Gln Leu Phe Ile Gln Trp Leu Leu Asn Gly
            20                  25

<210> SEQ ID NO 91
<211> LENGTH: 33
<212> TYPE: PRT
<213> ORGANISM: Artificial Sequence
<220> FEATURE:
<223> OTHER INFORMATION: GLP/glucagon analogue

<400> SEQUENCE: 91

His Ser Gln Gly Thr Phe Thr Ser Asp Tyr Ser Lys Tyr Leu Asp Glu
1               5                   10                  15

Glu Ala Val Arg Leu Phe Ile Glu Leu Leu Leu Asn Gly Gly Tyr Tyr
            20                  25                  30

Tyr

<210> SEQ ID NO 92
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 92

His Ser Gln Gly Thr Phe Thr Ser Asp Tyr Ser His Tyr Leu Asp Ser
1               5                   10                  15

Gln Ala Val Lys Leu Phe Ile Gln Trp Leu Leu Asn Thr

```
<210> SEQ ID NO 93
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 93

His Ser Gln Gly Thr Phe Thr Ser Asp Tyr Ser His Tyr Leu Asn Ser
1               5                   10                  15

Gln Ala Val Lys Leu Phe Ile Glu Trp Leu Leu Asn Thr
            20                  25

<210> SEQ ID NO 94
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 94

His Ser Gln Gly Thr Phe Thr Ser Asp Tyr Ser His Tyr Leu Asp Ser
1               5                   10                  15

Gln Ala Val Lys Leu His Ile Gln Trp Leu Leu Asn Thr
            20                  25

<210> SEQ ID NO 95
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 95

His Ser Gln Gly Thr Phe Thr Ser Asp Tyr Ser His Tyr Leu Asp Ser
1               5                   10                  15

Gln Ala Val His Lys Phe Ile Gln Trp Leu Leu Asn Thr
            20                  25

<210> SEQ ID NO 96
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 96

His Ser Gln Gly Thr Phe Thr Ser Asp Tyr Ser Lys Tyr Leu Asp Ser
1               5                   10                  15
```

Gln Ala Val Lys Asp Phe Ile Gln Trp Leu Leu Asn Thr
            20                  25

<210> SEQ ID NO 97
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 97

His Ser Gln Gly Thr Phe Thr Ser Asp Tyr Ser His Tyr Leu Asp Glu
1               5                   10                  15

Glu Ala Val Arg Leu Phe Ile Glu Trp Leu Leu Asn Gly Gly
            20                  25                  30

<210> SEQ ID NO 98
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 98

His Ser Gln Gly Thr Phe Thr Ser Asp Tyr Ser His Tyr Leu Asp Glu
1               5                   10                  15

Glu Ala Val Arg Leu Phe Ile Glu Trp Leu Leu Asn Gly
            20                  25

<210> SEQ ID NO 99
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 99

His Ser Gln Gly Thr Phe Thr Ser Asp Tyr Ser Lys Tyr Leu Asp Ser
1               5                   10                  15

Gln Ala Val Lys Leu Phe Ile Glu Trp Leu Thr Asn Thr
            20                  25

<210> SEQ ID NO 100
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 100

His Ser Gln Gly Thr Phe Thr Ser Asp Tyr Ser His Tyr Leu Asp Ser
1               5                   10                  15

Gln Ala Val Lys Leu Phe Ile Glu Trp Leu Leu Asn Thr
            20                  25

<210> SEQ ID NO 101
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 101

His Ser Gln Gly Thr Phe Thr Ser Asp Tyr Ser Lys Tyr Leu Asp Ser
1               5                   10                  15

Gln Ala Val His Leu Phe Ile Glu Trp Leu Leu Asn Thr
            20                  25

<210> SEQ ID NO 102
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 102

His Ser Gln Gly Thr Phe Thr Ser Asp Tyr Ser Lys Tyr Leu Asp Ser
1               5                   10                  15

Gln Ala Val Lys Leu Phe Ile Glu Trp Leu Lys Asn Thr
            20                  25

<210> SEQ ID NO 103
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 103

His Ser Gln Gly Thr Phe Thr Ser Asp Tyr Ser Lys Tyr Leu Asp Ser
1               5                   10                  15

Glu Ala Val Lys Leu Phe Ile Glu Trp Leu Val Asn Thr
            20                  25

<210> SEQ ID NO 104
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 104

His Ser Gln Gly Thr Phe Thr Ser Asp Tyr Ser Arg Tyr Leu Glu Ser
1               5                   10                  15

Gln Ala Val Arg Leu Phe Ile Gln Trp Leu Val Asn Thr
            20                  25

<210> SEQ ID NO 105
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 105

His Ser Gln Gly Thr Phe Thr Ser Asp Tyr Ser Lys Tyr Leu Glu Ser
1               5                   10                  15

Gln Ala Val Lys Leu Phe Ile Glu Trp Leu Leu Asn Thr
            20                  25

<210> SEQ ID NO 106
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 106

His Ser Gln Gly Thr Phe Thr Ser Asp Tyr Ser His Tyr Leu Glu Ser
1               5                   10                  15

Gln Ala Val Arg Leu Phe Ile Gln Trp Leu Leu Asn Thr
            20                  25

<210> SEQ ID NO 107
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 107

His Ser Gln Gly Thr Phe Thr Ser Asp Tyr Ser His Tyr Leu Glu Ser
1               5                   10                  15

Gln Ala Val Arg Leu Phe Ile Gln Trp Leu Val Asn Thr
            20                  25

<210> SEQ ID NO 108
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 108

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly Gly
            20                  25                  30

<210> SEQ ID NO 109

```
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 109

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly
            20                  25

<210> SEQ ID NO 110
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 110

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly Arg
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 111

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly Gly Pro
            20                  25                  30

<210> SEQ ID NO 112
<211> LENGTH: 34
<212> TYPE: PRT
<213> ORGANISM: Artificial Sequence
<220> FEATURE:
<223> OTHER INFORMATION: GLP/glucagon analogue

<400> SEQUENCE: 112

His Ser Gln Gly Thr Phe Thr Ser Asp Tyr Ser Lys Tyr Leu Asp Ser
1               5                   10                  15

Gln Ala Val His Leu Phe Ile Gln Trp Leu Leu Asn Gly Arg Pro Ser
            20                  25                  30

Ser Gly

<210> SEQ ID NO 113
<211> LENGTH: 29
<212> TYPE: PRT
<213> ORGANISM: Artificial Sequence
<220> FEATURE:
<223> OTHER INFORMATION: GLP/glucagon analogue
```

```
<220> FEATURE:
<221> NAME/KEY: MOD_RES
<222> LOCATION: (29)..(29)
<223> OTHER INFORMATION: AMIDATION

<400> SEQUENCE: 113

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Val Asn Thr
            20                  25

<210> SEQ ID NO 114
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 114

His Ser Gln Gly Thr Phe Thr Ser Asp Tyr Ser Lys Tyr Leu Glu Ser
1               5                   10                  15

Gln Ala Val Arg Leu Phe Ile Glu Trp Leu Leu Asn Thr
            20                  25

<210> SEQ ID NO 115
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 115

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Thr
            20                  25

<210> SEQ ID NO 116
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 116

His Ser Gln Gly Thr Phe Thr Ser Asp Tyr Ser Lys Tyr Leu Glu Ser
1               5                   10                  15

Glu Ala Val His Leu Phe Ile Glu Trp Leu Leu Asn Thr
            20                  25

<210> SEQ ID NO 117
<211> LENGTH: 29
<212> TYPE: PRT
<213> ORGANISM: Artificial Sequence
<220> FEATURE:
```

<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 117

His Ser Gln Gly Thr Phe Thr Ser Asp Tyr Ser His Tyr Leu Glu Ser
1               5                   10                  15

Glu Ala Val His Leu Phe Ile Glu Trp Leu Leu Asn Thr
            20                  25

<210> SEQ ID NO 118
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 118

His Ser Gln Gly Thr Phe Thr Ser Asp Tyr Ser Lys Tyr Leu Glu Ser
1               5                   10                  15

Glu Ala Val Arg Leu Phe Ile Gln Trp Leu Leu Asn Thr His
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 119

His Ser Gln Gly Thr Phe Thr Ser Asp Tyr Ser Lys Tyr Leu Asp Ser
1               5                   10                  15

Glu Ala Val Arg Leu Phe Ile Glu Trp Leu Val Asn Thr His
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 120

His Ser Gln Gly Thr Phe Thr Ser Asp Tyr Ser His Tyr Leu Asp Ser
1               5                   10                  15

Gln Ala Val His Leu Phe Ile Glu Trp Leu Lys Asn Thr His
            20                  25                  30

<210> SEQ ID NO 121
<211> LENGTH: 29
<212> TYPE: PRT
<213> ORGANISM: Artificial Sequence

```
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 121

His Ser Gln Gly Thr Phe Thr Ser Asp Tyr Ser Lys Tyr Leu Glu Ser
1               5                   10                  15

Glu Ala Val Lys Leu Phe Ile Glu Trp Leu Leu Asn Thr
            20                  25

<210> SEQ ID NO 122
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 122

His Ser Gln Gly Thr Phe Thr Ser Asp Tyr Ser His Tyr Leu Glu Ser
1               5                   10                  15

Gln Ala Val His Leu Phe Ile Glu Trp Leu Leu Asn Gly
            20                  25

<210> SEQ ID NO 123
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 123

His Ser Gln Gly Thr Phe Thr Ser Asp Tyr Ser Lys Tyr Leu Glu Gly
1               5                   10                  15

Glu Ala Val Lys Leu Phe Ile Gln Trp Leu Leu Asn Thr
            20                  25

<210> SEQ ID NO 124
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 124

His Ser Gln Gly Thr Phe Thr Ser Asp Tyr Ser His Tyr Leu Asp Ser
1               5                   10                  15

Gln Ala Val His His Phe Ile Gln Trp Leu Leu Asn Thr
            20                  25

<210> SEQ ID NO 125
<211> LENGTH: 29
<212> TYPE: PRT
```

<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 125

His Ser Gln Gly Thr Phe Thr Ser Asp Tyr Ser Lys Tyr Leu Glu Ser
1               5                   10                  15

Gln Ala Val His Leu Phe Ile Glu Trp Leu Lys Asn Gly
            20                  25

<210> SEQ ID NO 126
<211> LENGTH: 39
<212> TYPE: PRT
<213> ORGANISM: Artificial Sequence
<220> FEATURE:
<223> OTHER INFORMATION: GLP/glucagon analogue

<400> SEQUENCE: 126

His Ser Gln Gly Thr Phe Thr Ser Asp Tyr Ser Lys Tyr Leu Asp Ser
1               5                   10                  15

Gln Ala Val His Leu Phe Ile Gln Trp Leu Leu Asn Gly Gly Pro Ser
            20                  25                  30

Ser Gly Ala Pro Pro Pro Ser
        35

<210> SEQ ID NO 127
<211> LENGTH: 5
<212> TYPE: PRT
<213> ORGANISM: Artificial Sequence
<220> FEATURE:
<223> OTHER INFORMATION: Cleavable linker

<400> SEQUENCE: 127

Asp Asp Asp Asp Tyr
1               5

<210> SEQ ID NO 128
<211> LENGTH: 5
<212> TYPE: PRT
<213> ORGANISM: Artificial Sequence
<220> FEATURE:
<223> OTHER INFORMATION: Cleavable linker

<400> SEQUENCE: 128

His Pro Phe His Leu
1               5

<210> SEQ ID NO 129
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 129

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr

```
            20                  25

<210> SEQ ID NO 130
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 130

His Ser Gln Gly Thr Phe Thr Ser Asp Tyr Ser Lys Tyr Leu Asp Ser
1               5                   10                  15

Gln Ala Val Lys Leu Phe Asp Gln Trp Leu Leu Asn Thr
            20                  25

<210> SEQ ID NO 131
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 131

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Thr His
            20                  25                  30

<210> SEQ ID NO 132
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 132

His Ser Gln Gly Thr Phe Thr Ser Asp Tyr Ser Lys Tyr Leu Glu Ser
1               5                   10                  15

Glu Ala His Arg Leu Phe Ile Glu Trp Leu Leu Asn Thr
            20                  25

<210> SEQ ID NO 133
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 133

His Ser Gln Gly Thr Phe Thr Ser Asp Tyr Ser Lys Tyr Leu Glu Ser
1               5                   10                  15

Glu Ala Val Arg His Phe Ile Glu Trp Leu Leu Asn Thr
            20                  25
```

```
<210> SEQ ID NO 134
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 134

His Ser Gln Gly Thr Phe Thr Ser Asp Tyr Ser Lys Tyr Leu Glu Ser
1               5                   10                  15

Glu Ala Val Arg Leu Phe Ile Glu Trp Leu His Asn Thr
            20                  25

<210> SEQ ID NO 135
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is alpha-amino isobutyric acid
<220> FEATURE:
<221> NAME/KEY: MISC_FEATURE
<222> LOCATION: (29)..(29)
<223> OTHER INFORMATION: Xaa is alpha-amino isobutyric acid
<220> FEATURE:
<221> NAME/KEY: MOD_RES
<222> LOCATION: (30)..(30)
<223> OTHER INFORMATION: AMIDATION

<400> SEQUENCE: 135

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 136
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 136

His Ser Gln Gly Thr Phe Thr Ser Asp Tyr Ser His Tyr Leu Glu Gly
1               5                   10                  15

Glu Ala Val His Leu Phe Ile Glu Trp Leu Leu Asn Thr
            20                  25

<210> SEQ ID NO 137
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION
```

-continued

<400> SEQUENCE: 137

His Ser Gln Gly Thr Phe Thr Ser Asp Tyr Ser Lys Tyr Leu Glu Gly
1               5                   10                  15

Glu Ala Val Lys Leu Phe Ile Glu Trp Leu Val Asn Thr
            20                  25

<210> SEQ ID NO 138
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 138

His Ser Gln Gly Thr Phe Thr Ser Asp Tyr Ser His Tyr Leu Asn Ser
1               5                   10                  15

Gln Ala Val Lys Leu Phe Ile Gln Trp Leu Leu Asn Thr
            20                  25

<210> SEQ ID NO 139
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 139

His Ser Gln Gly Thr Phe Thr Ser Asp Tyr Ser His Tyr Leu Glu Ser
1               5                   10                  15

Gln Ala Val Lys Leu Phe Ile Gln Trp Leu Leu Asn Thr
            20                  25

<210> SEQ ID NO 140
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 140

His Ser Gln Gly Thr Phe Thr Ser Asp Tyr Ser His Tyr Leu Gln Ser
1               5                   10                  15

Gln Ala Val Lys Leu Phe Ile Gln Trp Leu Leu Asn Thr
            20                  25

<210> SEQ ID NO 141
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

```
<400> SEQUENCE: 141

His Ser Gln Gly Thr Phe Thr Ser Asp Tyr Ser His Tyr Leu Asp Ser
1               5                   10                  15

Gln Ala Val Arg Leu Phe Ile Gln Trp Leu Leu Asn Thr His
            20                  25                  30

<210> SEQ ID NO 142
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 142

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly His
            20                  25                  30

<210> SEQ ID NO 143
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 143

His Ser Gln Gly Thr Phe Thr Ser Asp Tyr Ser His Tyr Leu Asp Ser
1               5                   10                  15

Gln Ala Val Arg Leu Phe Ile Gln Trp Leu Leu Asn Gly
            20                  25

<210> SEQ ID NO 144
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 144

His Ser Gln Gly Thr Phe Thr Ser Asp Tyr Ser His Tyr Leu Asp Ser
1               5                   10                  15

Gln Ala Val Arg Leu Phe Ile Glu Trp Leu Leu Asn Gly
            20                  25

<210> SEQ ID NO 145
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
```

```
<223> OTHER INFORMATION: AMIDATION

<400> SEQUENCE: 145

His Ser Gln Gly Thr Phe Thr Ser Asp Tyr Ser His Tyr Leu Asp Ser
1               5                   10                  15

Gln Ala Val Lys Leu Phe Ile Gln Trp Leu Leu Asn Gly
            20                  25

<210> SEQ ID NO 146
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 146

His Ser Gln Gly Thr Phe Thr Ser Asp Tyr Ser His Tyr Leu Asp Ser
1               5                   10                  15

Gln Ala Val Lys Leu Phe Ile Gln Trp Leu Leu Asn Thr His
            20                  25                  30

<210> SEQ ID NO 147
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 147

His Ser Gln Gly Thr Phe Thr Ser Asp Tyr Ser His Tyr Leu Glu Ser
1               5                   10                  15

Arg Ala Val His Leu Phe Ile Gln Trp Leu Leu Asn Thr
            20                  25

<210> SEQ ID NO 148
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 148

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Gly
            20                  25

<210> SEQ ID NO 149
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
```

<222> LOCATION: (30)..(30)
<223> OTHER INFORMATION: AMIDATION

<400> SEQUENCE: 149

His Ser Gln Gly Thr Phe Thr Ser Asp Tyr Ser His Tyr Leu Glu Ser
1               5                   10                  15

Gln Ala Val Arg Leu Phe Ile Gln Trp Leu Leu Asn Thr His
            20                  25                  30

<210> SEQ ID NO 150
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 150

His Ser Gln Gly Thr Phe Thr Ser Asp Tyr Ser His Tyr Leu Glu Ser
1               5                   10                  15

Gln Ala Val Arg Leu Phe Ile Gln Trp Leu Leu Asn Gly
            20                  25

<210> SEQ ID NO 151
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 151

His Ser Gln Gly Thr Phe Thr Ser Asp Tyr Ser His Tyr Leu Asp Ser
1               5                   10                  15

Glu Ala Val Arg Leu Phe Ile Glu Trp Leu Leu Asn Gly Arg
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 152

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Gly Arg
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: GLP/glucagon analogue
<220> FEATURE:

```
<221> NAME/KEY: MOD_RES
<222> LOCATION: (30)..(30)
<223> OTHER INFORMATION: AMIDATION

<400> SEQUENCE: 153

His Ser Gln Gly Thr Phe Thr Ser Asp Tyr Ser His Tyr Leu Glu Ser
1               5                   10                  15

Gln Ala Val Arg Leu Phe Ile Gln Trp Leu Leu Asn Gly Arg
            20                  25                  30

<210> SEQ ID NO 154
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 154

His Ser Gln Gly Thr Phe Thr Ser Asp Tyr Ser Lys Tyr Leu Asp Arg
1               5                   10                  15

Ala Arg Ala Asp Asp Phe Val Ala Trp Leu Lys Ser Thr
            20                  25

<210> SEQ ID NO 155
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (39)..(39)
<223> OTHER INFORMATION: Xaa is K x 6
<220> FEATURE:
<221> NAME/KEY: MOD_RES
<222> LOCATION: (39)..(39)
<223> OTHER INFORMATION: AMIDATION

<400> SEQUENCE: 155

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Xaa
        35

<210> SEQ ID NO 156
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 156

His Ser Gln Gly Thr Phe Thr Ser Asp Tyr Ser His Tyr Leu Glu Ser
1               5                   10                  15

Gln Ala Val His Leu Phe Ile Glu Trp Leu Val Asn Gly
            20                  25
```

<210> SEQ ID NO 157
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 157

His Ser Gln Gly Thr Phe Thr Ser Asp Tyr Ser His Tyr Leu Glu Ser
1               5                   10                  15

Gln Ala Val His Leu Phe Ile Glu Trp Leu Leu Asn Thr
            20                  25

<210> SEQ ID NO 158
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 158

His Ser Gln Gly Thr Phe Thr Ser Asp Tyr Ser His Tyr Leu Glu Ser
1               5                   10                  15

Lys Ala Val His Leu Phe Ile Gln Trp Leu Leu Asn Gly
            20                  25

<210> SEQ ID NO 159
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 159

His Ser Gln Gly Thr Phe Thr Ser Asp Tyr Ser His Tyr Leu Glu Ser
1               5                   10                  15

Arg Ala Val His Leu Phe Ile Gln Trp Leu Leu Asn Gly
            20                  25

<210> SEQ ID NO 160
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 160

His Ser Gln Gly Thr Phe Thr Ser Asp Tyr Ser Lys Tyr Leu Asp Ser
1               5                   10                  15

Glu Ala Val Lys Leu Phe Ile Glu Trp Leu Leu Asn Gly
            20                  25

<210> SEQ ID NO 161
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 161

His Ser Gln Gly Thr Phe Thr Ser Asp Tyr Ser His Tyr Leu Asp Ser
1               5                   10                  15

Gln Ala Val His Leu Phe Ile Glu Trp Leu Lys Asn Gly
            20                  25

<210> SEQ ID NO 162
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 162

His Ser Gln Gly Thr Phe Thr Ser Asp Tyr Ser Lys Tyr Leu Glu Ser
1               5                   10                  15

Glu Ala Val Arg His Phe Ile Glu Trp Leu Leu Asn Gly
            20                  25

<210> SEQ ID NO 163
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 163

His Ser Gln Gly Thr Phe Thr Ser Asp Tyr Ser His Tyr Leu Asp Ser
1               5                   10                  15

Gln Ala Val Lys Leu Phe Ile Glu Trp Leu Leu Asn Gly
            20                  25

<210> SEQ ID NO 164
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 164

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Gly

```
                    20                  25

<210> SEQ ID NO 165
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 165

His Ser Gln Gly Thr Phe Thr Ser Asp Tyr Ser His Tyr Leu Glu Ser
1               5                   10                  15

Gln Ala Val Arg Leu Phe Ile Gln Trp Leu Val Asn Gly
            20                  25

<210> SEQ ID NO 166
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 166

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly
            20                  25

<210> SEQ ID NO 167
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 167

His Ser Gln Gly Thr Phe Thr Ser Asp Tyr Ser Lys Tyr Leu Asp Ser
1               5                   10                  15

Gln Ala Val His Leu Phe Ile Glu Trp Leu Leu Asn Gly
            20                  25

<210> SEQ ID NO 168
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 168

His Ser Gln Gly Thr Phe Thr Ser Asp Tyr Ser Lys Tyr Leu Glu Ser
1               5                   10                  15
```

```
Gln Ala Val His Leu Phe Ile Glu Trp Leu Leu Asn Gly
            20                  25
```

```
<210> SEQ ID NO 169
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 169

His Ser Gln Gly Thr Phe Thr Ser Asp Tyr Ser Lys Tyr Leu Asp Ser
1               5                   10                  15

Arg Ala Val His Leu Phe Ile Glu Trp Leu Leu Asn Gly
            20                  25
```

```
<210> SEQ ID NO 170
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 170

His Ser Gln Gly Thr Phe Thr Ser Asp Tyr Ser Lys Tyr Leu Glu Glu
1               5                   10                  15

Glu Ala Val His Leu Phe Ile Glu Trp Leu Leu Asn Gly
            20                  25
```

```
<210> SEQ ID NO 171
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 171

His Ser Gln Gly Thr Phe Thr Ser Asp Tyr Ser His Tyr Leu Glu Glu
1               5                   10                  15

Glu Ala Val His Leu Phe Ile Glu Trp Leu Leu Asn Gly
            20                  25
```

```
<210> SEQ ID NO 172
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 172

His Ser Gln Gly Thr Phe Thr Ser Asp Tyr Ser Lys Tyr Leu Glu Glu
1               5                   10                  15
```

Glu Ala Val His Leu Phe Ile Glu Trp Leu Leu Asn Thr
            20                  25

<210> SEQ ID NO 173
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 173

His Ser Gln Gly Thr Phe Thr Ser Asp Tyr Ser His Tyr Leu Glu Glu
1               5                   10                  15

Glu Ala Val His Leu Phe Ile Glu Trp Leu Leu Asn Thr
            20                  25

<210> SEQ ID NO 174
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 174

His Ser Gln Gly Thr Phe Thr Ser Asp Tyr Ser His Tyr Leu Glu Glu
1               5                   10                  15

Gln Ala Val His Leu Phe Ile Glu Trp Leu Leu Asn Gly
            20                  25

<210> SEQ ID NO 175
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 175

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Thr
            20                  25

<210> SEQ ID NO 176
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 176

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Thr Gly Pro
            20                  25                  30

<210> SEQ ID NO 177
<211> LENGTH: 29
<212> TYPE: PRT
<213> ORGANISM: Artificial Sequence
<220> FEATURE:
<223> OTHER INFORMATION: GLP/glucagon analogue

<400> SEQUENCE: 177

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly
            20                  25

<210> SEQ ID NO 178
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 178

His Ser Gln Gly Thr Phe Thr Ser Asp Tyr Ser His Tyr Leu Asp Ser
1               5                   10                  15

Gln Ala Val Arg Leu Phe Ile Glu Trp Leu Leu Asn Gly Gly Pro
            20                  25                  30

<210> SEQ ID NO 179
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 179

His Ser Gln Gly Thr Phe Thr Ser Asp Tyr Ser Lys Tyr Leu Asp Ser
1               5                   10                  15

Gln Ala Val His Leu Phe Ile Glu Trp Leu Leu Asn Gly Gly Pro
            20                  25                  30

<210> SEQ ID NO 180
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 180

His Ser Gln Gly Thr Phe Thr Ser Asp Tyr Ser His Tyr Leu Asp Ser
1               5                   10                  15

Gln Ala Val His Leu Phe Ile Glu Trp Leu Leu Asn Gly Gly Pro
            20                  25                  30

<210> SEQ ID NO 181
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 181

His Ser Gln Gly Thr Phe Thr Ser Asp Tyr Ser His Tyr Leu Asp Ser
1               5                   10                  15

Gln Ala Val His Leu Phe Ile Gln Trp Leu Leu Asn Gly Gly Pro

<210> SEQ ID NO 182
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 182

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly Pro
            20                  25                  30

<210> SEQ ID NO 183
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 183

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 184

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly His
            20                  25                  30

<210> SEQ ID NO 185
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 185

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly His His
            20                  25                  30

<210> SEQ ID NO 186
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 186

His Ser Gln Gly Thr Phe Thr Ser Asp Tyr Ser His Tyr Leu Asp Ser
1               5                   10                  15

Gln Ala Val His Leu Phe Ile Gln Trp Leu Leu Asn Gly Gly His
            20                  25                  30

<210> SEQ ID NO 187
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 187

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Gly Gly Pro
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 188

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Thr His
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 189

His Ser Gln Gly Thr Phe Thr Ser Asp Tyr Ser His Tyr Leu Asp Ser
1               5                   10                  15

Gln Ala Val His Leu Phe Ile Gln Trp Leu Leu Asn Thr His
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 190

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr His
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: GLP/glucagon analogue

```
<400> SEQUENCE: 191

His Ser Gln Gly Thr Phe Thr Ser Asp Tyr Ser Lys Tyr Leu Glu Ser
1               5                   10                  15

Glu Ala Val Arg His Phe Ile Glu Trp Leu Leu Asn Thr His
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 192

His Ser Gln Gly Thr Phe Thr Ser Asp Tyr Ser His Tyr Leu Asp Ser
1               5                   10                  15

Gln Ala Val Arg Leu Phe Ile Gln Trp Leu Leu Asn Thr His
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 193

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Thr His
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 194

His Ser Gln Gly Thr Phe Thr Ser Asp Tyr Ser His Tyr Leu Asp Ser
1               5                   10                  15

Lys Ala Val His Leu Phe Ile Gln Trp Leu Leu Asn Gly His
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 195

His Ser Gln Gly Thr Phe Thr Ser Asp Tyr Ser His Tyr Leu Glu Ser
1               5                   10                  15

Gln Ala Val Arg Leu Phe Ile Gln Trp Leu Val Asn Thr His
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: GLP/glucagon analogue
```

<400> SEQUENCE: 196

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly His
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 197

His Ser Gln Gly Thr Phe Thr Ser Asp Tyr Ser Lys Tyr Leu Asp Ser
1               5                   10                  15

Gln Ala Val Arg Leu Phe Ile Glu Trp Leu Leu Asn Gly Arg
            20                  25                  30

<210> SEQ ID NO 198
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 198

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Leu Asn Thr
            20                  25

<210> SEQ ID NO 199
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 199

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr His
            20                  25                  30

<210> SEQ ID NO 200
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 200

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr Arg
            20                  25                  30

<210> SEQ ID NO 201
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 201

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Thr His
            20                  25                  30

<210> SEQ ID NO 202
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 202

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Thr Arg
            20                  25                  30

<210> SEQ ID NO 203
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 203

His Ser Gln Gly Thr Phe Thr Ser Asp Tyr Ser His Tyr Leu Asp Ser
1               5                   10                  15

Gln Ala Val His Leu Phe Ile Glu Trp Leu Leu Asn Thr His
            20                  25                  30

<210> SEQ ID NO 204
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 204

His Ser Gln Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 205
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 205

His Ser Gln Gly Thr Phe Thr Ser Asp Tyr Ser His Tyr Leu Asp Glu
1               5                   10                  15

Gln Ala Val His Leu Phe Ile Glu Trp Leu Lys Asn Thr His
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 206

His Ser Gln Gly Thr Phe Thr Ser Asp Tyr Ser His Tyr Leu Asp Ser
1               5                   10                  15

Glu Ala Val His Leu Phe Ile Glu Trp Leu Lys Asn Thr His
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 207

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Thr His
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: GLP/glucagon analogue

<400> SEQUENCE: 208

His Ser Gln Gly Thr Phe Thr Ser Asp Tyr Ser Lys Tyr Leu Glu Ser
1               5                   10                  15

```
Gln Ala Val Arg Leu Phe Ile Glu Trp Leu Leu Asn Thr His
            20                  25                  30
```

<210> SEQ ID NO 209
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 209

```
His Ser Gln Gly Thr Phe Thr Ser Asp Tyr Ser His Tyr Leu Asp Ser
1               5                   10                  15

Arg Ala Val His Leu Phe Ile Gln Trp Leu Lys Asn Thr His
            20                  25                  30
```

<210> SEQ ID NO 210
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 210

```
His Ser Gln Gly Thr Phe Thr Ser Asp Tyr Ser His Tyr Leu Glu Ser
1               5                   10                  15

Arg Ala Val His Leu Phe Ile Gln Trp Leu Lys Asn Thr His
            20                  25                  30
```

<210> SEQ ID NO 211
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 211

```
His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Thr
            20                  25
```

<210> SEQ ID NO 212
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 212

```
His Ser Gln Gly Thr Phe Thr Ser Asp Tyr Ser Lys Tyr Leu Glu Gln
```

```
1               5                   10                  15
Glu Ala Val Arg Leu Phe Ile Glu Trp Leu Leu Asn Thr
            20                  25
```

<210> SEQ ID NO 213
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 213

```
His Ser Gln Gly Thr Phe Thr Ser Asp Tyr Ser Lys Tyr Leu Gln Glu
1               5                   10                  15

Glu Ala Val Arg Leu Phe Ile Glu Trp Leu Leu Asn Thr
            20                  25
```

<210> SEQ ID NO 214
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 214

```
His Ser Gln Gly Thr Phe Thr Ser Asp Tyr Ser Lys Tyr Leu Gln Gln
1               5                   10                  15

Glu Ala Val Arg Leu Phe Ile Glu Trp Leu Leu Asn Thr
            20                  25
```

<210> SEQ ID NO 215
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 215

```
His Ser Gln Gly Thr Phe Thr Ser Asp Tyr Ser Lys Tyr Leu Gln Gln
1               5                   10                  15

Gln Ala Val Arg Leu Phe Ile Glu Trp Leu Leu Asn Thr
            20                  25
```

<210> SEQ ID NO 216
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 216

His Ser Gln Gly Thr Phe Thr Ser Asp Tyr Ser Lys Tyr Leu Gln Gln
1               5                   10                  15

Gln Ala Val Arg Leu Phe Ile Glu Trp Leu Leu Asn Thr
            20                  25

<210> SEQ ID NO 217
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 217

His Ser Gln Gly Thr Phe Thr Ser Asp Tyr Ser Lys Tyr Leu Gln Glu
1               5                   10                  15

Gln Ala Val Arg Leu Phe Ile Glu Trp Leu Leu Asn Thr
            20                  25

<210> SEQ ID NO 218
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 218

His Ser Gln Gly Thr Phe Thr Ser Asp Tyr Ser His Tyr Leu Asp Glu
1               5                   10                  15

Arg Ala Val His Leu Phe Ile Gln Trp Leu Leu Asn Thr
            20                  25

<210> SEQ ID NO 219
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 219

His Ser Gln Gly Thr Phe Thr Ser Asp Tyr Ser His Tyr Leu Asp Glu
1               5                   10                  15

Gln Ala Val His Leu Phe Ile Glu Trp Leu Lys Asn Gly
            20                  25

<210> SEQ ID NO 220
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 220

His Ser Gln Gly Thr Phe Thr Ser Asp Tyr Ser Lys Tyr Leu Glu Glu
1               5                   10                  15

Glu Ala Val Arg His Phe Ile Glu Trp Leu Leu Asn Thr
            20                  25

<210> SEQ ID NO 221
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 221

His Ser Gln Gly Thr Phe Thr Ser Asp Tyr Ser His Tyr Leu Asp Glu
1               5                   10                  15

Gln Ala Val His Leu Phe Ile Glu Trp Leu Leu Asn Gly
            20                  25

<210> SEQ ID NO 222
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 222

His Ser Gln Gly Thr Phe Thr Ser Asp Tyr Ser His Tyr Leu Asp Glu
1               5                   10                  15

Gln Ala Val His Leu Phe Ile Glu Trp Leu Lys Asn Gly His
            20                  25                  30

<210> SEQ ID NO 223
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 223

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Val Asn Thr His
            20                  25                  30

<210> SEQ ID NO 224
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

```
<400> SEQUENCE: 224

His Ser Gln Gly Thr Phe Thr Ser Asp Tyr Ser Lys Tyr Leu Asp Ser
1               5                   10                  15

Glu Ala Val Lys Leu Phe Ile Glu Trp Leu Val Asn Thr His
            20                  25                  30

<210> SEQ ID NO 225
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 225

His Ser Gln Gly Thr Phe Thr Ser Asp Tyr Ser His Tyr Leu Asp Ser
1               5                   10                  15

Glu Ala Val Arg Leu Phe Ile Glu Trp Leu Val Asn Thr His
            20                  25                  30

<210> SEQ ID NO 226
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 226

His Ser Gln Gly Thr Phe Thr Ser Asp Tyr Ser Lys Tyr Leu Asp Ser
1               5                   10                  15

Glu Ala Val Arg Leu Phe Ile Glu Trp Leu Leu Asn Thr His
            20                  25                  30

<210> SEQ ID NO 227
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 227

His Ser Gln Gly Thr Phe Thr Ser Asp Tyr Ser His Tyr Leu Glu Glu
1               5                   10                  15

Gln Ala Val His Leu Phe Ile Glu Trp Leu Lys Asn Gly
            20                  25

<210> SEQ ID NO 228
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION
```

<400> SEQUENCE: 228

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Gly
            20                  25

<210> SEQ ID NO 229
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 229

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr Gly His
            20                  25                  30

<210> SEQ ID NO 230
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 230

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Gly Gly His
            20                  25                  30

<210> SEQ ID NO 231
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 231

His Ser Gln Gly Thr Phe Thr Ser Asp Tyr Ser Lys Tyr Leu Glu Glu
1               5                   10                  15

Glu Ala Val Arg Leu Phe Ile Gln Trp Leu Leu Asn Gly Gly His
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 232

His Ser Gln Gly Thr Phe Thr Ser Asp Tyr Ser Lys Tyr Leu Glu Glu
1               5                   10                  15

Glu Ala Val His Leu Phe Ile Glu Trp Leu Leu Asn Gly Gly His
            20                  25                  30

<210> SEQ ID NO 233
<211> LENGTH: 31
<212> TYPE: PRT
<213> ORGANISM: Artificial Sequence
<220> FEATURE:

<223> OTHER INFORMATION: GLP/glucagon analogue

<400> SEQUENCE: 233

His Ser Gln Gly Thr Phe Thr Ser Asp Tyr Ser His Tyr Leu Glu Glu
1               5                   10                  15

Glu Ala Val His Leu Phe Ile Glu Trp Leu Leu Asn Gly Gly His
            20                  25                  30

<210> SEQ ID NO 234
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 234

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Lys His
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 235

His Ser Gln Gly Thr Phe Thr Ser Asp Tyr Ser Lys Tyr Leu Glu Glu
1               5                   10                  15

Glu Ala Val Arg His Phe Ile Glu Trp Leu Leu Asn Gly Gly His
            20                  25                  30

<210> SEQ ID NO 236
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 236

His Ser Gln Gly Thr Phe Thr Ser Asp Tyr Ser Lys Tyr Leu Glu Glu
1               5                   10                  15

Glu Ala Val His Leu Phe Ile Gln Trp Leu Leu Asn Gly Gly His
            20                  25                  30

<210> SEQ ID NO 237
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 237

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 238
<211> LENGTH: 31
<212> TYPE: PRT
<213> ORGANISM: Artificial Sequence

```
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 238

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 239
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 239

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Gly Gly His
            20                  25                  30

<210> SEQ ID NO 240
<211> LENGTH: 31
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (30)..(30)
<223> OTHER INFORMATION: AMIDATION

<400> SEQUENCE: 240

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Gly Gly His
            20                  25                  30

<210> SEQ ID NO 241
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (29)..(29)
<223> OTHER INFORMATION: AMIDATION

<400> SEQUENCE: 241

His Ser Gln Gly Thr Phe Thr Ser Asp Tyr Ser His Tyr Leu Glu Ser
1               5                   10                  15

Gln Ala Val Arg Leu Phe Ile Glu Trp Leu Leu Asn Thr
            20                  25

<210> SEQ ID NO 242
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
```

-continued

```
<221> NAME/KEY: MOD_RES
<222> LOCATION: (29)..(29)
<223> OTHER INFORMATION: AMIDATION

<400> SEQUENCE: 242

His Ser Gln Gly Thr Phe Thr Ser Asp Tyr Ser His Tyr Leu Glu Ser
1               5                   10                  15

Glu Ala Val Arg His Phe Ile Glu Trp Leu Leu Asn Thr
            20                  25

<210> SEQ ID NO 243
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 243

His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Gly Gly His
            20                  25                  30

<210> SEQ ID NO 244
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 244

His Ser Gln Gly Thr Phe Thr Ser Asp Tyr Ser His Tyr Leu Asp Ser
1               5                   10                  15

Gln Ala Val Arg Leu Phe Ile Gln Trp Leu Leu Asn Gly Gly His
            20                  25                  30

<210> SEQ ID NO 245
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 245

His Ser Gln Gly Thr Phe Thr Ser Asp Tyr Ser Lys Tyr Leu Glu Ser
1               5                   10                  15

Glu Ala Val Arg His Phe Ile Glu Trp Leu Leu Asn Gly Gly His
            20                  25                  30

<210> SEQ ID NO 246
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 246

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Gly Gly His
            20                  25                  30

<210> SEQ ID NO 247
<211> LENGTH: 31
```

```
<212> TYPE: PRT
<213> ORGANISM: Artificial Sequence
<220> FEATURE:
<223> OTHER INFORMATION: GLP/glucagon analogue

<400> SEQUENCE: 247

His Ser Gln Gly Thr Phe Thr Ser Asp Tyr Ser His Tyr Leu Asp Ser
1               5                   10                  15

Gln Ala Val Arg Leu Phe Ile Gln Trp Leu Leu Asn Thr Gly His
            20                  25                  30

<210> SEQ ID NO 248
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 248

His Ser Gln Gly Thr Phe Thr Ser Asp Tyr Ser Lys Tyr Leu Glu Ser
1               5                   10                  15

Glu Ala Val Arg His Phe Ile Glu Trp Leu Leu Asn Thr Gly His
            20                  25                  30

<210> SEQ ID NO 249
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 249

His Ser Gln Gly Thr Phe Thr Ser Asp Tyr Ser His Tyr Leu Asp Ser
1               5                   10                  15

Arg Ala Val His Leu Phe Ile Gln Trp Leu Leu Asn Thr Gly His
            20                  25                  30

<210> SEQ ID NO 250
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 250

His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Thr Gly His
            20                  25                  30

<210> SEQ ID NO 251
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 251

His Ser Gln Gly Thr Phe Thr Ser Asp Tyr Ser Lys Tyr Leu Glu Glu
1               5                   10                  15

Gln Ala Val Arg His Phe Ile Glu Trp Leu Leu Asn Gly Gly His
            20                  25                  30

<210> SEQ ID NO 252
```

```
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 252

His Ser Gln Gly Thr Phe Thr Ser Asp Tyr Ser Lys Tyr Leu Glu Glu
1               5                   10                  15
Gln Ala Val His Leu Phe Ile Glu Trp Leu Leu Asn Gly Gly His
            20                  25                  30

<210> SEQ ID NO 253
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 253

His Ser Gln Gly Thr Phe Thr Ser Asp Tyr Ser His Tyr Leu Glu Glu
1               5                   10                  15
Gln Ala Val Arg Leu Phe Ile Gln Trp Leu Leu Asn Gly Gly His
            20                  25                  30

<210> SEQ ID NO 254
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 254

His Ser Gln Gly Thr Phe Thr Ser Asp Tyr Ser Lys Tyr Leu Glu Ser
1               5                   10                  15
Gln Ala Val Arg Leu Phe Ile Glu Trp Leu Leu Asn Thr Gly His
            20                  25                  30

<210> SEQ ID NO 255
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 255

His Ser Gln Gly Thr Phe Thr Ser Asp Tyr Ser Lys Tyr Leu Glu Ser
1               5                   10                  15
Glu Ala Val Arg Leu Phe Ile Glu Trp Leu Leu Asn Thr Gly His
            20                  25                  30

<210> SEQ ID NO 256
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 256

His Ser Gln Gly Thr Phe Thr Ser Asp Tyr Ser Lys Tyr Leu Glu Glu
1               5                   10                  15
Glu Ala Val Arg Leu Phe Ile Gln Trp Leu Leu Asn Thr Gly His
            20                  25                  30
```

```
<210> SEQ ID NO 257
<211> LENGTH: 31
<212> TYPE: PRT
<213> ORGANISM: Artificial Sequence
<220> FEATURE:
<223> OTHER INFORMATION: GLP/glucagon analogue

<400> SEQUENCE: 257

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Val Asn Gly Gly His
            20                  25                  30

<210> SEQ ID NO 258
<211> LENGTH: 29
<212> TYPE: PRT
<213> ORGANISM: Artificial Sequence
<220> FEATURE:
<223> OTHER INFORMATION: GLP/glucagon analogue

<400> SEQUENCE: 258

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr
            20                  25

<210> SEQ ID NO 259
<211> LENGTH: 29
<212> TYPE: PRT
<213> ORGANISM: Artificial Sequence
<220> FEATURE:
<223> OTHER INFORMATION: GLP/glucagon analogue

<400> SEQUENCE: 259

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly
            20                  25

<210> SEQ ID NO 260
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
```

```
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2,
      His-His-NH2 or Lys-His, and Xaa (32)..(39) are absent; or [see
      misc feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-
      Ser-Gly, and Xaa (35)..(39) are absent; or [see misc feature 30
      (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 260

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35
```

<210> SEQ ID NO 261
<211> LENGTH: 10
<212> TYPE: PRT
<213> ORGANISM: Artificial Sequence
<220> FEATURE:
<223> OTHER INFORMATION: GLP/glucagon analogue

<400> SEQUENCE: 261

Gly Pro Ser Ser Gly Ala Pro Pro Pro Ser
1               5                   10

<210> SEQ ID NO 262
<211> LENGTH: 10
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MOD_RES
<222> LOCATION: (10)..(10)
<223> OTHER INFORMATION: AMIDATION

<400> SEQUENCE: 262

Gly Pro Ser Ser Gly Ala Pro Pro Pro Ser
1               5                   10

<210> SEQ ID NO 263
<211> LENGTH: 4
<212> TYPE: PRT
<213> ORGANISM: Artificial Sequence
<220> FEATURE:
<223> OTHER INFORMATION: GLP/glucagon analogue

<400> SEQUENCE: 263

Gly Tyr Tyr Tyr
1

<210> SEQ ID NO 264
<211> LENGTH: 5
<212> TYPE: PRT
<213> ORGANISM: Artificial Sequence
<220> FEATURE:
<223> OTHER INFORMATION: GLP/glucagon analogue

<400> SEQUENCE: 264

Arg Pro Ser Ser Gly
1               5

<210> SEQ ID NO 265
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn or Glu

```
<220> FEATURE:
<221> NAME/KEY: misc_feature
<222> LOCATION: (16)..(16)
<223> OTHER INFORMATION: Xaa is Ser, Glu or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile or Arg
<220> FEATURE:
<221> NAME/KEY: misc_feature
<222> LOCATION: (19)..(19)
<223> OTHER INFORMATION: Xaa is Ala or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu or His
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (28)..(28)
<223> OTHER INFORMATION: Xaa is Lys or Asn
<220> FEATURE:
<221> NAME/KEY: misc_feature
<222> LOCATION: (29)..(29)
<223> OTHER INFORMATION: Xaa is Gly, Thr, Arg, Gly-NH2, Thr-NH2 or
      Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2 or His-NH2, and Xaa (31)..(39) are
      absent; or Xaa (30)..(31) are Gly-Pro, and Xaa (32)..(39) are
      absent; [see misc feature 30 (2)].
<220> FEATURE:
<221> NAME/KEY: misc_feature
<222> LOCATION: (30)..(39)
<223> OTHER INFORMATION: (2): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 265

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 266
<211> LENGTH: 39
<212> TYPE: PRT
<213> ORGANISM: Artificial Sequence
```

-continued

```
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2,
      His-His-NH2 or Lys-His, and Xaa (32)..(39) are absent; or [see
```

```
      misc feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 266

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 267
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
```

```
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 267

His Ser Gln Gly Thr Phe Thr Ser Asp Tyr Ser Xaa Tyr Leu Xaa Xaa
1               5                   10                  15

Xaa Ala Val Xaa Xaa Phe Ile Glu Trp Leu Xaa Asn Xaa Xaa Xaa Xaa
            20                  25                  30

Xaa Xaa Xaa Xaa Xaa Xaa Xaa
        35

<210> SEQ ID NO 268
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp, Gln, Lys, His or Glu
<220> FEATURE:
<221> NAME/KEY: misc_feature
<222> LOCATION: (16)..(16)
<223> OTHER INFORMATION: Xaa is Ser or Glu
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
```

```
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 268

His Ser Gln Gly Thr Phe Thr Ser Asp Tyr Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 269
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Glu
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
```

```
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 269

His Ser Gln Gly Thr Phe Thr Ser Asp Tyr Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 270
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
```

```
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 270

His Ser Gln Gly Thr Phe Thr Ser Asp Tyr Ser Lys Tyr Leu Asp Ser
1               5                   10                  15

Xaa Xaa Xaa Xaa Xaa Phe Xaa Xaa Xaa Leu Xaa Xaa Xaa Xaa Xaa Xaa
                20                  25                  30

Xaa Xaa Xaa Xaa Xaa Xaa Xaa
        35

<210> SEQ ID NO 271
```

```
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 271

His Ser Gln Gly Thr Phe Thr Ser Asp Tyr Ser His Tyr Leu Asp Ser
```

```
                1               5                    10                   15
Xaa Xaa Xaa Xaa Xaa Phe Xaa Xaa Xaa Leu Xaa Xaa Xaa Xaa Xaa Xaa
                        20                   25                   30
Xaa Xaa Xaa Xaa Xaa Xaa Xaa
            35
```

```
<210> SEQ ID NO 272
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
```

```
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 272

His Ser Gln Gly Thr Phe Thr Ser Asp Tyr Ser Lys Tyr Leu Glu Ser
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 273
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
```

```
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 273

His Ser Gln Gly Thr Phe Thr Ser Asp Tyr Ser His Tyr Leu Glu Ser
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 274
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
```

```
  His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are
      absent; or Xaa (30)..(34) are Arg-Pro-Ser-Ser-Gly, and Xaa
      (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 274

His Ser Gln Gly Thr Phe Thr Ser Asp Tyr Ser Lys Tyr Leu Asp Glu
1               5                   10                  15

Xaa Xaa Xaa Xaa Xaa Phe Xaa Xaa Xaa Leu Xaa Xaa Xaa Xaa Xaa Xaa
                20                  25                  30

Xaa Xaa Xaa Xaa Xaa Xaa Xaa
        35

<210> SEQ ID NO 275
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
```

```
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 275

His Ser Gln Gly Thr Phe Thr Ser Asp Tyr Ser His Tyr Leu Asp Glu
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 276
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
```

```
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 276

His Ser Gln Gly Thr Phe Thr Ser Asp Tyr Ser Lys Tyr Leu Glu Glu
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 277
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
```

```
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 277

His Ser Gln Gly Thr Phe Thr Ser Asp Tyr Ser His Tyr Leu Glu Glu
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 278
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
```

```
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu or Gln
<220> FEATURE:
<221> NAME/KEY: misc_feature
<222> LOCATION: (20)..(20)
<223> OTHER INFORMATION: Xaa is Lys, Arg or His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
```

Gly-Pro-Ser-Ser-Gly-Ala-Pro-Pro-Pro-Ser-NH2.

<400> SEQUENCE: 278

His Xaa Gln Gly Thr Phe Thr Ser Asp Xaa Ser Xaa Tyr Leu Xaa Xaa
1               5                   10                  15

Xaa Ala Val Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 279
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].

-continued

```
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 279

His Xaa Gln Gly Thr Phe Thr Ser Asp Xaa Ser Xaa Tyr Leu Xaa Xaa
1               5                   10                  15

Glu Ala Val His Leu Phe Xaa Xaa Xaa Leu Xaa Xaa Xaa Xaa Xaa Xaa
                20                  25                  30

Xaa Xaa Xaa Xaa Xaa Xaa Xaa
                35

<210> SEQ ID NO 280
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
```

```
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 280

His Xaa Gln Gly Thr Phe Thr Ser Asp Xaa Ser Xaa Tyr Leu Xaa Xaa
1               5                   10                  15

Gln Ala Val His Leu Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 281
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
```

```
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 281

His Xaa Gln Gly Thr Phe Thr Ser Asp Xaa Ser Xaa Tyr Leu Xaa Xaa
1               5                   10                  15

Glu Ala Val His His Phe Xaa Xaa Xaa Leu Xaa Xaa Xaa Xaa Xaa Xaa
                20                  25                  30

Xaa Xaa Xaa Xaa Xaa Xaa Xaa
                35

<210> SEQ ID NO 282
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
```

```
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
    His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
    Arg, Gly, Arg-NH2, Gly-NH2, His-NH2, or His, and Xaa (31)..(39)
    are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
    His-His, His-Pro, Gly-Pro-NH2, Gly-His-NH2, His-Pro-NH2, His-His-
    NH2 or Lys-His, and Xaa (32)..(39) are absent; or [see misc
    feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
    Xaa (34)..(39) are absent; or Xaa (30)..(34) are Arg-Pro-Ser-Ser-
    Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
    Gly-Pro-Ser-Ser-Gly-Ala-Pro-Pro-Pro-Ser or
    Gly-Pro-Ser-Ser-Gly-Ala-Pro-Pro-Pro-Ser-NH2.

<400> SEQUENCE: 282

His Xaa Gln Gly Thr Phe Thr Ser Asp Xaa Ser Xaa Tyr Leu Xaa Xaa
1               5                   10                  15

Gln Ala Val His His Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 283
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
    acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
```

```
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 283

His Xaa Gln Gly Thr Phe Thr Ser Asp Xaa Ser Xaa Tyr Leu Xaa Xaa
1               5                   10                  15

Glu Ala Val Arg Leu Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 284
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
```

```
                    acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 284

His Xaa Gln Gly Thr Phe Thr Ser Asp Xaa Ser Xaa Tyr Leu Xaa Xaa
1               5                   10                  15

Gln Ala Val Arg Leu Phe Xaa Xaa Xaa Leu Xaa Xaa Xaa Xaa Xaa
            20                  25                  30

Xaa Xaa Xaa Xaa Xaa Xaa Xaa
        35
```

```
<210> SEQ ID NO 285
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.
```

```
<400> SEQUENCE: 285

His Xaa Gln Gly Thr Phe Thr Ser Asp Xaa Ser Xaa Tyr Leu Xaa Xaa
1               5                   10                  15

Glu Ala Val Arg His Phe Xaa Xaa Xaa Leu Xaa Xaa Xaa Xaa Xaa Xaa
            20                  25                  30

Xaa Xaa Xaa Xaa Xaa Xaa Xaa
                35

<210> SEQ ID NO 286
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
```

```
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 286

His Xaa Gln Gly Thr Phe Thr Ser Asp Xaa Ser Xaa Tyr Leu Xaa Xaa
1               5                   10                  15

Gln Ala Val Arg His Phe Xaa Xaa Xaa Leu Xaa Xaa Xaa Xaa Xaa Xaa
            20                  25                  30

Xaa Xaa Xaa Xaa Xaa Xaa Xaa
            35

<210> SEQ ID NO 287
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
```

```
        Arg, Gly, Arg-NH2, Gly-NH2, His-NH2, or His, and Xaa (31)..(39)
        are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
        His-His, His-Pro, Gly-Pro-NH2, Gly-His-NH2, His-Pro-NH2, His-His-
        NH2 or Lys-His, and Xaa (32)..(39) are absent; or [see misc
        feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
        Xaa (34)..(39) are absent; or Xaa (30)..(34) are Arg-Pro-Ser-Ser-
        Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
        Gly-Pro-Ser-Ser-Gly-Ala-Pro-Pro-Pro-Ser or
        Gly-Pro-Ser-Ser-Gly-Ala-Pro-Pro-Pro-Ser-NH2.

<400> SEQUENCE: 287

His Xaa Gln Gly Thr Phe Thr Ser Asp Xaa Ser Xaa Tyr Leu Xaa Xaa
1               5                   10                  15

Glu Ala Val Lys Leu Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 288
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
        acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
```

```
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 288

His Xaa Gln Gly Thr Phe Thr Ser Asp Xaa Ser Xaa Tyr Leu Xaa Xaa
1               5                   10                  15

Gln Ala Val Lys Leu Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 289
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
```

```
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
     His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
     Arg, Gly, Arg-NH2, Gly-NH2, His-NH2, or His, and Xaa (31)..(39)
     are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
     His-His, His-Pro, Gly-Pro-NH2, Gly-His-NH2, His-Pro-NH2, His-His-
     NH2 or Lys-His, and Xaa (32)..(39) are absent; or [see misc
     feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
     Xaa (34)..(39) are absent; or Xaa (30)..(34) are Arg-Pro-Ser-Ser-
     Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
     Gly-Pro-Ser-Ser-Gly-Ala-Pro-Pro-Pro-Ser or
     Gly-Pro-Ser-Ser-Gly-Ala-Pro-Pro-Pro-Ser-NH2.

<400> SEQUENCE: 289

His Xaa Gln Gly Thr Phe Thr Ser Asp Xaa Ser Xaa Tyr Leu Xaa Xaa
1               5                   10                  15

Glu Ala Val Lys His Phe Xaa Xaa Xaa Leu Xaa Xaa Xaa Xaa Xaa Xaa
            20                  25                  30

Xaa Xaa Xaa Xaa Xaa Xaa Xaa
            35

<210> SEQ ID NO 290
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
     acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
```

```
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
     His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
     Arg, Gly, Arg-NH2, Gly-NH2, His-NH2, or His, and Xaa (31)..(39)
     are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
     His-His, His-Pro, Gly-Pro-NH2, Gly-His-NH2, His-Pro-NH2, His-His-
     NH2 or Lys-His, and Xaa (32)..(39) are absent; or [see misc
     feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
     Xaa (34)..(39) are absent; or Xaa (30)..(34) are Arg-Pro-Ser-Ser-
     Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
     Gly-Pro-Ser-Ser-Gly-Ala-Pro-Pro-Pro-Ser or
     Gly-Pro-Ser-Ser-Gly-Ala-Pro-Pro-Pro-Ser-NH2.

<400> SEQUENCE: 290

His Xaa Gln Gly Thr Phe Thr Ser Asp Xaa Ser Xaa Tyr Leu Xaa Xaa
1               5                   10                  15

Gln Ala Val Lys His Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 291
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
     acid
<220> FEATURE:
```

```
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Lys, Leu or Val
<220> FEATURE:
<221> NAME/KEY: misc_feature
<222> LOCATION: (29)..(29)
<223> OTHER INFORMATION: Xaa is Gly, Thr, His, Gly-NH2, Thr-NH2 or
      His-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 291

His Xaa Gln Gly Thr Phe Thr Ser Asp Xaa Ser Xaa Tyr Leu Xaa Xaa
1               5                   10                  15
```

Xaa Xaa Xaa Xaa Xaa Phe Ile Xaa Trp Leu Xaa Asn Xaa Xaa Xaa Xaa
                20                  25                  30

Xaa Xaa Xaa Xaa Xaa Xaa Xaa
        35

<210> SEQ ID NO 292
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (27)..(27)
<223> OTHER INFORMATION: Xaa is Lys or Leu
<220> FEATURE:
<221> NAME/KEY: misc_feature
<222> LOCATION: (29)..(29)
<223> OTHER INFORMATION: Xaa is Gly, Thr, Gly-NH2 or Thr-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and

```
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 292

His Xaa Gln Gly Thr Phe Thr Ser Asp Xaa Ser Xaa Tyr Leu Xaa Xaa
1               5                   10                  15

Xaa Xaa Xaa Xaa Xaa Phe Ile Glu Trp Leu Xaa Asn Xaa Xaa Xaa Xaa
            20                  25                  30

Xaa Xaa Xaa Xaa Xaa Xaa Xaa
        35

<210> SEQ ID NO 293
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (29)..(29)
<223> OTHER INFORMATION: Xaa is Gly or Gly-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
```

<221> NAME/KEY: misc_feature
<222> LOCATION: (30)..(39)
<223> OTHER INFORMATION: (2): or Xaa (30)..(31) are Gly-Pro, Gly-His, His-His, His-Pro, Gly-Pro-NH2, Gly-His-NH2, His-Pro-NH2, His-His-NH2 or Lys-His, and Xaa (32)..(39) are absent; or [see misc feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and Xaa (34)..(39) are absent; or Xaa (30)..(34) are Arg-Pro-Ser-Ser-Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are Gly-Pro-Ser-Ser-Gly-Ala-Pro-Pro-Pro-Ser or Gly-Pro-Ser-Ser-Gly-Ala-Pro-Pro-Pro-Ser-NH2.

<400> SEQUENCE: 293

His Xaa Gln Gly Thr Phe Thr Ser Asp Xaa Ser Xaa Tyr Leu Xaa Xaa
1               5                   10                  15

Xaa Xaa Xaa Xaa Xaa Phe Ile Glu Trp Leu Leu Asn Xaa Xaa Xaa Xaa
            20                  25                  30

Xaa Xaa Xaa Xaa Xaa Xaa Xaa
        35

<210> SEQ ID NO 294
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:

```
<221> NAME/KEY: misc_feature
<222> LOCATION: (29)..(29)
<223> OTHER INFORMATION: Xaa is Gly or Gly-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 294

His Xaa Gln Gly Thr Phe Thr Ser Asp Xaa Ser Xaa Tyr Leu Xaa Xaa
1               5                   10                  15

Xaa Xaa Xaa Xaa Xaa Phe Ile Glu Trp Leu Lys Asn Xaa Xaa Xaa Xaa
            20                  25                  30

Xaa Xaa Xaa Xaa Xaa Xaa Xaa
        35

<210> SEQ ID NO 295
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
```

```
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (29)..(29)
<223> OTHER INFORMATION: Xaa is Thr or Thr-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 295

His Xaa Gln Gly Thr Phe Thr Ser Asp Xaa Ser Xaa Tyr Leu Xaa Xaa
1               5                   10                  15

Xaa Xaa Xaa Xaa Xaa Phe Ile Glu Trp Leu Leu Asn Xaa Xaa Xaa Xaa
            20                  25                  30

Xaa Xaa Xaa Xaa Xaa Xaa Xaa
        35

<210> SEQ ID NO 296
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
```

```
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (29)..(29)
<223> OTHER INFORMATION: Xaa is Thr or Thr-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2, His-His-
      NH2 or Lys-His, and Xaa (32)..(39) are absent; or [see misc
      feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
      Xaa (34)..(39) are absent; or Xaa (30)..(34) are Arg-Pro-Ser-Ser-
      Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 296

His Xaa Gln Gly Thr Phe Thr Ser Asp Xaa Ser Xaa Tyr Leu Xaa Xaa
1               5                   10                  15

Xaa Xaa Xaa Xaa Xaa Phe Ile Glu Trp Leu Lys Asn Xaa Xaa Xaa Xaa
                20                  25                  30

Xaa Xaa Xaa Xaa Xaa Xaa Xaa
            35

<210> SEQ ID NO 297
<211> LENGTH: 31
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
```

```
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
     His-NH2 or Arg-NH2
<220> FEATURE:
<221> NAME/KEY: misc_feature
<222> LOCATION: (30)..(31)
<223> OTHER INFORMATION: Xaa (30)..(31) is absent; or Xaa (30) is
     His-NH2 and Xaa (31) is absent; or Xaa (30)..(31) is Gly-Pro,
     Gly-His, Gly-His-NH2, or His-His.

<400> SEQUENCE: 297

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa
            20                  25                  30

<210> SEQ ID NO 298
<211> LENGTH: 31
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
```

```
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(31)
<223> OTHER INFORMATION: Xaa (30)..(31) is absent; or Xaa (30) is
      His-NH2 and Xaa (31) is absent; or Xaa (30)..(31) is Gly-Pro,
      Gly-His, or His-His

<400> SEQUENCE: 298

His Xaa Gln Gly Thr Phe Thr Ser Asp Xaa Ser Xaa Tyr Leu Xaa Xaa
 1               5                  10                  15

Xaa Xaa Xaa Xaa Xaa Phe Xaa Xaa Xaa Leu Xaa Xaa Xaa Xaa Xaa
                20                  25                  30
```

-continued

```
<210> SEQ ID NO 299
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp, Gln, Glu, Lys or His
<220> FEATURE:
<221> NAME/KEY: misc_feature
<222> LOCATION: (16)..(16)
<223> OTHER INFORMATION: Xaa is Ser, Glu or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His;
<220> FEATURE:
<221> NAME/KEY: misc_feature
<222> LOCATION: (21)..(21)
<223> OTHER INFORMATION: Xaa is Glu, Tyr, Leu or His
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp or Lys
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys or Asn
<220> FEATURE:
<221> NAME/KEY: misc_feature
<222> LOCATION: (29)..(29)
<223> OTHER INFORMATION: Xaa is Gly, His, Thr, Gly-NH2, His-NH2 or
      Thr-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2, Gly-NH2, His-NH2, or His, and Xaa (31)..(39)
      are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
      His-His, His-Pro, Gly-Pro-NH2, Gly-His-NH2, His-Pro-NH2 or His-
      His-NH2, and Xaa (32)..(39) are absent; or [see misc feature 30
      (3)].
<220> FEATURE:
<221> NAME/KEY: misc_feature
```

```
<222> LOCATION: (30)..(39)
<223> OTHER INFORMATION: (3): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 299

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa
        35

<210> SEQ ID NO 300
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His;
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp or Lys
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (29)..(29)
<223> OTHER INFORMATION: Xaa is Gly, Thr, Gly-NH2 or Thr-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 300

His Ser Gln Gly Thr Phe Thr Ser Asp Xaa Ser Xaa Tyr Leu Xaa Xaa
```

```
      1               5              10              15
Xaa Xaa Xaa Xaa Xaa Phe Ile Xaa Xaa Leu Xaa Asn Xaa Xaa Xaa Xaa
             20              25              30
Xaa Xaa Xaa Xaa Xaa Xaa Xaa
        35

<210> SEQ ID NO 301
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (15)..(15)
<223> OTHER INFORMATION: Xaa is Asp, Gln, Glu, Lys or His
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(20)
<223> OTHER INFORMATION: Xaa-Xaa-Xaa is Ala-Val-Arg or Ala-Val-His;
<220> FEATURE:
<221> NAME/KEY: misc_feature
<222> LOCATION: (21)..(21)
<223> OTHER INFORMATION: Xaa is Glu, Tyr, Leu, His or Asp
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp or Lys
<220> FEATURE:
<221> NAME/KEY: misc_feature
<222> LOCATION: (27)..(27)
<223> OTHER INFORMATION: Xaa is Val, Met or Leu
<220> FEATURE:
<221> NAME/KEY: misc_feature
<222> LOCATION: (29)..(29)
<223> OTHER INFORMATION: Xaa is Gly or Gly-NH2
<220> FEATURE:
<221> NAME/KEY: misc_feature
<222> LOCATION: (30)..(39)
<223> OTHER INFORMATION: (1) Xaa (30)..(39) are absent; Xaa (30) is Arg,
      Gly, Arg-NH2 or Gly-NH2, and Xaa (31)..(39) are absent; or
      Xaa (30)..(31) are Gly-Pro, and Xaa (32)..(39) are absent; or [see
      misc feature 30 (2)].
<220> FEATURE:
<221> NAME/KEY: misc_feature
<222> LOCATION: (30)..(39)
<223> OTHER INFORMATION: (2): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 301
```

```
His Xaa Gln Gly Thr Phe Thr Ser Asp Xaa Ser Lys Tyr Leu Xaa Xaa
1               5                   10                  15

Xaa Xaa Xaa Xaa Xaa Phe Xaa Xaa Leu Xaa Lys Xaa Xaa Xaa Xaa
            20                  25                  30

Xaa Xaa Xaa Xaa Xaa Xaa Xaa
        35
```

<210> SEQ ID NO 302
<211> LENGTH: 31
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp, Gln, Glu, Lys or His
<220> FEATURE:
<221> NAME/KEY: misc_feature
<222> LOCATION: (16)..(16)
<223> OTHER INFORMATION: Xaa is Ser or Glu
<220> FEATURE:
<221> NAME/KEY: misc_feature
<222> LOCATION: (17)..(17)
<223> OTHER INFORMATION: Xaa is Glu or Gln
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His;
<220> FEATURE:
<221> NAME/KEY: misc_feature
<222> LOCATION: (21)..(21)
<223> OTHER INFORMATION: Xaa is  Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val, Lys or Leu
<220> FEATURE:
<221> NAME/KEY: misc_feature
<222> LOCATION: (29)..(29)
<223> OTHER INFORMATION: Xaa is Gly, His, Thr, Gly-NH2, His-NH2 or
      Thr-NH2
<220> FEATURE:
<221> NAME/KEY: misc_feature
<222> LOCATION: (30)..(31)
<223> OTHER INFORMATION: Xaa (30)..(39) are absent; Xaa (30) is Gly,
      Gly-NH2, His-NH2, or His, and Xaa (31)..(39) are absent; or Xaa
      (30)..(31) are Gly-Pro, Gly-His, His-His, His-Pro, Gly-Pro-NH2,
      Gly-His-NH2, His-Pro-NH2, His-His-NH2, and Xaa (32)..(39) are
      absent.

<400> SEQUENCE: 302

```
His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Xaa Xaa
            20                  25                  30
```

<210> SEQ ID NO 303
<211> LENGTH: 31
<212> TYPE: PRT
<213> ORGANISM: Artificial Sequence
<220> FEATURE:
<223> OTHER INFORMATION: GLP/glucagon analogue
<220> FEATURE:

<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Glu
<220> FEATURE:
<221> NAME/KEY: misc_feature
<222> LOCATION: (17)..(17)
<223> OTHER INFORMATION: Xaa is Glu or Gln
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
    Ala-Val-His;
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (27)..(27)
<223> OTHER INFORMATION: Xaa is Lys or Leu
<220> FEATURE:
<221> NAME/KEY: misc_feature
<222> LOCATION: (29)..(29)
<223> OTHER INFORMATION: Xaa is Gly, Thr, Gly-NH2 or Thr-NH2
<220> FEATURE:
<221> NAME/KEY: misc_feature
<222> LOCATION: (30)..(31)
<223> OTHER INFORMATION: Xaa (30)..(31) are absent; or Xaa (30) is
    His-NH2, and Xaa (31) is absent; or Xaa (30)..(31) are Gly-Pro,
    Gly-His, or His-His.

<400> SEQUENCE: 303

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Glu Trp Leu Xaa Asn Xaa Xaa Xaa
            20                  25                  30

<210> SEQ ID NO 304
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
    acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg

```
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
     His-NH2 or Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
     Arg, Gly, Arg-NH2, Gly-NH2, His-NH2, or His, and Xaa (31)..(39)
     are absent; or [see misc feature 30 (2)].
<220> FEATURE:
<221> NAME/KEY: misc_feature
<222> LOCATION: (30)..(39)
<223> OTHER INFORMATION: (2): or Xaa (30)..(31) are Gly-Pro, Gly-His,
     His-His, His-Pro, Gly-Pro-NH2, Gly-His-NH2, His-Pro-NH2, His-His-
     NH2 or Lys-His, and Xaa (32)..(39) are absent; or [see misc
     feature 30 (3)].
<220> FEATURE:
<221> NAME/KEY: misc_feature
<222> LOCATION: (30)..(39)
<223> OTHER INFORMATION: (3): or Xaa (30)..(33) are Gly-Tyr-Tyr-Tyr and
     Xaa (34)..(39) are absent; or Xaa (30)..(34) are Arg-Pro-Ser-Ser-
     Gly, and Xaa (35)..(39) are absent; or [see misc feature 30 (4)].
<220> FEATURE:
<221> NAME/KEY: misc_feature
<222> LOCATION: (30)..(39)
<223> OTHER INFORMATION: (4): or Xaa (30)..(39) are
     Gly-Pro-Ser-Ser-Gly-Ala-Pro-Pro-Pro-Ser or
     Gly-Pro-Ser-Ser-Gly-Ala-Pro-Pro-Pro-Ser-NH2.

<400> SEQUENCE: 304

His Xaa Gln Gly Thr Phe Thr Ser Asp Xaa Ser Xaa Tyr Leu Xaa Ser
1               5                   10                  15

Xaa Xaa Xaa Xaa Xaa Phe Xaa Xaa Xaa Leu Xaa Xaa Xaa Xaa Xaa
            20                  25                  30

Xaa Xaa Xaa Xaa Xaa Xaa Xaa
        35

<210> SEQ ID NO 305
<211> LENGTH: 39
<212> TYPE: PRT
<213> ORGANISM: Artificial Sequence
```

```
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn or Glu
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile or Arg
<220> FEATURE:
<221> NAME/KEY: misc_feature
<222> LOCATION: (19)..(19)
<223> OTHER INFORMATION: Xaa is Ala or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu or His
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (28)..(28)
<223> OTHER INFORMATION: Xaa is Lys or Asn
<220> FEATURE:
<221> NAME/KEY: misc_feature
<222> LOCATION: (29)..(29)
<223> OTHER INFORMATION: Xaa is Gly, Thr, Arg, Gly-NH2, Thr-NH2 or
      Arg-NH2
<220> FEATURE:
<221> NAME/KEY: misc_feature
<222> LOCATION: (30)..(39)
<223> OTHER INFORMATION: (1): Xaa (30)..(39) are absent; Xaa (30) is
      Arg, Gly, Arg-NH2 or Gly-NH2 or His-NH2, and Xaa (31)..(39) are
      absent; or Xaa (30)..(31) are Gly-Pro, and Xaa (32)..(39) are
      absent; or [see misc feature 30 (2)].
<220> FEATURE:
<221> NAME/KEY: misc_feature
<222> LOCATION: (30)..(39)
<223> OTHER INFORMATION: (2): or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 305
```

-continued

```
His Xaa Gln Gly Thr Phe Thr Ser Asp Xaa Ser Xaa Tyr Leu Xaa Ser
1               5                   10                  15

Xaa Xaa Xaa Xaa Xaa Phe Xaa Xaa Leu Xaa Xaa Xaa Xaa Xaa Xaa
            20                  25                  30

Xaa Xaa Xaa Xaa Xaa Xaa Xaa
        35

<210> SEQ ID NO 306
<211> LENGTH: 16
<212> TYPE: PRT
<213> ORGANISM: Artificial Sequence
<220> FEATURE:
<223> OTHER INFORMATION: partial GLP/glucagon analogue
<220> FEATURE:
<221> NAME/KEY: misc_feature
<222> LOCATION: (2)..(2)
<223> OTHER INFORMATION: Ser may be optionally replaced by a alpha-
      aminoisobutyric acid residue
<220> FEATURE:
<221> NAME/KEY: misc_feature
<222> LOCATION: (12)..(12)
<223> OTHER INFORMATION: Lys may be optionally replaced by Arg
<220> FEATURE:
<221> NAME/KEY: misc_feature
<222> LOCATION: (15)..(15)
<223> OTHER INFORMATION: Asp may be optionally replaced by a neutural
      amino acid residue, for example Asn
<220> FEATURE:
<221> NAME/KEY: misc_feature
<222> LOCATION: (16)..(16)
<223> OTHER INFORMATION: Ser may be optionally replaced by Gly

<400> SEQUENCE: 306

His Ser Gln Gly Thr Phe Thr Ser Asp Tyr Ser Lys Tyr Leu Asp Ser
1               5                   10                  15

<210> SEQ ID NO 307
<211> LENGTH: 8
<212> TYPE: PRT
<213> ORGANISM: Artificial Sequence
<220> FEATURE:
<223> OTHER INFORMATION: partial GLP/glucagon analogue
<220> FEATURE:
<221> NAME/KEY: misc_feature
<222> LOCATION: (1)..(1)
<223> OTHER INFORMATION: Glu  may be replaced by Gln or by Arg
<220> FEATURE:
<221> NAME/KEY: misc_feature
<222> LOCATION: (2)..(2)
<223> OTHER INFORMATION: Ala may be replaced by Arg
<220> FEATURE:
<221> NAME/KEY: misc_feature
<222> LOCATION: (4)..(4)
<223> OTHER INFORMATION: Arg may be replaced by Gln or His
<220> FEATURE:
<221> NAME/KEY: misc_feature
<222> LOCATION: (5)..(5)
<223> OTHER INFORMATION: Leu may be replaced by Tyr
<220> FEATURE:
<221> NAME/KEY: misc_feature
<222> LOCATION: (8)..(8)
<223> OTHER INFORMATION: Glu may be replaced by Gln

<400> SEQUENCE: 307

Glu Ala Val Arg Leu Phe Ile Glu
1               5

<210> SEQ ID NO 308
<211> LENGTH: 5
<212> TYPE: PRT
<213> ORGANISM: Artificial Sequence
<220> FEATURE:
```

<223> OTHER INFORMATION: partial GLP/glucagon analogue

<400> SEQUENCE: 308

Tyr Leu Leu Asn Thr
1               5

<210> SEQ ID NO 309
<211> LENGTH: 5
<212> TYPE: PRT
<213> ORGANISM: Artificial Sequence
<220> FEATURE:
<223> OTHER INFORMATION: partial GLP/glucagon analogue

<400> SEQUENCE: 309

Tyr Leu Met Asn Thr
1               5

<210> SEQ ID NO 310
<211> LENGTH: 5
<212> TYPE: PRT
<213> ORGANISM: Artificial Sequence
<220> FEATURE:
<223> OTHER INFORMATION: partial GLP/glucagon analogue

<400> SEQUENCE: 310

Trp Leu Leu Asn Thr
1               5

<210> SEQ ID NO 311
<211> LENGTH: 5
<212> TYPE: PRT
<213> ORGANISM: Artificial Sequence
<220> FEATURE:
<223> OTHER INFORMATION: partial GLP/glucagon analogue

<400> SEQUENCE: 311

Trp Leu Met Asn Thr
1               5

<210> SEQ ID NO 312
<211> LENGTH: 5
<212> TYPE: PRT
<213> ORGANISM: Artificial Sequence
<220> FEATURE:
<223> OTHER INFORMATION: partial GLP/glucagon analogue

<400> SEQUENCE: 312

Leu Leu Leu Asn Thr
1               5

<210> SEQ ID NO 313
<211> LENGTH: 5
<212> TYPE: PRT
<213> ORGANISM: Artificial Sequence
<220> FEATURE:
<223> OTHER INFORMATION: partial GLP/glucagon analogue

<400> SEQUENCE: 313

Leu Leu Met Asn Thr
1               5

<210> SEQ ID NO 314
<211> LENGTH: 30
<212> TYPE: PRT
<213> ORGANISM: Artificial Sequence
<220> FEATURE:
<223> OTHER INFORMATION: GLP/glucagon analogue

```
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His or Arg

<400> SEQUENCE: 314

His Xaa Gln Gly Thr Phe Thr Ser Asp Xaa Ser His Tyr Leu Xaa Xaa
1               5                   10                  15

Xaa Xaa Xaa His Xaa Phe Xaa Xaa Xaa Leu Xaa Xaa Xaa His
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
```

```
<222> LOCATION: (10)..(10)
<223> OTHER INFORMATION: Xaa is Tyr or Val
<220> FEATURE:
<221> NAME/KEY: misc_feature
<222> LOCATION: (15)..(15)
<223> OTHER INFORMATION: Xaa is Asp, Asn or Glu
<220> FEATURE:
<221> NAME/KEY: misc_feature
<222> LOCATION: (16)..(16)
<223> OTHER INFORMATION: Xaa is Ser, Glu or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile or Arg
<220> FEATURE:
<221> NAME/KEY: misc_feature
<222> LOCATION: (19)..(19)
<223> OTHER INFORMATION: Xaa is Ala or Val
<220> FEATURE:
<221> NAME/KEY: misc_feature
<222> LOCATION: (21)..(21)
<223> OTHER INFORMATION: Xaa is Glu, Tyr, Leu or His
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (28)..(28)
<223> OTHER INFORMATION: Xaa is Lys or Asn
<220> FEATURE:
<221> NAME/KEY: misc_feature
<222> LOCATION: (29)..(29)
<223> OTHER INFORMATION: Xaa is Gly, Thr or Arg

<400> SEQUENCE: 315

His Xaa Gln Gly Thr Phe Thr Ser Asp Xaa Ser His Tyr Leu Xaa Xaa
1               5                   10                  15

Xaa Xaa Xaa His Xaa Phe Xaa Xaa Xaa Leu Xaa Xaa Xaa His
                20                  25                  30

<210> SEQ ID NO 316
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
```

```
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
     His-NH2 or Arg-NH2
<220> FEATURE:
<221> NAME/KEY: misc_feature
<222> LOCATION: (30)..(30)
<223> OTHER INFORMATION: Xaa is absent; Arg; Gly; His; Arg-NH2; Gly-NH2;
     or His-NH2

<400> SEQUENCE: 316

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa
            20                  25                  30

<210> SEQ ID NO 317
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
```

```
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn or Glu
<220> FEATURE:
<221> NAME/KEY: misc_feature
<222> LOCATION: (16)..(16)
<223> OTHER INFORMATION: Xaa is Ser, Glu or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile or Arg
<220> FEATURE:
<221> NAME/KEY: misc_feature
<222> LOCATION: (19)..(19)
<223> OTHER INFORMATION: Xaa is Ala or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu or His
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (28)..(28)
<223> OTHER INFORMATION: Xaa is Lys or Asn
<220> FEATURE:
<221> NAME/KEY: misc_feature
<222> LOCATION: (29)..(29)
<223> OTHER INFORMATION: Xaa is Gly, Thr, Arg, Gly-NH2, Thr-NH2 or
      Arg-NH2
<220> FEATURE:
<221> NAME/KEY: misc_feature
<222> LOCATION: (30)..(30)
<223> OTHER INFORMATION: Xaa is absent; Arg; Gly; His; Arg-NH2; Gly-NH2;
      or His-NH2

<400> SEQUENCE: 317

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa
            20                  25                  30

<210> SEQ ID NO 318
<211> LENGTH: 30
<212> TYPE: PRT
<213> ORGANISM: Artificial Sequence
```

```
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser, Gly or an alpha-amino isobutyric
      acid
<220> FEATURE:
<221> NAME/KEY: misc_feature
<222> LOCATION: (10)..(10)
<223> OTHER INFORMATION: Xaa is Tyr, Leu or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn, Gln, Glu, Lys or His
<220> FEATURE:
<221> NAME/KEY: misc_feature
<222> LOCATION: (16)..(16)
<223> OTHER INFORMATION: Xaa is Ser, Glu, Gln or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile, His or Arg
<220> FEATURE:
<221> NAME/KEY: misc_feature
<222> LOCATION: (19)..(19)
<223> OTHER INFORMATION: Xaa is Ala, His or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu, His or Lys
<220> FEATURE:
<221> NAME/KEY: misc_feature
<222> LOCATION: (23)..(23)
<223> OTHER INFORMATION: Xaa is Ile, His or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys, His or Leu
<220> FEATURE:
<221> NAME/KEY: misc_feature
<222> LOCATION: (28)..(28)
<223> OTHER INFORMATION: Xaa is Lys, His or Asn
<220> FEATURE:
<221> NAME/KEY: misc_feature
<222> LOCATION: (29)..(29)
<223> OTHER INFORMATION: Xaa is Gly, Thr, His, Arg, Gly-NH2, Thr-NH2,
      His-NH2 or Arg-NH2
<220> FEATURE:
<221> NAME/KEY: misc_feature
<222> LOCATION: (30)..(30)
<223> OTHER INFORMATION: Xaa is absent; Arg-NH2; Gly-NH2; or His-NH2.

<400> SEQUENCE: 318

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa
```

20          25          30

<210> SEQ ID NO 319
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: MISC_FEATURE
<222> LOCATION: (2)..(2)
<223> OTHER INFORMATION: Xaa is Ser or an alpha-amino isobutyric acid
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys, His or Arg
<220> FEATURE:
<221> NAME/KEY: misc_feature
<222> LOCATION: (15)..(15)
<223> OTHER INFORMATION: Xaa is Asp, Asn or Glu
<220> FEATURE:
<221> NAME/KEY: misc_feature
<222> LOCATION: (16)..(16)
<223> OTHER INFORMATION: Xaa is Ser, Glu or Gly
<220> FEATURE:
<221> NAME/KEY: misc_feature
<222> LOCATION: (17)..(17)
<223> OTHER INFORMATION: Xaa is Glu, Gln, Arg, Ser or Lys
<220> FEATURE:
<221> NAME/KEY: misc_feature
<222> LOCATION: (18)..(18)
<223> OTHER INFORMATION: Xaa is Ala, Ile or Arg
<220> FEATURE:
<221> NAME/KEY: misc_feature
<222> LOCATION: (19)..(19)
<223> OTHER INFORMATION: Xaa is Ala or Val
<220> FEATURE:
<221> NAME/KEY: misc_feature
<222> LOCATION: (20)..(20)
<223> OTHER INFORMATION: Xaa is Lys, Arg, His or Gln
<220> FEATURE:
<221> NAME/KEY: misc_feature
<222> LOCATION: (21)..(21)
<223> OTHER INFORMATION: Xaa is Glu, Tyr, Leu or His
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp, His, Lys, Tyr or Leu
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (28)..(28)
<223> OTHER INFORMATION: Xaa is Lys or Asn
<220> FEATURE:
<221> NAME/KEY: misc_feature
<222> LOCATION: (29)..(29)
<223> OTHER INFORMATION: Xaa is Gly, Thr, Arg, Gly-NH2, Thr-NH2 or
      Arg-NH2
<220> FEATURE:
<221> NAME/KEY: misc_feature
<222> LOCATION: (30)..(30)
<223> OTHER INFORMATION: Xaa is absent; Arg-NH2; Gly-NH2; or His-NH2.

-continued

```
<400> SEQUENCE: 319

His Xaa Gln Gly Thr Phe Thr Ser Asp Xaa Ser Xaa Tyr Leu Xaa Xaa
1               5                   10                  15

Xaa Xaa Xaa Xaa Xaa Phe Xaa Xaa Xaa Leu Xaa Xaa Xaa Xaa
            20                  25                  30

<210> SEQ ID NO 320
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (10)..(10)
<223> OTHER INFORMATION: Xaa is Tyr or Val
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Gly or Ser
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (25)..(25)
<223> OTHER INFORMATION: Xaa is Trp or Lys
<220> FEATURE:
<221> NAME/KEY: misc_feature
<222> LOCATION: (27)..(27)
<223> OTHER INFORMATION: Xaa is Val, Met, Lys or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 320

His Ser Gln Gly Thr Phe Thr Ser Asp Xaa Ser Xaa Tyr Leu Xaa Xaa
1               5                   10                  15

Xaa Xaa Xaa Xaa Xaa Phe Ile Xaa Xaa Leu Xaa Asn Xaa Xaa Xaa Xaa
            20                  25                  30

Xaa Xaa Xaa Xaa Xaa Xaa Xaa
        35
```

```
<210> SEQ ID NO 321
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 321

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Xaa Xaa Xaa
                20                  25                  30

Xaa Xaa Xaa Xaa Xaa Xaa Xaa
        35

<210> SEQ ID NO 322
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
```

```
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 322

His Ser Gln Gly Thr Phe Thr Ser Asp Tyr Ser Lys Tyr Leu Xaa Xaa
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
            35

<210> SEQ ID NO 323
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
```

-continued

```
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 323

His Ser Gln Gly Thr Phe Thr Ser Asp Tyr Ser His Tyr Leu Xaa Xaa
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
            35

<210> SEQ ID NO 324
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 324

His Ser Gln Gly Thr Phe Thr Ser Asp Tyr Ser Xaa Tyr Leu Asp Xaa
1               5                   10                  15

Xaa Xaa Xaa Xaa Xaa Phe Ile Xaa Trp Leu Xaa Asn Xaa Xaa Xaa Xaa
            20                  25                  30
```

Xaa Xaa Xaa Xaa Xaa Xaa Xaa
        35

<210> SEQ ID NO 325
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 325

His Ser Gln Gly Thr Phe Thr Ser Asp Tyr Ser Xaa Tyr Leu Glu Xaa
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
        35

<210> SEQ ID NO 326
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature

```
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 326

His Ser Gln Gly Thr Phe Thr Ser Asp Tyr Ser Xaa Tyr Leu Xaa Ser
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
        35

<210> SEQ ID NO 327
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Gly or Ser
<220> FEATURE:
<221> NAME/KEY: misc_feature
<222> LOCATION: (17)..(17)
<223> OTHER INFORMATION: Xaa is Glu or Gln
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
```

```
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 327

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
        35

<210> SEQ ID NO 328
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 328

His Ser Gln Gly Thr Phe Thr Ser Asp Tyr Ser Xaa Tyr Leu Xaa Xaa
1               5                   10                  15

Xaa Ala Val Arg Xaa Phe Ile Xaa Trp Leu Xaa Asn Xaa Xaa Xaa Xaa
```

```
                    20                  25                  30

Xaa Xaa Xaa Xaa Xaa Xaa Xaa
        35

<210> SEQ ID NO 329
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 329

His Ser Gln Gly Thr Phe Thr Ser Asp Tyr Ser Xaa Tyr Leu Xaa Xaa
1               5                   10                  15

Xaa Ala Val Lys Xaa Phe Ile Xaa Trp Leu Xaa Asn Xaa Xaa Xaa Xaa
                20                  25                  30

Xaa Xaa Xaa Xaa Xaa Xaa Xaa
        35

<210> SEQ ID NO 330
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
```

```
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 330

His Ser Gln Gly Thr Phe Thr Ser Asp Tyr Ser Xaa Tyr Leu Xaa Xaa
1               5                   10                  15

Xaa Ala Val His Xaa Phe Ile Xaa Trp Leu Xaa Asn Xaa Xaa Xaa Xaa
            20                  25                  30

Xaa Xaa Xaa Xaa Xaa Xaa Xaa
        35

<210> SEQ ID NO 331
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
```

```
<221> NAME/KEY: misc_feature
<222> LOCATION: (29)..(29)
<223> OTHER INFORMATION: Xaa is Thr, Gly, Thr-NH2 or

```
<210> SEQ ID NO 333
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 333

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Gln Trp Leu Xaa Asn Xaa Xaa Xaa Xaa
            20                  25                  30

Xaa Xaa Xaa Xaa Xaa Xaa Xaa
            35

<210> SEQ ID NO 334
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
```

```
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 334

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Glu Trp Leu Xaa Asn Xaa Xaa Xaa Xaa
            20                  25                  30

Xaa Xaa Xaa Xaa Xaa Xaa Xaa
        35

<210> SEQ ID NO 335
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
```

```
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 335

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Leu Asn Xaa Xaa Xaa Xaa
            20                  25                  30

Xaa Xaa Xaa Xaa Xaa Xaa Xaa
        35

<210> SEQ ID NO 336
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (29)..(29)
<223> OTHER INFORMATION: Xaa is Thr, Gly, Thr-NH2 or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 336

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Val Asn Xaa Xaa Xaa Xaa
            20                  25                  30

Xaa Xaa Xaa Xaa Xaa Xaa Xaa
        35
```

```
<210> SEQ ID NO 337
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
     Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr or Thr-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
     or Arg-NH2, and Xaa (31)..(39) are absent; or Xaa (30)..(39) are
     Gly-Pro-Ser-Ser-Gly-Ala-Pro-Pro-Pro-Ser or
     Gly-Pro-Ser-Ser-Gly-Ala-Pro-Pro-Pro-Ser-NH2.

<400> SEQUENCE: 337

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
        35

<210> SEQ ID NO 338
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
```

```
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Gly or Gly-NH2
<220> FEATURE:
<221> NAME/KEY: misc_feature
<222> LOCATION: (30)..(39)
<223> OTHER INFORMATION: Xaa (30)..(39) are absent; Xaa (30) is Arg, Gly
      or Arg-NH2, and Xaa (31)..(39) are absent; or Xaa (30)..(39) are
      Gly-Pro-Ser-Ser-Gly-Ala-Pro-Pro-Pro-Ser or
      Gly-Pro-Ser-Ser-Gly-Ala-Pro-Pro-Pro-Ser-NH2.

<400> SEQUENCE: 338

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Xaa Xaa Xaa
            20                  25                  30

Xaa Xaa Xaa Xaa Xaa Xaa Xaa
        35

<210> SEQ ID NO 339
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
```

-continued

```
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr or Gly
<220> FEATURE:
<221> NAME/KEY: MOD_RES
<222> LOCATION: (29)..(29)
<223> OTHER INFORMATION: AMIDATION

<400> SEQUENCE: 339

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa
            20                  25

<210> SEQ ID NO 340
<211> LENGTH: 29
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr or Gly

<400> SEQUENCE: 340

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa
            20                  25
```

```
<210> SEQ ID NO 341
<211> LENGTH: 30
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr or Gly

<400> SEQUENCE: 341

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Gly
            20                  25                  30

<210> SEQ ID NO 342
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
```

<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr or Gly

<400> SEQUENCE: 342

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Gly Pro Ser
            20                  25                  30

Ser Gly Ala Pro Pro Pro Ser
        35

<210> SEQ ID NO 343
<211> LENGTH: 39
<212> TYPE: PRT
<213> ORGANISM: Artificial Sequence
<220> FEATURE:
<223> OTHER INFORMATION: GLP/glucagon analogue
<220> FEATURE:
<221> NAME/KEY: misc_feature
<222> LOCATION: (12)..(12)
<223> OTHER INFORMATION: Xaa is Lys or His
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Ser or Gly
<220> FEATURE:
<221> NAME/KEY: misc_feature
<222> LOCATION: (17)..(17)
<223> OTHER INFORMATION: Xaa is Glu, Gln, Arg or Lys
<220> FEATURE:
<221> NAME/KEY: misc_feature
<222> LOCATION: (18)..(20)
<223> OTHER INFORMATION: Xaa-Xaa-Xaa is Ala-Val-Arg, Ala-Val-Lys or
      Ala-Val-His
<220> FEATURE:
<221> NAME/KEY: misc_feature
<222> LOCATION: (21)..(21)
<223> OTHER INFORMATION: Xaa is Leu or His
<220> FEATURE:
<221> NAME/KEY: misc_feature
<222> LOCATION: (24)..(24)
<223> OTHER INFORMATION: Xaa is Glu or Gln
<220> FEATURE:
<221> NAME/KEY: misc_feature
<222> LOCATION: (27)..(27)
<223> OTHER INFORMATION: Xaa is Val or Leu
<220> FEATURE:
<221> NAME/KEY: misc_feature
<222> LOCATION: (29)..(29)
<223> OTHER INFORMATION: Xaa is Thr or Gly
<220> FEATURE:
<221> NAME/KEY: MOD_RES
<222> LOCATION: (39)..(39)
<223> OTHER INFORMATION: AMIDATION -continued

```
<400> SEQUENCE: 343

His Ser Gln Gly Thr Phe Thr Ser Asp Tyr Ser Xaa Tyr Leu Xaa Xaa
1               5                   10                  15

Xaa Xaa Xaa Xaa Xaa Phe Ile Xaa Trp Leu Xaa Asn Xaa Gly Pro Ser
            20                  25              30

Ser Gly Ala Pro Pro Pro Ser
            35
```

COMPOUNDS AND THEIR EFFECTS ON FEEDING BEHAVIOUR

CROSS-REFERENCE TO RELATED APPLICATIONS

This application is a U.S. national stage filing under 35 U.S.C. § 371 of international application No. PCT/GB2011/001010, filed Jul. 4, 2011, and designating the United States.

1. FIELD OF THE INVENTION

This application relates to the use of agents to control appetite, feeding, food intake, energy expenditure, calorie intake and carbohydrate tolerance, particularly in the field of diabetes and obesity. It also relates to use of said agents as neuroprotective or cardioprotective agents.

2. BACKGROUND OF THE INVENTION

According to the National Health and Nutrition Examination Survey (NHANES III, 1988 to 1994), between one third and one half of men and women in the United States are overweight. In the United States, sixty percent of men and fifty-one percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia. Recently it has been shown that considerable weight loss can effectively cure type 2 diabetes (Lim et al, Diabetologia June 2011).

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have proven to have serious adverse side effects, and have had to be withdrawn again. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects as well as subjects who are of normal weight.

A number of derivatives of peptides deriving from the pro-glucagon molecule have been proposed for use in treatment of obesity and/or diabetes. Pro-glucagon is a precursor peptide of glucagon and several other hormones including oxyntomodulin (OXM) and GLP1 (glucagon-like peptide 1). The present invention is based on the discovery that hybrid peptide molecules containing sequence from both the GLP1 peptide and the glucagon peptide in which specific residues are deleted and/or substituted can be administered to a subject in order to cause decreased food intake, decreased calorific intake, decreased appetite, an increase in energy metabolism, enhanced insulin release and/or carbohydrate tolerance. In many cases such analogues exhibit improved potency and/or longer duration of action and fewer side effects than hybrid molecules based solely on the native residues of GLP1 and/or glucagon.

GLP1 and glucagon may be considered to have opposite effects on circulating glucose concentration. GLP1 is produced in vivo in the intestinal L cell in response to the presence of nutrients in the lumen of the gut. Once in the circulation, native GLP1 has a half-life of only a few minutes in humans due to rapid degradation by the enzyme dipeptidyl peptidase. GLP1 possesses a number of physiological functions including increasing insulin secretion from the pancreas in a glucose-dependent manner, decreasing glucagon secretion from the pancreas, inhibiting gastric emptying and decreasing food intake by increasing satiety. Increased insulin secretion leads to a decrease in circulating glucose concentration.

Glucagon is released in vivo when blood glucose levels fall low and has the activity of causing the liver to convert stored glycogen into glucose which is released into the bloodstream raising blood glucose levels. In this respect the action of glucagon may be regarded as opposite to that of insulin, and because insulin secretion is promoted by GLP1, it may therefore be regarded as having the opposite activity of GLP1. However, the interaction between the various hormones is complex because glucose also stimulates the release of insulin so that newly released glucose in the bloodstream as a result of glycogenlysis can be taken up and used by insulin dependent tissues. It has been proposed that a hybrid molecule with activities at the receptors for both GLP1 and of glucagon may be used for the treatment of type II diabetes (non-insulin dependent diabetes mellitus). Pan et al. discloses a peptide which a GLP1 agonist and a glucagon antagonist (Pan et al. Journal of Biological Chemistry, vol. 281, no. 18, p. 12501-12515, 5 May 2006). Some of the peptides disclosed in Pan et al. also contain sequences derived from exendin-4 which is an animal venom. The half-life of the compounds disclosed in Pan et al. are disappointing and it is proposed that PEGylation may be used to increase the circulatory half-life of the proteins to allow once a week dosing. However, PEGylation may result in a reduced activity due to steric hindrances. Pan et al. suggests that stability may be proved by adding a positive charge at residue 12 or by substituting methionine at position 27 to leucine in an attempt to mitigate oxidative degradation.

Runge et al. (British Journal of Pharmacology 2003, vol. 138, p. 787 to 794) discloses a hybrid peptide molecule comprising residues 7 to 20 of GLP1 and residues 15 to 29 of glucagon, and a further hybrid molecule comprising residues 1 to 14 of glucagon and residues 21 to 27 of GLP1.

3. SUMMARY OF THE INVENTION

The present invention is based on the discovery that peptides wherein residues in common with GLP and glucagon are generally unchanged, but other residues are altered in accordance with the invention, cause prolonged reductions in appetite and usually bind to both the GLP1 and glucagon receptors. The invention is also based on the realization that there are therapeutic advantages to the provision of a hybrid molecule that is both a GLP1 receptor agonist and a glucagon receptor agonist. The present disclosure provides evidence that such hybrid molecules have the ability to reduce appetite and therefore food intake and also change energy metabolism so as to promote weight loss. It is expected that such agents will be more effective at promoting weight loss than agents which are solely appetite suppressants.

A first aspect of the invention provides a compound that is a peptide having a sequence represented by formula I $$A\text{-}B \quad (I)$$

wherein A represents a region of the peptide having a sequence His1-Xaa2-Gln3-Gly4-Thr5-Phe6-Thr7-Ser8-Asp9-Xaa10-Ser11-Xaa12-Tyr13-Leu14-Xaa15-Xaa16-Xaa17-Xaa18-Xaa19-Xaa20-Xaa21-Phe22-Xaa23-Xaa24-Xaa25-Leu26-Xaa27-Xaa28-Xaa29;
wherein B is absent, —NH$_2$ or a region of the peptide having a sequence selected from:
  a) Arg30;
  b) Gly30;
  c) Arg30-NH$_2$;
  d) Gly30-NH$_2$;
  e) Gly30-Pro31-Ser32-Ser33-Gly34-Ala35-Pro36-Pro37-Pro38-Ser39;
  f) Gly30-Pro31-Ser32-Ser33-Gly34-Ala35-Pro36-Pro37-Pro38-Ser39-NH$_2$;
  g) His30-NH$_2$;
  h) Gly30-Pro31;
  i) Gly30-Tyr31-Tyr32-Tyr33;
  j) Arg30-Pro31-Ser32-Ser33-Gly34;
  k) His30;
  l) Gly30-His31;
  m) His30-His31;
  n) His30-Pro31;
  o) Gly30-Pro31-NH$_2$;
  p) Gly30-His31-NH$_2$;
  q) His30-Pro31-NH$_2$;
  r) His30-His31-NH$_2$; and
  s) Lys30-His31,
wherein —NH$_2$ represents C-terminal amidation of the peptide;
wherein Xaa2 is Ser2, Gly2 or an α-aminoisobutyric acid residue;
  Xaa10 is Tyr10, Leu10 or Val10;
  Xaa12 is Lys12, His12 or Arg12;
  Xaa15 is Asp15, Asn15, Gln15, Glu15, Lys15 or His15;
  Xaa16 is Ser16, Glu16, Gln16 or Gly16;
  Xaa17 is Glu17, Gln17, Arg17, Ser17 or Lys17;
  Xaa18 is Ala18, Ile18, His18 or Arg18;
  Xaa19 is Ala19, His19 or Val19;
  Xaa20 is Lys20, Arg20, His20 or Gln20;
  Xaa21 is Glu21, Tyr21, Leu21, His21 or Lys21;
  Xaa23 is Ile23, His23 or Val23;
  Xaa24 is Glu24 or Gln24;
  Xaa25 is Trp25, His25, Lys25, Tyr25 or Leu25;
  Xaa27 is Val27, Met27, Lys27, His27 or Leu27;
  Xaa28 is Lys28, His28 or Asn28;
  Xaa29 is Gly29, Thr29, His29 or Arg29;
or a compound that is a variant and/or derivative of said peptide; or a salt and/or solvate of said peptide or said compound,
with the proviso that at least one of the following criteria apply:
  t) an α-aminoisobutyric acid residue is present at position 2 of the peptide sequence;
  u) Val10 is present at position 10 of the peptide sequence;
  v) Ser17 is present at position 17 of the peptide sequence;
  w) Ile18 is present at position 18 of the peptide sequence;
  x) His25 is present at position 25 of the peptide sequence;
  y) Lys25 is present at position 25 of the peptide sequence;
  z) Leu27 is present at position 27 of the peptide sequence;
  aa) Val 27 is present at position 27 of the peptide sequence;
  ab) B is absent;
  ac) B is —NH$_2$;
  ad) B is Gly30-Pro31-Ser32-Ser33-Gly34-Ala35-Pro36-Pro37-Pro38-Ser39;
  ae) B is Gly30-Pro31-Ser32-Ser33-Gly34-Ala35-Pro36-Pro37-Pro38-Ser39-NH$_2$;
  and/or
  af) B is His30-NH$_2$.

According to a further aspect of the invention there is provided a compound that is a peptide having the sequence represented by formula IA:

$$A\text{-}B \quad (IA)$$

wherein A represents a region of the peptide having a sequence His1-Xaa2-Gln3-Gly4-Thr5-Phe6-Thr7-Ser8-Asp9-Xaa10-Ser11-Xaa12-Tyr13-Leu14-Xaa15-Xaa16-Xaa17-Xaa18-Xaa19-Xaa20-Xaa21-Phe22-Xaa23-Xaa24-Xaa25-Leu26-Xaa27-Xaa28-Xaa29;
wherein B is absent, —NH$_2$ or a region of the peptide having a sequence selected from:
  a) Arg30
  b) Gly30
  c) Arg30-NH$_2$
  d) Gly30-NH$_2$
  e) Gly30-Pro31-Ser32-Ser33-Gly34-Ala35-Pro36-Pro37-Pro38-Ser39
  f) Gly30-Pro31-Ser32-Ser33-Gly34-Ala35-Pro36-Pro37-Pro38-Ser39-NH$_2$
  g) His30-NH$_2$; and
  h) Gly30-Pro31
wherein —NH$_2$ represents C-terminal amidation of the peptide;
wherein Xaa2 is Ser2 or an α-aminoisobutyric acid residue,
  Xaa10 is Tyr10 or Val10,
  Xaa12 is Lys12, His12 or Arg12,
  Xaa15 is Asp15, Asn15 or Glu15,
  Xaa16 is Ser16, Glu16 or Gly16,
  Xaa17 is Glu17, Gln17, Arg17, Ser17 or Lys17,
  Xaa18 is Ala18, Ile18 or Arg18,
  Xaa19 is Ala19 or Val19,
  Xaa20 is Lys20, Arg20, His20 or Gln20,
  Xaa21 is Glu21, Tyr21, Leu21 or His21,
  Xaa23 is Ile23 or Val23,
  Xaa24 is Glu24 or Gln24,
  Xaa25 is Trp25, His25, Lys25, Tyr25 or Leu25, Xaa27 is Val27, Met27, Lys27 or Leu27,
Xaa28 is Lys28 or Asn28,
Xaa29 is Gly29, Thr29 or Arg29;
or a compound that is a variant and/or derivative of said peptide; or a salt and/or solvate of said peptide or said compound
with the proviso that at least one of the following criteria apply:
a) an α-aminoisobutyric acid residue is present at position 2 of the peptide sequence
b) Val10 is present at position 10 of the peptide sequence.
c) Ser17 is present at position 17 of the peptide sequence.
d) Ile18 is present at position 18 of the peptide sequence,
e) His25 is present at position 25 of the peptide sequence,
f) Lys25 is present at position 25 of the peptide sequence,
g) Leu27 is present at position 27 of the peptide sequence.
h) Val 27 is present at position 27 of the peptide sequence,
i) B is absent,
j) B is —$NH_2$,
k) B is Gly30-Pro31-Ser32-Ser33-Gly34-Ala35-Pro36-Pro37-Pro38-Ser39, or
l) B is Gly30-Pro31-Ser32-Ser33-Gly34-Ala35-Pro36-Pro37-Pro38-Ser39-$NH_2$.

According to a further aspect of the invention, there is provided a compound according to the invention for use as a medicament.

According to a further aspect of the invention, there is provided a pharmaceutical composition comprising a compound according to the invention together with a pharmaceutically acceptable carrier and optionally other therapeutic ingredients.

According to a further aspect of the invention, there is provided a compound according to the invention, or a pharmaceutical composition comprising a compound according to the invention, for use in the treatment of obesity or diabetes.

According to a further aspect of the invention, there is provided a compound according to the invention, or a pharmaceutical composition comprising a compound according to the invention, for use as a medicament for providing neuroprotection, for providing cardioprotection, or for preventing or treating neurodegeneration.

According to another aspect of the invention, there is provided a compound according to the invention, or a pharmaceutical composition comprising a compound according to the invention, for use in the reduction of appetite in a subject, for use in the reduction of food intake in a subject, for use in the reduction of calorie intake in a subject, for use in increasing energy expenditure in a subject, or for use in enhancing insulin release, for use in improving carbohydrate tolerance and/or improving carbohydrate metabolism in a subject.

According to a further aspect of the invention, there is provided a method for treating a disease or disorder or other non-desired physiological state comprising subcutaneous administration of a compound according to the invention, or a pharmaceutical composition comprising a compound according to the invention.

According to the invention there is further provided a method for treating obesity or diabetes in the subject in need thereof comprising administering to the subject a compound according to the invention, or a pharmaceutical composition comprising a compound according to the invention.

According to the invention there is further provided a method for treating a neurodegenerative disease or for proving neuroprotection, or for providing cardioprotection, in the subject in need thereof comprising administering to the subject a compound according to the invention, or a pharmaceutical composition comprising a compound according to the invention.

There is further provided use of a compound according to the invention for the manufacture of a medicament for the treatment of obesity or diabetes.

There is further provided use of a compound according to the invention for the manufacture of a medicament for the treatment of a neurodegenerative disease or for providing neuroprotection, or for providing cardioprotection.

There is further provided use of a compound according to the invention for the manufacture of a medicament for the reduction of appetite in a subject, for the reduction of food intake in a subject, for the reduction of calorie intake in a subject, for increasing energy expenditure in a subject, for use in enhancing insulin release, for use in improving carbohydrate tolerance and/or improving carbohydrate metabolism in a subject.

4. BRIEF DESCRIPTION OF THE DRAWINGS

FIG. 1 shows sequences of example compounds and summary food intake data.

5. SEQUENCE LISTING

Figure 2:
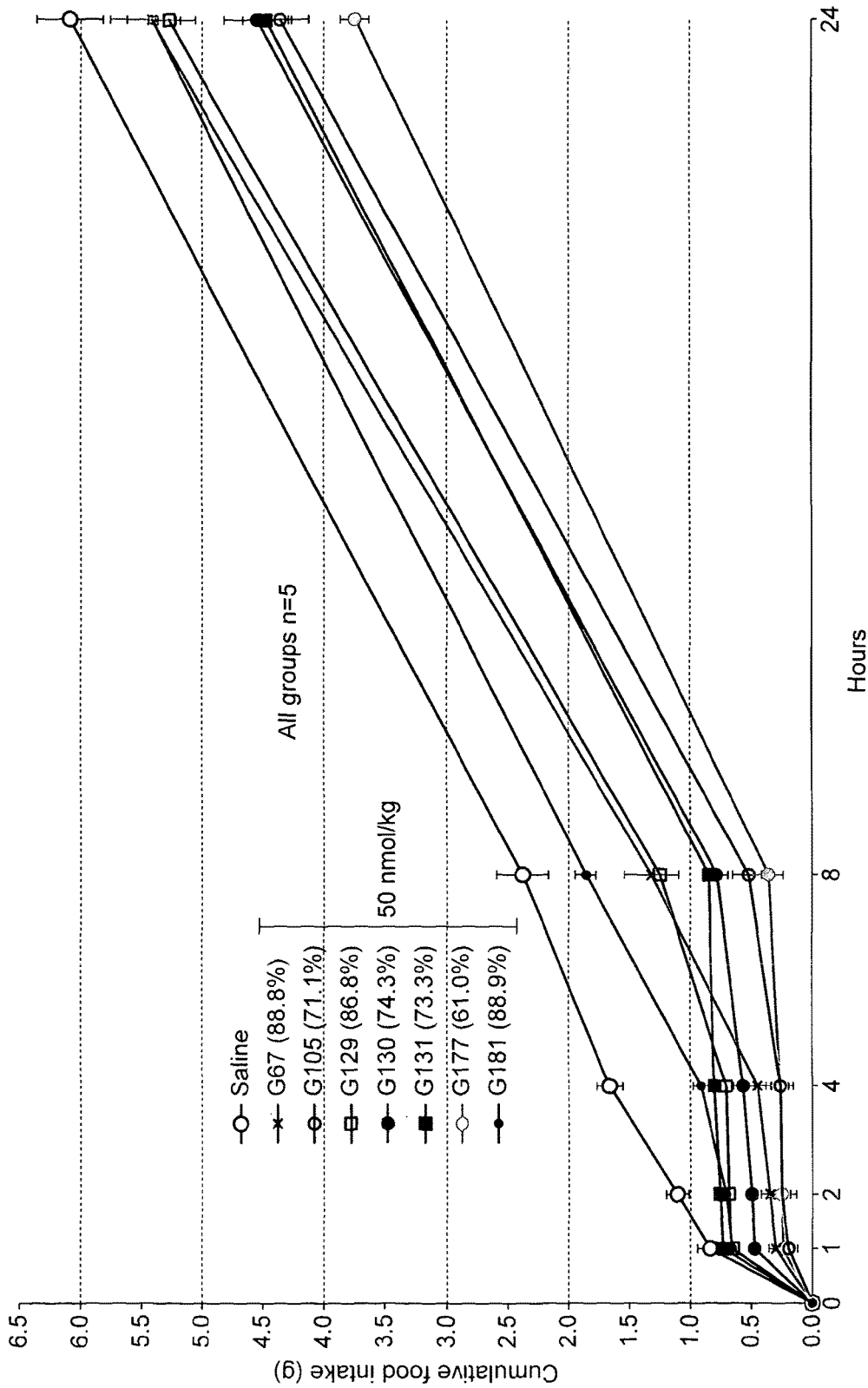
FIGS. 2 to 11 show more detailed food intake data for selected example compounds.
Figure 3:
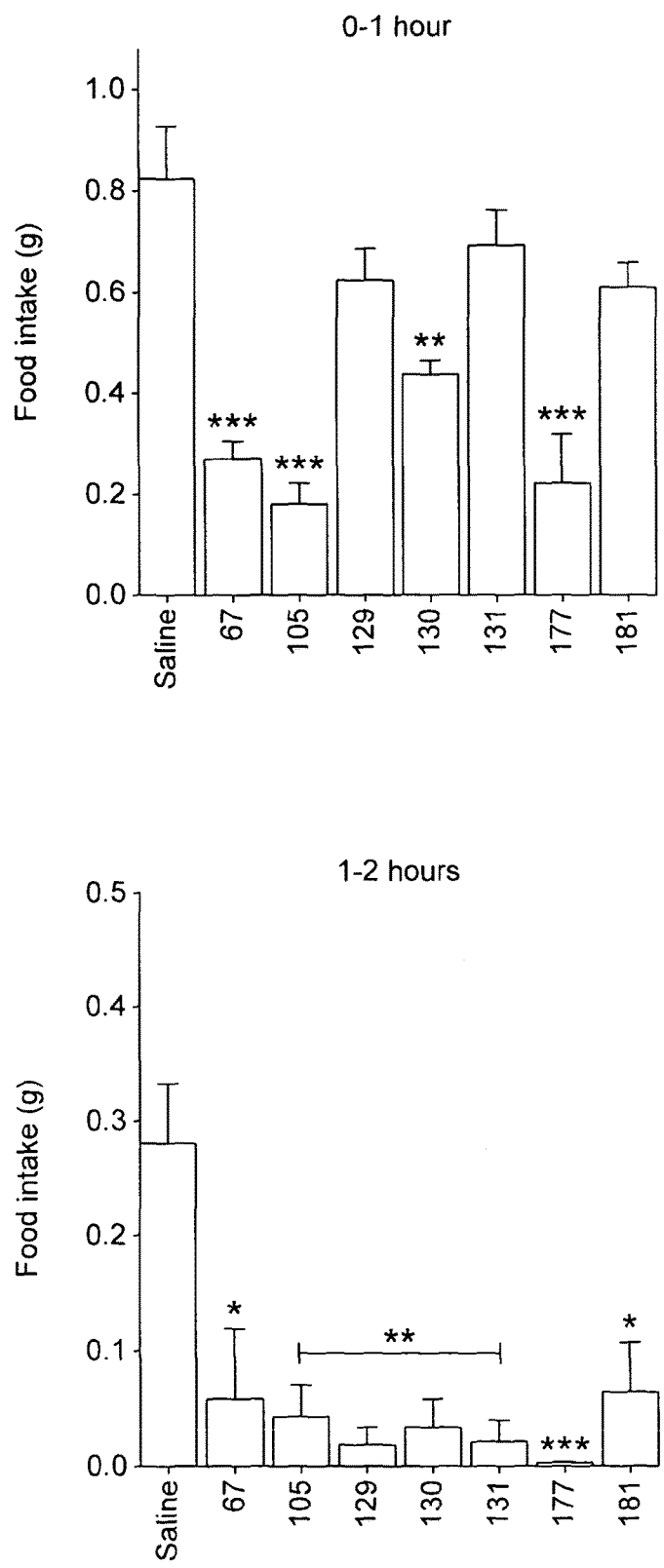
Figure 4:
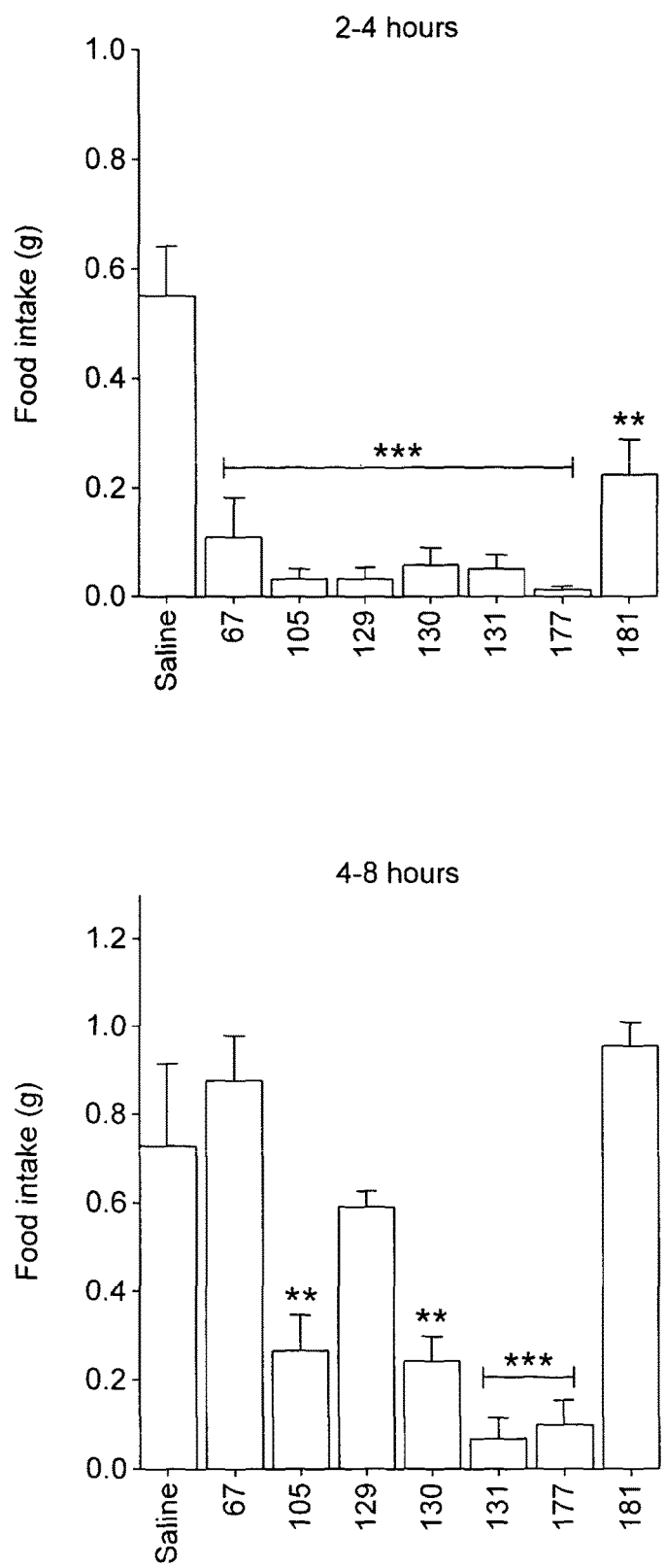
Figure 5:
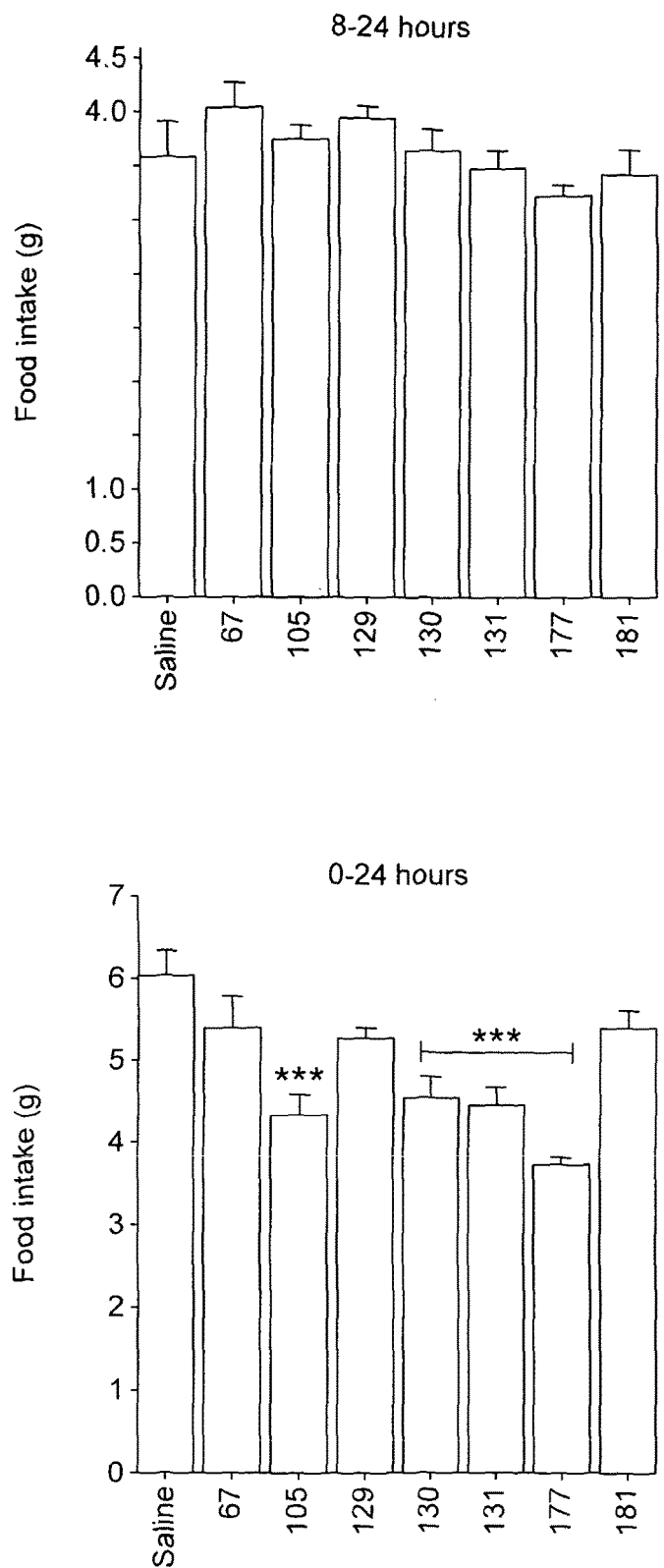

The amino acid sequences listed in the application are shown using standard letter abbreviations for amino acids. The specific sequences given in FIG. 1, FIG. 6 and the Examples relate to specific preferred embodiments of the invention. "AIB" is the abbreviation used for an α-amino isobutyric acid residue. Specific compounds are referred to herein by a numeric identifier/compound no. (i.e. compound 285, peptide 285). On occasion that numeric identifier may have a "G" suffix (i.e. compound G285). The G suffix serves solely to distinguish the subject matter of this application from the Applicant's other projects. The G suffix does not signify anything else and numeric identifiers with and without the suffix refer to the same compound and may be used interchangeably.

6. DEFINITIONS

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity (which is sometimes referred to as being "overweight" rather than obesity) corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J Clin. Nutr.* 45:1035-47, 1987). Ideal body weight will vary among species and individuals based on height, body build, bone structure, and sex.

Cardioprotection refers to the protection of cardiac cells (and especially the myocardial cells) from apoptosis, necrotic cell death or degeneration (loss of function). Cardioprotection is most often required following myocardial infarction, but may also be used in subjects suffering from ischemic heart disease (for example angina)

Conservative substitutions: The replacement of an amino acid residue by another, biologically similar residue in a polypeptide. The term "conservative variation" also includes the use of a substituted amino acid, i.e. an amino acid with one or more atoms replaced with another atom or group, in place of a parent amino acid provided that the polypeptide retains its activity or provided that antibodies raised to the substituted polypeptide also immunoreact with the unsubstituted polypeptide Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Energy Metabolism: The body has to expend a certain amount of energy to maintain normal metabolism. In civilized man this is often set at about 2,800 Calories daily. If food consumption does not provide this, weight loss results. However, energy metabolism is also regulated and, for example, administration of glucagon is thought to increase the metabolic rate so that a greater food intake is required to achieve energy balance and maintain weight. Thus, if food intake is maintained at the usual level, but energy metabolism is increased, weight loss will result. Reduction of food intake is normally thought to cause a decrease of energy metabolism which may allow the body to maintain weight in spite of the reduction of food intake. An agent which enhanced energy metabolism and reduced food intake would thus be likely to produce a much greater loss of body fat stores and weight.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

GLP1: Glucagon-like peptide 1 (GLP1) is derived from the transcription product of the proglucagon gene. The biologically active forms of GLP1 are truncated forms known as GLP1$_{(7-37)}$ and GLP1$_{(7-36)}$-NH$_2$.

```
The sequence of human GLP1(7-36)-HN2 is
                                        [SEQ ID NO 2]
His-Ala-Glu-Gly-Thr-Phe-Thr-Ser-Asp-Val-Ser-Ser- Tyr-Leu-Glu-Gly-Gln-Ala-Ala-Lys-Glu-Phe-Ile-Ala- Trp-Leu-Val-Lys-Gly-Arg-NH2.
```

Glucagon: Glucagon is a peptide derived from the proglucagon gene. It is a 29-amino acid polypeptide in humans and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu. [SEQ ID NO 1]

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is uncharged, a hyperpolarized cell requires a stronger excitatory stimulus to reach threshold.

Neuroprotection refers to the protection of neurons within the nervous system (preferably within the central nervous system) from apoptosis, necrotic cell death or degeneration (loss of function). Neuroprotective treatments, including those relating to various aspects of the present invention may be required following a brain injury (for example those following physical trauma or non-traumatic injury such as stroke, brain tumours, infection, poisoning, hypoxia, ischemia, encephalopathy or substance abuse). Neuroprotective treatments, including those relating to various aspects of the present invention may also be indicated in subjects having a chronic neurodegenerative disease such as Alzheimer's disease, Parkinson's disease Gehrig's disease or Huntington's disease.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 kg/m$^2$ to 29.9 k g/m$^2$ is overweight, while a BMI of 30 kg/m$^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Pam. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m$^2$ to 29.9 kg/m$^2$ PEGylated and PEGylation: the process of reacting a poly (alkylene glycol), preferably an activated poly(alkylene glycol) to form a covalent bond. A facilitator may be used, for example an amino acid, e.g. lysine. Although "PEGylation" is often carried out using poly(ethylene glycol) or derivatives thereof, such as methoxy poly(ethylene glycol), the term is not limited herein to the use of methoxy poly (ethylene glycol) but also includes the use of any other useful poly(alkylene glycol), for example poly(propylene glycol).

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focussing which is an electrophoretic method that utilises a pH gradient contained within a polyacrylamide gel.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH 4 and pH 10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure.

7. DETAILED DESCRIPTION

A first aspect of the invention provides a compound that is a peptide having a sequence represented by formula I $$A-B \qquad (I)$$

wherein A represents a region of the peptide having a sequence His1-Xaa2-Gln3-Gly4-Thr5-Phe6-Thr7-Ser8-Asp9-Xaa10-Ser11-Xaa12-Tyr13-Leu14-Xaa15-Xaa16-Xaa17-Xaa18-Xaa19-Xaa20-Xaa21-Phe22-Xaa23-Xaa24-Xaa25-Leu26-Xaa27-Xaa28-Xaa29;

wherein B is absent, —NH$_2$ or a region of the peptide having a sequence selected from:
  a) Arg30;
  b) Gly30;
  c) Arg30-NH$_2$;
  d) Gly30-NH$_2$;
  e) Gly30-Pro31-Ser32-Ser33-Gly34-Ala35-Pro36-Pro37-Pro38-Ser39;
  f) Gly30-Pro31-Ser32-Ser33-Gly34-Ala35-Pro36-Pro37-Pro38-Ser39-NH$_2$;
  g) His30-NH$_2$;
  h) Gly30-Pro31;
  i) Gly30-Tyr31-Tyr32-Tyr33;
  j) Arg30-Pro31-Ser32-Ser33-Gly34;
  k) His30;
  l) Gly30-His31;

m) His30-His31;
n) His30-Pro31;
o) Gly30-Pro31-NH$_2$;
p) Gly30-His31-NH$_2$;
q) His30-Pro31-NH$_2$;
r) His30-His31-NH$_2$; and
s) Lys30-His31, wherein —NH$_2$ represents C-terminal amidation of the peptide;

wherein Xaa2 is Ser2, Gly2 or an α-aminoisobutyric acid residue;

Xaa10 is Tyr10, Leu10 or Val10;
Xaa12 is Lys12, His12 or Arg12;
Xaa15 is Asp15, Asn15, Gln15, Glu15, Lys15 or His15;
Xaa16 is Ser16, Glu16, Gln16 or Gly16;
Xaa17 is Glu17, Gln17, Arg17, Ser17 or Lys17;
Xaa18 is Ala18, Ile18, His18 or Arg18;
Xaa19 is Ala19, His19 or Val19;
Xaa20 is Lys20, Arg20, His20 or Gln20;
Xaa21 is Glu21, Tyr21, Leu21, His21 or Lys21;
Xaa23 is Ile23, His23 or Val23;
Xaa24 is Glu24 or Gln24;
Xaa25 is Trp25, His25, Lys25, Tyr25 or Leu25;
Xaa27 is Val27, Met27, Lys27, His27 or Leu27;
Xaa28 is Lys28, His28 or Asn28;
Xaa29 is Gly29, Thr29, His29 or Arg29;

or a compound that is a variant and/or derivative of said peptide; or a salt and/or solvate of said peptide or said compound, with the proviso that at least one of the following criteria apply:

t) an α-aminoisobutyric acid residue is present at position 2 of the peptide sequence;
u) Val10 is present at position 10 of the peptide sequence;
v) Ser17 is present at position 17 of the peptide sequence;
w) Ile18 is present at position 18 of the peptide sequence;
x) His25 is present at position 25 of the peptide sequence;
y) Lys25 is present at position 25 of the peptide sequence;
z) Leu27 is present at position 27 of the peptide sequence;
aa) Val 27 is present at position 27 of the peptide sequence;
ab) B is absent;
ac) B is —NH$_2$;
ad) B is Gly30-Pro31-Ser32-Ser33-Gly34-Ala35-Pro36-Pro37-Pro38-Ser39;
ae) B is Gly30-Pro31-Ser32-Ser33-Gly34-Ala35-Pro36-Pro37-Pro38-Ser39-NH$_2$;
and/or
af) B is His30-NH$_2$.

According to certain embodiments at least, 1, 2, 3, 4, 5, 6, 7, 8, 9, 10, 11, 12, 13, 14 or 15 of the following criteria A to O apply to the compounds of Formula (I):

A, Xaa2 is Ser2.
B, Xaa10 is Tyr10.
C, Xaa12 is Lys12 or His12.
D, Xaa15 is Asp15, Gln15, Lys15, His15, or Glu15.
E, Xaa16 is Ser16 or Glu16.
F, Xaa17 is Glu17 or Gln17.
G, Xaa18-Xaa19-Xaa20 is Ala18-Val19-His20, Ala18-Val19-Lys20 or Ala18-Val19-Arg20.
H, Xaa21 is His21 or Leu21.
I, Xaa23 is Ile23.
J, Xaa24 is Glu24 or Gln24.
K, Xaa25 is Trp25.
L, Xaa27 is Lys27, Leu27 or Val27.
M, Xaa28 is Asn28.
N, Xaa29 is Thr29, His29 or Gly29
O. B is —NH$_2$ or a region of the peptide having a sequence selected from Gly30, His30, Gly30-NH$_2$, His30-NH$_2$, His30-Pro31, Gly30-Pro31, Gly30-His31, His30-His31, His30-Pro31-NH$_2$, Gly30-Pro31-NH$_2$, Gly30-His31-NH$_2$ or His30-His31-NH$_2$.

All combinations of the features listed above are contemplated, including:
A+B, A+C, A+D, A+E, A+F, A+G, A+H, A+I, A+J, A+K, A+L, A+M, A+N, A+O,
B+C, B+D, B+E, B+F, B+G, B+H, B+I, B+J, B+K, B+L, B+M, B+N, B+O,
C+D, C+E, C+F, C+G, C+H, C+I, C+J, C+K, C+L, C+M, C+N, C+O,
D+E, D+F, D+G, D+H, D+I, D+J, D+K, D+L, D+M, D+N, D+O
E+F, E+G, E+H, E+I, E+J, E+K, E+L, E+M, E+N, E+O
F+G, F+H, F+I, F+J, F+K, F+L, F+M, F+N, F+O
G+H, G+I, G+J, G+K, G+L, G+M, G+N, G+O
J+K, J+L, J+M, J+N, J+O
K+L, K+M, K+N, K+O
L+M, L+N, L+O,
M_N, M+O and
N+O, optionally in combination with a third, fourth, fifth, sixth, seventh, eight, ninth, tenth, eleventh, twelfth, thirteenth, fourteenth or fifteenth feature A to O.

According to certain embodiments of the compound of Formula (I), Xaa2 is Ser2 or an α-aminoisobutyric acid residue.

According to certain embodiments of the compound of Formula (I), Xaa24 is Glu24 or Gln24.

According to certain embodiments of the compound of Formula (I), Xaa2 is Ser2, Xaa10 is Tyr10, Xaa18 is Ala18, Xaa19 is Val19, Xaa23 is Ile23, Xaa24 is Glu24, Xaa25 is Trp25, and Xaa28 is Asn28.

According to certain embodiments of the compound of formula (I), Xaa2 is Ser2, Xaa10 is Tyr10, Xaa12 is Lys12 or His12, Xaa15 is Asp15, Gln15, Lys15, His15, or Glu15, and Xaa16 is Ser16 or Glu16. Preferably, Xaa2 is Ser2, Xaa10 is Tyr10, Xaa12 is Lys12 or His12, Xaa15 is Asp15 or Glu15, and Xaa16 is Ser16 or Glu16. In certain embodiments, Xaa2 is Ser2, Xaa10 is Tyr10, Xaa12 is Lys12, Xaa15 is Asp15, and Xaa16 is Ser16. In certain embodiments, Xaa2 is Ser2, Xaa10 is Tyr10, Xaa12 is His12, Xaa15 is Asp15, and Xaa16 is Ser16. In certain embodiments, Xaa2 is Ser2, Xaa10 is Tyr10, Xaa12 is Lys12, Xaa15 is Glu15, and Xaa16 is Ser16. In certain embodiments, Xaa2 is Ser2, Xaa10 is Tyr10, Xaa12 is His12, Xaa15 is Glu15, and Xaa16 is Ser16. In certain embodiments, Xaa2 is Ser2, Xaa10 is Tyr10, Xaa12 is Lys12, Xaa15 is Asp15, and Xaa16 is Glu16. In certain embodiments, Xaa2 is Ser2, Xaa10 is Tyr10, Xaa12 is His12, Xaa15 is Asp15, and Xaa16 is Glu16. In certain embodiments, Xaa2 is Ser2, Xaa10 is Tyr10, Xaa12 is Lys12, Xaa15 is Glu15, and Xaa16 is Glu16. In certain embodiments, Xaa2 is Ser2, Xaa10 is Tyr10, Xaa12 is His12, Xaa15 is Glu15, and Xaa16 is Glu16.

According to certain embodiments of the compound of Formula (I) Xaa17 is Glu17 or Gln17, Xaa18 is Ala18, Xaa19 is Val19, Xaa20 is His20, Arg20 or Lys20, and Xaa21 is Leu21 or His21. In certain embodiments, Xaa17 is Glu17, Xaa18 is Ala18, Xaa19 is Val19, Xaa20 is His20, and Xaa21 is Leu21. In certain embodiments, Xaa17 is Gln17, Xaa18 is Ala18, Xaa19 is Val19, Xaa20 is His20, and Xaa21 is Leu21. In certain embodiments, Xaa17 is Glu17, Xaa18 is Ala18, Xaa19 is Val19, Xaa20 is His20, and Xaa21 is His21. In certain embodiments, Xaa17 is Gln17, Xaa18 is Ala18, Xaa19 is Val19, Xaa20 is His20, and Xaa21 is His21. In certain embodiments, Xaa17 is Glu17, Xaa18 is Ala18, Xaa19 is Val19, Xaa20 is Arg20, and Xaa21 is Leu21. In certain embodiments, Xaa17 is Gln17, Xaa18 is Ala18, Xaa19 is Val19, Xaa20 is Arg20, and Xaa21 is Leu21. In certain embodiments, Xaa17 is Glu17, Xaa18 is Ala18, Xaa19 is Val19, Xaa20 is Arg20, and Xaa21 is His21. In certain embodiments, Xaa17 is Gln17, Xaa18 is Ala18, Xaa19 is Val19, Xaa20 is Arg20, and Xaa21 is His21. In certain embodiments, Xaa17 is Glu17, Xaa18 is Ala18, Xaa19 is Val19, Xaa20 is Lys20, and Xaa21 is Leu21. In certain embodiments, Xaa17 is Gln17, Xaa18 is Ala18, Xaa19 is Val19, Xaa20 is Lys20, and Xaa21 is Leu21. In certain embodiments, Xaa17 is Glu17, Xaa18 is Ala18, Xaa19 is Val19, Xaa20 is Lys20, and Xaa21 is His21. In certain embodiments, Xaa17 is Gln17, Xaa18 is Ala18, Xaa19 is Val19, Xaa20 is Lys20, and Xaa21 is His21.

According to certain embodiments of the compound of Formula (I), Xaa23 is Ile23, Xaa24 is Glu24 or Gln24, Xaa25 is Trp25, Xaa27 is Lys27, Leu27 or Val27, Xaa28 is Asn28 and Xaa29 is Thr29, His29 or Gly29. Preferably, Xaa23 is Ile23, Xaa24 is Glu24, Xaa25 is Trp25, Xaa27 is Leu27 or Lys27, Xaa28 is Asn28, and Xaa29 is Gly29 or Thr29. In certain embodiments, Xaa23 is Ile23, Xaa24 is Glu24, Xaa25 is Trp25, Xaa27 is Leu27, Xaa28 is Asn28, and Xaa29 is Gly29. In certain embodiments, Xaa23 is Ile23, Xaa24 is Glu24, Xaa25 is Trp25, Xaa27 is Lys27, Xaa28 is Asn28, and Xaa29 is Gly29. In certain embodiments, Xaa23 is Ile23, Xaa24 is Glu24, Xaa25 is Trp25, Xaa27 is Leu27, Xaa28 is Asn28, and Xaa29 is Thr29. In certain embodiments, Xaa23 is Ile23, Xaa24 is Glu24, Xaa25 is Trp25, Xaa27 is Lys27, Xaa28 is Asn28, and Xaa29 is Thr29.

In certain embodiments of the compound of Formula (I), B is —NH$_2$ or a region of the peptide having the sequence Gly30-Pro31, Gly30-His31, His30-NH$_2$, Gly30-His31-NH$_2$, or His30-His31. In certain embodiments, B is —NH$_2$ or a region of the peptide having a sequence selected from Gly30-Pro31, Gly30-His31, His30-NH$_2$ or His30-His31.

According to certain preferred embodiments of the compound of Formula (I),
Xaa2 is Ser2 or an α-aminoisobutyric acid residue;
Xaa10 is Tyr10 or Val10;
Xaa12 is Lys12 or His12;
Xaa15 is Asp15, Glu15, Gln15, Lys15 or His15;
Xaa16 is Ser16, Glu16 or Gly16;
Xaa17 is Glu17, Gln17, Arg17, Ser17 or Lys17;
Xaa18 to Xaa20 is Ala18-Val19-Arg20, Ala18-Val19-Lys20 or Ala18-Val19-His20;
Xaa21 is Glu21, Tyr21, Leu21, or His21;
Xaa23 is Ile23 or Val23;
Xaa24 is Glu24 or Gln24;
Xaa25 is Trp25 or Lys25;
Xaa28 is Lys28 or Asn28; and
Xaa29 is Gly29, His29 or Thr29;
and B is absent, —NH$_2$ or a region of the peptide having a sequence selected from: Arg30, Gly30, His30, Arg30-NH$_2$, Gly30-NH$_2$, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, His30-NH$_2$, Gly30-Pro31, Gly30-His31, His30-Pro31, His30-His31, Gly30-Pro31-NH$_2$, Gly30-His31-NH$_2$, His30-Pro31-NH$_2$, and His30-His31-NH$_2$.

According to certain preferred embodiments of the compounds of Formula (I),
Xaa2 is Ser2;
Xaa10 is Tyr10 or Val10;
Xaa12 is Lys12 or His12;
Xaa15 is Asp15 or Glu15;
Xaa16 is Gly16 or Ser16;
Xaa17 is Gln17, Glu17, Arg17 or Lys17;
Xaa18 to Xaa20 is Ala18-Val19-Arg20, Ala18-Val19-Lys20 or Ala18-Val19-His20;
Xaa21 is Leu21 or His21;
Xaa23 is Ile23;
Xaa24 is Glu24 or Gln24;
Xaa25 is Trp25 or Lys25;
Xaa27 is Leu27, Lys27, Met 27 or Val27;
Xaa28 is Asn28; and
Xaa29 is Thr29 or Gly29;
and B is absent, —NH$_2$ or a region of the peptide having a sequence selected from: Arg30, Gly30, Arg30-NH$_2$, Gly30-Pro31-Ser32-Ser33-Gly34-Ala35-Pro36-Pro37-Pro38-Ser39, and Gly30-Pro31-Ser32-Ser33-Gly34-Ala35-Pro36-Pro37-Pro38-Ser39-NH$_2$,
with the proviso that at least one of the following criteria apply:
a) an α-aminoisobutyric acid residue is present at position 2 of the peptide sequence
b) Val10 is present at position 10 of the peptide sequence.
c) Ser17 is present at position 17 of the peptide sequence.
d) Ile18 is present at position 18 of the peptide sequence,
e) His25 is present at position 25 of the peptide sequence,
f) Lys25 is present at position 25 of the peptide sequence,
g) Leu27 is present at position 27 of the peptide sequence.
h) Val 27 is present at position 27 of the peptide sequence,
i) B is absent,
j) B is —NH$_2$,
k) B is Gly30-Pro31-Ser32-Ser33-Gly34-Ala35-Pro36-Pro37-Pro38-Ser39, or
l) B is Gly30-Pro31-Ser32-Ser33-Gly34-Ala35-Pro36-Pro37-Pro38-Ser39-NH$_2$.

According to certain preferred embodiments of the compounds of Formula (I),
Xaa2 is Ser2 or an α-aminoisobutyric acid residue;
Xaa10 is Tyr10 or Val10;
Xaa12 is Lys12;
Xaa15 is Asp15, Glu15, Gln15, Lys15, or His15;
Xaa16 is Ser16 or Gly16;
Xaa17 is Glu17, Gln17, Arg17, Ser17 or Lys17;
Xaa18-Xaa19-Xaa20 is Ala18-Val19-Arg20 or Ala18-Val19-His20;
Xaa21 is Glu21, Tyr21, Leu21, His21 or Asp21;
Xaa23 is Ile23 or Val23;
Xaa25 is Trp25 or Lys25;
Xaa27 is Val27, Met27 or Leu27;
Xaa28 is Lys28; and
Xaa29 is Gly29;
and B is absent, —NH$_2$ or a region of the peptide having a sequence selected from:
Arg30, Gly30, Arg30-NH$_2$, Gly30-NH$_2$, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, His30-NH$_2$, and Gly30-Pro31;
with the proviso that at least one of the following criteria apply:
a) an α-aminoisobutyric acid residue is present at position 2 of the peptide sequence;
b) Val10 is present at position 10 of the peptide sequence;
c) Ser17 is present at position 17 of the peptide sequence;
d) Lys25 is present at position 25 of the peptide sequence;
e) Leu27 is present at position 27 of the peptide sequence;

f) Val 27 is present at position 27 of the peptide sequence;
g) B is absent;
h) B is —NH$_2$;
i) B is Gly30-Pro31-Ser32-Ser33-Gly34-Ala35-Pro36-Pro37-Pro38-Ser39, and/or
j) B is Gly30-Pro31-Ser32-Ser33-Gly34-Ala35-Pro36-Pro37-Pro38-Ser39-NH$_2$.

According to certain preferred embodiments of the compounds of Formula (I),
Xaa2 is Ser2;
Xaa10 is Tyr10;
Xaa12 is Lys12 or His12;
Xaa15 is Asp15, Glu15, Gln15, Lys15 or His15;
Xaa16 is Ser16 or Glu16;
Xaa17 is Glu17 or Gln17;
Xaa18 to Xaa20 is Ala18-Val19-Arg20, Ala18-Val19-Lys20 or Ala18-Val19-His20;
Xaa21 is Leu21 or His21;
Xaa23 is Ile23;
Xaa24 is Glu24 or Gln24;
Xaa25 is Trp25;
Xaa27 is Lys27, Leu27 or Val27;
Xaa28 is Asn28; and
Xaa29 is Gly29, His29 or Thr29;
and B is —NH$_2$ or a region of the peptide having a sequence selected from Gly30, His30, Gly30-NH$_2$, His30-NH$_2$, His30-Pro31, Gly30-Pro31, Gly30-His31, His30-His31, His30-Pro31-NH$_2$, Gly30-Pro31-NH$_2$, Gly30-His31-NH$_2$ or His30-His31-NH$_2$.

According to certain preferred embodiments of the compounds of Formula (I),
Xaa2 is Ser2;
Xaa10 is Tyr10;
Xaa12 is Lys12 or His12;
Xaa15 is Asp15 or Glu15;
Xaa16 is Ser16 or Glu16;
Xaa17 is Glu17 or Gln17;
Xaa18 to Xaa20 is Ala18-Val19-Arg20, Ala18-Val19-Lys20 or Ala18-Val19-His20;
Xaa21 is Leu21 or His21;
Xaa23 is Ile23;
Xaa24 is Glu24;
Xaa25 is Trp25;
Xaa27 is Lys27 or Leu27;
Xaa28 is Asn28; and
Xaa29 is Gly29 or Thr29;
and B is —NH$_2$ or a region of the peptide having a sequence selected from His30-NH$_2$, Gly30-Pro31, Gly30-His31, and His30-His31.

According to a further aspect of the invention there is provided a compound that is a peptide in the sequence represented by formula IA:

A-B    (IA)

wherein A represents a region of the peptide having a sequence His1-Xaa2-Gln3-Gly4-Thr5-Phe6-Thr7-Ser8-Asp9-Xaa10-Ser11-Xaa12-Tyr13-Leu14-Xaa15-Xaa16-Xaa17-Xaa18-Xaa19-Xaa20-Xaa21-Phe22-Xaa23-Xaa24-Xaa25-Leu26-Xaa27-Xaa28-Xaa29;
wherein B is absent, —NH$_2$ or a region of the peptide having a sequence selected from:
a) Arg30
b) Gly30
c) Arg30-NH$_2$
d) Gly30-NH$_2$
e) Gly30-Pro31-Ser32-Ser33-Gly34-Ala35-Pro36-Pro37-Pro38-Ser39
f) Gly30-Pro31-Ser32-Ser33-Gly34-Ala35-Pro36-Pro37-Pro38-Ser39-NH$_2$
g) His30-NH$_2$ and
h) Gly30-Pro31 wherein —NH$_2$ represents C-terminal amidation of the peptide;
wherein Xaa2 is Ser2 or an α-aminoisobutyric acid residue,
Xaa10 is Tyr10 or Val10,
Xaa12 is Lys12, His12 or Arg12,
Xaa15 is Asp15, Asn15 or Glu15,
Xaa16 is Ser16, Glu16 or Gly16,
Xaa17 is Glu17, Gln17, Arg17, Ser17 or Lys17,
Xaa18 is Ala18, Ile18 or Arg18,
Xaa19 is Ala19 or Val19,
Xaa20 is Lys20, Arg20, His20 or Gln20,
Xaa21 is Glu21, Tyr21, Leu21 or His21;
Xaa23 is Ile23 or Val23,
Xaa24 is Glu24 or Gln24,
Xaa25 is Trp25, His25, Lys25, Tyr25 or Leu25,
Xaa27 is Val27, Met27, Lys27 or Leu27,
Xaa28 is Lys28 or Asn28,
Xaa29 is Gly29, Thr29 or Arg29;
or a compound that is a variant and/or derivative of said peptide; or a salt and/or solvate of said peptide or said compound
with the proviso that at least one of the following criteria apply:
a) an α-aminoisobutyric acid residue is present at position 2 of the peptide sequence
b) Val10 is present at position 10 of the peptide sequence.
c) Ser17 is present at position 17 of the peptide sequence.
d) Ile18 is present at position 18 of the peptide sequence,
e) His25 is present at position 25 of the peptide sequence,
f) Lys25 is present at position 25 of the peptide sequence,
g) Leu27 is present at position 27 of the peptide sequence.
h) Val 27 is present at position 27 of the peptide sequence,
i) B is absent,
j) B is —NH$_2$,
k) B is Gly30-Pro31-Ser32-Ser33-Gly34-Ala35-Pro36-Pro37-Pro38-Ser39, or
l) B is Gly30-Pro31-Ser32-Ser33-Gly34-Ala35-Pro36-Pro37-Pro38-Ser39-NH$_2$.

The compounds of the invention may be variant compounds of said peptide of formula (I) or (IA) wherein up to five specified amino acid residues are substituted by alternative amino acid residues.

A compound of the invention may be a variant of said peptide of formula (I) or (IA) wherein up to four specified amino acid residues are substituted by alternative residues.

A compound of the invention may be a variant of said peptide of formula (I) or (IA) wherein up to three specified amino acid residues are substituted by alternative amino acid residues.

A compound of the invention may be a variant of said peptide of formula (I) or (IA) wherein up to two specified amino acid residues are substituted by alternative amino acid residues.

A compound of the invention may be a variant of said peptide of formula (I) or (IA) wherein up to one specified amino acid residue is substituted by an alternative amino acid residue.

According to certain embodiments the compounds of the invention are not variant compounds, that is to say they are compounds of Formula (I) or (IA) with no further residue changes or derivatives thereof.

According to certain embodiments the compounds of the invention are neither variant compounds nor derivative compounds, that is to say they are compounds of Formula (I) or (IA) with no further residue changes or derivatisation.

According to certain embodiments at least, 1, 2, 3, 4, 5, 6, 7, 8, 9, or 10 of the following criteria A to J apply to the compounds of Formula (I) or (IA):
A, Xaa2 is an aminoisobutyric acid residue.
B, Xaa12 is Lys12.
C, Xaa16 is Ser16 or Gly16.
D, Xaa18-Xaa19-Xaa20 is Ala18-Val19-Arg20.
E, Xaa24 is Glu24.
F, Xaa25 is Trp25 or Lys25.
G, Xaa27 is Val27, Met27 or Leu27.
H, Xaa28 is Lys28.
I, Xaa29 is Gly29
J, B is absent —NH$_2$ or a region of the peptide having the sequence Arg30 or Arg30-NH$_2$.

According to certain preferred embodiments of the compounds of Formula (I) or (IA), Xaa16 is Ser16.

According to certain embodiments of the compounds of Formula (I) or (IA), the sequence of Xaa1 to Xaa16 may be mostly or wholly based on the sequence His1-Ser2-Gln3-Gly4-Thr5-Phe6-Thr7-Ser8-Asp9-Tyr10-Ser11-Lys12-Tyr13-Leu14-Asp15-Ser16 with Ser2 optionally replaced by an α-aminoisobutyric acid residue and one or more charged residues replaced by corresponding uncharged residues to lower the total number of charged residues in the molecule. For example Asp15 may optionally be replaced with a neutral amino acid residue for example Asn15. Additionally Ser16 may optionally be replaced by Gly16 and/or Lys12 replaced by Arg12.

According to certain embodiments of the compounds of Formula (I) or (IA), the sequence Xaa17 to Xaa24 may be mostly or wholly based on the residues Glu17-Ala18-Val19-Arg20-Leu21-Phe22-Ile23-Glu24 with one or more charged residues replaced by corresponding uncharged residues. For example Glu17 and Glu24 may be replaced by Gln17 and/or Gln24, and Arg20 may be replaced by Gln20 or His20. Alternatively, Glu17 may be replaced by Arg17 and Ala18 may be replaced by Arg18. Additionally Leu21 may be replaced by Tyr21.

According to certain embodiments of the compounds of Formula (I) or (IA), the sequence Xaa25 to Xaa29 may be:
Tyr25-Leu26-Leu27-Asn28-Thr29,
Tyr25-Leu26-Met27-Asn28-Thr29,
Trp25-Leu26-Leu27-Asn28-Thr29,
Trp25-Leu26-Met27-Asn28-Thr29,
Leu25-Leu26-Leu27-Asn28-Thr29, or
Leu25-Leu26-Met27-Asn28-Thr29.

According to certain embodiments of the compounds of Formula (I) or (IA), the sequence contains at least 3 His residues. Preferred positions for these residues include positions 12, 20 and 30.

According to certain embodiments of the compounds of Formula (I) or (IA), the region B is absent, —NH$_2$, Arg30, Gly30, His30, Arg30-NH$_2$, Gly30-NH$_2$ or His30-NH$_2$. Preferably region B is —NH$_2$, Arg30-NH$_2$, Gly30-NH$_2$ or His30-NH$_2$.

According to certain embodiments of the compounds of Formula (I) or (IA), one or more of the following features are preferred:
A, Xaa2 is Ser2
B, Xaa10 is Tyr10 or Val10
C, Xaa12 is Lys12 or His12
D, Xaa15 is Aps15 or Glu15
E, Xaa16 is Gly16 or Ser16
F, Xaa17 is Gln17, Glu17, Arg17 or Lys17
G, Xaa18 to Xaa20 is Ala18-Val19-Arg20, Ala18-Val19-Lys20 or Ala18-Val19-His20,
H, Xaa21 is Leu21 or His21
I, Xaa23 is Ile23
J, Xaa24 is Glu24 or Gln24
K, Xaa25 is Trp25 or Lys25
L, Xaa27 is Leu27, Lys27, Met 27 or Val27
M, Xaa28 is Asn 28
N, Xaa29 is Thr29 or Gly29
O, B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent.

According to certain embodiments of the compounds of Formula (I) or (IA), one or more of the following features are preferred:
A, Xaa2 is Ser2
B, Xaa10 is Tyr10
C, Xaa12 is Lys12 or His12
D, Xaa15 is Aps15 or Glu15
E, Xaa16 is Gly16 or Ser16
F, Xaa17 is Gln17, Glu17, Arg17 or Lys17
G, Xaa18 to Xaa20 is Ala18-Val19-Arg20, Ala18-Val19-Lys20 or Ala18-Val19-His20
H, Xaa21 is Leu21 or His21
I, Xaa23 is Ile23
J, Xaa24 is Glu24 or Gln24
K, Xaa25 is Trp25
L, Xaa27 is Leu27 or Val27
M, Xaa28 is Asn 28
N, Xaa29 is Thr29 or Gly29
O, B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent All combinations of the features listed above are contemplated, including:
A+B, A+C, A+D, A+E, A+F, A+G, A+H, A+I, A+J, A+K, A+L, A+M, A+N, A+O,
B+C, B+D, B+E, B+F, B+G, B+H, B+I, B+J, B+K, B+L, B+M, B+N, B+O,
C+D, C+E, C+F, C+G, C+H, C+I, C+J, C+K, C+L, C+M, C+N, C+O,
D+E, D+F, D+G, D+H, D+I, D+J, D+K, D+L, D+M, D+N, D+O
E+F, E+G, E+H, E+I, E+J, E+K, E+L, E+M, E+N, E+O
F+G, F+H, F+I, F+J, F+K, F+L, F+M, F+N, F+O
G+H, G+I, G+J, G+K, G+L, G+M, G+N, G+O
J+K, J+L, J+M, J+N, J+O
K+L, K+M, K+N, K+O
L+M, L+N, L+O, and
N+O, in combination with a third, fourth, fifth, sixth, seventh, eight, ninth, tenth, eleventh, twelfth, thirtieth, fourteenth or fifteenth feature A to O.

According to certain embodiments of the compounds of Formula (I) or (IA), all of the following features apply:
Xaa2 is Ser2
Xaa10 is Tyr10 or Val10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24

Xaa25 is Trp25 or Lys25
Xaa27 is Leu27, Lys27, Met 27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39-Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29

B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12 or His12
Xaa15 is Asp15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA) all of the following features apply:
Xaa2 is Ser2
Xaa10 is Tyr10
Xaa12 is Lys12 or His12
Xaa15 is Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12 or His12
Xaa15 is Asp15 or Glu15
Xaa16 is Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29

B is Arg30-NH$_2$, Arg30, —NH$_2$, Gly30, Gly30-Pro31-Ser32-Ser33-Gly34-Ala35-Pro36-Pro37-Pro38-Ser39-Gly30-Pro31-Ser32-Ser33-Gly34-Ala35-Pro36-Pro37-Pro38-Ser39-NH$_2$, or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Glu17 or Gln17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39-Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Lys20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:

Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$, or absent According to certain embodiments of the compounds of Formula (I) or (IA), all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA), all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16

Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Gln24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24
Xaa25 is Trp25
Xaa27 is Leu27 or Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Val27
Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27

Xaa28 is Asn 28
Xaa29 is Thr29 or Gly29
B is Arg30-NH$_2$, Arg30, —NH$_2$, Gly30, Gly30-Pro31-Ser32-Ser33-Gly34-Ala35-Pro36-Pro37-Pro38-Ser39, Gly30-Pro31-Ser32-Ser33-Gly34-Ala35-Pro36-Pro37-Pro38-Ser39-NH$_2$ or absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is, NH$_2$, According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is absent According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is, Gly30

According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Gly30-Pro31-Ser32-Ser33-Gly34-Ala35-Pro36-Pro37-Pro38-Ser39.

According to certain embodiments of the compounds of Formula (I) or (IA) all of the following features apply:
Xaa2 is Ser2
Xaa10 is Tyr10
Xaa12 is Lys12 or His12
Xaa15 is Asp15 or Glu15
Xaa16 is Gly16 or Ser16
Xaa17 is Gln17, Glu17, Arg17 or Lys17
Xaa18 to Xaa20 is Ala18-Val19-Arg20, Ala18-Val19-Lys20 or Ala18-Val19-His20
Xaa21 is Leu21 or His21
Xaa23 is Ile23
Xaa24 is Glu24 or Gln24
Xaa25 is Trp25
Xaa27 is Leu27 or Val27
Xaa28 is Asn 28
Xaa29 is Thr29 or Gly29
B is Gly30-Pro31-Ser32-Ser33-Gly34-Ala35-Pro36-Pro37-Pro38-Ser39-NH2.

According to certain embodiments, the compounds of the invention may be the compounds specifically disclosed in FIG. 1 or any of the Examples.

Compounds of the invention may be produced by recombinant methods well known in the art or alternatively they may be produced by synthetic methods, again well known in the art.

Activities:

Compounds of the invention are preferably active at both the human glucagon and GLP1 receptors. This may be assessed by an in vitro or cellular binding assay or by a reporter assay. Preferably, the compounds show binding to human glucagon receptors and human GLP1 receptors with affinity of at least $1/20,000^{th}$, $1/10,000^{th}$, $1/5,000^{th}$, $1/1,1000^{th}$ or $1/400^{th}$ of the respective affinity of human glucagon and human GLP. More preferably, the compounds show affinity similar to that of human glucagon and human GLP. It is a surprising discovery that binding to the receptors does not need to be as strong as that of the natural ligands. For example, compound G57 has $1/204^{th}$ of the affinity for human GLP1 receptor as does human GLP1 and yet shows acceptable activity in respect of modulation of food intake.

Methods of assessing activity of compounds at the GLP1 and glucagon receptors are well known. For example, Mukai et al (2009) Biochem. Biophys. Re. Comm. 28993):523-6 discloses a method of assaying for GLP1 receptor binding and Thermo Scientific (Lafayette, Colo., USA) market an in vitro glucagon receptor assay.

The activity at both receptors is preferably longer lasting in vivo than, respectively, native glucagon and GLP1.

The invention also provides a compound of the invention for use as a medicament.

The invention also provides a pharmaceutical composition comprising a compound of the invention together with a pharmaceutically acceptable carrier and optionally other therapeutic ingredients. According to certain embodiments the pharmaceutical composition is present in a syringe or other administration device for subcutaneous administration to humans.

The invention also provides a method of treating or preventing a disease or disorder or other non-desired physiological state comprising subcutaneous administration of a compound of the invention or of a pharmaceutical composition of the invention.

According to certain embodiments the disease or disorder or other non-desired physiological state is obesity or diabetes. According to other embodiments it may be being the physiological state of being overweight. According to other embodiments it may be being of a non-desired weight despite not being obese or overweight.

According to other embodiments the disease or disorder or other non-desired physiological state is neurodegeneration. Such neurodegeneration may be caused by apoptosis, necrosis or loss of function of neuronal cells, preferably in the CNS. Neurodegeneration treated or prevented may be that following a brain injury (for example following physical trauma or following a non-traumatic injury such a stroke, tumour, hypoxia, poisoning, infection, ischemia, encephalopathy or substance abuse). Alternatively or additionally, neurodegeneration may be prevented or treated in a subject having (or diagnosed as having a predisposition to) a chronic neurodegenerative disease such as Alzheimer's Parkinson, Gehrig's or Huntington's disease. In such circumstances the treatment would be regarded as neuroprotective. According to certain preferred embodiments, the treatment is neuroprotective following cerebral ischemic or neuroprotective in a subject having a neurodegenerative disease or diagnosed as having a predisposition to a neurodegenerative disease.

According to other embodiments the disease or disorder or other non-desired physiological state is cardiac degeneration (in particular myocardial degeneration by apoptosis, necrosis or loss of function of myocardial cells). According to certain preferred embodiments that treatment is protective of myocardial function following myocardiac infarction.

The invention also provides use of a compound of the invention or a pharmaceutical composition of the invention for use in the reduction of appetite in the subject for use in the reduction of food intake in the subject, for use in the reduction of calorie intake in the subject, for use in increasing energy expenditure in a subject, or for use in enhancing insulin release, for use in improving carbohydrate tolerance and/or improving carbohydrate metabolism in a subject. Such use may relate to treating subjects with a pre-diabetic state such as insulin insensitivity or pre-diabetes.

The invention also provides use of a compound of the invention or a pharmaceutical composition of the invention for use in the myocardial protecting in a subject following myocardial infarction or for use in neuroprotection in a subject following cerebral ischemia or stroke or for use in neuroprotection in a subject having a chronic neurodegenerative disease. Various features of neuroprotective or cardioprotective use of the compound or composition may be as outlined above in relation to methods of the invention.

The invention also provides a method for treating obesity or diabetes in a subject comprising administering to a subject compound of the invention or a pharmaceutical composition of the invention The subject may be overweight, obese or diabetic. Alternatively, the subject may be of normal weight (this includes but is not limited to subjects who were previously overweight or obese and who wish to prevent a return to an unhealthy weight). In some cases where the subject is of a normal weight aspects of the invention may relate to cosmetic treatment rather than to therapeutic treatment.

The invention also provides a method of neuroprotection or cardioprotection in a subject in need thereof comprising administering to a subject compound of the invention or a pharmaceutical composition of the invention In the case of neuroprotection the subject may have experienced previously a brain injury, stroke or other even causing cerebral ischemia. Alternatively, the subject may have or have been diagnosed with a predisposition to develop a chronic neurodegenerative disease. In the case of cardioprotection the subject may have experienced previously an event causing myocardial ischemia such as a myocardial infarction and angina.

According to certain embodiments the compound is to be administered parentally. According to other embodiments the compound is to be administered subcutaneously, intravenously, intramuscularly, intranasally, transdermally or sublingually. According to other embodiments the compound is to be administered orally.

The invention also provides use of a compound of the invention for the manufacture of a medicament for the treatment of obesity, diabetes or other non-desired physiological state.

The invention also provides use of a compound of the invention for the manufacture of a medicament for cardioprotection or neuroprotection of a subject who may be as described above in reference to other aspects of the invention.

The invention also provides use of a compound for the manufacture of a medicament for reduction of appetite in the subject or the reduction of food intake in a subject, for the reduction of calorie intake in a subject, or for increasing energy expenditure in a subject, or for use in enhancing insulin release, for use in improving carbohydrate tolerance and/or improving carbohydrate metabolism in a subject. Such use may relate to treating subjects with a pre-diabetic state such as insulin insensitivity or pre-diabetes.

Compounds of formula (I) include, but are not limited to, the compounds specifically described in the Examples herein.

Compounds according to the present invention preferably have a more sustained effect on food intake reduction or have a stronger effect on food intake reduction than human GLP1. Preferably they have an effect on food intake reduction which is at least as strong as native human GLP1 but which is more sustained. Increased duration of appetite suppression can be particularly important to avoid the effect known as "escape". A short duration of appetite suppressant may reduce appetite or the time covered by one meal and in that meal the subject typically eats less food. If, however, the appetite suppressant is then metabolized or otherwise removed from circulation then by the time of the next meal the subject can regain its "normal" appetite. In view of the subject having eaten a small meal at the previous mealtime, the subject may in fact have an increased appetite at the time of the second meal. If the subject satisfies that appetite it is possible for the food intake over the two meals in total to be no lower than the food intake would have been without the appetite suppressant. That is to say, the subject may have "escaped" from the effects of the appetite suppressant. "Escape" can be reduced by using additional doses of appetite suppressant or by using an appetite suppressant with a longer duration of action. If the subject has a reduced appetite for longer, then the degree to which it can make up the deficit from one meal in the next meal is reduced and as there is a practical limit to total capacity in a particular single meal.

Criteria for Compounds of the Invention

Preferably, the compounds of the invention fulfil some or more preferably all, of the following criteria.
1) Sustained bioactivity at both the human glucagon and human GLP1 receptors resulting in inhibition of appetite and enhancement of energy expenditure.
2) High solubility in aqueous solution at pH 5 to allow an effective dose to be administered in a low volume injection (thereby resulting in lower pain of injection). Solubility may be easily assessed by simple in vitro tests and solubility may also be predicted with reasonable accuracy from primary peptide sequences. Solubility may be improved by:—i) avoiding clustering of uncharged residues; ii) increasing charged residues to at least 5, 10, 15, 20 or 25% of the peptides total number of residues; or iii) limiting hydrophobic residues to less than 5, 10, 15, 20 or 25% of the peptides total number of residues.
3) Long period of activity in vivo (as assessed in humans or an animal model) so as to permit injections no more frequently than daily and preferably twice, or more preferably, once a week, whilst still producing acceptable therapeutic or cosmetic benefits.
4) Good weight loss or appetite suppression (as assessed in human subjects or an animal model).
5) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm (Jameson & Wolf (1988) Comput. Appl. Biosci. 4(1): 181-6), or the PREDITOP algorithm (Pellequer & Westhof, (1993) J. Mol. Graph. 11(3):204-10, or using the methods of Kolaskar & Tongankar (1990) FEBS Leu. 10:276(1-2):172-4.

Zinc & Solubility

Enhanced solubility at pH 5 may be provided by ensuring at least 1 (and preferably 2, 3, 4 or more) histidine residue in the peptide. Histidine is unique among naturally occurring amino acids in that it is not charged at pH 7.4 (i.e. under physiological conditions in the circulation or subcutaneously following subcutaneous injection), but that it is fully charged at pH 5 since the pI of the NH side chain group of histidine is about 6.0. The inclusion of histidine residues in compounds of the invention therefore increases solubility at pH 5 which is a desirable feature. Histidine residues also bring an additional advantage in that when the compound injected subcutaneously, the solubility falls and this leads to subcutaneous precipitation of peptide. This is unexpected because in vitro zinc precipitation of His-containing peptides (as used for example in the purification of insulin) is typically slower and not expected to be sufficiently rapid in vivo to prevent dispersion of the subcutaneous precipitate. The precipitate will resolubilise over time and this will produce an advantageous slow-release effect. The inclusion of histidine residues is especially advantageous wherein the compound is to be formulated into a pharmaceutical composition containing zinc ions. This is because at pH 7.4 but not at pH 5 zinc ions coordinate with histidine residues and result in a further reduction in the compound's solubility which can contribute to increased precipitation at a subcutaneous injection site, or which can contribute to increased stability of the precipitate. A zinc-containing precipitate will more gradually re-dissolve because the solubilisation is dependent on the zinc washing out of the injection site into the circulation and/or surrounding tissue fluid, increasing the longevity of the release into the circulation and decreasing the frequency of injections needed to sustain a useful biological effect.

Accordingly, peptides of the invention preferably contain at least 1, 2, 3, 4 or 5 histidine residues and compositions of the invention preferably contain zinc ions (preferably at a ratio of 1:4, 1:2, 1:1, 2:1 or 4:1 with peptide molecules) or at a ratio which is a range between any two of the whole number ratios given immediately above.

According to certain embodiments of various aspects of the invention, especially embodiments relating to weight loss, appetite suppression, obesity, carbohydrate metabolism and diabetes, compounds of the invention have one, several or all of the following features:
A) Sufficient solubility between pH 4 and pH5 to permit an effective dose to be administered in a volume of less than 1 ml, less than 0.5 ml or less than 0.3 ml
B) Good inhibition of food intake in both mice and rats (which is taken to provide a more certain indication of good inhibition of food intake in humans than is good inhibition in a single rodent species only.
C) Activation of cAMP signaling in human embryonic kidney cells over-expressing the human GLP1 Receptor, and in a second set of sells the human glucagon receptor,
D) One, several or all of the further 1 to 5 features listed above.

Variants:

Variants include compounds of the invention comprising an amino acid sequence represented by formula (I) having up to five amino acids (e.g. 1, 2, 3, 4 or 5) replaced with a different amino acid (e.g., conservative substitutions and non-conservative substitutions; see, e.g., Table 1 below) which retain at least one of the biological activities (for example food intake suppression or receptor binding) of a corresponding non-variant molecule (i.e., a compound having the formula given in formula I with no further residue changes or a derivative thereof) when in a compound of the invention.

Typically conservative substitutions are the replacements, for one another, among the aliphatic amino acids Ala, Val, Leu and Ile; interchange of Ser and Thr containing hydroxy residues, interchange of the acidic residues Asp and Glu, interchange between the amide residues Asn and Gln, interchange of the basic residues Lys and Arg, interchange of the aromatic residues Phe and Tyr, and interchange of the small-sized amino acids Ala, Ser, Thr, Met and Gly. Guidance concerning how to make phenotypically silent amino acid substitutions, i.e. substitutions that do not alter the expressed phenotype, is provided in Bowie et al., *Science* 247:1306-1310, 1990.

TABLE 1

Non-limiting examples of conservative amino acid substitutions

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |

TABLE 1-continued

Non-limiting examples of conservative amino acid substitutions

| Original Residue | Conservative Substitutions |
| --- | --- |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variants further include compounds in which up to five amino acids (e.g. 1, 2, 3, 4 or 5) are replaced with an amino acid present at the equivalent position of a corresponding peptide derived from a species other than human.

Derivatives

A compound of the invention may comprise the structure of formula (I) modified by well-known processes including amidation, glycosylation, carbamylation, acylation, for example acetylation, sulfation, phosphylation, cyclization, lipidization and PEGylation. The structure of formula (I) may be modified at random positions within the molecule, or at predetermined positions within the molecule and may include one, two, three or more attached chemical moieties.

A compound of the invention may be a fusion protein, whereby the structure of formula (I) is fused to another protein or polypeptide (the fusion partner) using recombinant methods known in the art. Alternatively, such a fusion protein may be synthetically synthesized by any known method. Such a fusion protein comprises the structure of formula (I). Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers D-D-D-D-Y [SEQ ID NO 127], G-P-R, A-G-G and H-P-F-H-L [SEQ ID NO 128], which can be cleaved by enterokinase, thrombin, ubiquitin cleaving enzyme and renin, respectively. See, e.g., U.S. Pat. No. 6,410,707.

A compound of the invention may be a physiologically functional derivative of the structure of formula (I). The term "physiologically functional derivative" is used herein to denote a chemical derivative of a compound of formula (I) having the same physiological function as the corresponding unmodified compound of formula (I). For example, a physiologically functionally derivative may be convertible in the body to a compound of formula (I). According to the present invention, examples of physiologically functional derivatives include esters, amides, and carbamates; preferably esters and amides.

Pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include, but are not limited to, the following: lauroyl ($C_{12}H_{23}$), palmityl ($C_{15}H_{31}$), oleyl ($C_{15}H_{29}$), stearyl ($C_{17}H_{35}$), cholate; and deoxycholate.

Methods for lipidization of sulfhydryl-containing compounds with fatty acid derivatives are disclosed in U.S. Pat. No. 5,936,092; U.S. Pat. No. 6,093,692; and U.S. Pat. No. 6,225,445. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in a lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$), oleyl ($C_{15}H_{29}$), stearyl ($C_{17}H_{35}$), cholate; and deoxycholate.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A compound of the invention may be a PEGylated structure of formula (I). PEGylated compounds of the invention may provide additional advantages such as increased solubility, stability and circulating time of the polypeptide, or decreased immunogenicity (see U.S. Pat. No. 4,179,337).

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any, on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

Salts and solvates of compounds of the invention that are suitable for use in a medicament are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable salts or solvates.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

Conditions:

The invention provides a pharmaceutical composition comprising a compound of formula (I) together with a pharmaceutically acceptable carrier and optionally other therapeutic ingredients, together with related methods. In some embodiments, the pharmaceutical composition is present in a syringe or other administration device for subcutaneous administration to humans.

The invention further provides the compound of formula (I) or a variant, derivative, salt or solvate thereof for use as a medicament.

The invention also provides a compound of formula (I) or a variant, derivative, salt or solvate thereof, or a pharmaceutical composition comprising a compound of formula (I), for use in the treatment of obesity or diabetes.

The invention further provides a compound of formula (I), or a pharmaceutical composition comprising a compound of formula (I), for use in reduction of appetite in a subject, for use in reduction of food intake in a subject, or for use in reduction of calorie intake in a subject.

The invention further provides a compound of formula (I), or a pharmaceutical composition comprising a compound of formula (I), for use in increasing energy expenditure in a subject.

The invention further provides a compound of formula (I), or a pharmaceutical composition comprising a compound of formula (I), for use in enhancing insulin release and/or improving carbohydrate metabolism in a subject. Administration of glucagon is known to cause carbohydrate tolerance to worsen (i.e. the ability of the subject to metabolise carbohydrate released into the blood stream, for example from the gut, is worsened). However, despite having activity at the glucagon receptor, unexpectedly the compounds of the invention do not demonstrate disadvantageous carbohydrate intolerance, without wishing to be bound by theory it is suggested that this is because their activity at the GLP1 receptor promotes sufficient insulin release to counter this effect.

The invention further provides the use of a compound of formula (I) or a variant, derivative, salt or solvate thereof for the manufacture of a medicament for the treatment of obesity or diabetes. The invention also provides the use of a compound of formula (I) or a variant, derivative salt or solvate thereof for the manufacture of a medicament for reducing appetite in a subject, reducing food intake in a subject, reducing calorie intake in a subject, increasing energy expenditure in a subject or enhancing insulin release and/or improving carbohydrate metabolism in a subject.

The increase in energy expenditure noted in relation to various aspects of the invention may manifest as a lessening of the normal reduction in energy expenditure seen following reduced food intake, or it may manifest as an absolute increase in energy expenditure for example by the promotion of increased physical activity levels or by an increase in the basal metabolic rate.

The invention further provides a method of treating obesity or diabetes in a subject in need thereof comprising administering to the subject an effective amount of a compound of formula (I) or a variant, derivative, salt or solvate thereof, or a pharmaceutical composition comprising a compound of formula (I). The invention also provides a method of reducing appetite in a subject, reducing food intake in a subject, reducing calorie intake in a subject, increasing energy expenditure in a subject, or enhancing insulin release and/or improving carbohydrate metabolism in a subject, comprising administering to the subject an effective amount of a compound of formula (I), or a pharmaceutical composition comprising a compound of formula (I).

In some embodiments, the compound is administered parentally. In some embodiments, the compound is administered subcutaneously, intravenously, intramuscularly, intranasally, transdermally or sublingually. In other embodiments the compound may be administered orally.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, *Nature* 404:635-43; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e.g., Kopelman, Nature 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

The present invention further provides a method (and also related compounds and compositions) for increasing energy expenditure in a subject. The method includes, for example, peripherally administering a therapeutically effective amount of a compound of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry, that alter food intake coordinately and reciprocally alter energy expenditure. Energy expenditure is a result of cellular metabolism, protein synthesis, metabolic rate, and calorie utilization. Thus, in this aspect of the invention, administration of a compound of formula (I) or a variant, derivative salt or solvate thereof results in increased energy expenditure, and decreased efficiency of calorie utilization.

The invention also provides a method for improving a lipid profile in a subject. The invention also provides a method for alleviating a condition or disorder that can be alleviated by reducing nutrient availability.

Appetite can be measured by any means known to one of skill in the art. For example, decreased appetite can be assessed by a psychological assessment. For example, administration of a compound of the invention results in a change in perceived hunger, satiety, and/or fullness. Hunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

A compound of the invention may be used for weight control and treatment, for example reduction or prevention of obesity, in particular any one or more of the following: preventing and reducing weight gain; inducing and promoting weight loss; and reducing obesity as measured by the Body Mass Index. A compound of the invention may be used in the control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. A compound of the invention may be used in maintaining any one or more of a desired body weight, a desired Body Mass Index, a desired appearance and good health.

A subject may be a subject who desires weight loss, for example female and male subjects who desire a change in their appearance. A subject may desire decreased feelings of hunger, for example the subject may be a person involved in a lengthy task that requires a high level of concentration, for example soldiers on active duty, air traffic controllers, or truck drivers on long distance routes, etc.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

According to the present invention, a compound of formula (I) or a variant, derivative, salt or solvate thereof is preferably used in the treatment of a human. However, while the compounds of the invention will typically be used to treat human subjects they may also be used to treat similar or identical conditions in other vertebrates for example other primates; farm animals for example swine, cattle and poultry; sport animals for example horses; or companion animals for example dogs and cats.

Use in Protection of Neuronal Cells and Cardiac Cells.

J. Cereb. Blood Flow Metab. 2011 Apr. 13 (Teramoto S et al) discusses the use of both GLP1 and exendin-4 to confer cardioprotection after myocardial infarction, and demonstrates that exendin-4 may be used to provide neuroprotection against cerebral ischemia-reperfusion injury.

The study showed that mice receiving a transvenous injection of exendin-4, after a 60-minute focal cerebral ischemia showed significantly reduced infarct volume and improved functional deficit as well as suppressed oxidative stress, inflammatory response, and cell death after reperfusion. The study provided evidence that the protective effect of exendin-4 is mediated through increased intracellular cAMP levels and suggested that Exendin-4 is potentially useful in the treatment of acute ischemic stroke.

Aspects of the present invention relating to neuroprotection and cardiac protection are supported by the inventor's observation that compounds of the present invention result in elevated intracellular cAMP, particularly in HELA cells with extra receptors.

Compositions

While it is possible for the active ingredient to be administered alone, it is preferable for it to be present in a pharmaceutical formulation or composition. Accordingly, the invention provides a pharmaceutical formulation comprising a compound of formula (I), or a variant or derivative thereof, or a salt or solvate thereof, as defined above and a pharmaceutically acceptable excipient. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2 S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Preferably, compositions according to the invention are suitable for subcutaneous administration, for example by injection. According to certain embodiments the composition may contain metal ion for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions as described in more detail above.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) or variant, derivative, salt or solvate thereof can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to compounds of the invention and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention are also suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

A compound of the invention may be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by a continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990). In another aspect of the disclosure, compounds of the invention are delivered by way of an implanted pump, described, for example, in U.S. Pat. No. 6,436,091; U.S. Pat. No. 5,939,380; U.S. Pat. No. 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a compound of the invention may be administered as a single pulse dose, as a bolus dose, or as pulse doses administered over time. Thus, in pulse doses, a bolus administration of a compound of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

In one embodiment, a therapeutically effective amount of a compound of the invention is administered with a therapeutically effective amount of another agent, for example an additional appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, and fluoxetine. The compound of the invention can be administered simultaneously with the additional appetite suppressant, or it may be administered sequentially. Thus, in one embodiment, the compound of the invention is formulated and administered with an appetite suppressant as a single dose.

A compound of the invention may be administered whenever the effect, e.g., appetite suppression, decreased food intake, increased energy expenditure or decreased caloric intake, is desired, or slightly before to whenever the effect is desired, such as, but not limited to about 10 minutes, about 15 minutes, about 30 minutes, about 60 minutes, about 90 minutes, or about 120 minutes, before the time the effect is desired.

The therapeutically effective amount of a compound of the invention will be dependent on the molecule utilized, the subject being treated, the severity and type of the affliction, and the manner and route of administration. For example, a therapeutically effective amount of a compound of the invention may vary from about 0.01 µg per kilogram (kg) body weight to about 1 g per kg body weight, for example about 0.1 µg to about 20 mg per kg body weight, for example about 1 µg to about 5 mg per kg body weight, or about 5 µg to about 1 mg per kg body weight.

In one embodiment of the invention, a compound of the invention may be administered to a subject at from 4 to 1333 nmol per kg bodyweight, for example from 5 to 1000 nmol per kg bodyweight, for example at from 10 to 750 nmol per kg bodyweight, for example at from 20 to 500 mmol per kg bodyweight, in particular at from 30 to 240 nmol per kg bodyweight. For a 75 kg subject, such doses correspond to dosages of from 300 nmol to 100 µmol, for example from 375 nmol to 75 µmol, for example from 750 nmol to 56.25 µmol, for example from 1.5 to 37.5 µmol, in particular from 2.25 to 18 µmol. The invention also contemplates dosages ranges bounded by any of the specific dosages mentioned herein.

In an alternative embodiment, a compound of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 µmol per kg body weight. In one specific, non-limiting example, a compound of the invention is administered in a dose of about 1 nmol or more, 2 nmol or more, or 5 nmol or more. In this example, the dose of the compound of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of compounds of the invention are within the range of from 1 to 100 nmols, from 2 to 90 mols, from 5 to 80 nmols.

In one specific, non-limiting example, from about 1 to about 50 nmol of a compound of the invention is administered, for example about 2 to about 20 nmol, for example about 10 nmol is administered as a subcutaneous injection. The exact dose is readily determined by one of skill in the art based on the potency of the specific compound utilized, the route of delivery of the compound and the age, weight, sex and physiological condition of the subject.

Suitable doses of compounds of the invention also include those that result in a reduction in calorie intake, food intake, or appetite, or increase in energy expenditure that is equivalent to the reduction in calorie intake, food intake, or appetite, or to increase the energy expenditure, caused by the normal postprandial level of GLP1. Examples of doses include, but are not limited to, doses that produce the effect demonstrated when the serum levels of GLP1 are from about 40 pM to about 60 pM, or from about 40 pM to about 45 pM, or about 43 pM.

The doses discussed above may be given, for example, once, twice, three-times or four-times a day or once or twice a week. Preferably a dose may be given no more frequently than once a week. Alternatively, they may be given once every 2, 3 or 4 days. According to certain embodiments they may be administered once shortly before each meal to be taken.

Specific Sequences of the Invention

According to certain specific embodiments of the invention the compound has an amino acid sequence given in one of the specific sequences set out in FIG. 1, wherein AIB represents alpha-aminoisobutyric acid.

The invention is illustrated by the following non-limiting Examples.

Materials and Methods:

Animals

Male C57BL/6 mice (Harlan) or male Wistar rats (Charles River Ltd, Margate, UK) were used for all animal experiments.

Peptide Synthesis

Peptides were made by a standard automated fluorenylmethoxycarbonyl (Fmoc) solid phase peptide synthesis (SPPS) method. Peptide synthesis was carried out on a tryclic amide linker resin. Amino acids were attached using the Fmoc strategy. Each amino acid was added sequentially from the C- to the N-termini. Peptide couplings were mediated by the reagent TBTU. Peptide cleavage from the resin was achieved with trifluoracetic acid in the presence of scavengers.

Peptides were purified by reverse phase HPLC. Full quality control was performed on all purified peptides and peptides were shown to be greater than 95% pure by HPLC in two buffer systems. Amino acid analysis following acid hydrolysis confirmed the amino acid composition. MALDI-MS showed the expected molecular ion.

Example 1

Acute Feeding Studies in Mice

Mice were individually housed in IVC cages. Animals were randomised into treatment groups, with stratification by body weight. Mice were fasted overnight (16 hrs) prior to peptide or vehicle administration. All peptide solutions were prepared freshly, immediately prior to administration. The vehicle used for all studies was 5% v/v water and 95% v/v sodium chloride (0.9% w/v). Peptide and vehicle were administered by subcutaneous injection, with dosage corrected for bodyweight. The injection volume was 50 µl. Vehicle or peptide was administered at 09:00 and animals were returned to their home cage with a known amount of food. Food intake was measured at 1, 2, 4, 8 and 24 hours post injection. All statistics are calculated using a one-way ANOVA with Dunnett's post-test or one-way ANOVA with Bonferroni post-test.

Cellular Assays

Cells (Chinese hamster ovary hGcgR, or Human embryonic kidney hGLP1R) were plated at a density of 150000 cells/ml in 24 well plates. The cells were left for 18 hours, and were then serum starved for 1 hour by replacing with serum free media. The media was then replaced with that containing the example compound at 12 concentrations in duplicate ranging from 0 up to 30 nM (1 analogue per 24 well plate). Each plate was incubated for exactly 30 minutes. The incubation media was removed, and replaced with 120 ul of lysis buffer (0.1 M HCl 0.5% TritonX). 120 ul of sample (or a dilution thereof so as to hit ELISA standard curve) was added to an eppendorf tube, and was spun for 3 minutes at >5000 g to remove cell debris. 100 ul of sample was added to an ELISA plate (Direct cyclic AMP Enzyme Immunoassay Kit—Enzolifesciences). The ELISA assay was run as described in the manual.

Results

FIG. 1 shows the amino acid sequences of example compounds of the invention (each compound is identified by a unique compound number (or G no.) with the exception of the first three lines which give the native sequences of human glucagon, GLP1 and of exendin4), the result of binding experiments, the results of experiments in which the appetite suppressant effects in mice were determined, the result of pair feeding studies, solubility studies, and rat pharmacokinetic studies.

The column headed "hGLP1R man" shows strength of binding to the human GLP1 Receptor of each compound analogue as a ratio relative to human GLP1. A value of less than 1.0 indicates binding to the human GLP1 receptor greater than that shown by human GLP1. The column headed "rGLP1R Rat" shows strength of binding to the rat GLP1 Receptor of each compound analogue as a ratio relative to human GLP1. A value of less than 1.0 indicates binding to the rat GLP1 receptor greater than that shown by human GLP1. The column headed "rGLP1R Mouse" shows strength of binding to the mouse GLP1 Receptor of each compound analogue as a ratio relative to human GLP1. A value of less than 1.0 indicates binding to the mouse GLP1 receptor greater than that shown by human GLP1. The column headed "hGLP1R cAMP" shows signaling in human embryonic kidney cells or chinese hamster ovary cells over-expressing human GLP1 receptor. The data is scaled so that a value of 1 represents baseline cAMP signaling level and cAMP signaling and other values represent fold-differences in cAMP signalling.

The column headed "hGlucR Man" shows strength of binding to the human glucagon receptor as a ratio relative to human glucagon. A value of less than 1.0 indicates binding to the human glucagon receptor greater than that shown by human glucagon. The column headed" hGluc cAMP" shows signaling in human embryonic kidney cells or Chinese hamster ovary cells over-expressing human glucagon receptor. The data is scaled so that a value of 1 represents baseline cAMP signaling level and cAMP signaling and other values represent fold-differences in cAMP signalling.

The columns headed "0–1 Mouse", "0–4 Mouse", "0–8 Mouse", "4–8 Mouse", "8–24 Mouse" and "0–24 Mouse" show the reduction in food intake relative to saline during the indicated time periods since compound administration in hours. A value of greater than 1.0 indicates a reduction of food intake better than that achieved with saline. The column headed "pair feeding" shows the performance of selected compounds in pair feeding studies (see Examples 4 and 5 below) ranked from 0=worst to 5=best. The column headed "mouse 8+24 shows cumulative reduction in food intake in mice relative to saline control over the 0 to 8 and 8 to 24 hour time periods. The column headed "rat 8+24" shows the data from an equivalent rat feeding experiment A value of above 1 demonstrates a combination of good appetite suppression immediately following compound administration (during 0 to 8 hours) and a continued suppression (or at least minimal rebound in feeding) during the 8 to 24 hour time period.

The column headed "sol pH<5" shows a score for solubility at 20 mg/ml at a pH of between 4 and 5 where 1=fully soluble and 2 and 3 show partial solubility. The column headed "sol pH7.4" shows a score for solubility at 20 mg/ml of a sample which pH has been raised from between pH4 and pH5 to 7.4, wherein 5=fully precipitated, 4=partial precipitated.

The columns with a heading including the abbreviation "PK" show the results of pharmacokinetic studies in rats administered a single 0.5 mg dose of a slow-release zinc-containing formulation of the peptide in saline containing 0.5 zinc ions (as zinc chloride) per molecule of peptide and peptide present at a concentration of 10 mg/ml. Blood plasma levels of the administered peptide were measured at intervals subsequently. The "PK peak" column shows the approximate timing in hours of the peak (highest) measured plasma level of the peptide following administration. The "PK 3d/4d" column shows that measured plasma concentration of the peptide expressed as a ratio of the earlier measured peak concentration at 3 or 4 days following the peak. The scale is linear, so for example a value of 0.5 indicates that 3 or 4 days following the peak concentration, levels of the peptide in the circulation are at half the peak level. The column headed "PK 7d" shows a corresponding value. The "PK rating" column shows a score for overall pharmacokinetic performance wherein a long and stable plasma concentration of administered peptide is preferred and 0 is poor, 2 is acceptable and 5 is good.

Example 2—Administration of Compounds to Mice

Mice were injected with saline or with compound numbers 67, 105, 129, 130, 131, 177 or 181. Food intake was measured at time intervals over 24 hours. The results are shown in FIGS. 2 to 5 show that all compounds tested show a reduction in food intake at least in some time periods and that there is no overall increase in food intake during the first 24 hours as a whole indicating that no "escape" takes place during that period.

Example 3—Further Feeding Studies in Mice and Rats

Figure 6:
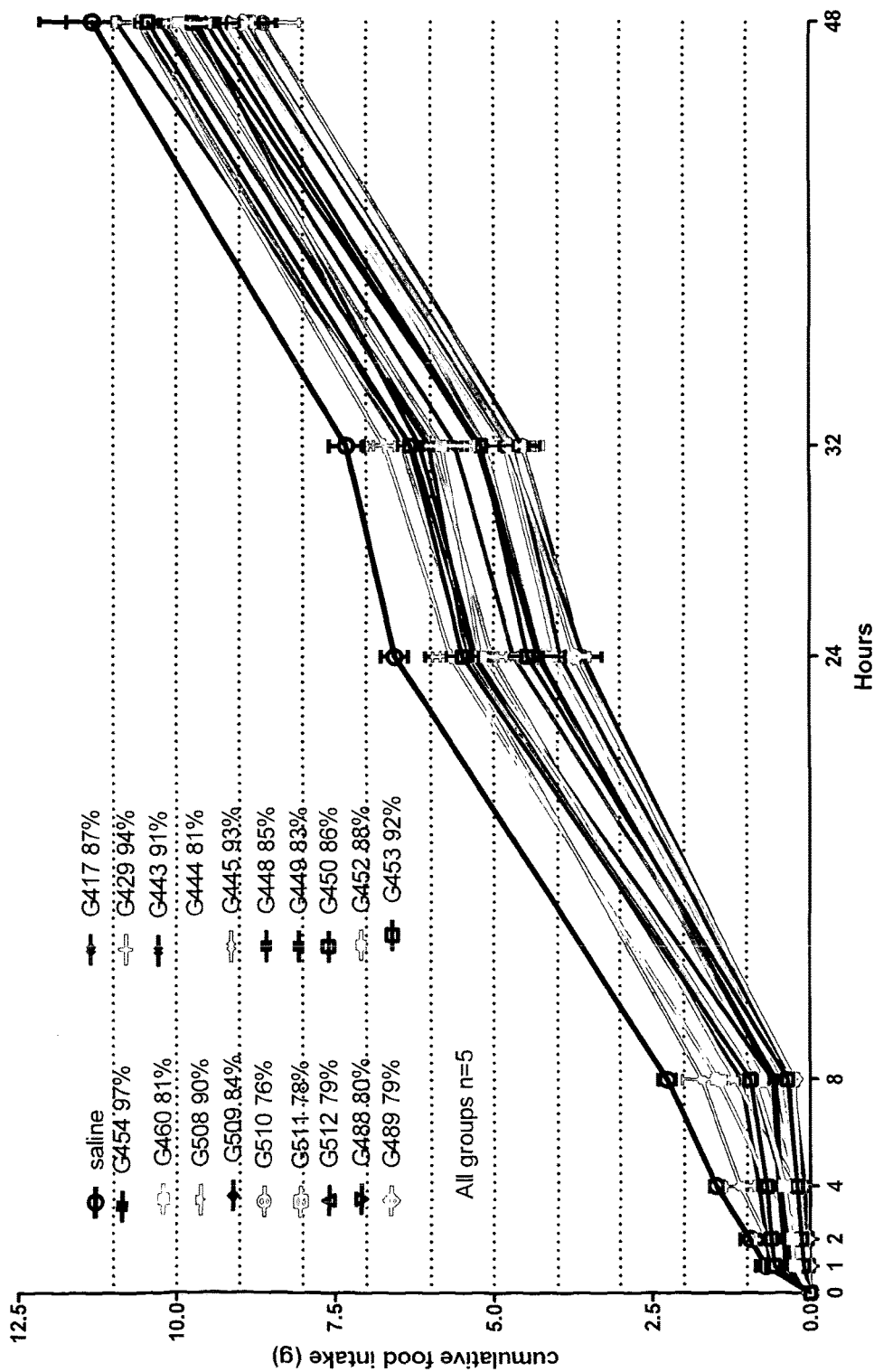

Further feeding studies in mice were carried out as described above in Example 1 using compound numbers 454, 460, 508, 509, 510, 512, 488, 489, 417, 429, 443, 444, 445, 448, 449, 450, 452 and 453, except that food intake was additionally measured at 32 and 24 hours post injection, and that the peptide was administered with zinc ions. The results are shown in FIG. 6.

Figure 7:
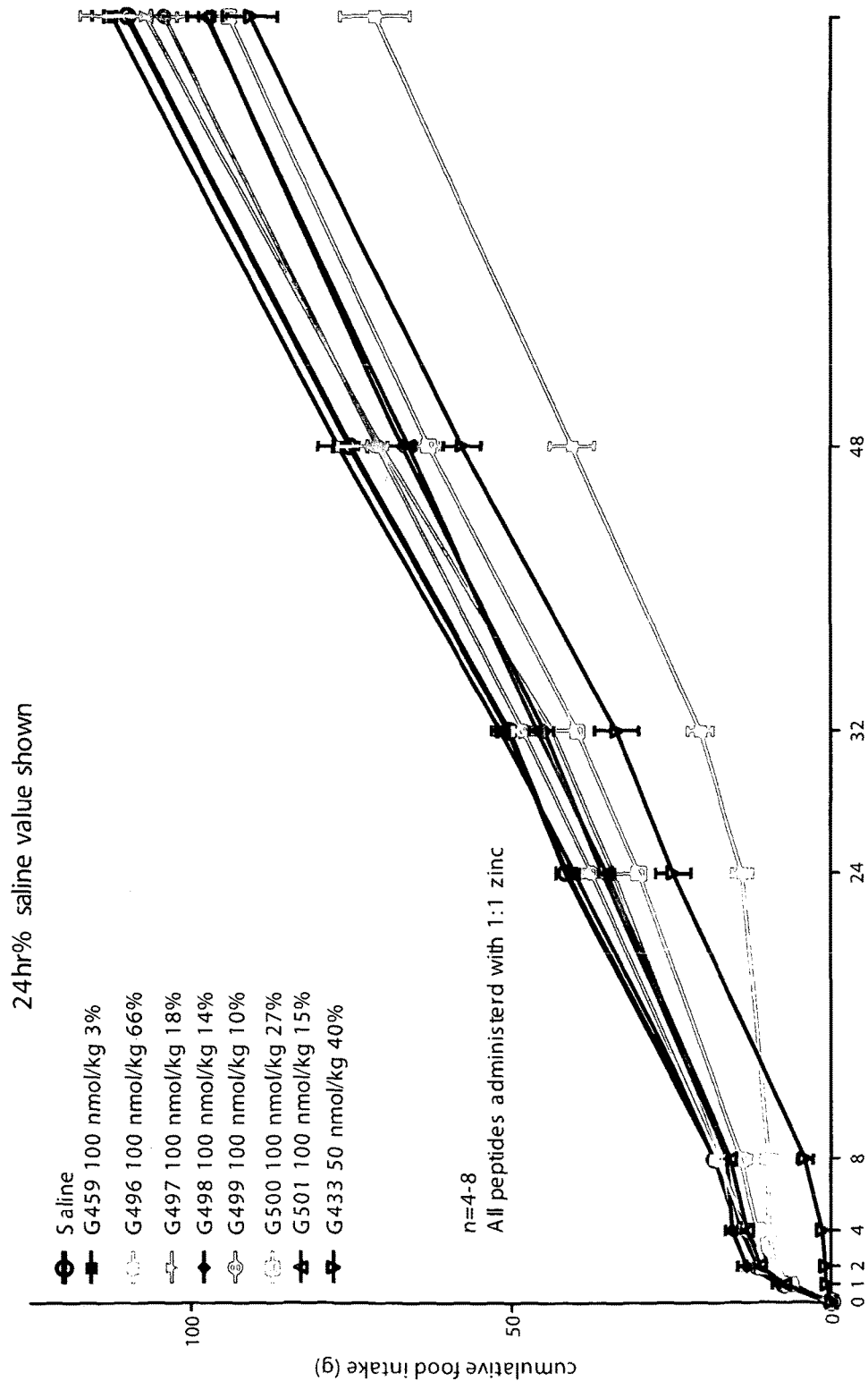
Figure 8:
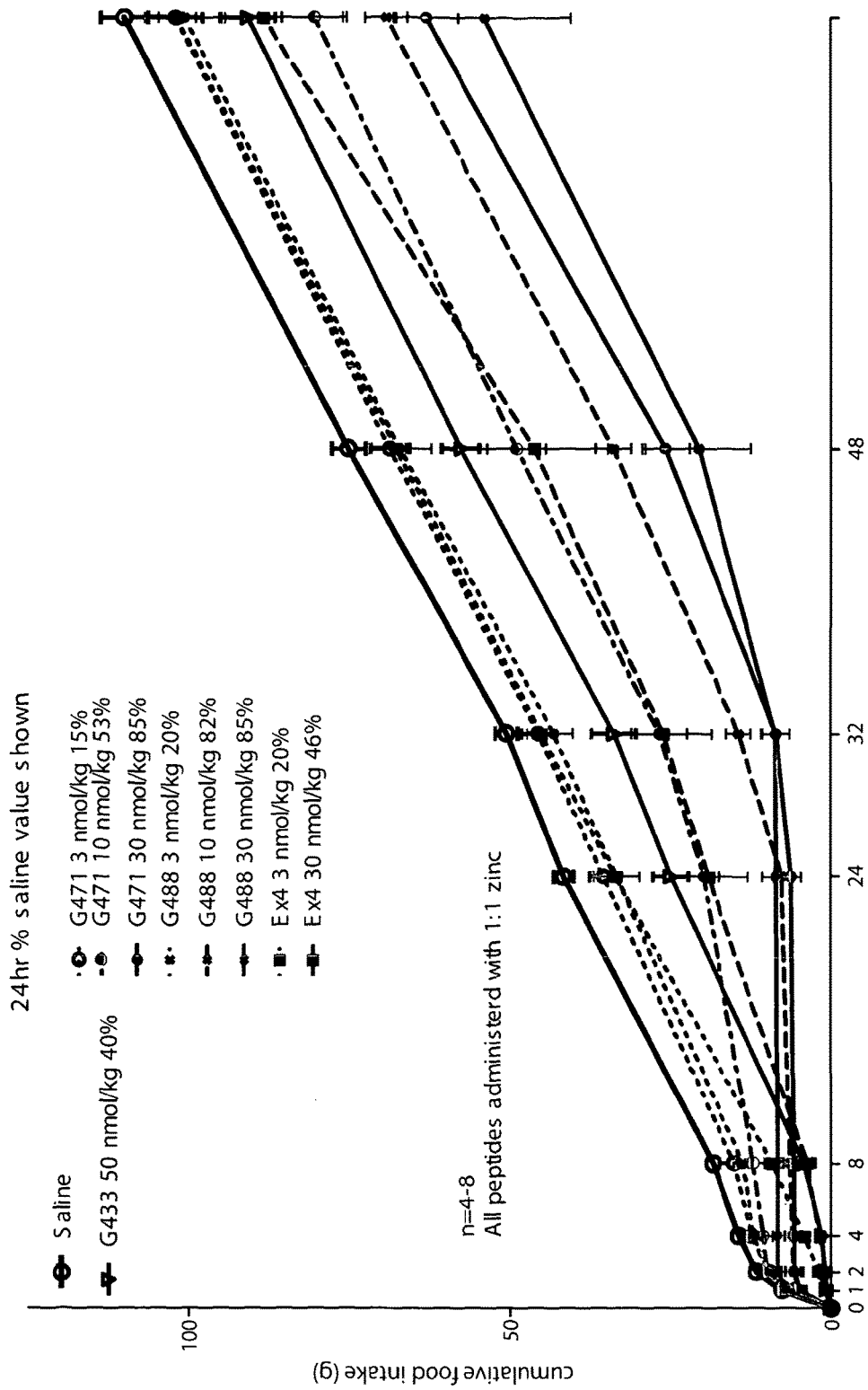
Figure 9:
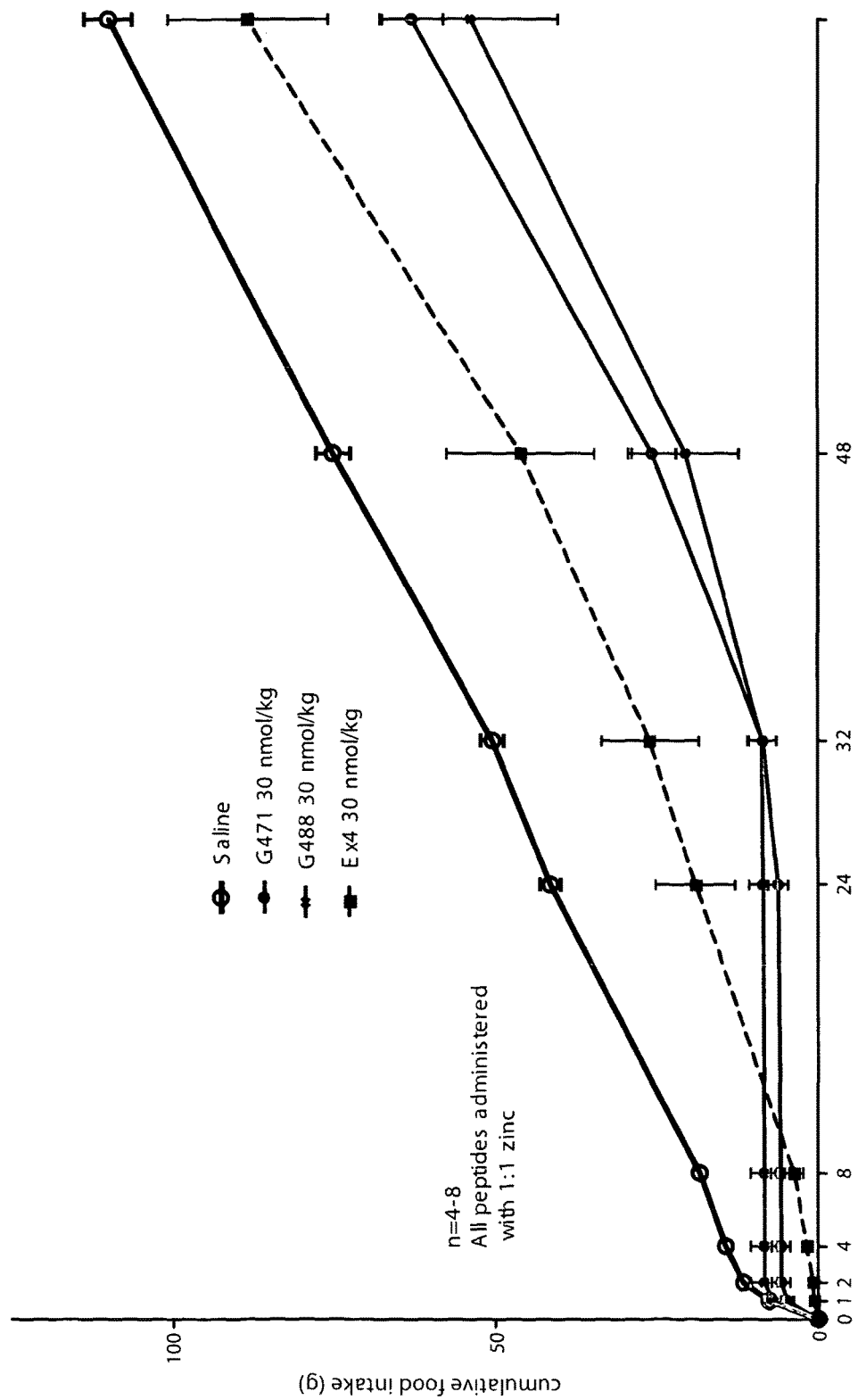

Further feeding studies were carried out as described above in Example 1, using compound numbers 459 (100 nmol/kg), 496 (100 nmol/kg), 497 (100 nmol/kg), 498 (100 nmol/kg), 499 (100 nmol/kg), 500 (100 nmol/kg), 501 (100 nmol/kg), 433 (50 nmol/kg), 471 (3 nmol/kg; 10 nmol/kg; 30 nmol/kg), 488 (3 mmol/kg; 10 nmol/kg; 30 nmol/kg) and exendin-4 (3 nmol/kg; 30 nmol/kg) at the indicated dosage levels, except that the studies were carries out in groups of rats, food intake was additionally measured at 32, 48 and 72 hours, and the peptide formulation contained 1 zinc ion per molecule of peptide. The results are shown in FIGS. 7-9.

Figure 10:
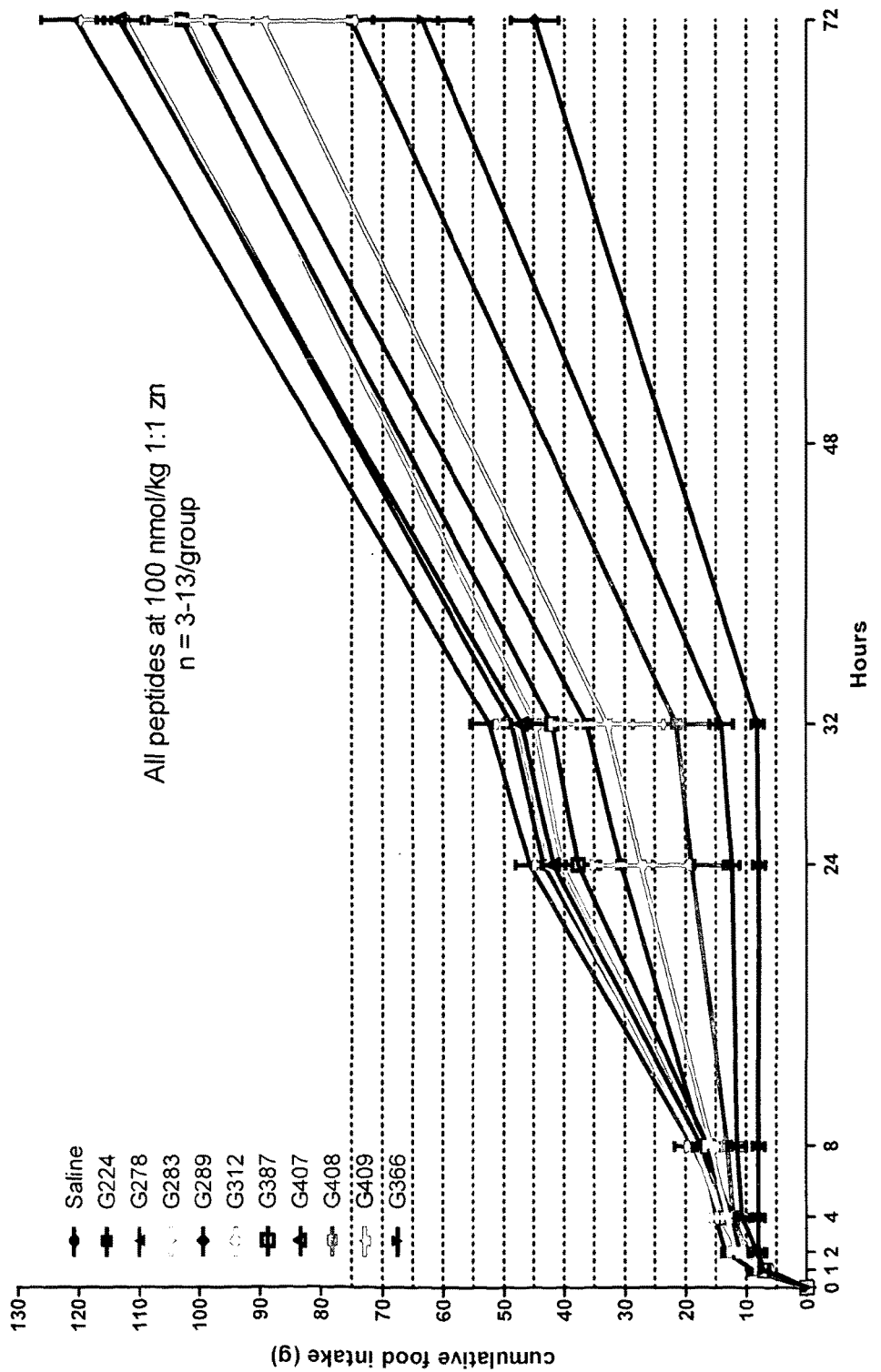
Figure 11:
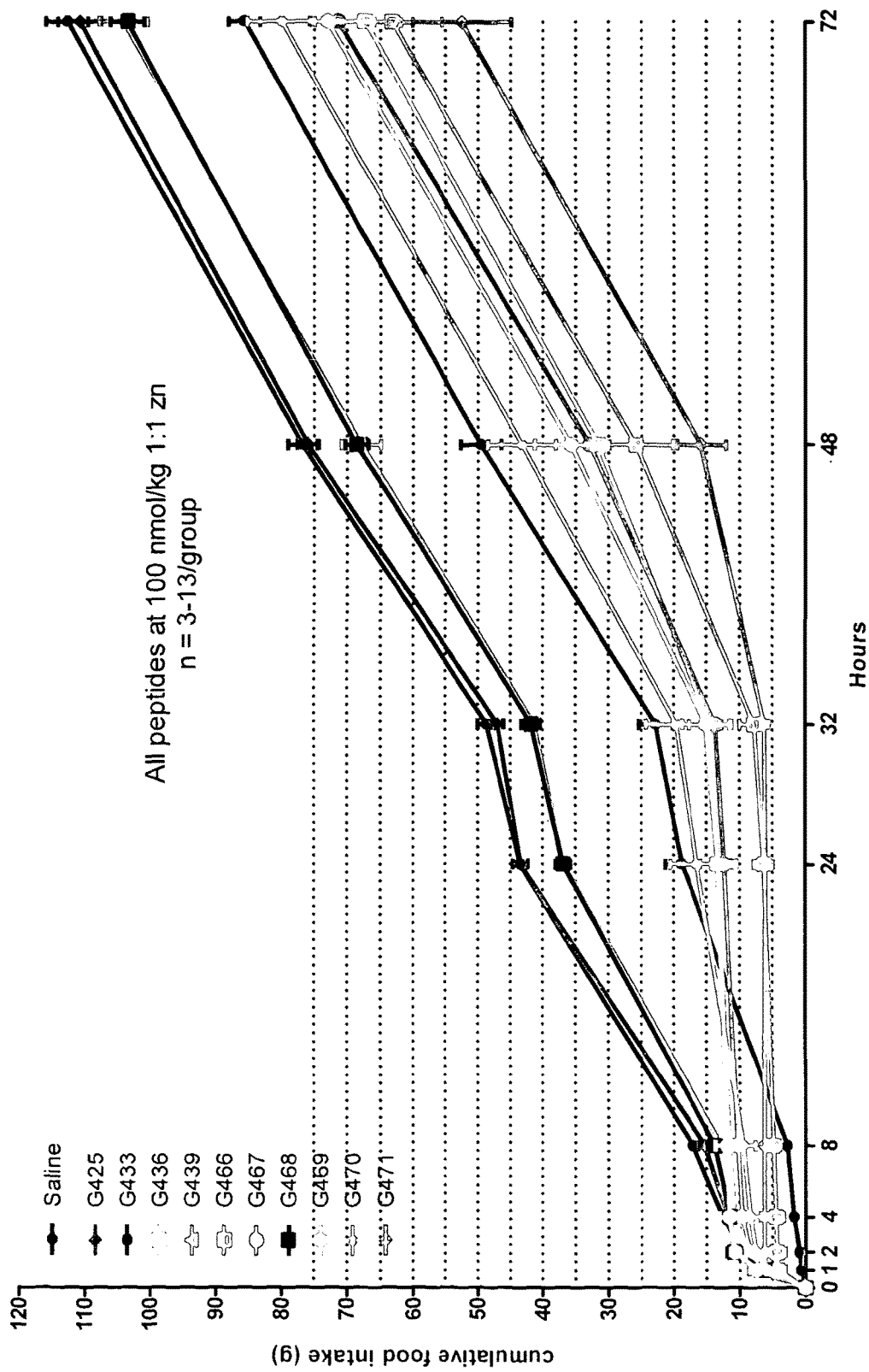

Further feeding studies were carried out as described above in Example 1, using compound numbers 224, 278, 283, 289, 312, 387, 407, 408, 409, 366, 425, 433, 436, 439, 466, 467, 468, 469, 470, and 471 (all at 100 nmol/kg dosage levels), except that the studies were carries out in groups of rats, food intake was additionally measured at 32, 48 and 72 hours, and the peptide formulation contained 1 zinc ion per molecule of peptide. The results are shown in FIGS. 10 and 11.

Example 4—Pair Feeding in Rats

Method

Pair feeding is a technique used to separate the weight loss observed in a cohort of animals which has been caused by appetite suppression from the weight loss caused by the induction of metabolic changes. Pair-feeding studies require daily measurement of body weight (BW) and food intake (FI). In pair-feeding studies, rats were divided into three weight-matched groups. Group 1 (the "saline" group) were given a daily injection of saline and allowed access to ad libitum food. Group 2 (identified by the code of the compound administered) were given daily injection of a selected compound of the invention and allowed access to ad libitum food. Group 3 (identified by the code of the compound administered in the corresponding group 2 and the "PF" suffix) were given a daily saline injection and access to only the same amount of food (one day behind) as that which had been consumed by the group 2 animals.

In the first pair-feeding experiment Male Wistar rats with a mean starting weight of 367 g, received, saline (n=9), exendin-4 at 30 nmol/kg (n=8) marketed by Lilly as Byetta™ as used as a reference compound, compound 285 at 100 nmol/kg (n=8), compound 373 at 50 nmol/kg (n=8), or compound 398 at 200 nmol/kg (n=8)

Sequences of compounds are as shown below:

```
Exendin-4
                                        [SEQ ID NO 3]
His Gly Glu Gly Thr Phe Thr Ser Asp Leu Ser Lys
Gln Met Glu Glu Glu Ala Val Arg Leu Phe Ile Glu
Trp Leu Lys Asn Gly Gly Pro Ser Ser Gly Ala Pro
Pro Pro Ser 285 (also identified as G285)
                                       [SEQ ID NO 87]
His Ser Gln Gly Thr Phe Thr Ser Asp Tyr Ser His
Tyr Leu Asp Ser Lys Ala Val His Leu Phe Ile Gln
Trp Leu Leu Asn Gly-NH2

373 (also identified as G373)
                                      [SEQ ID NO 125]
His Ser Gln Gly Thr Phe Thr Ser Asp Tyr Ser Lys
Tyr Leu Glu Ser Gln Ala Val His Leu Phe Ile Glu
Trp Leu Lys Asn Gly-NH2

398 (also identified as G398)
                                      [SEQ ID NO 109]
His Ser Gln Gly Thr Phe Thr Ser Asp Tyr Ser Lys
Tyr Leu Asp Ser Gln Ala Val Arg Leu Phe Ile Glu
Trp Leu Leu Asn Gly-NH2
```

Results

A summary of the performance of selected compounds of the invention in pair feeding studies is shown in FIG. 1, wherein a score of 1 indicates relatively poor performance (i.e. similar weight change in group 2 and group 3 animals) and a score of 5 corresponds to very good performance (i.e., substantially more weight lost or substantially less weight gained in group 2 animals compared to group 3 animals)

Figure 12B:
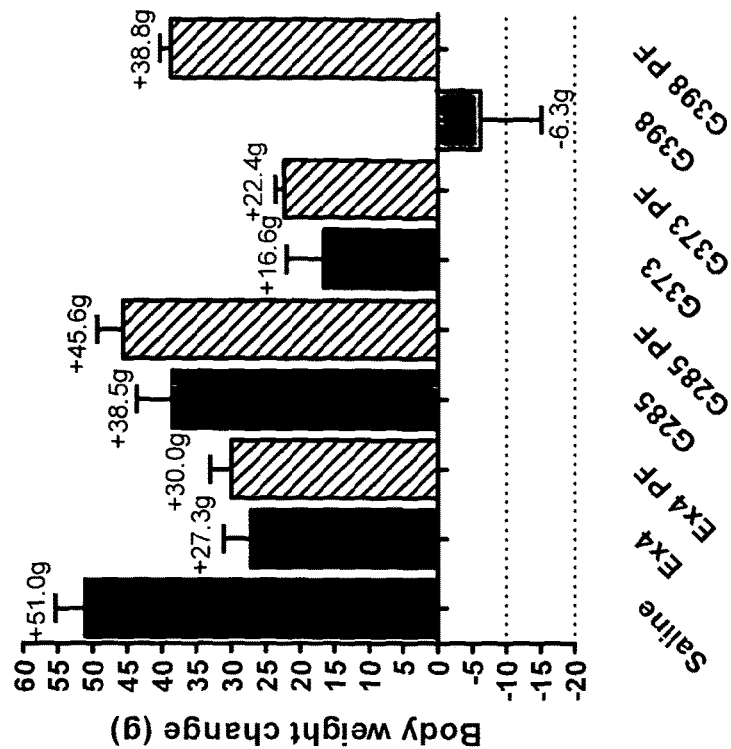
FIGS. 12 to 21 show the result of pair feeding studies using compounds of the invention.
Figure 12A:
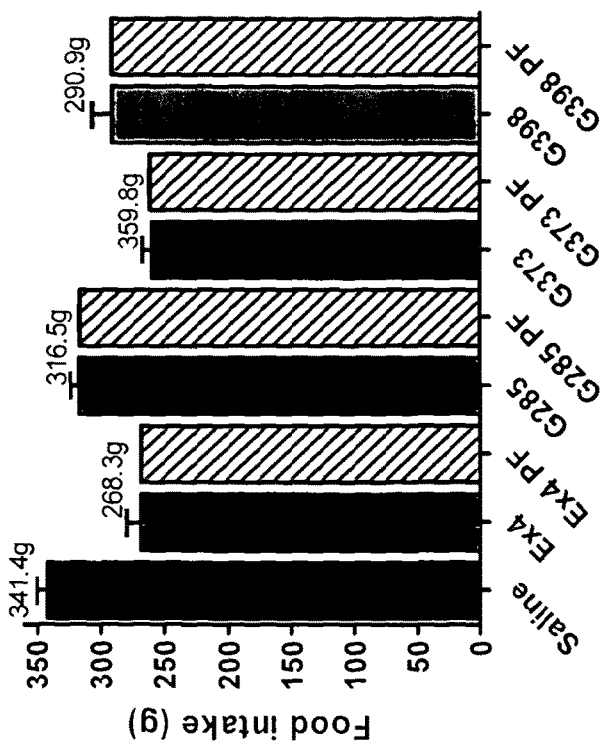

FIG. 12 shows the pair feeding results for compound 285 (G285), 373 (G373) and 398 (G398) and also for reference compound exendin-4 (Ex4) and the saline control. FIG. 12*a* shows the total food intake over 10 days for the groups of rats. It can be seen that exendin-4 and all compound of the invention resulted in less overall food intake. FIG. 12*b* shows the overall body weight change by the end of the 10 day test period. It can be seen that the picture for body weight change is does not correspond directly to food intake change for all compounds tested. Firstly, all compounds of the invention and also comparator compound exendin-4 showed lower body weight gain than the saline control group. But it can be seen that for compounds of the invention, that the lower gain in body weight is not entirely accounted for by reduced food intake in all tested compounds. If that had been the case the "PF" columns of FIG. 12*b* would be the same as the corresponding non-PF column. Whilst this is approximately the case for exendin-4, suggesting that that comparator compound's mechanism is action is weight loss caused solely by appetite suppression, compound 285 and 373, and to a greater extent, compound 398 of the invention show lower weight gains than the corresponding paired feeding groups suggesting that compounds of the invention have a mechanism of action which is not solely via reduction in appetite, but also works via changes in metabolism.

FIGS. 13, 14, 15 and 16 show the full data summarised in FIG. 12*b* together with 95% confidence intervals and demonstrate that the tested compounds influence on body weight manifests relative to the saline control animals throughout the 10 day test period and that the divergence between the paired group 2 and group 3 animals exists throughout the test period also.

Example 5—Further Paired Feeding Studies

Method

Further paired feeding studies were carried out as described in Example 4, but with compound of the invention 237 (also known as G237) which has the sequence given below

```
                                      [SEQ ID NO 126]
His Ser Gln Gly Thr Phe Thr Ser Asp Tyr Ser Lys

Tyr Leu Asp Ser Gln Ala Val His Leu Phe Ile Gln

Trp Leu Leu Asn Gly Gly Pro Ser Ser Gly Ala Pro

Pro Pro Ser
```

Figure 13:
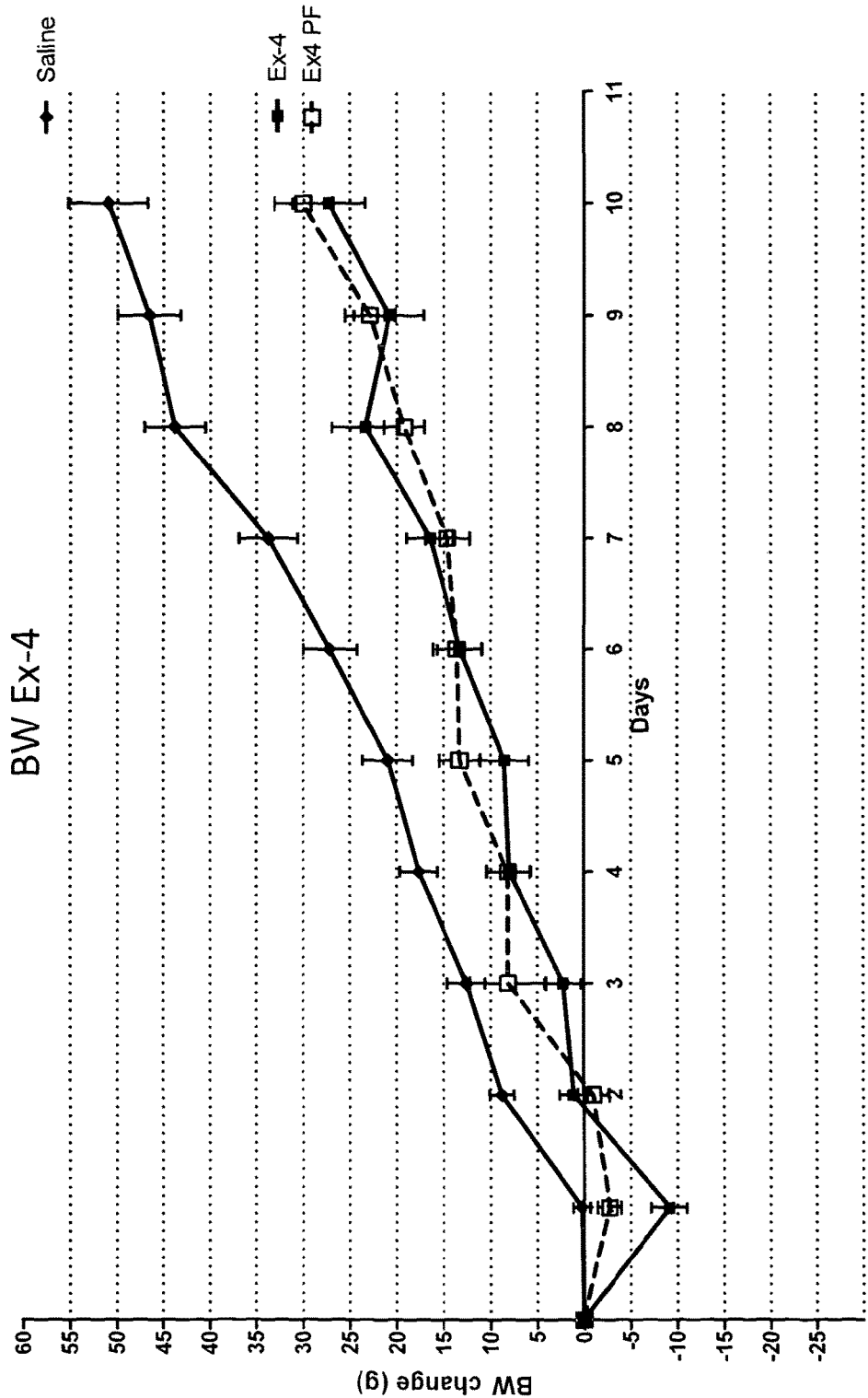
Figure 14:
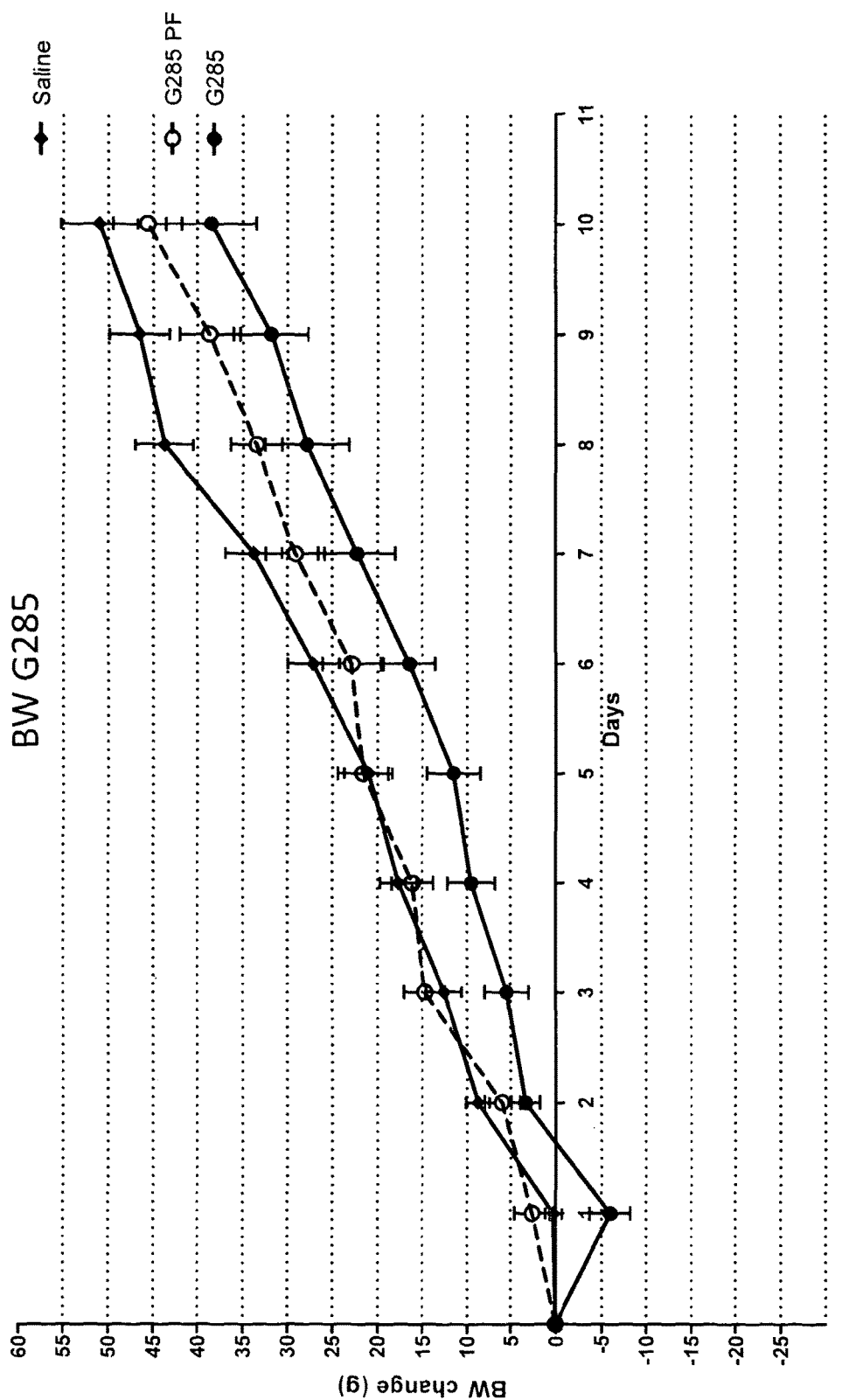
Figure 15:
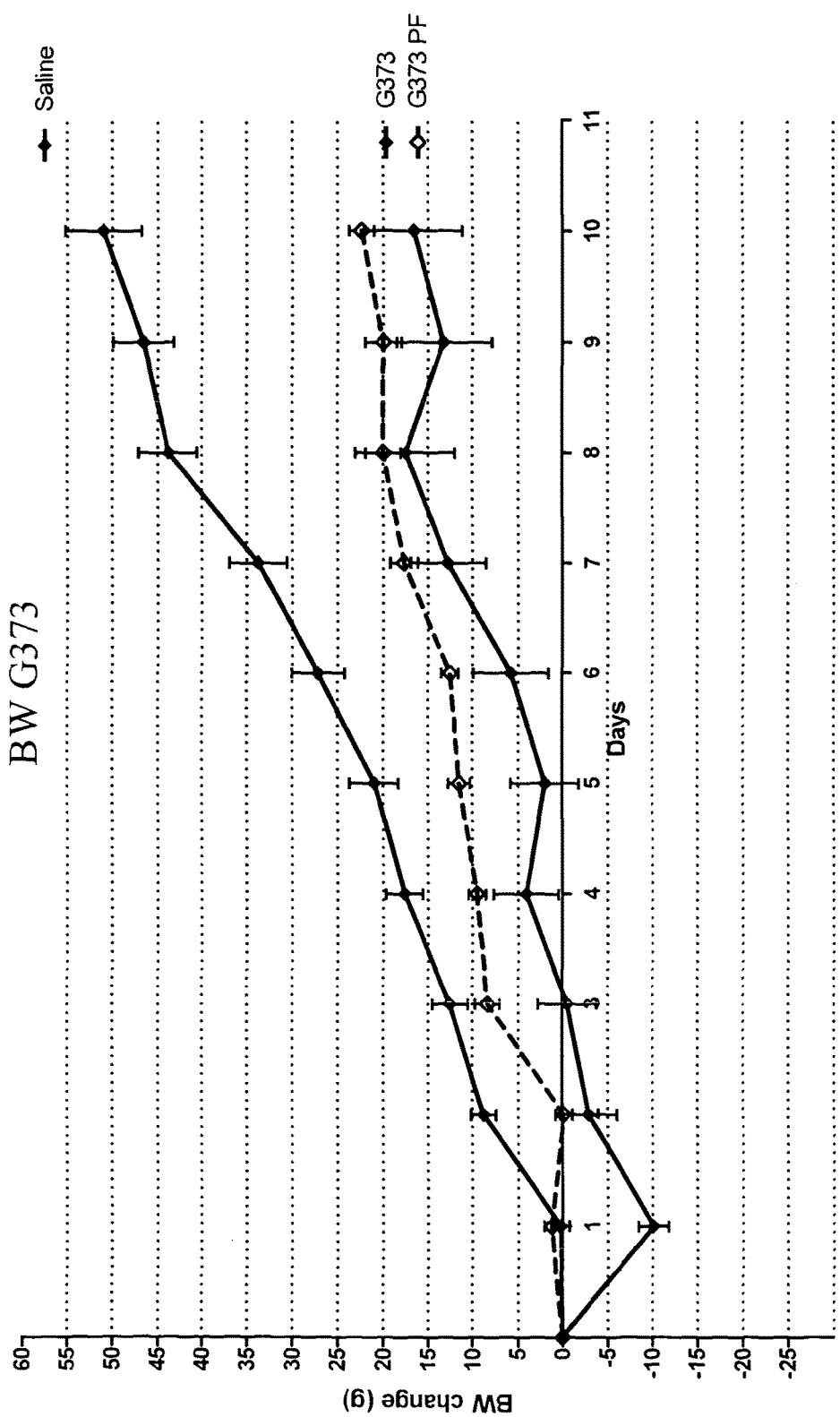
Figure 16:
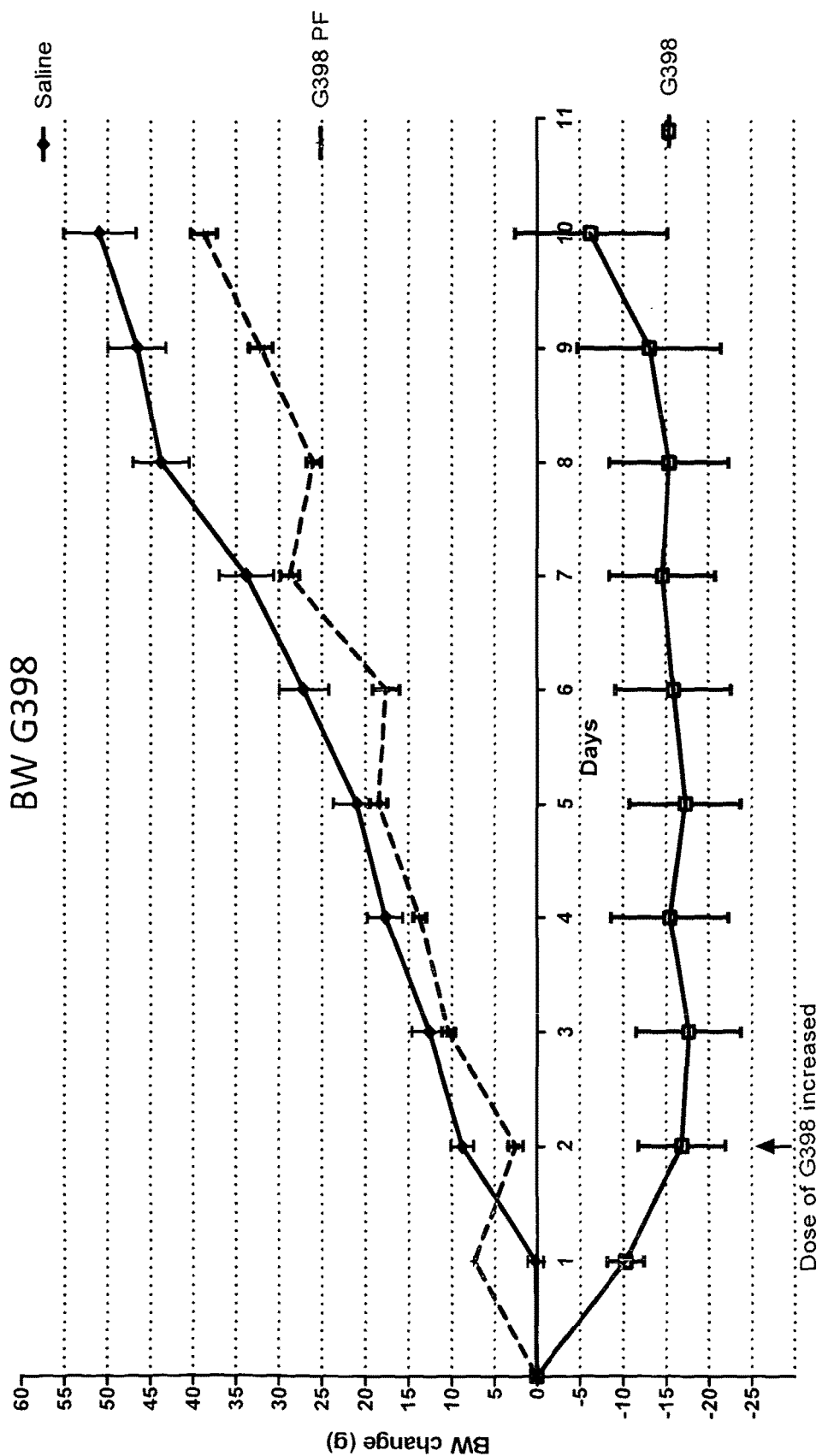
Figure 17:
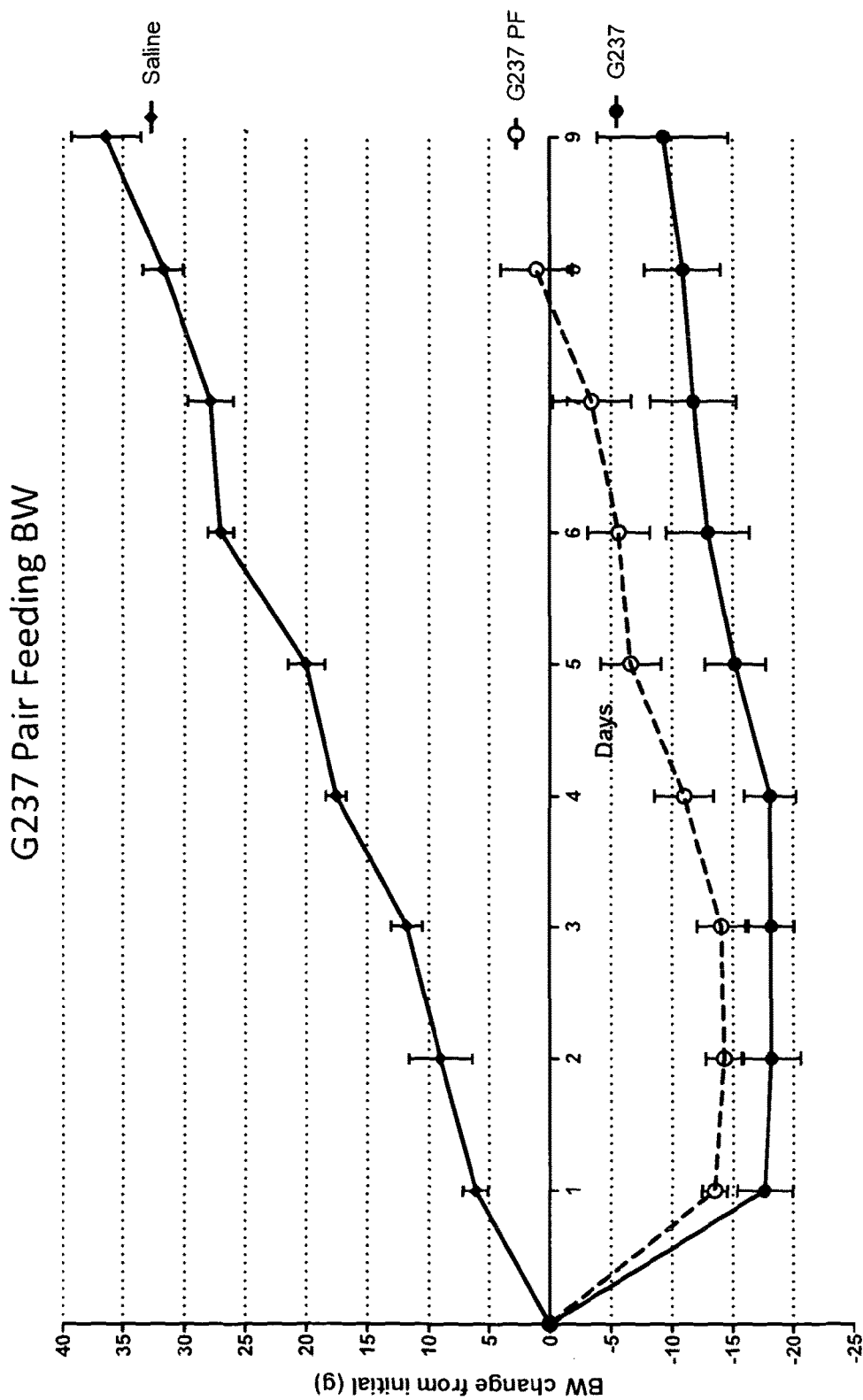

Compound 237 was administered at 100 nmol/kg daily (n=9). Comparator compound exendin-4 was administered at 10 nmol/kg daily on days 1 and 2 with a change in dose at day 3 to 30 nmol/kg which was maintained for all subsequent days. FIG. 13 provides evidence that compound 237 mediates a reduction in body weight compared to the saline control. Evidence that this reduction in body weight is not solely mediated by a reduction in food intake is provided by the "G237 PF" group which received no compound 237 but had their food intake reduced by the same amount as the "G237" group. This suggests that compound 237 has a metabolic effect on the body that contributes to body weight loss.

Example 6—Further Paired Feeding Studies

Figure 18:
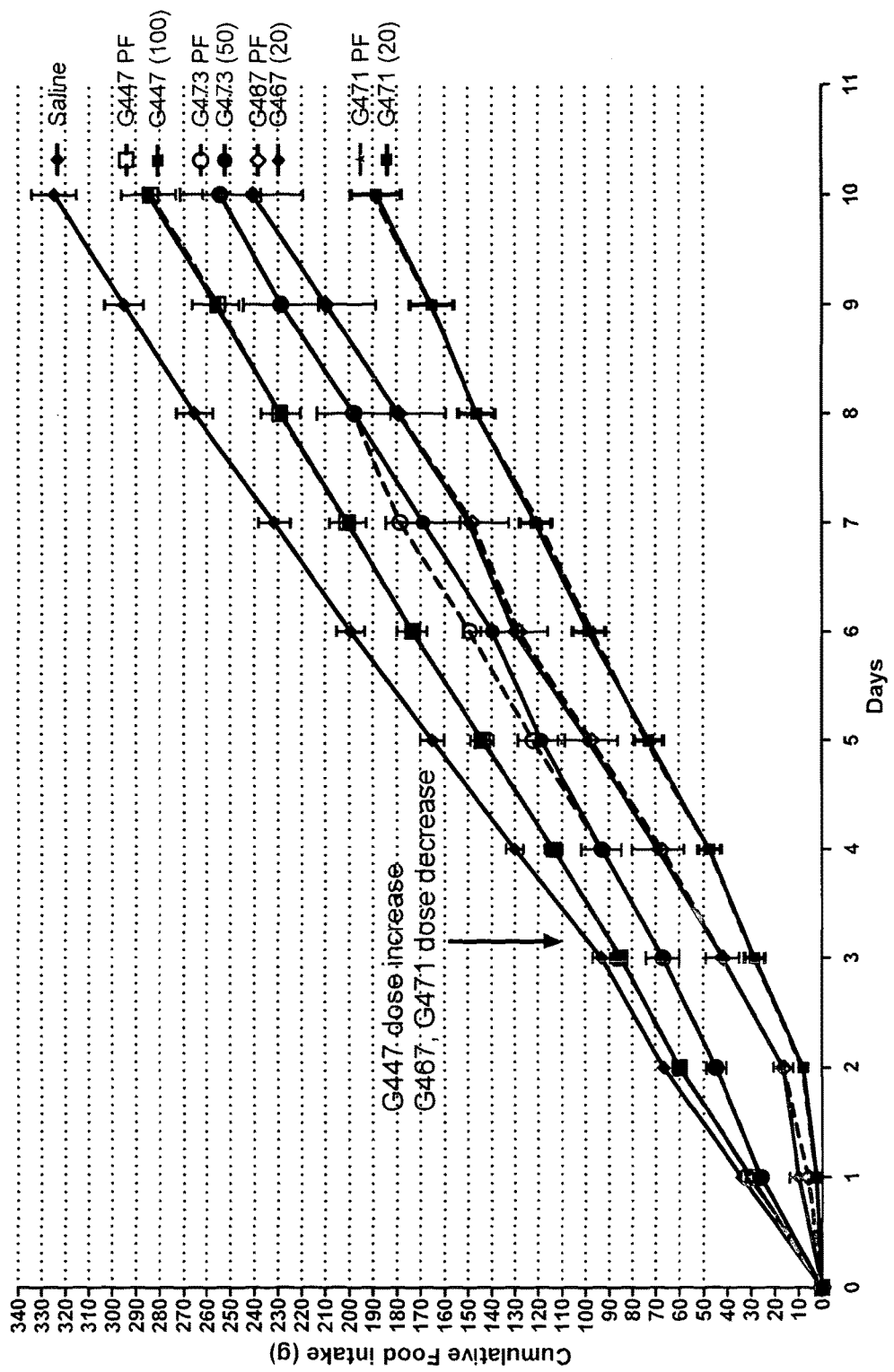
Figure 19:
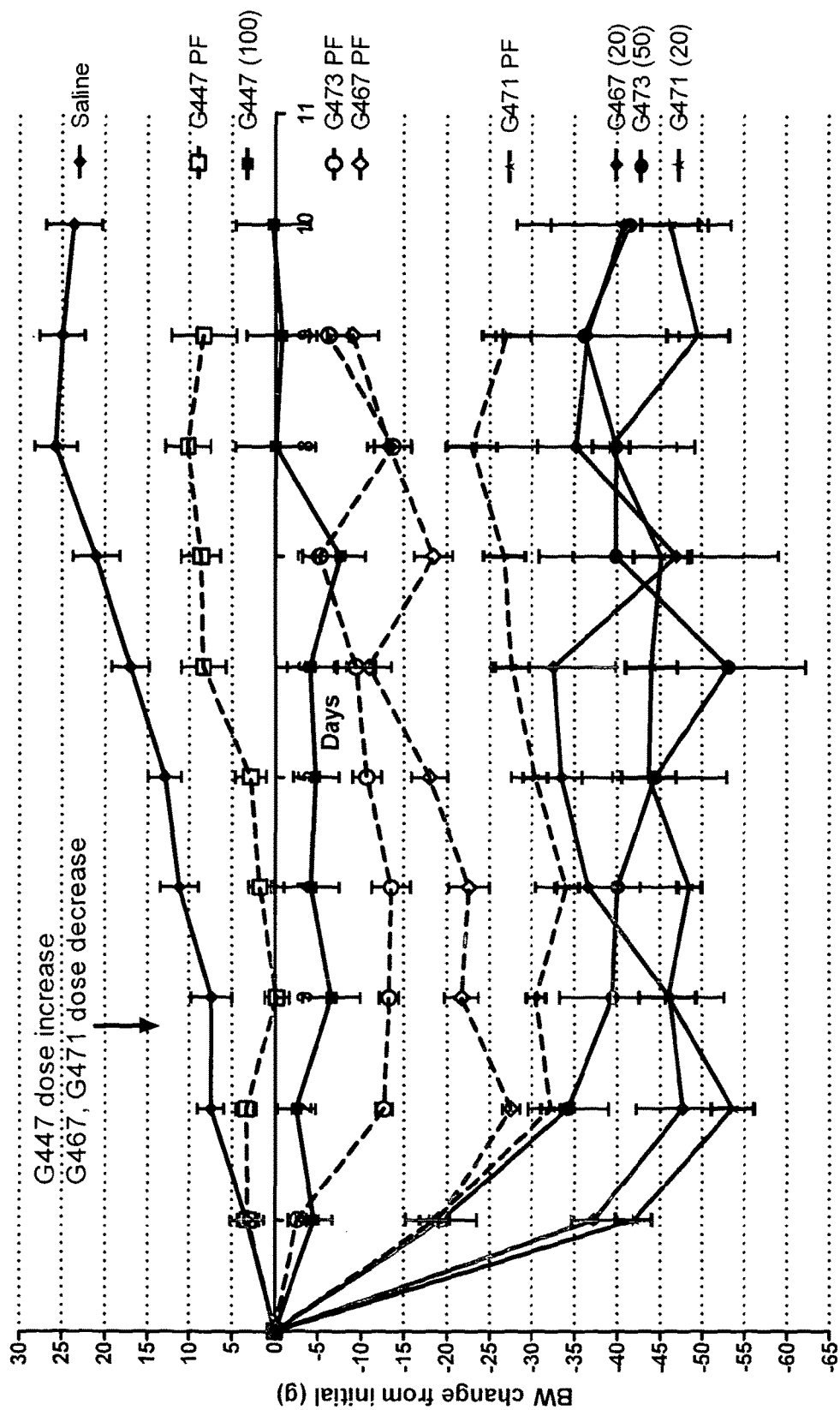

Further paired feeding studies were carried out as described in Example 4, but with compounds 447 (100 nmol/kg; 50 nmol/kg on days 1,2), 473 (50 nmol/kg), 467 (20 nmol/kg; 50 nmol/kg on days 1,2) and 471 (20 nmol/kg; 50 nmol/kg on days 1,2) at the indicated dosage levels for 10 days. The peptide formulations contained 1 zinc ion (as zinc chloride) per molecule of peptide. The results are shown in FIGS. 18 and 19.

Example 7—Further Paired Feeding Studies

Figure 20:
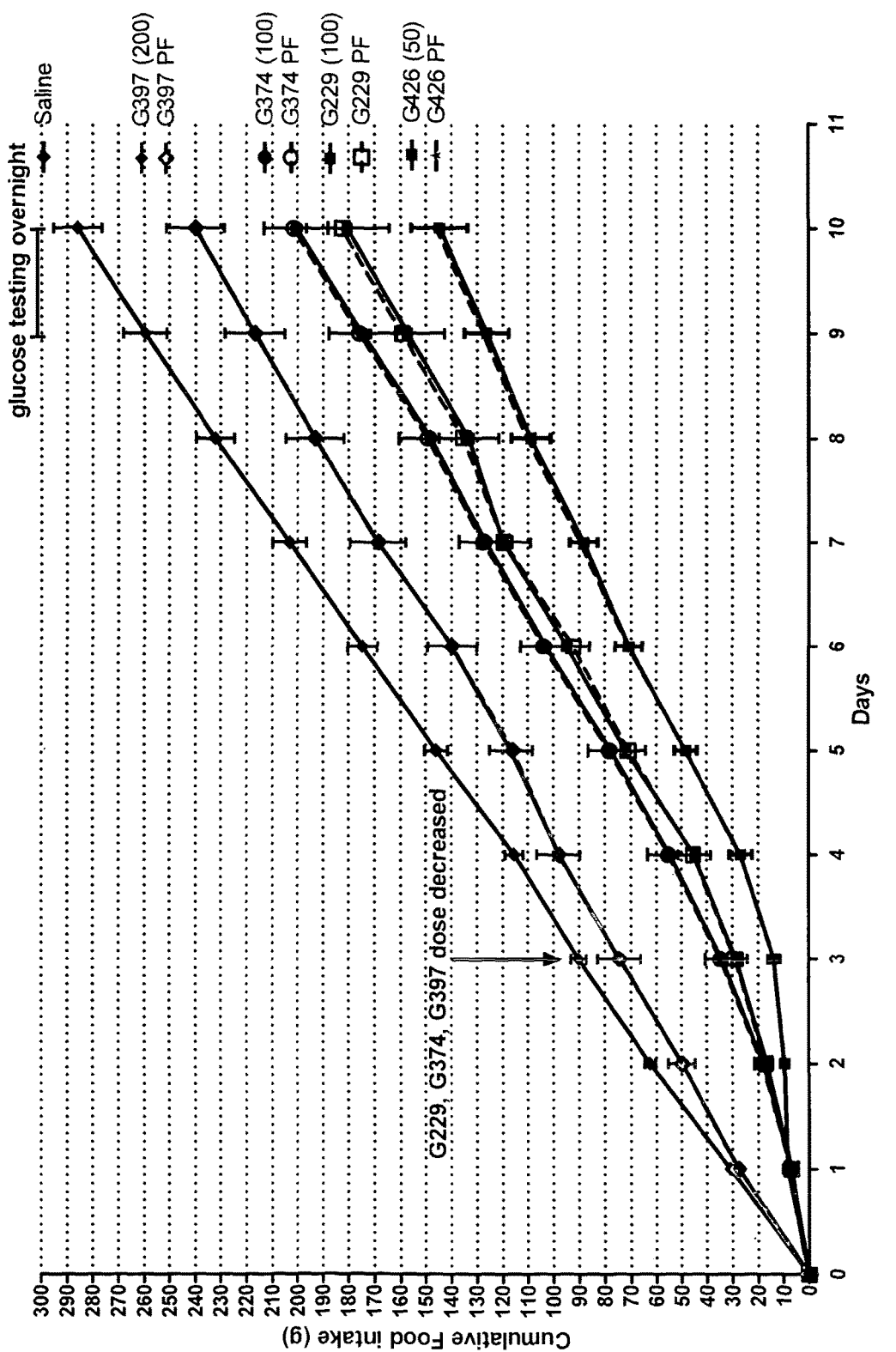
Figure 21:
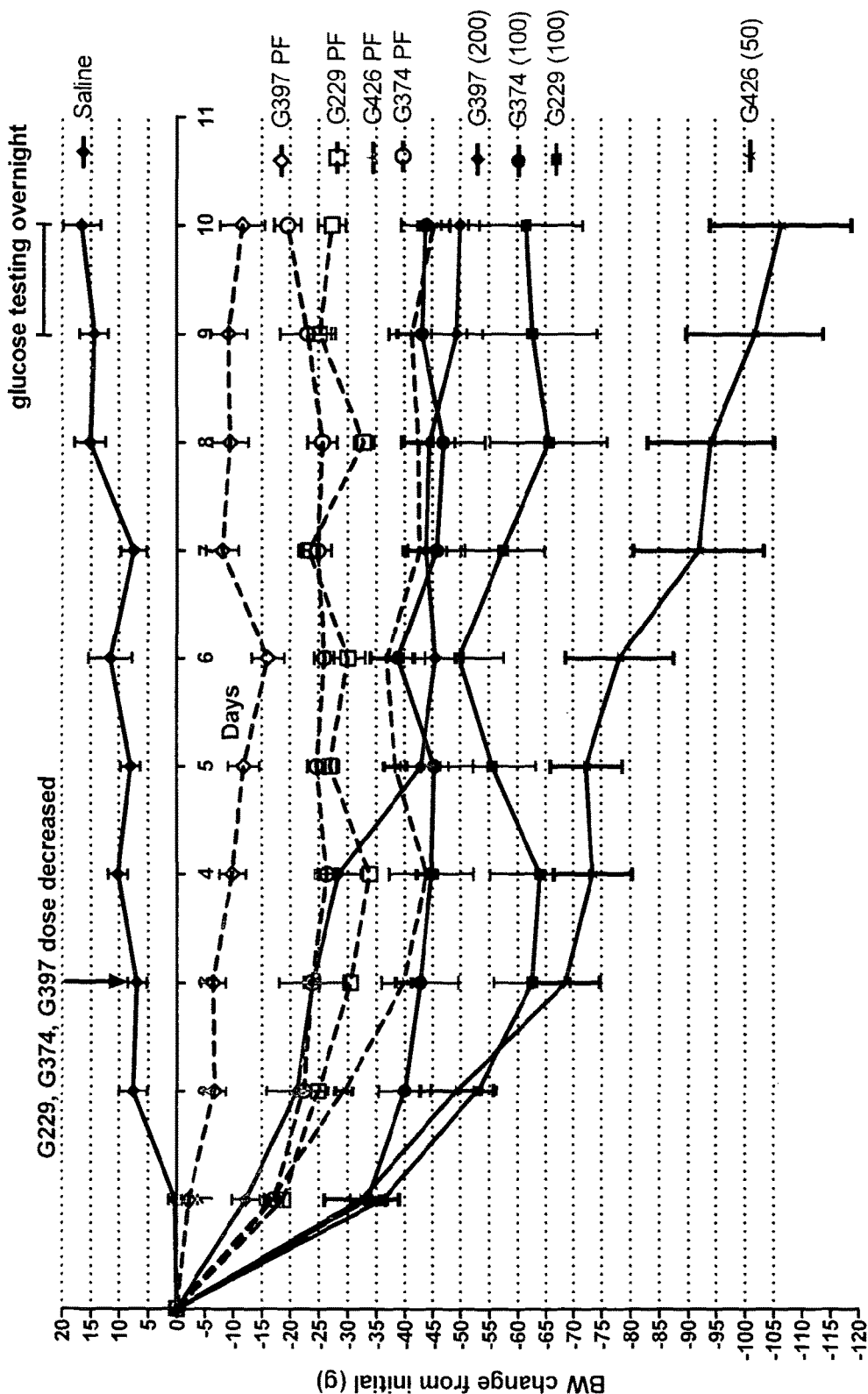

Further paired feeding studies were carried out as described in Example 4, but with compounds 229 (100 nmol/kg; 200 nmol/kg on days 1-3), 374 (100 nmol/kg; 200 nmol/kg on days 1-3), 397 (200 nmol/kg), and 426 (50 nmol/kg; 200 nmol/kg on days 1-3) at the indicated dosage levels for 10 days. The peptide formulations contained 1 zinc ion (as zinc chloride) per molecule of peptide. The results are shown in FIGS. 20 and 21.

Figure 22:
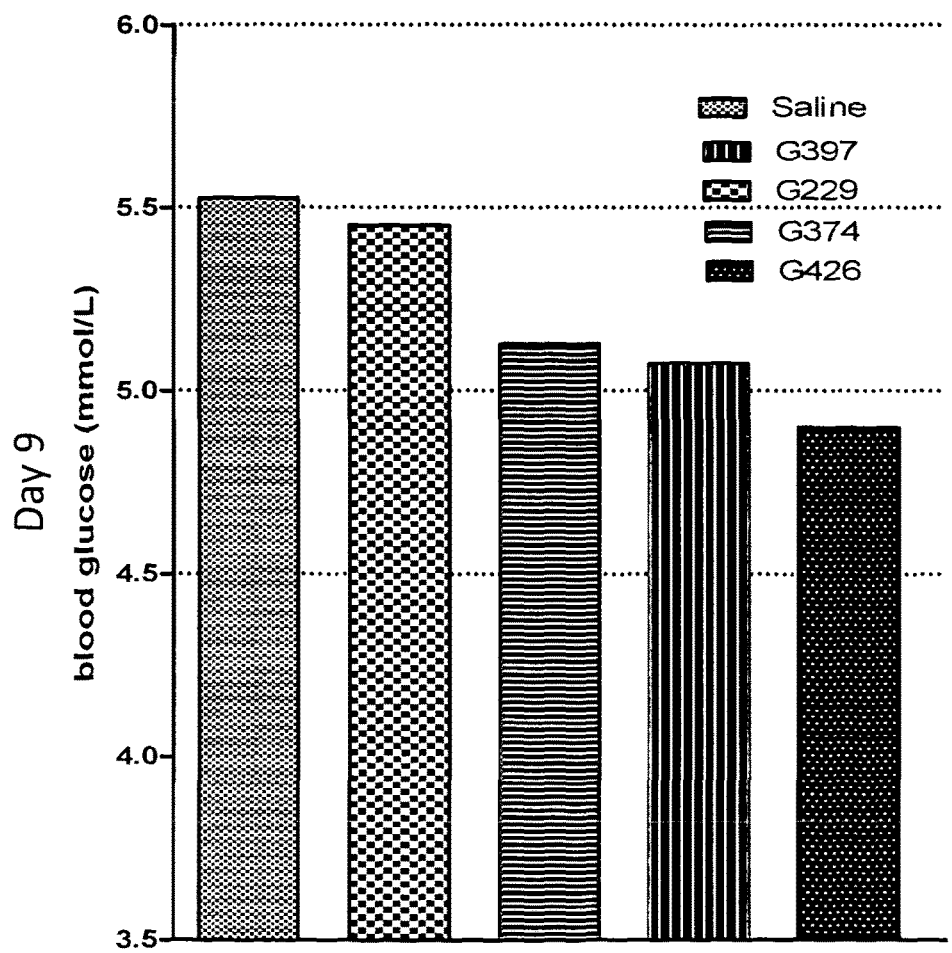
FIG. 22 shows the day-9 blood glucose levels of rats used in the pair feeding study of Example 7.

Blood glucose levels were measured on day 9. FIG. 22 shows that blood glucose levels on day 9 for peptides G397, G229, G374 and G426 were either the same or lower than for the saline control.

Example 8—Rat Pharmacokinetic Studies

Figure 23:
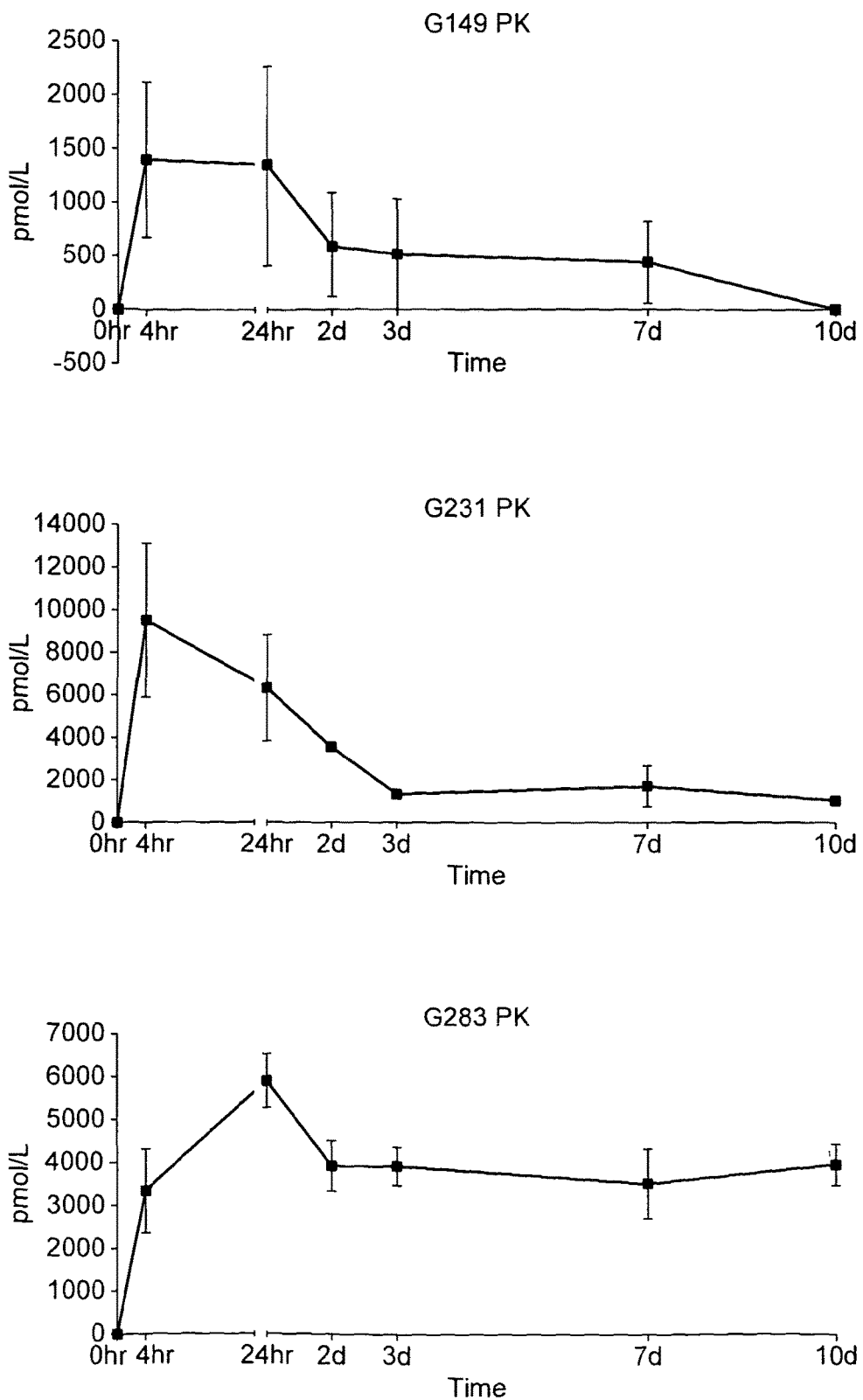
FIGS. 23 to 25 show the results of rat pharmacokinetic studies with compounds of the invention.
Figure 24:
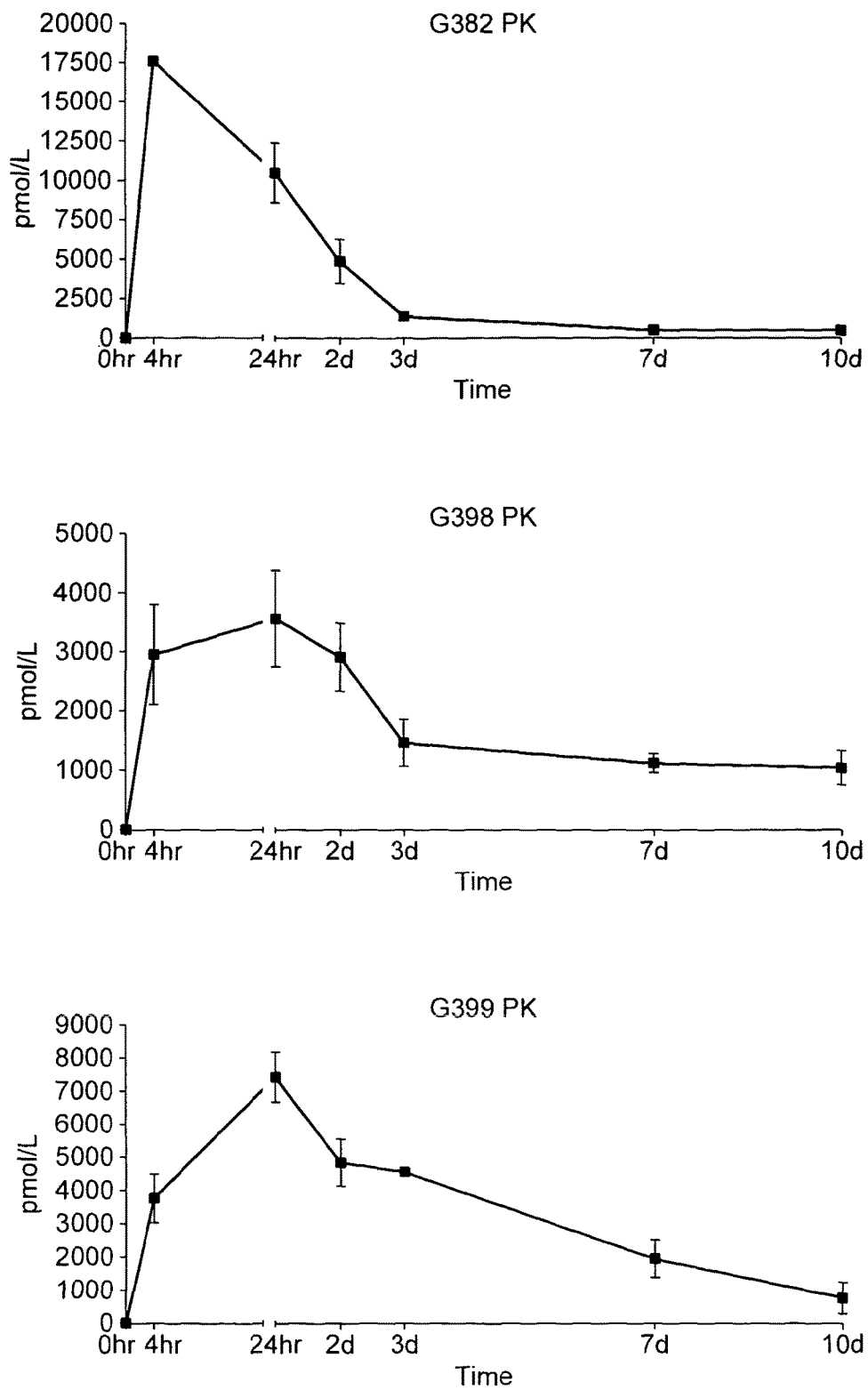
Figure 25:
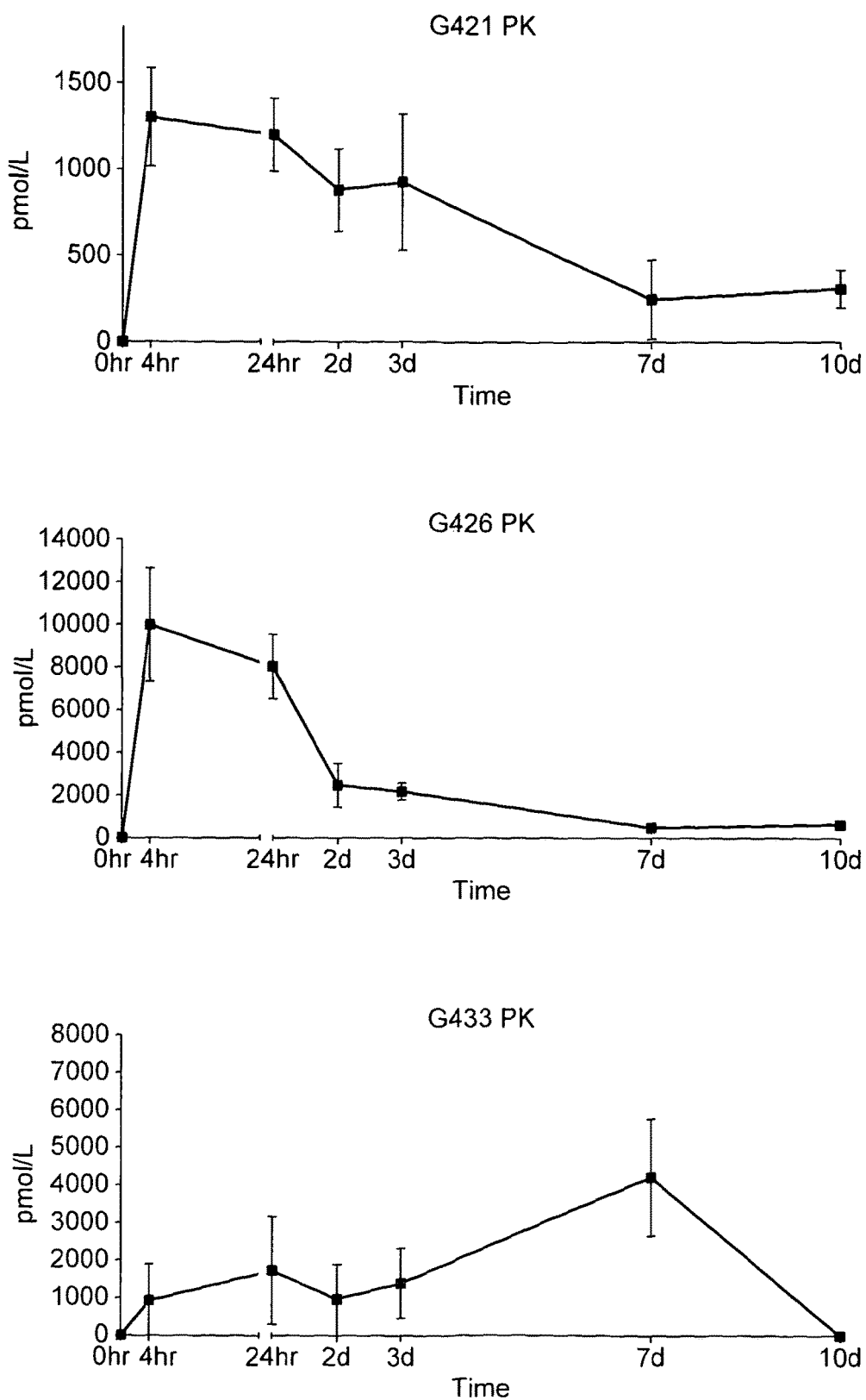

Rats were injected subcutaneously with peptides 149, 233, 283, 332, 398, 399, 421, 426 or 433. Each injection was of 20 μl total volume/rat containing 0.5 mg peptide and 1 zinc ion (as $ZnCl_2$) per peptide molecule. Blood was collected at 4 h, 24 h, 2 d, 3 d, 7 d and 10 d. The results are presented in FIGS. 23 to 25.

The invention claimed is:

1. A compound that is a peptide having a sequence represented by formula I

A-B    (I)

wherein A represents a region of the peptide having a sequence His1-Xaa2-Gln3-Gly4-Thr5-Phe6-Thr7-Ser8-Asp9-Xaa10-Ser11-Xaa12-Tyr13-Leu14-Xaa15-Xaa16-Xaa17-Xaa18-Xaa19-Xaa20-Xaa21-Phe22-Xaa23-Xaa24-Xaa25-Leu26-Xaa27-Xaa28-Xaa29;

wherein B is a region of the peptide having a sequence selected from

His30-His31; and

His30-His31-HN$_2$, wherein —NH$_2$ represents C-terminal amidation of the peptide;

wherein Xaa2 is Ser2, or an α-aminoisobutyric acid residue;

Xaa10 is Tyr10 or Val10;
Xaa12 is Lys12, His12, or Arg12;
Xaa15 is Asp15, Asn15, or Glu15;
Xaa16 is Ser16, Glu16, or Gly16;
Xaa17 is Glu17, Gln17, Arg17, Ser17 or Lys17;
Xaa18 is Ala18, Ile18, or Arg18;
Xaa19 is Ala19 or Val19;
Xaa20 is Lys20, Arg20, His20 or Gln20;
Xaa21 is Glu21, Tyr21, Leu21, or His21;
Xaa23 is Ile23 or Val23;
Xaa24 is Glu24 or Gln24;
Xaa25 is Trp25, His25, Lys25, Tyr25 or Leu25;
Xaa27 is Val27, Lys27, or Leu27;
Xaa28 is Lys28 or Asn28;
Xaa29 is Gly29, Thr29, or Arg29;

or a salt and/or solvate of said compound, with the proviso that at least one of the following criteria apply:

an α-aminoisobutyric acid residue is present at position 2 of the peptide sequence;
Val10 is present at position 10 of the peptide sequence;
Ser17 is present at position 17 of the peptide sequence;
Ile18 is present at position 18 of the peptide sequence;
His25 is present at position 25 of the peptide sequence;
Lys25 is present at position 25 of the peptide sequence;
Leu27 is present at position 27 of the peptide sequence; and
Val 27 is present at position 27 of the peptide sequence.

2. A compound as claimed in claim 1 wherein:

Xaa2 is Ser2 or an α-aminoisobutyric acid residue;
Xaa10 is Tyr10 or Val10;
Xaa12 is Lys12 or His12;
Xaa15 is Asp15 or Glu15;
Xaa16 is Ser16, Glu16 or Gly16;
Xaa17 is Glu17, Gln17, Arg17, Ser17 or Lys17;
Xaa18 to Xaa20 is Ala18-Val19-Arg20, Ala18-Val19-Lys20 or Ala18-Val19-His20;
Xaa21 is Glu21, Tyr21, Leu21 or His21;
Xaa23 is Ile23 or Val23;
Xaa25 is Trp25 or Lys25;
Xaa28 is Lys28 or Asn28; and
Xaa29 is Gly29 or Thr29;

wherein B is a region of the peptide having a sequence selected from:

His30-His31 and His30-His31-NH$_2$.

3. A compound as claimed in claim 2, wherein

Xaa2 is Ser2;
Xaa10 is Tyr10;
Xaa16 is Ser16 or Glu16;
Xaa17 is Glu17 or Gln17;
Xaa21 is Leu21 or His21;
Xaa23 is Ile23;
Xaa25 is Trp25;
Xaa27 is Lys27, Leu27 or Val27;
Xaa28 is Asn28;

wherein B is a region of the peptide having a sequence selected from His30-His31 or His30-His31-NH$_2$.

4. A compound as claimed in claim 1, wherein B is a region of the peptide having a sequence which is His30-His31.

5. A pharmaceutical composition comprising a compound as claimed in claim 1 together with a pharmaceutically acceptable carrier and optionally other therapeutic ingredients.

6. The pharmaceutical composition as claimed in claim 5 wherein said compound comprises at least 3 His residues, and wherein the composition has a pH of less than 5.0 prior to administration and wherein the composition comprises at least one zinc ion for every 4 molecules of peptide.

7. A method of treating or preventing a disease or disorder or other non-desired physiological state in a subject comprising administering to the subject a compound as claimed in claim 1.

8. The method as claimed in claim 7, wherein the method is a method of treating obesity or diabetes in a subject in need thereof, a method of reducing appetite in a subject, a method of reducing food intake in a subject, a method of reducing calorie intake in a subject, a method of increasing the energy expenditure of a subject, a method of enhancing insulin release in a subject, a method of improving carbohydrate tolerance in a subject, a method of improving carbohydrate metabolism in a subject, a method of cardiac protection in a subject following myocardial infarction, a method of neuroprotection in a subject having cerebral ischemia and/or a method of neuroprotection in a subject having or diagnosed as being at risk of a chronic neurodegenerative disease.

9. The method of claim 8 wherein the subject is overweight.

10. The method of claim 8 wherein the compound is administered parentally.

11. The method of claim 8 wherein the compound is administered subcutaneously, intravenously, intramuscularly, intranasally, transdermally or sublingually.

12. A method of treating or preventing a disease or disorder or other non-desired physiological state in a subject comprising administering to the subject a pharmaceutical composition as claimed in claim 5.

13. The method as claimed in claim 12, wherein the method is a method of treating obesity or diabetes in a subject in need thereof, a method of reducing appetite in a subject, a method of reducing food intake in a subject, a method of reducing calorie intake in a subject, a method of increasing the energy expenditure of a subject, a method of enhancing insulin release in a subject, a method of improving carbohydrate tolerance in a subject, a method of improving carbohydrate metabolism in a subject, a method of cardiac protection in a subject following myocardial infarction, a method of neuroprotection in a subject having cerebral ischemia and/or a method of neuroprotection in a subject having or diagnosed as being at risk of a chronic neurodegenerative disease.

14. The method as claimed in claim 13 wherein the subject is overweight, obese and/or diabetic.

15. The method as claimed in claim 12, wherein the pharmaceutical composition is administered subcutaneously.

* * * * *